(12) United States Patent
Barlaam et al.

(10) Patent No.: US 8,399,460 B2
(45) Date of Patent: Mar. 19, 2013

(54) CHROMENONE DERIVATIVES

(75) Inventors: Bernard Chistrophe Barlaam, Reims (FR); Sebastien Louis Degorce, Reims (FR); Christine Marie Paul Lambert-Van Der Brempt, Reims (FR); Remy Robert Morgentin, Reims (FR); Patrick Ple, Reims (FR)

(73) Assignee: Astrazeneca AB, Macclesfield, Cheshire (GB)

( * ) Notice: Subject to any disclaimer, the term of this patent is extended or adjusted under 35 U.S.C. 154(b) by 123 days.

(21) Appl. No.: 12/909,968

(22) Filed: Oct. 22, 2010

(65) Prior Publication Data

US 2011/0098271 A1    Apr. 28, 2011

(30) Foreign Application Priority Data

Oct. 27, 2009   (EP) .................................... 09306017

(51) Int. Cl.
     *A61K 31/535*    (2006.01)
     *C07D 413/04*    (2006.01)
(52) U.S. Cl. ..................... 514/233.5; 544/151
(58) Field of Classification Search ............... 514/233.5; 544/151
See application file for complete search history.

(56) References Cited

U.S. PATENT DOCUMENTS

2006/0276470 A1    12/2006   Jackson et al.

FOREIGN PATENT DOCUMENTS

| WO | 90/06921 A1 | 6/1990 |
|---|---|---|
| WO | 01/53266 A1 | 7/2001 |
| WO | 2004/016607 A1 | 2/2004 |
| WO | 2007/045876 A1 | 4/2007 |
| WO | 2008064244 A2 | 5/2008 |
| WO | 2009/130253 A1 | 10/2009 |
| WO | 2010/134082 A1 | 11/2010 |

OTHER PUBLICATIONS

Chen, Jack S.; Zhou, Linda J.; Entin-Meer, Michal; Yang, Xiaodong; Donker, Mila; Knight, Zachary A.; Weiss, William; Shokat, Kevan M.; Haas-Kogan, Daphne; Stokoe, David. Characterization of structurally distinct, isoform-selective phosphoinositide 3'-kinase inhibitors in combination with radiation in the treatment of glioblastoma. Molecular Cancer Therapeutics (2008), 7(4), 841-850. CODEN: MCTOCF ISSN:1535-7163. CAN 149:44464 AN 2008:465521 CAPLUS.

Fan, Qi-Wen; Knight, Zachary A.; Goldenberg, David D.; Yu, Wei; Mostov, Keith E.; Stokoe, David; Shokat, Kevan M.; Weiss, William A. A dual PI3 kinase/mTOR inhibitor reveals emergent efficacy in glioma. Cancer Cell (2006), 9(5), 341-349. CODEN: CCAECI ISSN:1535-6108. CAN 145:159270 AN 2006:519423 CAPLUS.

Torbett, Neil E.; Luna-moran, Antonio; Knight, Zachary A.; Houk, Andrew; Moasser, Mark; Weiss, William; Shokat, Kevan M.; Stokoe, David. A chemical screen in diverse breast cancer cell lines reveals genetic enhancers and suppressors of sensitivity to PI3K isoform-selective inhibition. Biochemical Journal (2008), 415(1), 97-110. CODEN: BIJOAK ISSN:0264-6021. CAN 149:548423 AN 2008:1106700 CAPLUS.

Griffin et al., "Selective Benzopyranone and Pyrimido[2,1-alpha]isoquinolin-4-one Inhibitors of DNA-Dependent Protein Kinase: Synthesis, Structure—Activity Studies, and Radiosensitization of a Human Tumor Cell Line in Vitro", Journal of Medicinal Chemistry 48(2): 569-585 (2005).

*Primary Examiner* — Rebecca Anderson
(74) *Attorney, Agent, or Firm* — Astrazeneca AB

(57) ABSTRACT

The invention concerns chromenone derivatives of Formula I

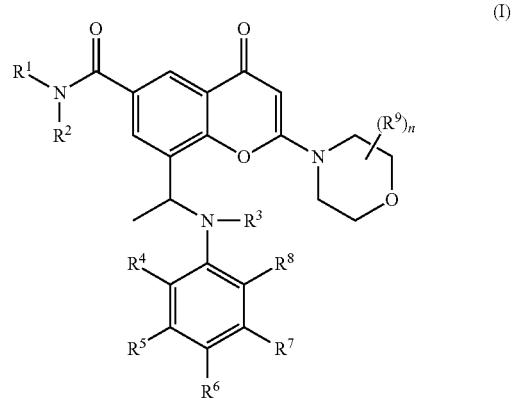

or a pharmaceutically-acceptable salts thereof, wherein each of $R^1$, $R^2$, $R^3$, $R^4$, $R^5$, $R^6$, $R^7$, $R^8$, n and $R^9$ has any of the meanings defined hereinbefore in the description; processes for their preparation, pharmaceutical compositions containing them and their use in the manufacture of a medicament for use in the treatment of cell proliferative disorders.

15 Claims, 9 Drawing Sheets

CHROMENONE DERIVATIVES

This application claims the benefit under 35 U.S.C. §119 (a)-(d) of application Ser. No. 09306017.6 (EP) filed on 27 Oct. 2009.

The invention concerns certain novel chromenone derivatives, or pharmaceutically-acceptable salts thereof, which possess anti-cancer activity and are accordingly useful in methods of treatment of the human or animal body. The invention also concerns processes for the manufacture of said chromenone derivatives, pharmaceutical compositions containing them and their use in therapeutic methods, for example in the manufacture of medicaments for use in the prevention or treatment of cancers in a warm-blooded animal such as man, including use in the prevention or treatment of cancer.

The present invention also relates to chromenone derivatives that are selective inhibitors of phosphoinositide (PI) 3-kinase β, and are, for example, useful for anti-tumour therapy. Further, the present invention also relates to the use of chromenone derivatives of the invention that are selective inhibitors of phosphoinositide (PI) 3-kinase β, in anti-tumour therapy Inhibitors of PI 3-kinase β may be effective in the treatment of tumours which are deficient in the gene PTEN (phosphatase and tensin homologue deleted on chromosome 10) and this relates to a further feature of the invention.

In the area of cancer it has in recent years been discovered that a cell may become cancerous by virtue of the transformation of a portion of its DNA into an oncogene, that is a gene which, on activation, leads to the formation of malignant tumour cells (Bradshaw, *Mutagenesis*, 1986, 1, 91). Several such oncogenes give rise to the production of peptides, which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al., *Ann. Reports in Med. Chem.*, 1989, Chpt. 13). The first group of tyrosine kinases to be identified arose from such viral oncogenes, for example pp $60^{v\text{-}Src}$ tyrosine kinase (otherwise known as v-Src), and the corresponding tyrosine kinases in normal cells, for example pp $60^{c\text{-}Src}$ tyrosine kinase (otherwise known as c-Src).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43-73) based on families of growth factors, which bind to different receptor tyrosine kinases. The classification includes Class I receptor tyrosine kinases comprising the EGF family of receptor tyrosine kinases such as the EGF, TGFα, Neu and erbB receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth. Various classes of non-receptor tyrosine kinases are known including the Src family such as the Src, Lyn, Fyn and Yes tyrosine kinases.

Further, it is also known that certain kinases belong to the class of serine/threonine kinases which are located intracellularly and downstream of tyrosine kinase activation and are involved in the transmission of biochemical signals such as those that influence tumour cell growth. Such serine/threonine signalling pathways include the Raf-MEK-ERK cascade and those downstream of PI 3-KINASE such as PDK-1, AKT and mTOR (Blume-Jensen and Hunter, *Nature*, 2001, 411, 355).

It is also known that certain other kinases belong to the class of lipid kinases, which are located intracellularly and are also involved in the transmission of biochemical signals such as those that influence tumour cell growth and invasiveness. Various classes of lipid kinases are known including the aforementioned PI 3-kinase family, which is alternatively known as the phosphatidylinositol-3-kinase family.

It is now well understood that deregulation of oncogenes and tumour-suppressor genes contributes to the formation of malignant tumours, for example by way of increased cell proliferation or increased cell survival. It is also now known that signalling pathways mediated by the PI 3-kinase family have a central role in a number of cell processes including proliferation and survival, and deregulation of these pathways is a causative factor a wide spectrum of human cancers and other diseases (Katso et al., *Annual Rev. Cell Dev. Biol.*, 2001, 17: 615-617 and Foster et al., *J. Cell Science*, 2003, 116: 3037-3040).

The PI 3-kinase family of lipid kinases is a group of enzymes that phosphorylate the 3-position of the inositol ring of phosphatidylinositol (PI). Three major groups of PI 3-s kinase enzymes are known which are classified according to their physiological substrate specificity (Vanhaesebroeck et al., *Trends in Biol. Sci.*, 1997, 22, 267). Class III PI 3-kinase enzymes phosphorylate PI alone. In contrast, Class II PI 3-kinase enzymes phosphorylate both PI and PI 4-phosphate [abbreviated hereinafter to PI(4)P]. Class I PI 3-kinase enzymes phosphorylate PI, PI(4)P and PI 4,5-bisphosphate [abbreviated hereinafter to PI(4,5)P2], although only PI(4,5)P2 is believed to be the physiological cellular substrate. Phosphorylation of PI(4,5)P2 produces the lipid second messenger PI 3,4,5-triphosphate [abbreviated hereinafter to PI(3,4,5)P3]. More distantly related members of this superfamily are Class IV kinases such as mTOR and DNA-dependent kinase that phosphorylate serine/threonine residues within protein substrates. The most studied and understood of these lipid kinases are the Class I PI 3-kinase enzymes.

Class I PI 3-kinase is a heterodimer consisting of a p110 catalytic subunit and a regulatory subunit, and the family is further divided into Class Ia and Class Ib enzymes on the basis of regulatory partners and mechanism of regulation. Class Ia enzymes, include PI 3-kinase β, and consist of three distinct catalytic subunits (p110α, p110β and p110δ) that dimerise with five distinct regulatory subunits (p85α, p55α, p50α, p85β and p55γ), with all catalytic subunits being able to interact with all regulatory subunits to form a variety of heterodimers. Class Ia PI 3-kinase enzymes are generally activated in response to growth factor-stimulation of receptor tyrosine kinases, via interaction of the regulatory subunit SH2 domains with specific phospho-tyrosine residues of the activated receptor or adaptor proteins such as IRS-1. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzymes are activated in response to G-protein coupled receptor (GPCR) systems as well as by the mechanisms described above.

There is now considerable evidence indicating that Class Ia PI 3-kinase enzymes, which include PI 3-kinase β, contribute to tumourigenesis in a wide variety of human cancers, either directly or indirectly (Vivanco and Sawyers, *Nature Reviews Cancer*, 2002, 2, 489-501). For example, the p110α subunit is amplified in some tumours such as those of the ovary (Shayesteh et al., *Nature Genetics*, 1999, 21: 99-102) and cervix (Ma et al., *Oncogene*, 2000, 19: 2739-2744). Activating mutations within the catalytic site of p110α have been associated with various other tumours such as those of the colorectal region and of the breast and lung (Samuels et al., *Science*, 2004, 304, 554). Tumour-related mutations in p85α have also been identified in cancers such as those of the ovary and colon (Philp et al., *Cancer Research*, 2001, 61, 7426-7429). In addition to direct effects, it is believed that activation of Class Ia PI 3-kinase contributes to tumourigenic events that occur upstream in signalling pathways, for example by way of ligand-dependent or ligand-independent activation of receptor tyrosine kinases, GPCR systems or integrins (Vara et al., *Cancer Treatment Reviews*, 2004, 30, 193-204). Examples of such upstream signalling pathways include over-expression of the receptor tyrosine kinase Erb2 in a variety of tumours leading to activation of PI 3-kinase-mediated pathways (Harari et al., *Oncogene*, 2000, 19, 6102-6114) and over-expression of the oncogene Ras (Kauffmann-Zeh et al., *Nature*, 1997, 385, 544-548). In addition, Class Ia PI 3-kinases may contribute indirectly to tumourigenesis caused by various downstream signalling events. For example, loss of the effect of the PTEN tumour-suppressor phosphatase that catalyses conversion of PI(3,4,5)P3 back to PI(4,5)P2 is associated with a very broad range of tumours via deregulation of PI 3-kinase-mediated production of PI(3,4,5) P3 (Simpson and Parsons, *Exp. Cell Res.*, 2001, 264, 29-41). Furthermore, augmentation of the effects of other PI 3-kinase-mediated signalling events is believed to contribute to a variety of cancers, for example by activation of Akt (Nicholson and Anderson, *Cellular Signalling*, 2002, 14, 381-395).

In addition to a role in mediating proliferative and survival signalling in tumour cells, there is also good evidence that Class Ia PI 3-kinase enzymes will also contribute to tumourigenesis via its function in tumour-associated stromal cells. For example, PI 3-kinase signalling is known to play an important role in mediating angiogenic events in endothelial cells in response to pro-angiogenic factors such as VEGF (Abid et al., *Arterioscler. Thromb. Vasc. Biol.*, 2004, 24, 294-300). As Class I PI 3-kinase enzymes are also involved in motility and migration (Sawyer, *Expert Opinion Investig. Drugs*, 2004, 13, 1-19), PI 3-kinase inhibitors should provide therapeutic benefit via inhibition of tumour cell invasion and metastasis.

In addition, Class I PI 3-kinase enzymes play an important role in the regulation of immune cells with PI 3-kinase activity contributing to pro-tumourigenic effects of inflammatory cells (Coussens and Werb, *Nature*, 2002, 420, 860-867).

These findings suggest that pharmacological inhibitors of Class I PI 3-kinase enzymes should be of therapeutic value for treatment of the various forms of the disease of cancer comprising solid tumours such as carcinomas and sarcomas and the leukaemias and lymphoid malignancies. In particular, inhibitors of Class I PI 3-kinase enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

Generally, investigators have explored the physiological and pathological roles of the PI 3-kinase enzyme family using the aforementioned PI 3-kinase inhibitors LY294002 and wortmannin. Although use of those compounds may suggest a role for PI 3-kinase in a cellular event, they are not sufficiently selective within the PI 3-kinase family to allow dissection of the individual roles of the family members. For this reason, more potent and selective pharmaceutical PI 3-kinase inhibitors would be useful to allow a more complete understanding of PI 3-kinase function and to provide useful therapeutic agents.

In addition to tumourigenesis, there is evidence that Class I PI 3-kinase enzymes play a role in other diseases (Wymann et al., *Trends in Pharmacological Science*, 2003, 24, 366-376). Both Class Ia PI 3-kinase enzymes and the single Class Ib enzyme have important roles in cells of the immune system (Koyasu, *Nature Immunology*, 2003, 4, 313-319) and thus they are therapeutic targets for inflammatory and allergic indications Inhibition of PI 3-kinase is also, as described earlier, useful to treat cardiovascular disease via anti-inflammatory effects or directly by affecting cardiac myocytes (Prasad et al., *Trends in Cardiovascular Medicine*, 2003, 13, 206-212). Inhibition of PI 3-kinase is also useful to treat thrombosis. WO2004016607 provides a method of disrupting platelet aggregation and adhesion occurring under high shear conditions, and a method for inhibiting platelet activation induced by shear, where both methods comprise the administration of a selective PI 3-kinase β inhibitor. WO2004016607 also provides an antithrombotic method comprising administering an effective amount of a selective PI 3-kinase β inhibitor. According to the method, specific inhibition of thrombosis can be obtained without affecting normal haemostasis by targeting PI 3-kinase β that is important for shear-induced platelet activation. Said antithrombotic method therefore does not involve side effects caused by disruption of normal haemostasis, such as extending of bleeding time. Thus inhibitors of Class I PI 3-kinase enzymes, including inhibitors of PI 3-kinase β, are expected to be of value in the prevention and treatment of a wide variety of diseases in addition to cancer.

The compounds, i.e. the chromenone derivatives, of the invention have now surprisingly been found to possess potent anti-tumour activity, being useful in inhibiting the uncontrolled cellular proliferation which arises from malignant disease. Without wishing to imply that the compounds disclosed in the present invention possess pharmacological activity only by virtue of an effect on a single biological process, it is believed that the compounds provide an anti-tumour effect by way of inhibition of Class I PI 3-kinase enzymes, particularly by way of inhibition of the Class Ia PI 3-kinase enzymes and/or the Class Ib PI 3-kinase enzyme, more particularly by way of inhibition of the Class Ia PI 3-kinase enzymes, which include inhibition of PI 3-kinase β.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, benign prostatic hypertrophy (BPH), hypersensitivity reactions of the skin, blood vessel diseases (for example atherosclerosis and restenosis), allergic asthma, insulin-dependent diabetes, diabetic retinopathy and diabetic nephropathy.

Generally, the compounds of the present invention possess potent inhibitory activity against Class I PI 3-kinase enzymes, particularly against Class Ia PI 3-kinase enzymes, including against of PI 3-kinase β, whilst possessing less potent inhibitory activity against tyrosine kinase enzymes such as the receptor tyrosine kinases, for example EGF receptor tyrosine kinase and/or VEGF receptor tyrosine kinase, or against non-receptor tyrosine kinases such as Src. Furthermore, certain compounds of the present invention, possess substantially better potency against Class I PI 3-kinase enzymes, particularly against Class Ia PI 3-kinase enzymes, including against of PI 3-kinase β, than against EGF receptor tyrosine kinase or VEGF receptor tyrosine kinase or Src non-receptor tyrosine kinase. Such compounds possess sufficient potency against Class I PI 3-kinase enzymes that they may be used in an amount sufficient to inhibit Class I PI 3-kinase enzymes, particularly to inhibit Class Ia PI 3-kinase enzymes, including PI 3-kinase β, whilst demonstrating little activity against EGF receptor tyrosine kinase or VEGF receptor tyrosine kinase or Src non-receptor tyrosine kinase.

Figure 1:
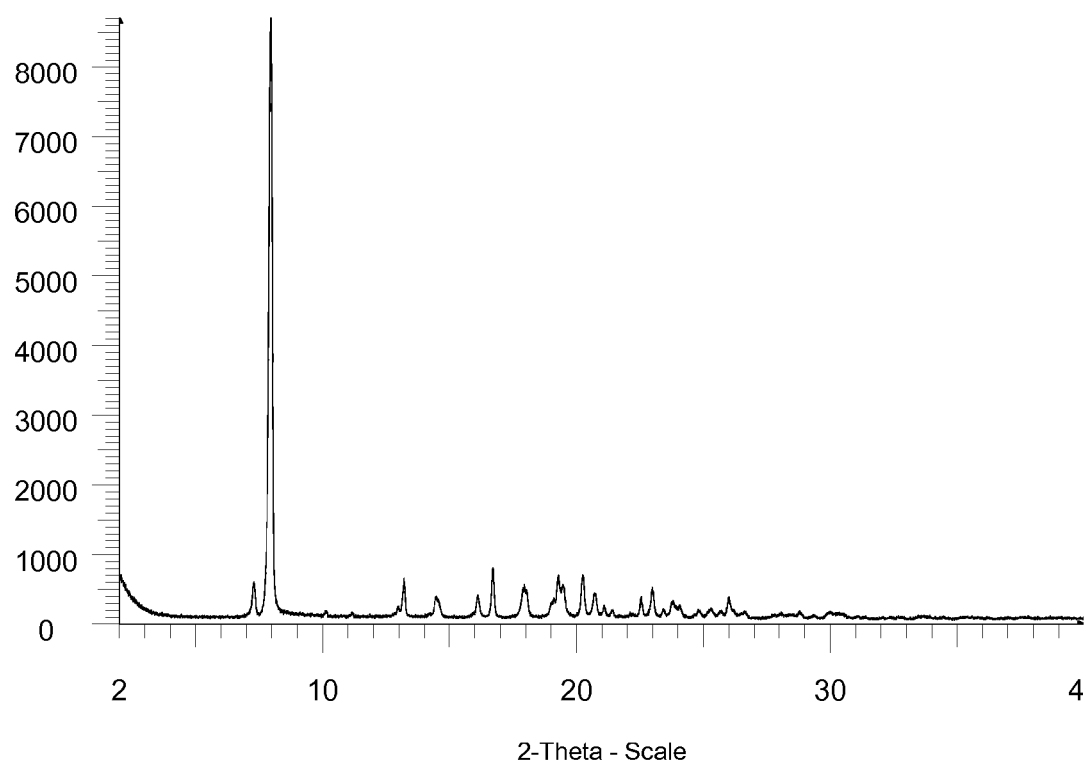
FIG. 1 shows an X-Ray Powder Diffraction Pattern of Form A of Example 3.06b.
Figure 2:
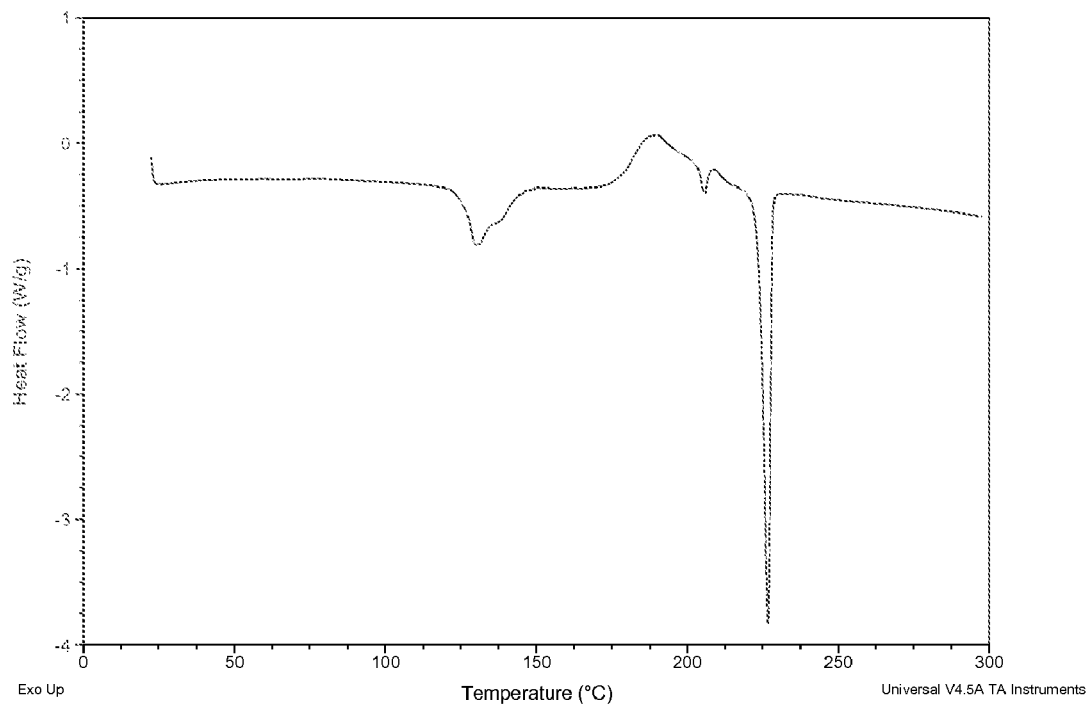
FIG. 2 shows a DSC Thermogram of Form A of Example 3.06b.
Figure 3:
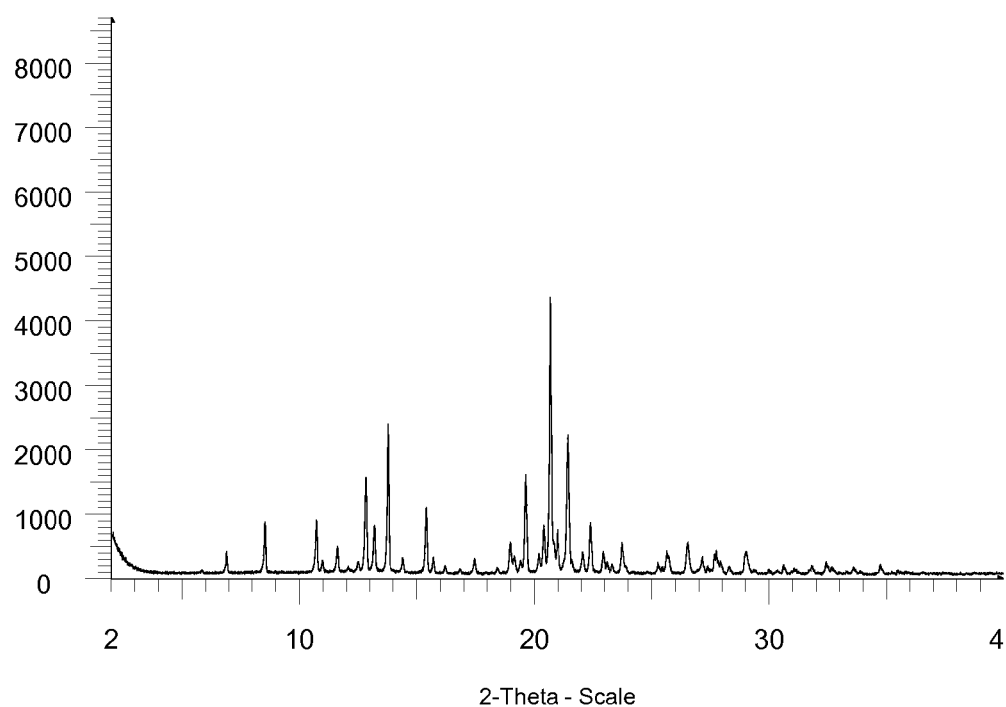
FIG. 3 shows an X-Ray Powder Diffraction Pattern of Form B of Example 3.06b.
Figure 4:
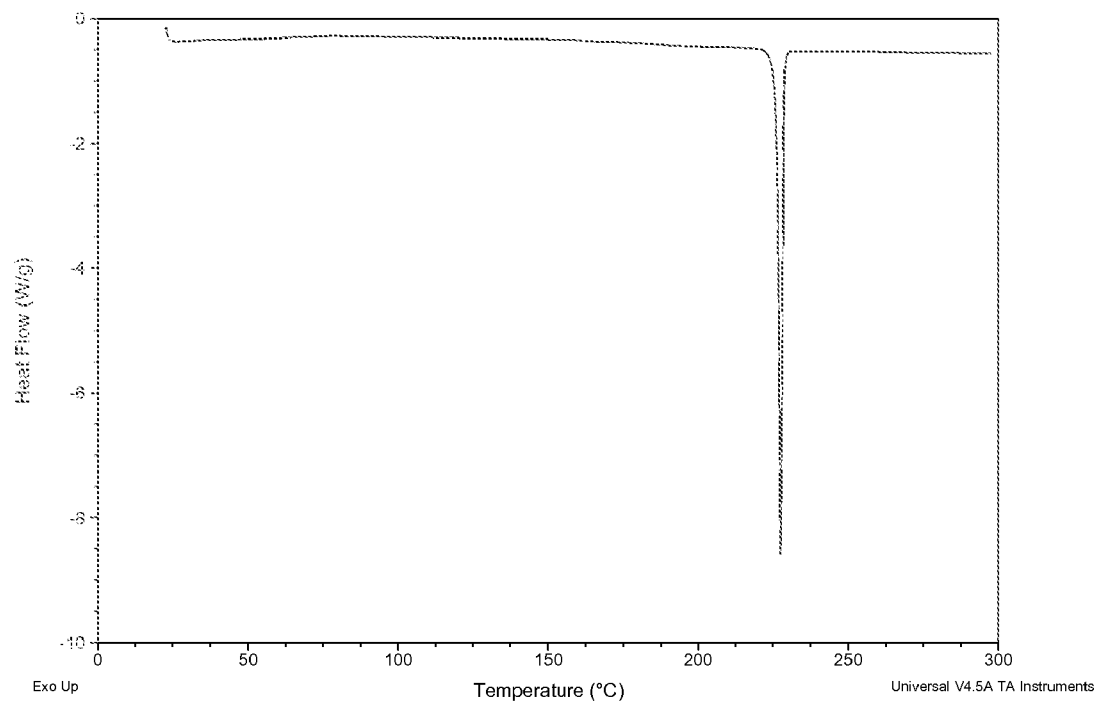
FIG. 4 shows a DSC Thermogram of Form B of Example 3.06b.
Figure 5:
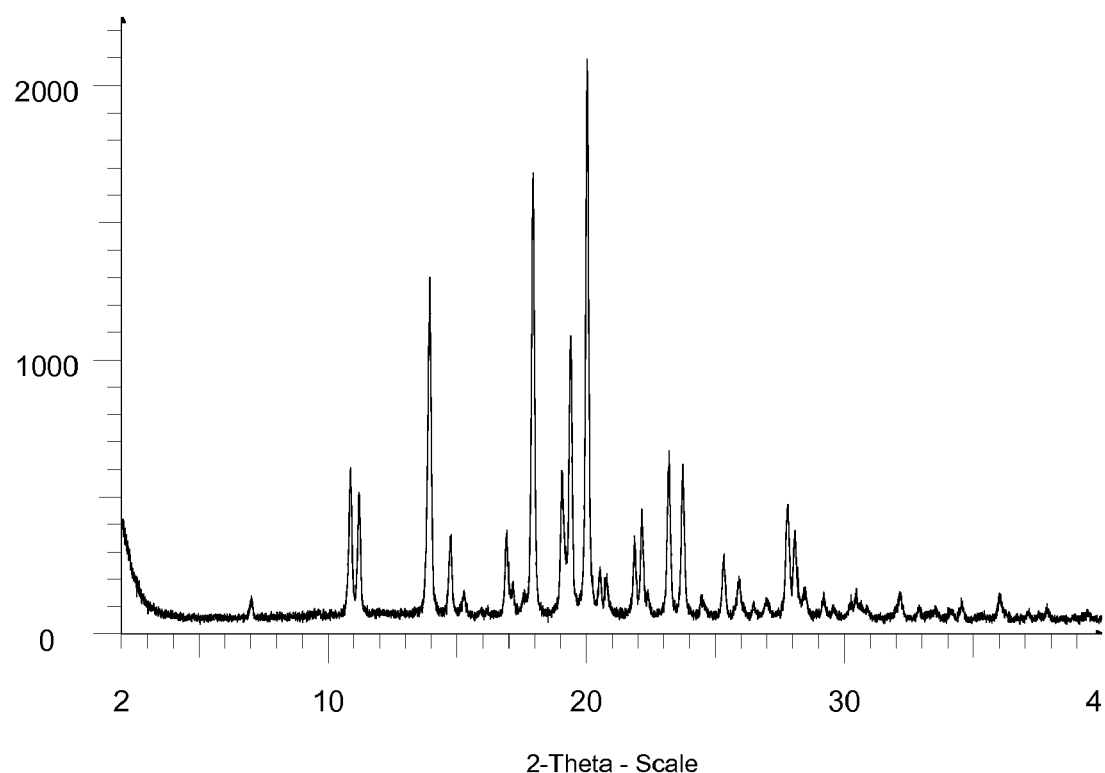
FIG. 5 shows an X-Ray Powder Diffraction Pattern of Form A of Example 3.13b.
Figure 6:
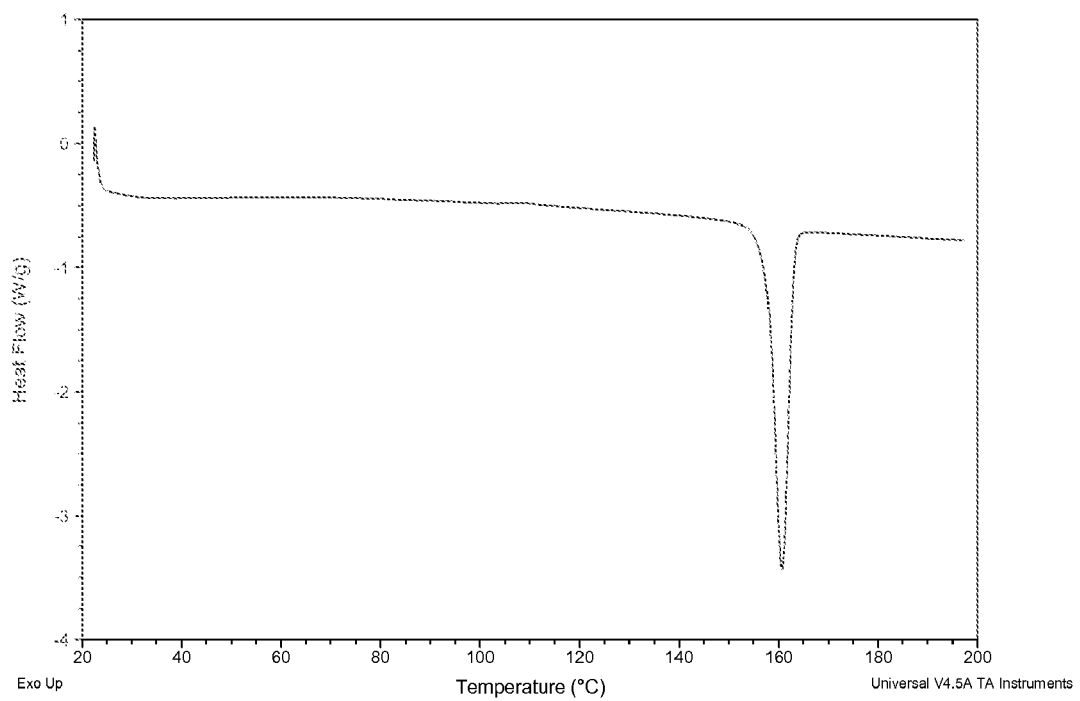
FIG. 6 shows a DSC Thermogram of Form A of Example 3.13b.
Figure 7:
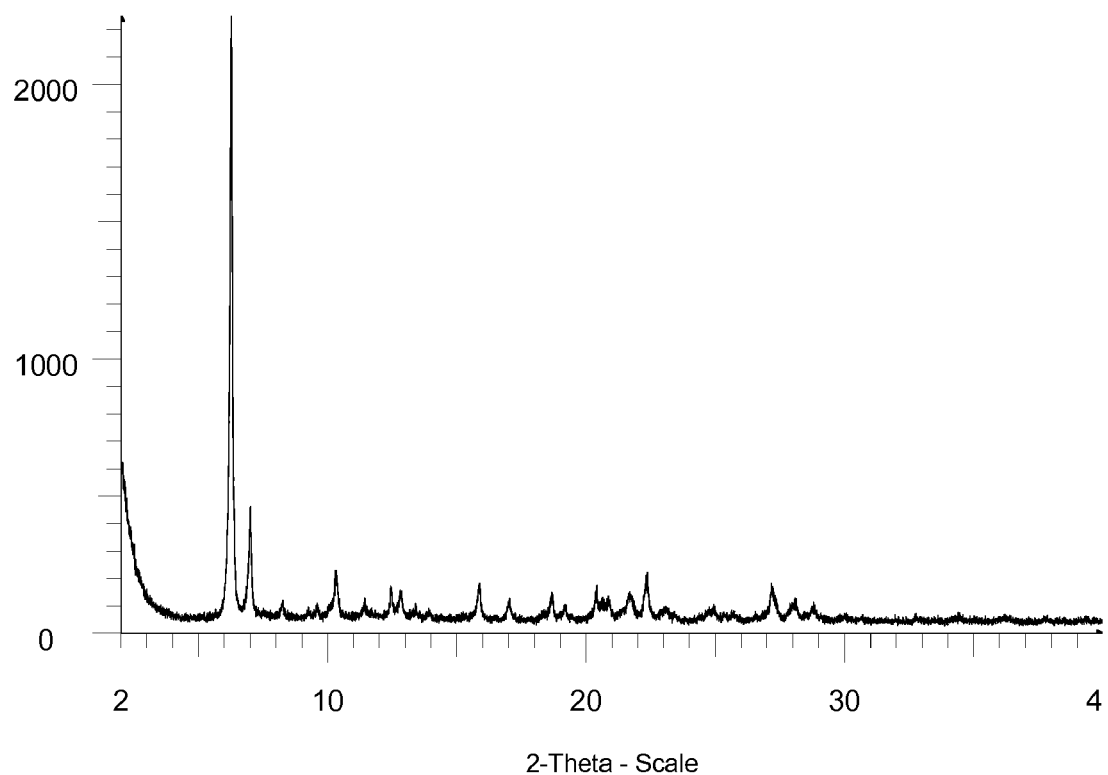
FIG. 7 shows an X-Ray Powder Diffraction Pattern of Form B of Example 3.13b.
Figure 8:
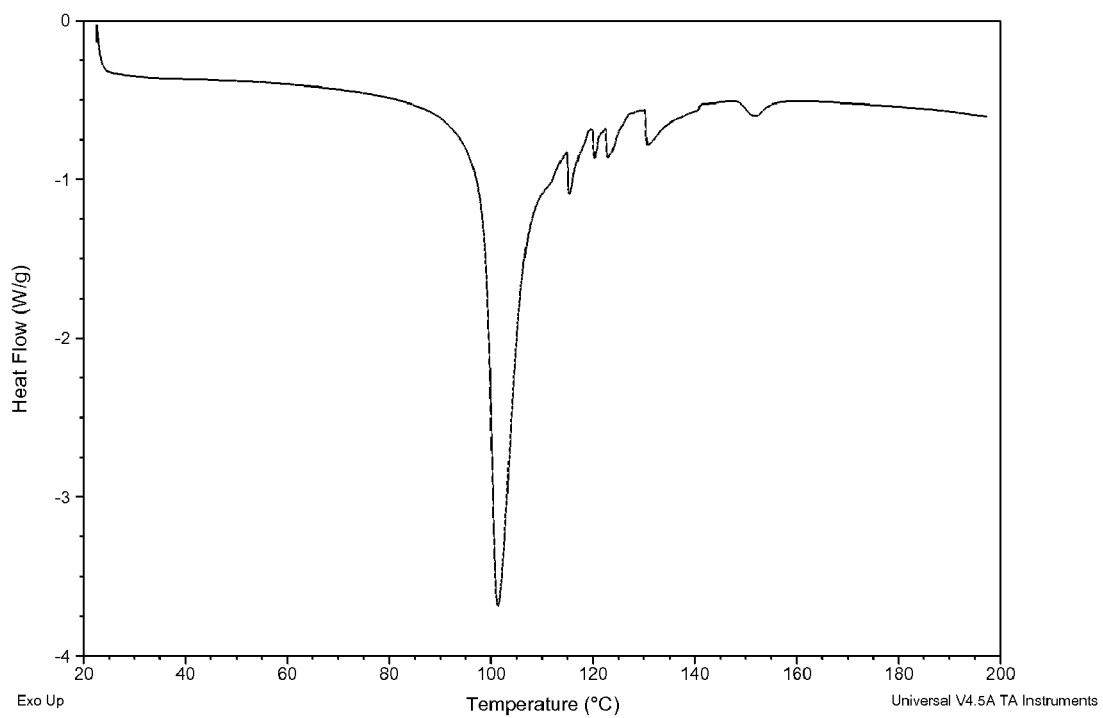
FIG. 8 shows a DSC Thermogram of Form B of Example 3.13b.
Figure 9:
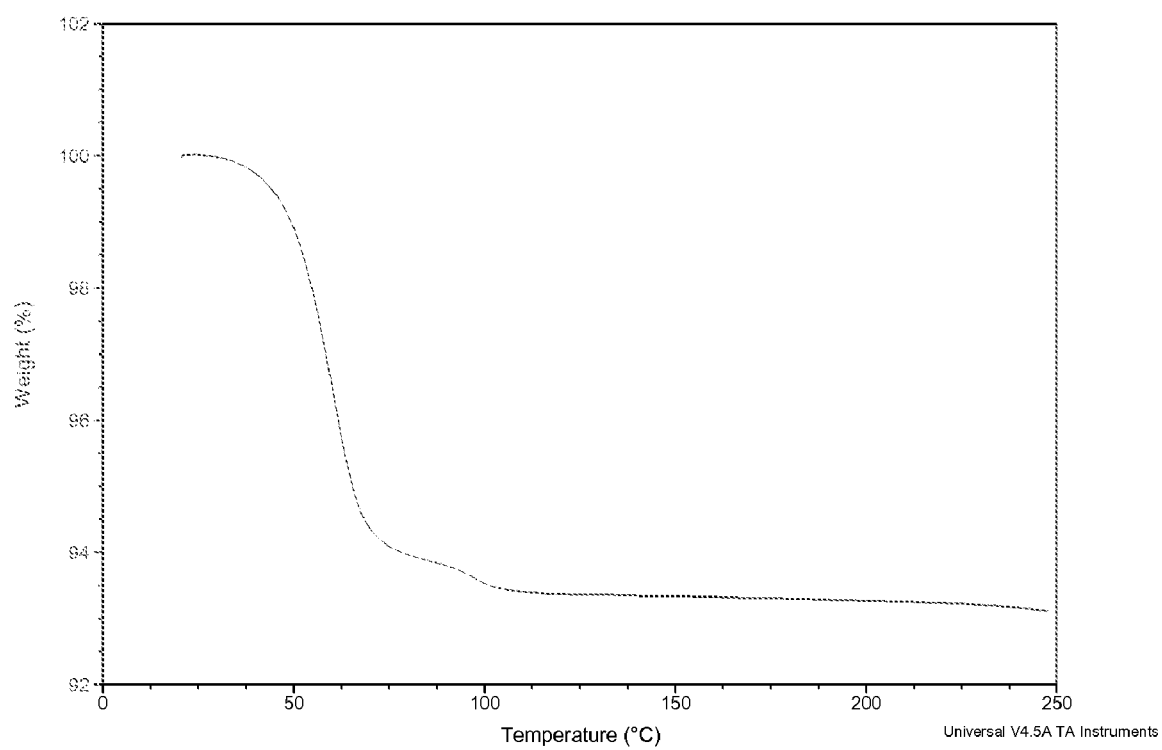
FIG. 9 shows a TGA Thermogram of Form B of Example 3.13b.

According to one aspect of the invention there is provided a chromenone derivative of the Formula I

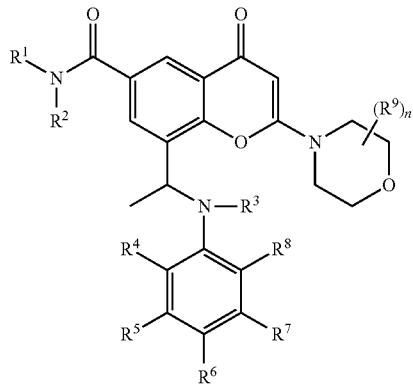

in which:
R$^1$ is H or (1-4C)alkyl optionally substituted by 1, 2 or 3 substituents independently selected from halogeno, hydroxy or (1-3C)alkoxy;
R$^2$ is (1-4C)alkyl or (1-4C)alkoxy, either of which can be optionally substituted by 1, 2 or 3 substituents independently selected from halogeno, hydroxy, (2-3C)alkenyl, (2-3C)alkynyl, (1-3C)alkoxy, cyano, (1-3C)alkylamino or di-[(1-3C)alkyl]amino; or
R$^1$ and R$^2$ together form a 3 to 8 membered nitrogen containing heterocyclyl ring system, which optionally contains 1 or 2 further heteroatoms selected from oxygen, nitrogen and sulphur, wherein a ring sulphur atom is optionally oxidised to form the S-oxide(s), said ring being optionally substituted by 1, 2 or 3 substituents independently selected from halogeno, hydroxy, (1-3C)alkyl, (2-3C)alkenyl, (2-3C)alkynyl, (1-3C)alkoxy, oxo, hydroxy-(1-3C)alkyl, halogeno-(1-3C)alkyl and (1-3C)alkoxy-(1-3C)alkyl;
R$^3$ is H or (1-3C)alkyl;
R$^4$ and R$^5$ are independently selected from H, halogeno, (1-3C)alkyl, (2-3C)alkenyl, (2-3C)alkynyl, (1-3C)alkoxy and cyano; or
R$^4$ and R$^5$ together form a phenyl ring or a 5 or 6 membered heterocyclyl ring or a 5 or 6 membered heteroaryl ring, wherein the heterocyclyl or heteroaryl ring contains 1, 2 or 3 heteroatoms selected from oxygen and nitrogen, said phenyl, heterocyclyl or heteroaryl ring being optionally substituted by 1, 2 or 3 substituents independently selected from halogeno, (1-3C)alkyl, (2-3C)alkenyl, (2-3C)alkynyl, (1-3C)alkoxy and cyano;
R$^6$, R$^7$ and R$^8$ are independently selected from H, halogeno, (1-3C)alkyl, (2-3C)alkenyl, (2-3C)alkynyl, (1-3C)alkoxy and cyano;
n is 0, 1, 2, 3 or 4;
each R$^9$ group is (1-3C)alkyl; or a pharmaceutically-acceptable salt thereof.

In this specification the generic term "(1-8C)alkyl" includes both straight-chain and branched-chain alkyl groups such as propyl, isopropyl and tert-butyl, and also (3-8C)cycloalkyl groups such as cyclopropyl, cyclobutyl, cyclopentyl, cyclohexyl and cycloheptyl, and also (3-6C)cycloalkyl-(1-2C)alkyl groups such as cyclopropylmethyl, 2-cyclopropylethyl, cyclobutylmethyl, 2-cyclobutylethyl, cyclopentylmethyl, 2-cyclopentylethyl, cyclohexylmethyl and 2-cyclohexylethyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes (3-6C)cycloalkyloxy groups and cycloalkyl-alkoxy groups having 4 to 6 carbon atoms, for example methoxy, ethoxy, propoxy, isopropoxy, cyclopropyloxy, cyclobutyloxy, cyclopentyloxy, cyclohexyloxy, cyclopropylmethoxy, 2-cyclopropylethoxy, cyclobutylmethoxy, 2-cyclobutylethoxy and cyclopentylmethoxy; (1-6C)alkylamino includes (3-6C)cycloalkylamino groups and N-(cycloalkylalkyl)amino groups having 4 to 6 carbon atoms, for example methylamino, ethylamino, propylamino, cyclopropylamino, cyclobutylamino, cyclohexylamino, cyclopropylmethylamino, 2-cyclopropylethylamino, cyclobutylmethylamino, 2-cyclobutylethylamino and cyclopentylmethylamino; and di-[(1-6Calkyl]amino includes di-[(3-6C)cycloalkyl]amino groups and di-[cycloalkylalkyl]amino groups in which the cycloalkylalkyl moiety has 4 to 6 carbon atoms, for example dimethylamino, diethylamino, dipropylamino, N-cyclopropyl-N-methylamino, N-cyclobutyl-N-methylamino, N-cyclohexyl-N-ethylamino, N-cyclopropylmethyl-N-methylamino, N-(2-cyclopropylethyl)-N-methylamino and N-cyclopentylmethyl-N-methylamino.

A person skilled in the art will appreciate that the terms "(1-6C)alkyl", "(1-4C)alkyl", "(1-3C)alkyl" and "(1-2C) alkyl" that are used herein refer to any of the alkyl groups defined above that posseses 1 to 6, 1 to 4, 1 to 3 and 1 to 2 carbon atoms respectively. The same convention applies to other terms used herein, such as, for example, "(1-6C) alkoxy", "(1-4C)alkoxy", "(1-3C)alkoxy" and "(1-2C) alkoxy".

For the avoidance of doubt, when, as defined hereinbefore, an $R^4$ and $R^5$ group together form a phenyl ring or a 5 or 6 membered heterocyclyl ring or a 5 or 6 membered heteroaryl ring, said ring includes the carbon atoms of the core phenyl group to which the $R^4$ and $R^5$ groups are attached. For example, when the $R^4$ and $R^5$ group together form a phenyl ring, then the ring system directly attached to the $N(R^3)$ group would be a napthyl ring:

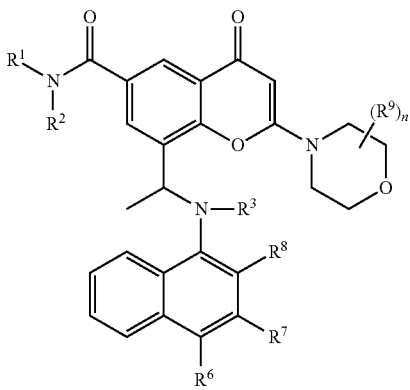

Similarly, when, as defined hereinbefore, the $R^4$ and $R^5$ group together form a pyridinyl ring, then the ring system directly attached to the $N(R^3)$ group would be a quinolinyl or isoquinolinyl ring.

It is to be understood that, insofar as certain of the compounds of Formula I defined above may exist in optically active or racemic forms by virtue of one or more asymmetric carbon atoms, the invention includes in its definition any such optically active or racemic form which possesses phosphoinositide (PI) 3-kinase inhibitory activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques.

A particular enantiomer of the compounds described herein may be more active that other enantiomers of the compound. For example, the (+) enantiomer of the title compound of Example 3.06 (i.e. the compound of Example 3.06a, where (+) signifies the optical rotation measured using the conditions described in Example 3.06a) is the enantiomer having the weaker activity. For the avoidance of doubt, the chiral centre in question is the carbon atom to which the groups methyl and —$N(R^3)$phenyl$(R^4)(R^5)(R^6)(R^7)(R^8)$ are attached.

Accordingly, in a further aspect of the invention, there is provided a chromenone derivative of the Formula I, or a pharmaceutically-acceptable salt thereof, wherein the chiral centre to which the groups methyl and —$N(R^3)$phenyl$(R^4)$ $(R^5)(R^6)(R^7)(R^8)$ are attached is in the (R)-stereochemical configuration. In a further aspect of the invention, there is provided a chromenone derivative of the Formula I, or a pharmaceutically-acceptable salt thereof, wherein the chiral centre to which the groups methyl and —$N(R^3)$phenyl$(R^4)$ $(R^5)(R^6)(R^7)(R^8)$ are attached is in the (S)-stereochemical configuration.

According to a further aspect of the invention there is provided a chromenone derivative of the Formula I, or a pharmaceutically-acceptable salt thereof, which is a single enantiomer being in an enantiomeric excess (% ee) of ≧95, ≧98% or ≧99%. In one embodiment of this aspect of the invention, the chiral centre to which the groups methyl and —$N(R^3)$phenyl$(R^4)(R^5)(R^6)(R^7)(R^8)$ are attached is in the (R)-stereochemical configuration. In a further embodiment of this aspect of the invention, the chiral centre to which the groups methyl and —$N(R^3)$phenyl$(R^4)(R^5)(R^6)(R^7)(R^8)$ are attached is in the (S)-stereochemical configuration.

According to a further aspect of the invention there is provided a pharmaceutical composition, which comprises a chromenone derivative of the Formula I, which is a single enantiomer being in an enantiomeric excess (% ee) of ≧95, ≧98% or ≧99% or a pharmaceutically-acceptable salt thereof, in association with a pharmaceutically-acceptable diluent or carrier. Conveniently, the single enantiomer is present in an enantiomeric excess (% ee) of ≧99%. In one embodiment of this aspect of the invention, the chiral centre to which the groups methyl and —$N(R^3)$phenyl$(R^4)(R^5)(R^6)$ $(R^7)(R^8)$ are attached is in the (R)-stereochemical configuration. In a further embodiment of this aspect of the invention, the chiral centre to which the groups methyl and —$N(R^3)$ phenyl$(R^4)(R^5)(R^6)(R^7)(R^8)$ are attached is in the (S)-stereochemical configuration.

Some compounds of formula (I) may exhibit polymorphism. It is to be understood that the present invention encompasses any polymorphic form, or mixtures thereof, which form possesses properties useful in the inhibition of phosphoinositide (PI) 3-kinase activity, it being well known in the art how to determine efficacy of a polymorphic form for the inhibition of phosphoinositide (PI) 3-kinase activity by the standard tests described hereinafter.

It is generally known that crystalline materials may be analysed using conventional techniques such as X-Ray Powder Diffraction (hereinafter XRPD) analysis, Differential Scanning calorimetry (hereinafter DSC), Thermal Gravimetric Analysis (hereinafter TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

As an example, the compound of Example 3.06b exhibits polymorphism and two crystalline forms have been identified Accordingly, a further aspect of the invention is Form A of (−)-8-(1-(3,5-difluorophenylamino)ethyl)-N,N-dimethyl-2-morpholino-4-oxo-4H-chromene-6-carboxamide, where the (−)- in the chemical name signifies the optical rotation measured using the conditions described in Example 3.06b.

Accordingly, a further aspect of the invention is Form B of (−)-8-(1-(3,5-difluorophenylamino)ethyl)-N,N-dimethyl-2-morpholino-4-oxo-4H-chromene-6-carboxamide.

According to a further aspect of the present invention, there is provided a crystalline form, Form A of (−)-8-(1-(3,5-difluorophenylamino)ethyl)-N,N-dimethyl-2-morpholino-4- oxo-4H-chromene-6-carboxamide, which has an X-ray powder diffraction pattern with at least one specific peak at about 2-theta=7.9°.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at about 2-theta=16.7°.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with at least two specific peaks at about 2-theta=7.9° and 16.7°.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with specific peaks at about 2-theta=7.9, 16.7, 20.3, 19.3, 13.2, 7.2, 19.5, 17.9, 23.0, 5.0°.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern substantially the same as the X-ray powder diffraction pattern shown in Figure A.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at 2-theta=7.9° plus or minus 0.5° 2-theta.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at 2-theta=16.7° plus or minus 0.5° 2-theta.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with at least two specific peaks at 2-theta=7.9° and 16.7° wherein said values may be plus or minus 0.5° 2-theta.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with specific peaks at 2-theta=7.9, 16.7, 20.3, 19.3, 13.2, 7.2, 19.5, 17.9, 23.0, 5.0° wherein said values may be plus or minus 0.5° 2-theta.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at 2-theta=7.9°.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at 2-theta=16.7°.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with at least two specific peaks at 2-theta=7.9° and 16.7°.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern with specific peaks at 2-theta=7.9, 16.7, 20.3, 19.3, 13.2, 7.2, 19.5, 17.9, 23.0, 5.0°.

According to a further aspect of the present invention, there is provided a crystalline form, Form A of (−)-8-(1-(3,5-difluorophenylamino)ethyl)-N,N-dimethyl-2-morpholino-4-oxo-4H-chromene-6-carboxamide, which has an X-ray powder diffraction pattern as shown in Figure A.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at about 2-theta=20.7°.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at about 2-theta=13.8°.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with at least two specific peaks at about 2-theta=20.7° and 13.8°.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with specific peaks at about 2-theta=20.7, 13.8, 21.5, 19.6, 12.8, 15.4, 10.7, 8.5, 22.4°

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern substantially the same as the X-ray powder diffraction pattern shown in Figure C.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at 2-theta=20.7° plus or minus 0.5° 2-theta.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at 2-theta=13.8° plus or minus 0.5° 2-theta.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with at least two specific peaks at 2-theta=20.7° and 13.8° wherein said values may be plus or minus 0.5° 2-theta.

According to a further aspect of the present invention, there is provided a crystalline form, Form B of (−)-8-(1-(3,5-difluorophenylamino)ethyl)-N,N-dimethyl-2-morpholino-4- oxo-4H-chromene-6-carboxamide, which has an X-ray powder diffraction pattern with specific peaks at 2-theta=20.7, 13.8, 21.5, 19.6, 12.8, 15.4, 10.7, 8.5, 22.4° wherein said values may be plus or minus 0.5° 2-theta.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at 2-theta=20.7°.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with at least one specific peak at 2-theta=13.8°.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with at least two specific peaks at 2-theta=20.7° and 13.8°.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern with specific peaks at 2-theta=20.7, 13.8, 21.5, 19.6, 12.8, 15.4, 10.7, 8.5, 22.4°.

According to a further aspect of the present invention, there is provided a crystalline form, Form B of (−)-8-(1-(3,5-difluorophenylamino)ethyl)-N,N-dimethyl-2-morpholino-4-oxo-4H-chromene-6-carboxamide, which has an X-ray powder diffraction pattern as shown in Figure C.

A further example of a compound exhibiting polymorphism is the compound of Example 3.13b.

Accordingly, a further aspect of the invention is Form A of (−)-N,N-dimethyl-2-morpholino-4-oxo-8-(1-(2,3,5-trifluorophenylamino)ethyl)-4H-chromene-6-carboxamide, where the (−)- in the chemical name signifies the optical rotation measured using the conditions described in Example 3.13b.

Accordingly, a further aspect of the invention is Form B of (−)-N,N-dimethyl-2-morpholino-4-oxo-8-(1-(2,3,5-trifluorophenylamino)ethyl)-4H-chromene-6-carboxamide.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at about 2-theta=20.0°.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at about 2-theta=18.0°.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least two specific peaks at about 2-theta=20.0° and 18.0°.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with specific peaks at about 2-theta=20.0, 18.0, 14.0, 19.4, 23.2, 23.8, 10.8, 19.1, 11.2, 27.8°.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern substantially the same as the X-ray powder diffraction pattern shown in Figure E.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at 2-theta=20.0° plus or minus 0.5° 2-theta.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at 2-theta=18.0° plus or minus 0.5° 2-theta.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least two specific peaks at 2-theta=20.0° and 18.0° wherein said values may be plus or minus 0.5° 2-theta.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with specific peaks at 2-theta=20.0, 18.0, 14.0, 19.4, 23.2, 23.8, 10.8, 19.1, 11.2, 27.8° wherein said values may be plus or minus 0.5° 2-theta.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at 2-theta=20.0°.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at 2-theta=18.0°.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least two specific peaks at 2-theta=20.0° and 18.0°.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern with specific peaks at 2-theta=20.0, 18.0, 14.0, 19.4, 23.2, 23.8, 10.8, 19.1, 11.2, 27.8°.

According to a further aspect of the invention there is provided a crystalline form, Form A of (−)-N,N-dimethyl-2-morpholino-4-oxo-8-(1-(2,3,5-trifluorophenylamino)ethyl)-4H-chromene-6-carboxamide, which has an X-ray powder diffraction pattern as shown in Figure E.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at about 2-theta=6.2°.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at about 2-theta=7.0°.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least two specific peaks at about 2-theta=6.2° and 7.0°.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with specific peaks at about 2-theta=6.2, 7.0, 10.3, 22.4, 15.9, 20.4, 27.2, 12.4, 18.7, 12.8°.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern substantially the same as the X-ray powder diffraction pattern shown in Figure G.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at 2-theta=6.2° plus or minus 0.5° 2-theta.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at 2-theta=7.0° plus or minus 0.5° 2-theta.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least two specific peaks at 2-theta=6.2° and 7.0° wherein said values may be plus or minus 0.5° 2-theta.

According to to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with specific peaks at 2-theta=6.2, 7.0, 10.3, 22.4, 15.9, 20.4, 27.2, 12.4, 18.7, 12.8° wherein said values may be plus or minus 0.5° 2-theta.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at 2-theta=6.2°.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least one specific peak at 2-theta=7.0°.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with at least two specific peaks at 2-theta=6.2° and 7.0°.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern with specific peaks at 2-theta=6.2, 7.0, 10.3, 22.4, 15.9, 20.4, 27.2, 12.4, 18.7, 12.8°.

According to a further aspect of the invention there is provided a crystalline form, Form B of (−)-N,N-dimethyl-2-morpholino-4-oxo-8-(1-(2,3,5-trifluorophenylamino)ethyl)-4H-chromene-6-carboxamide, which has an X-ray powder diffraction pattern as shown in Figure G.

It will be understood that 2-theta values of the X-ray powder diffraction patterns may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the crystalline Forms of the present invention described above, unless otherwise stated, are not limited to the crystals that provide X-ray powder diffraction patterns identical to the X-ray powder diffraction pattern shown in Figures A, C, E and G and any crystals providing X-ray powder diffraction patterns substantially the same as those shown in these Figures fall within the scope of the present invention. A person skilled in the art of X-ray powder diffraction is able to judge the substantial identity of X-ray powder diffraction patterns.

Persons skilled in the art of X-ray powder diffraction will also realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values (see Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.5° 2-theta, and such degree of a measurement error should be taken into account when considering the X-ray powder diffraction data. Furthermore, it should be understood that intensities might fluctuate depending on experimental conditions and sample preparation (preferred orientation).

Particular compounds of the invention are each of the Examples and pharmaceutically-acceptable salt(s) thereof, each of which provides a further independent aspect of the invention.

According to a further aspect of the invention there is provided a chromenone derivative of the Formula I, which is obtainable by following any of the Examples as disclosed herein.

A further feature is any of the scopes defined herein with the proviso that specific Examples, such as Example 1.00, 2.00, 3.00, 4.00 etc. are individually disclaimed.

It is to be understood that certain compounds of Formula I defined above may exhibit the phenomenon of tautomerism. It is to be understood that the present invention includes in its definition any such tautomeric form, or a mixture thereof, which possesses phosphoinositide (PI) 3-kinase inhibitory activity and is not to be limited merely to any one tautomeric form utilised within the formulae drawings or named in the Examples. In general, just one of any such tautomeric forms is named in the Examples that follow hereinafter or is presented in any relevant formulae drawings that follow hereinafter.

Suitable values for the generic radicals referred to above include those set out below.

A suitable value for the 3 to 8 membered nitrogen containing heterocyclyl ring system formed by the $R^1$ and $R^2$ groups of Formula I is, for example, a nitrogen containing non-aromatic saturated or partially saturated 3 to 8 membered ring, which optionally contains 1 or 2 further heteroatoms selected from oxygen, nitrogen and sulphur, wherein a ring sulphur atom is optionally oxidised to form the S-oxide(s). Suitable examples include azepanyl, oxazepanyl, aziridinyl, azetidinyl, pyrrolinyl, pyrrolidinyl, imidazolinyl, imidazolidinyl, pyrazolinyl, pyrazolidinyl, morpholinyl, thiomorpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl. In a particular group of compounds, particular examples of the heterocyclyl ring include azepanyl, oxazepanyl, azetidinyl, pyrrolidinyl, morpholinyl, thiomorpholinyl, piperidinyl, piperazinyl, and especially azepan-1-yl, 1,4-oxazepan-4-yl, azetidin-1-yl, pyrrolidine-1-yl, morpholin-4-yl, thiomorpholin-4-yl, piperidin-1-yl and piperazine-1-yl.

A suitable value for the 5 to 6 membered heterocyclyl ring formed by the $R^4$ and $R^5$ groups of Formula I is, for example, a non-aromatic saturated or partially saturated 5 or 6 membered ring, which contains 1, 2 or 3 heteroatoms selected from oxygen and nitrogen. Suitable examples include tetrahydrofuranyl, tetrahydropyranyl, pyrrolinyl, pyrrolidinyl, imidazolinyl, imidazolidinyl, pyrazolinyl, pyrazolidinyl, morpholinyl, piperidinyl, homopiperidinyl, piperazinyl, homopiperazinyl, dihydropyridinyl, tetrahydropyridinyl, dihydropyrimidinyl or tetrahydropyrimidinyl.

A suitable value for the 5 to 6 membered heteroaryl ring formed by the $R^4$ and $R^5$ groups of Formula I is, for example, an aromatic 5- or 6-membered monocyclic ring with 1, 2 or 3 ring heteroatoms selected from oxygen and nitrogen. Suitable examples include furanyl, pyrrolyl, oxazolyl, isoxazolyl, imidazolyl, pyrazolyl, oxadiazolyl, triazolyl, pyridinyl, pyridazinyl, pyrimidinyl, pyrazinyl or 1,3,5-triazinyl.

Suitable values for any of the 'R' groups ($R^1$ to $R^9$), include, for example: — for halogeno fluoro, chloro, bromo and iodo;
for (1-8C)alkyl: methyl, ethyl, propyl, isopropyl, tert-butyl, cyclobutyl, cyclohexyl, cyclohexylmethyl and 2-cyclopropylethyl;
for (2-8C)alkenyl: vinyl, isopropenyl, allyl and but-2-enyl;
for (2-8C)alkynyl: ethynyl, 2-propynyl and but-2-ynyl;
for (1-6C)alkoxy: methoxy, ethoxy, propoxy, isopropoxy and butoxy;
for (1-6C) alkylamino: methylamino, ethylamino, propylamino, isopropylamino and butylamino;
for di-[(1-6C)alkyl]amino: dimethylamino, diethylamino, N-ethyl-N-methylamino and diisopropylamino;
for halogeno-(1-6C)alkyl: chloromethyl, 2-fluoroethyl, 2-chloroethyl, 1-chloroethyl, 2,2-difluoroethyl, 2,2,2-trifluoroethyl, 3-fluoropropyl, 3-chloropropyl, 3,3-difluoropropyl and 3,3,3-trifluoropropyl;
for hydroxy-(1-6C)alkyl: hydroxymethyl, 2-hydroxyethyl, 1-hydroxyethyl and 3-hydroxypropyl; and
for (1-6C)alkoxy-(1-6C)alkyl: methoxymethyl, ethoxymethyl, 1-methoxyethyl, 2-methoxyethyl, 2-ethoxyethyl and 3-methoxypropyl.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic or citric acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine. A further suitable pharmaceutically-acceptable salt of a compound of the Formula I is, for example, a salt formed within the human or animal body after administration of a compound of the Formula I.

It is further to be understood that a suitable pharmaceutically-acceptable solvate of a compound of the Formula I also forms an aspect of the present invention. A suitable pharmaceutically-acceptable solvate is, for example, a hydrate such as a hemi-hydrate, a mono-hydrate, a di-hydrate or a tri-hydrate or an alternative quantity thereof It is further to be understood that a suitable pharmaceutically-acceptable pro-drug of a compound of the Formula I also forms an aspect of the present invention. Accordingly, the compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents: —
a) *Methods in Enzymology*, Vol. 42, p. 309-396, edited by K. Widder, et al. (Academic Press, 1985);
b) Design of Pro-drugs, edited by H. Bundgaard, (Elsevier, 1985);

c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1-6C)alkyl esters such as methyl, ethyl and tent-butyl, (1-6C)alkoxymethyl esters such as methoxymethyl esters, (1-6C)alkanoyloxymethyl esters such as pivaloyloxymethyl esters, 3-phthalidyl esters, (3-8C)cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C)alkoxycarbonyloxy-(1-6C)alkyl esters such as methoxycarbonyloxymethyl and 1-methoxycarbonyloxyethyl esters.

A suitable pharmaceutically-acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include (1-10C)alkanoyl groups such as acetyl, benzoyl, phenylacetyl and substituted benzoyl and phenylacetyl groups, (1-10C)alkoxycarbonyl groups such as ethoxycarbonyl, N,N-[di-(1-4C)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula I that possesses a carboxy group is, for example, an in vivo cleavable amide thereof, for example an amide formed with an amine such as ammonia, a (1-4C) alkylamine such as methylamine, a di-(1-4C)alkylamine such as dimethylamine, N-ethyl-N-methylamine or diethylamine, a (1-4C)alkoxy-(2-4C)alkylamine such as 2-methoxyethylamine, a phenyl-(1-4C)alkylamine such as benzylamine and amino acids such as glycine or an ester thereof.

A suitable pharmaceutically-acceptable pro-drug of a compound of the Formula I that possesses an amino group is, for example, an in vivo cleavable amide derivative thereof. Suitable pharmaceutically-acceptable amides from an amino group include, for example an amide formed with (1-10C) alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

For the avoidance of doubt it is to be understood that where in this specification a group is qualified by 'hereinbefore defined' or 'defined hereinbefore' the said group encompasses the first occurring and broadest definition as well as each and all of the particular definitions for that group.

Particular novel compounds of the invention include, for example, chromenone derivatives of the Formula I, or pharmaceutically-acceptable salts thereof, wherein, unless otherwise stated, each of $R^1$, $R^2$, $R^3$, $R^4$, $R^5$, $R^6$, $R^7$, $R^8$, n and $R^9$ has any of the meanings defined hereinbefore or in paragraphs (a) to (ii) hereinafter: —

(a) $R^1$ is H or (1-4C)alkyl;
(b) $R^1$ is H;
(c) $R^1$ is (1-4C)alkyl;
(d) $R^1$ is methyl or ethyl;
(e) $R^1$ is H, methyl or ethyl;
(f) $R^1$ is methyl;
(g) $R^2$ is (1-4C)alkyl optionally substituted by halogeno, hydroxy, (1-3C)alkoxy, cyano, (1-3C)alkylamino or di-[(1-3C)alkyl]amino;
(h) $R^2$ is (1-3C)alkyl optionally substituted by halogeno, hydroxy, (1-3C)alkoxy or di-[(1-3C)alkyl]amino;
(i) $R^2$ is (1-3C)alkyl optionally substituted by halogeno, hydroxy, methoxy or N,N-dimethylamino;
(j) $R^2$ is methyl, ethyl, propyl, 2-fluoroethyl, 2-hydroxyethyl, 2-methoxyethyl, 3-methoxypropyl, cyclopropylmethyl or 1-(N,N-dimethylamino)ethyl;
(k) $R^2$ is methyl;
(l) $R^1$ and $R^2$ are both methyl;
(m) $R^1$ and $R^2$ together form a 4 to 7 membered nitrogen containing heterocyclyl ring system, which optionally contains 1 further heteroatom selected from oxygen, nitrogen and sulphur, wherein a ring sulphur atom is optionally oxidised to form the S-oxide(s), said ring being optionally substituted by halogeno, hydroxy, (1-3C)alkyl, (1-3C)alkoxy or hydroxy-(1-3C)alkyl;
(n) $R^1$ and $R^2$ together form a nitrogen containing heterocyclyl ring system, selected from azepanyl, oxazepanyl, azetidinyl, pyrrolidinyl, morpholinyl, thiomorpholinyl, piperidinyl and piperazinyl, said ring being optionally substituted by halogeno, hydroxy, (1-3C)alkyl, (1-3C)alkoxy or hydroxy-(1-3C)alkyl;
(o) $R^1$ and $R^2$ together form a nitrogen containing heterocyclyl ring system, selected from azepan-1-yl, 1,4-oxazepan-4-yl, azetidin-1-yl, pyrrolidine-1-yl, morpholin-4-yl, thiomorpholin-4-yl, piperidine-1-yl and piperazine-1-yl, said ring being optionally substituted by halogeno, hydroxy, (1-3C)alkyl, (1-3C)alkoxy or hydroxy-(1-3C)alkyl;
(p) $R^3$ is H or methyl;
(q) $R^3$ is H;
(r) $R^3$ is methyl;
(s) $R^4$ and $R^5$ are independently selected from H, halogeno, (1-3C)alkyl, (2-3C)alkenyl, (2-3C)alkynyl, (1-3C)alkoxy and cyano;

(t) $R^4$ and $R^5$ are independently selected from H, fluoro, chloro, methyl, ethynyl, methoxy and cyano;
(u) $R^4$ and $R^5$ are independently selected from H or halogeno;
(v) $R^4$ and $R^5$ are independently selected from H, fluoro or chloro;
(w) $R^6$, $R^7$ and $R^8$ are independently selected from H, fluoro, chloro, methyl, ethynyl, methoxy and cyano;
(x) $R^6$, $R^7$ and $R^8$ are independently selected from H or halogeno;
(y) $R^6$ is H and $R^7$ and $R^8$ are independently selected from H, fluoro or chloro;
(z) $R^6$ and $R^8$ are H and $R^4$, $R^5$ and $R^7$ are halogeno;
(aa) $R^6$ and $R^8$ are H and $R^4$, $R^5$ and $R^7$ are fluoro;
(bb) $R^4$, $R^6$ and $R^8$ are H and $R^5$ and $R^7$ are halogeno;
(cc) $R^4$, $R^6$ and $R^8$ are H and $R^5$ and $R^7$ are fluoro;
(dd) n is 0;
(ee) n is 0 or 1;
(ff) n is 1;
(gg) $R^9$ is methyl or ethyl;
(hh) $R^9$ is methyl; or
(ii) n is 1 and $R^9$ is a methyl group located in the 2-position of the morpholine ring.

A particular group of compounds of the invention are chromenone derivatives of Formula I above wherein: —
$R^1$ is H or (1-4C)alkyl;
$R^2$ is (1-4C)alkyl optionally substituted by halogeno, hydroxy, (1-3C)alkoxy, cyano, (1-3C)alkylamino or di-[(1-3C)alkyl]amino; or
$R^1$ and $R^2$ together form a 4 to 7 membered nitrogen containing heterocyclyl ring system, which optionally contains 1 further heteroatom selected from oxygen, nitrogen and sulphur, wherein a ring sulphur atom is optionally oxidised to form the S-oxide(s), said ring being optionally substituted by halogeno, hydroxy, (1-3C)alkyl, (1-3C)alkoxy or hydroxy-(1-3C)alkyl;
$R^3$ is H or methyl;
$R^4$ and $R^5$ are independently selected from H, halogeno, (1-3C)alkyl, (2-3C)alkenyl, (2-3C)alkynyl, (1-3C)alkoxy and cyano;
$R^6$, $R^7$ and $R^8$ are independently selected from H, halogeno, (1-3C)alkyl, (2-3C)alkenyl, (2-3C)alkynyl, (1-3C)alkoxy and cyano;
n is 0; or a pharmaceutically-acceptable salt thereof.

A further particular group of compounds of the invention are chromenone derivatives of Formula I above wherein: —
$R^1$ is H, methyl or ethyl;
$R^2$ is (1-4C)alkyl optionally substituted by halogeno, hydroxy, (1-3C)alkoxy, cyano, (1-3C)alkylamino or di-[(1-3C)alkyl]amino; or
$R^1$ and $R^2$ together form a nitrogen containing heterocyclyl ring system, selected from azepanyl, oxazepanyl, azetidinyl, pyrrolidinyl, morpholinyl, thiomorpholinyl, piperidinyl and piperazinyl, said ring being optionally substituted by halogeno, hydroxy, (1-3C)alkyl, (1-3C)alkoxy or hydroxy-(1-3C)alkyl;
$R^3$ is H;
$R^4$ and $R^5$ are independently selected from H, fluoro or chloro;
$R^6$, $R^7$ and $R^8$ are independently selected from H or halogeno;
n is 0; or a pharmaceutically-acceptable salt thereof.

A further particular group of compounds of the invention are chromenone derivatives of Formula I above wherein: —
$R^1$ and $R^2$ are suitably as defined in any of paragraphs (a) to (g) and (m) to (o) above;
$R^3$ is suitably as defined in any one of paragraphs (p) to (q) above;
$R^4$ and $R^5$ are suitably as defined in any one of paragraphs (s), (u) to (v) above and is particularly as defined in any one of paragraphs (u) to (v) above;
$R^6$, $R^7$ and $R^8$ are suitably as defined in any one of paragraphs (x) to (y) above; and
n is suitably as defined in paragraph (dd) above.

A further particular group of compounds of the invention are chromenone derivatives of Formula I above or pharmaceutically-acceptable salt(s) thereof, wherein: —
$R^1$ and $R^2$ are suitably as defined in any of paragraphs (a) to (o) above, particularly as defined in paragraph (l) above;
$R^3$ is suitably as defined in any one of paragraphs (p) to (r) above;
$R^4$ and $R^5$ are suitably as defined in any one of paragraphs (s) to (v) above and is particularly as defined in paragraph (v) above;
$R^6$, $R^7$ and $R^8$ are suitably as defined in any one of paragraphs (w) to (cc) above and is particularly as defined in any one of paragraphs (z) to (cc) above; and
n and $R^9$ are suitably as defined in any one of paragraphs (dd) to (ii) above.

A further particular group of compounds of the invention are chromenone derivatives of Formula I above wherein: —
$R^1$ is H, methyl or ethyl;
$R^2$ is methyl, ethyl, cyclopropylmethyl, 2-fluoroethyl, 2-hydroxyethyl, 2-methoxyethyl, 3-methoxypropyl or 2-(dimethylamino)ethyl; or
$R^1$ and $R^2$ together form an optionally substituted nitrogen containing heterocyclyl ring system, selected from azepan-1-yl, 1,4-oxazepan-4-yl, azetidin-1-yl, 3-fluoroazetidin-1-yl, 3-hydroxyazetidin-1-yl, pyrrolidin-1-yl, (2R)-2-(hydroxymethyl)pyrrolidin-1-yl, (2S)-2-(hydroxymethyl)pyrrolidin-1-yl, morpholin-4-yl, thiomorpholin-4-yl, piperidin-1-yl, 4-hydroxypiperidin-1-yl, 4-methoxypiperidin-1-yl, piperazin-1-yl or 4-methylpiperazin-1-yl;
$R^3$ is H or methyl;
$R^4$ and $R^5$ are independently selected from H, fluoro or chloro;
$R^6$, $R^7$ and $R^8$ are independently selected from H, fluoro or chloro;
n is 0; or a pharmaceutically-acceptable salt thereof.

A further particular group of compounds of the invention are chromenone derivatives of Formula I above wherein: —
$R^1$ is methyl;
$R^2$ is methyl; or
$R^1$ and $R^2$ together form a pyrrolidin-1-yl ring;
$R^3$ is H;
$R^4$ and $R^5$ are independently selected from H or fluoro;
$R^6$ is H;
$R^7$ and $R^8$ are independently selected from H, fluoro or chloro;
n is 0; or a pharmaceutically-acceptable salt thereof.

A particular group of compounds of the invention are chromenone derivatives of Formula I above wherein: —
$R^1$ is H or (1-4C)alkyl;
$R^2$ is (1-4C)alkyl optionally substituted by halogeno, hydroxy, (1-3C)alkoxy, cyano, (1-3C)alkylamino or di-[(1-3C)alkyl]amino; or
$R^1$ and $R^2$ together form a 4 to 7 membered nitrogen containing heterocyclyl ring system, which optionally contains 1 further heteroatom selected from oxygen, nitrogen and sulphur, wherein a ring sulphur atom is optionally oxidised to form the S-oxide(s), said ring being optionally substituted by halogeno, hydroxy, (1-3C)alkyl, (1-3C)alkoxy or hydroxy-(1-3C)alkyl;

$R^3$ is H or methyl;
$R^4$ and $R^5$ are independently selected from H, halogeno, (1-3C)alkyl, (2-3C)alkenyl, (2-3C)alkynyl, (1-3C)alkoxy and cyano;
$R^6$, $R^7$ and $R^8$ are independently selected from H, halogeno, (1-3C)alkyl, (2-3C)alkenyl, (2-3C)alkynyl, (1-3C)alkoxy and cyano;
n is 0 or 1;
each $R^9$ group is methyl; or a pharmaceutically-acceptable salt thereof.

A particular group of compounds of the invention are chromenone derivatives of Formula I above wherein: —
$R^1$ is methyl;
$R^2$ is methyl or (2-hydroxy)ethyl; or
$R^1$ and $R^2$ together form a 6 membered nitrogen containing heterocyclyl ring system, said ring system being optionally substituted by hydroxy;
$R^3$ is H or methyl;
$R^4$ and $R^5$ are independently selected from H or halogeno;
$R^6$, $R^7$ and $R^8$ are independently selected from H or halogeno;
n is 1;
$R^9$ is a methyl group located in the 2-position of the morpholine ring; or a pharmaceutically-acceptable salt thereof.

A further particular group of compounds of the invention are chromenone derivatives of Formula I above wherein: —
$R^1$ is H, methyl or ethyl;
$R^2$ is (1-3C)alkyl optionally substituted by halogeno, hydroxy, (1-3C)alkoxy, cyano, (1-3C)alkylamino or di-[(1-3C)alkyl]amino; or
$R^1$ and $R^2$ together form a nitrogen containing heterocyclyl ring system, selected from azepanyl, oxazepanyl, azetidinyl, pyrrolidinyl, morpholinyl, thiomorpholinyl, piperidinyl and piperazinyl, said ring being optionally substituted by halogeno, hydroxy, (1-3C)alkyl, (1-3C)alkoxy or hydroxy-(1-3C)alkyl;
$R^3$ is H;
$R^4$ and $R^5$ are independently selected from H, halogeno, (1-3C)alkyl, (2-3C)alkenyl, (2-3C)alkynyl, (1-3C)alkoxy and cyano;
$R^6$, $R^7$ and $R^8$ are independently selected from H, halogeno, (1-3C)alkyl, (2-3C)alkenyl, (2-3C)alkynyl, (1-3C)alkoxy and cyano;
n is 0 or 1;
each $R^9$ group is (1-3C)alkyl; or a pharmaceutically-acceptable salt thereof.

A further particular group of compounds of the invention are chromenone derivatives of Formula I above wherein: —
$R^1$ is H, methyl or ethyl;
$R^2$ is methyl, ethyl, cyclopropylmethyl, 2-fluoroethyl, 2-hydroxyethyl, 2-methoxyethyl, 3-methoxypropyl or 2-(dimethylamino)ethyl; or
$R^1$ and $R^2$ together form an optionally substituted nitrogen containing heterocyclyl ring system, selected from azepan-1-yl, 1,4-oxazepan-4-yl, azetidin-1-yl, 3-fluoroazetidin-1-yl, 3-hydroxyazetidin-1-yl, pyrrolidin-1-yl, (2R)-2-(hydroxymethyl)pyrrolidin-1-yl, (2S)-2-(hydroxymethyl)pyrrolidin-1-yl, morpholin-4-yl, thiomorpholin-4-yl, piperidin-1-yl, 4-hydroxypiperidin-1-yl, 4-methoxypiperidin-1-yl, piperazin-1-yl or 4-methylpiperazin-1-yl;
$R^3$ is H or methyl;
$R^4$ and $R^5$ are independently selected from H, fluoro, chloro, methyl, ethynyl, methoxy and cyano;
$R^6$, $R^7$ and $R^8$ are independently selected from H, fluoro, chloro, methyl, ethynyl, methoxy and cyano;
n is 0 or 1;
$R^9$ is methyl; or a pharmaceutically-acceptable salt thereof.

A further particular group of compounds of the invention are chromenone derivatives of Formula I above wherein: —
$R^1$ is methyl;
$R^2$ is methyl;
$R^3$ is H or methyl;
$R^4$ and $R^5$ are independently selected from H or fluoro;
$R^6$ is H;
$R^7$ and $R^8$ are independently selected from H or fluoro;
n is 0; or a pharmaceutically-acceptable salt thereof.

Particular compounds of the invention are, for example, the chromenone derivatives of the Formula I that are disclosed within the Examples that are set out hereinafter.

For example, a particular compound of the invention is a chromenone derivative of the Formula I selected from any one of the following: —

N-(2-(dimethylamino)ethyl)-8-(1-(4-fluorophenylamino)ethyl)-2-morpholino-4-oxo-4H-chromene-6-carboxamide;

N-(2-(dimethylamino)ethyl)-8-(1-(3-fluorophenylamino)ethyl)-2-morpholino-4-oxo-4H-chromene-6-carboxamide;

N-(2-(dimethylamino)ethyl)-2-morpholino-4-oxo-8-(1-(phenylamino)ethyl)-4H-chromene-6-carboxamide;

8-(1-(3-chloro-2-fluorophenylamino)ethyl)-N-(2-(dimethylamino)ethyl)-2-morpholino-4-oxo-4H-chromene-6-carboxamide;

8-(1-(4-fluorophenylamino)ethyl)-N,N-dimethyl-2-morpholino-4-oxo-4H-chromene-6-carboxamide;

N-(2-(dimethylamino)ethyl)-8-(1-(4-fluorophenylamino)ethyl)-N-methyl-2-morpholino-4-oxo-4H-chromene-6-carboxamide;

8-(1-(3-chloro-4-fluorophenylamino)ethyl)-6-(4-hydroxypiperidine-1-carbonyl)-2-morpholino-4H-chromen-4-one;

8-(1-(3-chloro-4-fluorophenylamino)ethyl)-N-(2-hydroxyethyl)-N-methyl-2-morpholino-4-oxo-4H-chromene-6-carboxamide;

8-(1-(3-chloro-2-fluorophenylamino)ethyl)-N-(2-hydroxyethyl)-N-methyl-2-morpholino-4-oxo-4H-chromene-6-carboxamide;

8-(1-(3-chloro-2-fluorophenylamino)ethyl)-6-(4-hydroxypiperidine-1-carbonyl)-2-morpholino-4H-chromen-4-one;

8-(1-(3,5-difluorophenylamino)ethyl)-6-(morpholine-4-carbonyl)-2-morpholino-4H-chromen-4-one;

N-(2-(dimethylamino)ethyl)-8-(1-((4-fluorophenyl)(methyl)amino)ethyl)-2-morpholino-4-oxo-4H-chromene-6-carboxamide;

8-(1-((3,4-difluorophenyl)(methyl)amino)ethyl)-N-(2-(dimethylamino)ethyl)-2-morpholino-4-oxo-4H-chromene-6-carboxamide;

N-(2-(dimethylamino)ethyl)-8-(1-((4-fluorophenyl)(methyl)amino)ethyl)-N-methyl-2-morpholino-4-oxo-4H-chromene-6-carboxamide;

8-(1-(3,4-difluorophenylamino)ethyl)-N,N-dimethyl-2-morpholino-4-oxo-4H-chromene-6-carboxamide;

8-(1-(3-chloro-2-fluorophenylamino)ethyl)-N,N-dimethyl-2-morpholino-4-oxo-4H-chromene-6-carboxamide;

8-(1-(3-chloro-4-fluorophenylamino)ethyl)-N,N-dimethyl-2-morpholino-4-oxo-4H-chromene-6-carboxamide;

8-(1-(3,5-difluorophenylamino)ethyl)-N,N-dimethyl-2-morpholino-4-oxo-4H-chromene-6-carboxamide;

8-(1-((4-fluorophenyl)(methyl)amino)ethyl)-N,N-dimethyl-2-morpholino-4-oxo-4H-chromene-6-carboxamide;

8-(1-((3-chloro-4-fluorophenyl)(methyl)amino)ethyl)-N,N-dimethyl-2-morpholino-4-oxo-4H-chromene-6-carboxamide;

8-(1-(3-chlorophenylamino)ethyl)-N,N-dimethyl-2-morpholino-4-oxo-4H-chromene-6-carboxamide;

8-(1-(2,3-difluorophenylamino)ethyl)-N,N-dimethyl-2-morpholino-4-oxo-4H-chromene-6-carboxamide;
N,N-dimethyl-2-morpholino-4-oxo-8-(1-(3,4,5-trifluorophenylamino)ethyl)-4H-chromene-6-carboxamide;
8-(1-(3-fluorophenylamino)ethyl)-N,N-dimethyl-2-morpholino-4-oxo-4H-chromene-6-carboxamide;
N,N-dimethyl-2-morpholino-4-oxo-8-(1-(2,3,5-trifluorophenylamino)ethyl)-4H-chromene-6-carboxamide
8-(1-(3,5-difluorophenylamino)ethyl)-N,N-diethyl-2-morpholino-4-oxo-4H-chromene-6-carboxamide;
8-(1-(3,5-difluorophenylamino)ethyl)-2-morpholino-6-(pyrrolidine-1-carbonyl)-4H-chromen-4-one;
8-(1-(3,5-difluorophenylamino)ethyl)-6-(4-methylpiperazine-1-carbonyl)-2-morpholino-4H-chromen-4-one;
8-(1-(3,5-difluorophenylamino)ethyl)-2-morpholino-6-(piperazine-1-carbonyl)-4H-chromen-4-one;
8-(1-(3,5-difluorophenylamino)ethyl)-2-morpholino-6-(thiomorpholine-4-carbonyl)-4H-chromen-4-one;
6-(azepane-1-carbonyl)-8-(1-(3,5-difluorophenylamino)ethyl)-2-morpholino-4H-chromen-4-one;
8-(1-(3,5-difluorophenylamino)ethyl)-N-(2-hydroxyethyl)-N-methyl-2-morpholino-4-oxo-4H-chromene-6-carboxamide;
6-(azetidine-1-carbonyl)-8-(1-(3,5-difluorophenylamino)ethyl)-2-morpholino-4H-chromen-4-one;
8-(1-(3,5-difluorophenylamino)ethyl)-6-(4-hydroxypiperidine-1-carbonyl)-2-morpholino-4H-chromen-4-one;
8-(1-(3,5-difluorophenylamino)ethyl)-2-morpholino-6-(piperidine-1-carbonyl)-4H-chromen-4-one;
8-(1-(3,5-difluorophenylamino)ethyl)-N-ethyl-N-methyl-2-morpholino-4-oxo-4H-chromene-6-carboxamide;
8-(1-(3,5-difluorophenylamino)ethyl)-6-(3-hydroxyazetidine-1-carbonyl)-2-morpholino-4H-chromen-4-one;
8-(1-(3,5-difluorophenylamino)ethyl)-6-(3-fluoroazetidine-1-carbonyl)-2-morpholino-4H-chromen-4-one;
8-(1-(3,5-difluorophenylamino)ethyl)-N-(2-hydroxyethyl)-2-morpholino-4-oxo-4H-chromene-6-carboxamide;
8-(1-(3,5-difluorophenylamino)ethyl)-N-(2-methoxyethyl)-2-morpholino-4-oxo-4H-chromene-6-carboxamide;
8-(1-(3,5-difluorophenylamino)ethyl)-2-morpholino-4-oxo-N-propyl-4H-chromene-6-carboxamide;
8-(1-(3,5-difluorophenylamino)ethyl)-N-ethyl-2-morpholino-4-oxo-4H-chromene-6-carboxamide;
8-(1-(3,5-difluorophenylamino)ethyl)-N-(2-fluoroethyl)-2-morpholino-4-oxo-4H-chromene-6-carboxamide;
8-(1-(3,5-difluorophenylamino)ethyl)-N-(3-methoxypropyl)-2-morpholino-4-oxo-4H-chromene-6-carboxamide;
8-(1-(3,5-difluorophenylamino)ethyl)-6-((R)-2-(hydroxymethyl)pyrrolidine-1-carbonyl)-2-morpholino-4H-chromen-4-one;
8-(1-(3,5-difluorophenylamino)ethyl)-6-((S)-2-(hydroxymethyl)pyrrolidine-1-carbonyl)-2-morpholino-4H-chromen-4-one;
8-(1-(3,5-difluorophenylamino)ethyl)-N-methyl-2-morpholino-4-oxo-4H-chromene-6-carboxamide;
N-(cyclopropylmethyl)-8-(1-(3,5-difluorophenylamino)ethyl)-2-morpholino-4-oxo-4H-chromene-6-carboxamide;
8-(1-(3,5-difluorophenylamino)ethyl)-N-(2-methoxyethyl)-N-methyl-2-morpholino-4-oxo-4H-chromene-6-carboxamide;
8-(1-(3,5-difluorophenylamino)ethyl)-2-morpholino-6-(1,4-oxazepane-4-carbonyl)-4H-chromen-4-one; and
8-(1-(3,5-difluorophenylamino)ethyl)-6-(4-methoxypiperidine-1-carbonyl)-2-morpholino-4H-chromen-4-one; or a pharmaceutically-acceptable salt thereof.

According to a further aspect of the invention, a particular compound of the invention is a chromenone derivative of the Formula I selected from any one of the following: —
8-(1-(4-fluorophenylamino)ethyl)-N,N-dimethyl-2-morpholino-4-oxo-4H-chromene-6-carboxamide;
8-((1R)-1-(4-fluorophenylamino)ethyl)-N,N-dimethyl-2-morpholino-4-oxo-4H-chromene-6-carboxamide;
8-((1S)-1-(4-fluorophenylamino)ethyl)-N,N-dimethyl-2-morpholino-4-oxo-4H-chromene-6-carboxamide,
8-(1-(3,4-difluorophenylamino)ethyl)-N,N-dimethyl-2-morpholino-4-oxo-4H-chromene-6-carboxamide;
8-((1R)-1-(3,4-difluorophenylamino)ethyl)-N,N-dimethyl-2-morpholino-4-oxo-4H-chromene-6-carboxamide;
8-((1S)-1-(3,4-difluorophenylamino)ethyl)-N,N-dimethyl-2-morpholino-4-oxo-4H-chromene-6-carboxamide;
8-(1-(3,5-difluorophenylamino)ethyl)-N,N-dimethyl-2-morpholino-4-oxo-4H-chromene-6-carboxamide;
8-((1R)-1-(3,5-difluorophenylamino)ethyl)-N,N-dimethyl-2-morpholino-4-oxo-4H-chromene-6-carboxamide;
8-((1S)-1-(3,5-difluorophenylamino)ethyl)-N,N-dimethyl-2-morpholino-4-oxo-4H-chromene-6-carboxamide;
N,N-dimethyl-2-morpholino-4-oxo-8-(1-(2,3,5-trifluorophenylamino)ethyl)-4H-chromene-6-carboxamide;
N,N-dimethyl-2-morpholino-4-oxo-8-((1R)-1-(2,3,5-trifluorophenylamino)ethyl)-4H-chromene-6-carboxamide;
N,N-dimethyl-2-morpholino-4-oxo-8-((1S)-1-(2,3,5-trifluorophenylamino)ethyl)-4H-chromene-6-carboxamide;
8-(1-(3-chloro-5-fluorophenylamino)ethyl)-N,N-dimethyl-2-morpholino-4-oxo-4H-chromene-6-carboxamide;
8-((1R)-1-(3-chloro-5-fluorophenylamino)ethyl)-N,N-dimethyl-2-morpholino-4-oxo-4H-chromene-6-carboxamide;
8-((1S)-1-(3-chloro-5-fluorophenylamino)ethyl)-N,N-dimethyl-2-morpholino-4-oxo-4H-chromene-6-carboxamide;
8-(1-((3,5-difluorophenyl)(methyl)amino)ethyl)-N,N-dimethyl-2-morpholino-4-oxo-4H-chromene-6-carboxamide;
8-((1R)-1-((3,5-difluorophenyl)(methyl)amino)ethyl)-N,N-dimethyl-2-morpholino-4-oxo-4H-chromene-6-carboxamide;
8-((1S)-1-((3,5-difluorophenyl)(methyl)amino)ethyl)-N,N-dimethyl-2-morpholino-4-oxo-4H-chromene-6-carboxamide;
8-(1-((3,5-difluorophenyl)(methyl)amino)ethyl)-6-(4-hydroxypiperidine-1-carbonyl)-2-morpholino-4H-chromen-4-one;
8-((1R)-1-(3,5-difluorophenyl)(methyl)amino)ethyl)-6-(4-hydroxypiperidine-1-carbonyl)-2-morpholino-4H-chromen-4-one;
8-((1S)-1-((3,5-difluorophenyl)(methyl)amino)ethyl)-6-(4-hydroxypiperidine-1-carbonyl)-2-morpholino-4H-chromen-4-one;
8-(1-((3,5-difluorophenyl)(methyl)amino)ethyl)-N-(2-hydroxyethyl)-N-methyl-2-morpholino-4-oxo-4H-chromene-6-carboxamide;
8-((1R)-1-((3,5-difluorophenyl)(methyl)amino)ethyl)-N-(2-hydroxyethyl)-N-methyl-2-morpholino-4-oxo-4H-chromene-6-carboxamide;
8-((1S)-1-((3,5-difluorophenyl)(methyl)amino)ethyl)-N-(2-hydroxyethyl)-N-methyl-2-morpholino-4-oxo-4H-chromene-6-carboxamide;
8-(1-((3,5-difluorophenyl)(methyl)amino)ethyl)-6-(4-hydroxypiperidine-1-carbonyl)-2-morpholino-4H-chromen-4-one;
8-((1R)-1-(3,5-difluorophenyl)(methyl)amino)ethyl)-6-(4-hydroxypiperidine-1-carbonyl)-2-morpholino-4H-chromen-4-one;

8-((1S)-1-((3,5-difluorophenyl)(methyl)amino)ethyl)-6-(4-hydroxypiperidine-1-carbonyl)-2-morpholino-4H-chromen-4-one;

8-(1-(3,5-difluorophenylamino)ethyl)-N,N-dimethyl-2-((R)-2-methylmorpholino)-4-oxo-4H-chromene-6-carboxamide;

8-((1R)-1-(3,5-difluorophenylamino)ethyl)-N,N-dimethyl-2-((R)-2-methylmorpholino)-4-oxo-4H-chromene-6-carboxamide;

8-((1S)-1-(3,5-difluorophenylamino)ethyl)-N,N-dimethyl-2-((R)-2-methylmorpholino)-4-oxo-4H-chromene-6-carboxamide;

8-(1-(3,5-difluorophenylamino)ethyl)-N,N-dimethyl-2-((S)-2-methylmorpholino)-4-oxo-4H-chromene-6-carboxamide;

8-((1R)-1-(3,5-difluorophenylamino)ethyl)-N,N-dimethyl-2-((S)-2-methylmorpholino)-4-oxo-4H-chromene-6-carboxamide;

8-((1S)-1-(3,5-difluorophenylamino)ethyl)-N,N-dimethyl-2-((S)-2-methylmorpholino)-4-oxo-4H-chromene-6-carboxamide;

8-(1-((3,5-difluorophenyl)(methyl)amino)ethyl)-N,N-dimethyl-2-((R)-2-methylmorpholino)-4-oxo-4H-chromene-6-carboxamide;

8-((1R)-((3,5-difluorophenyl)(methyl)amino)ethyl)-N,N-dimethyl-2-((R)-2-methylmorpholino)-4-oxo-4H-chromene-6-carboxamide;

8-((1S)-1-((3,5-difluorophenyl)(methyl)amino)ethyl)-N,N-dimethyl-2-((R)-2-methylmorpholino)-4-oxo-4H-chromene-6-carboxamide;

8-(1-((3,5-difluorophenyl)(methyl)amino)ethyl)-N-(2-hydroxyethyl)-N-methyl-2-((R)-2-methylmorpholino)-4-oxo-4H-chromene-6-carboxamide;

8-((1R)-((3,5-difluorophenyl)(methyl)amino)ethyl)-N-(2-hydroxyethyl)-N-methyl-2-((R)-2-methylmorpholino)-4-oxo-4H-chromene-6-carboxamide;

8-((1S)-1-((3,5-difluorophenyl)(methyl)amino)ethyl)-N-(2-hydroxyethyl)-N-methyl-2-((R)-2-methylmorpholino)-4-oxo-4H-chromene-6-carboxamide;

8-(1-((3,5-difluorophenyl)(methyl)amino)ethyl)-6-(4-hydroxypiperidine-1-carbonyl)-2-((R)-2-methylmorpholino)-4H-chromen-4-one;

8-((1R)-((3,5-difluorophenyl)(methyl)amino)ethyl)-6-(4-hydroxypiperidine-1-carbonyl)-2-((R)-2-methylmorpholino)-4H-chromen-4-one;

8-((1S)-1-((3,5-difluorophenyl)(methyl)amino)ethyl)-6-(4-hydroxypiperidine-1-carbonyl)-2-((R)-2-methylmorpholino)-4H-chromen-4-one;

8-(1-(3,5-difluorophenylamino)ethyl)-N,N-dimethyl-2-((S)-3-methylmorpholino)-4-oxo-4H-chromene-6-carboxamide;

8-((1R)-1-(3,5-difluorophenylamino)ethyl)-N,N-dimethyl-2-((S)-3-methylmorpholino)-4-oxo-4H-chromene-6-carboxamide; and 8-((1S)-1-(3,5-difluorophenylamino)ethyl)-N,N-dimethyl-2-((S)-3-methylmorpholino)-4-oxo-4H-chromene-6-carboxamide; or a pharmaceutically-acceptable salt thereof.

According to a yet further aspect of the invention, a particular compound of the invention is a chromenone derivative of the Formula I selected from any one of the following: —

8-((1R)-1-(4-fluorophenylamino)ethyl)-N,N-dimethyl-2-morpholino-4-oxo-4H-chromene-6-carboxamide;

8-((1R)-1-(3,4-difluorophenylamino)ethyl)-N,N-dimethyl-2-morpholino-4-oxo-4H-chromene-6-carboxamide;

8-((1R)-1-(3,5-difluorophenylamino)ethyl)-N,N-dimethyl-2-morpholino-4-oxo-4H-chromene-6-carboxamide;

N,N-dimethyl-2-morpholino-4-oxo-8-((1R)-1-(2,3,5-trifluorophenylamino)ethyl)-4H-chromene-6-carboxamide;

8-((1R)-1-(3-chloro-5-fluorophenylamino)ethyl)-N,N-dimethyl-2-morpholino-4-oxo-4H-chromene-6-carboxamide;

8-((1R)-1-((3,5-difluorophenyl)(methyl)amino)ethyl)-N,N-dimethyl-2-morpholino-4-oxo-4H-chromene-6-carboxamide;

8-((1R)-1-(3,5-difluorophenyl)(methyl)amino)ethyl)-6-(4-hydroxypiperidine-1-carbonyl)-2-morpholino-4H-chromen-4-one;

8-((1R)-1-((3,5-difluorophenyl)(methyl)amino)ethyl)-N-(2-hydroxyethyl)-N-methyl-2-morpholino-4-oxo-4H-chromene-6-carboxamide;

8-((1R)-1-(3,5-difluorophenyl)(methyl)amino)ethyl)-6-(4-hydroxypiperidine-1-carbonyl)-2-morpholino-4H-chromen-4-one;

8-((1R)-1-(3,5-difluorophenylamino)ethyl)-N,N-dimethyl-2-((R)-2-methylmorpholino)-4-oxo-4H-chromene-6-carboxamide;

8-((1R)-1-(3,5-difluorophenylamino)ethyl)-N,N-dimethyl-2-((S)-2-methylmorpholino)-4-oxo-4H-chromene-6-carboxamide;

8-((1R)-1-((3,5-difluorophenyl)(methyl)amino)ethyl)-N,N-dimethyl-2-((R)-2-methylmorpholino)-4-oxo-4H-chromene-6-carboxamide;

8-((1R)-1-(3,5-difluorophenyl)(methyl)amino)ethyl)-N-(2-hydroxyethyl)-N-methyl-2-((R)-2-methylmorpholino)-4-oxo-4H-chromene-6-carboxamide;

8-((1R)-1-(3,5-difluorophenyl)(methyl)amino)ethyl)-6-(4-hydroxypiperidine-1-carbonyl)-2-((R)-2-methylmorpholino)-4H-chromen-4-one; and 8-((1R)-1-(3,5-difluorophenylamino)ethyl)-N,N-dimethyl-2-((S)-3-methylmorpholino)-4-oxo-4H-chromene-6-carboxamide; or a pharmaceutically-acceptable salt thereof.

According to a yet further aspect of the invention, a particular compound of the invention is a chromenone derivative of the Formula I selected from any one of the following: —

8-((1S)-1-(4-fluorophenylamino)ethyl)-N,N-dimethyl-2-morpholino-4-oxo-4H-chromene-6-carboxamide;

8-((1S)-1-(3,4-difluorophenylamino)ethyl)-N,N-dimethyl-2-morpholino-4-oxo-4H-chromene-6-carboxamide;

8-((1S)-1-(3,5-difluorophenylamino)ethyl)-N,N-dimethyl-2-morpholino-4-oxo-4H-chromene-6-carboxamide;

N,N-dimethyl-2-morpholino-4-oxo-8-((1S)-1-(2,3,5-trifluorophenylamino)ethyl)-4H-chromene-6-carboxamide;

8-((1S)-1-(3-chloro-5-fluorophenylamino)ethyl)-N,N-dimethyl-2-morpholino-4-oxo-4H-chromene-6-carboxamide;

8-((1S)-1-((3,5-difluorophenyl)(methyl)amino)ethyl)-N,N-dimethyl-2-morpholino-4-oxo-4H-chromene-6-carboxamide;

8-((1S)-1-((3,5-difluorophenyl)(methyl)amino)ethyl)-6-(4-hydroxypiperidine-1-carbonyl)-2-morpholino-4H-chromen-4-one;

8-((1S)-1-((3,5-difluorophenyl)(methyl)amino)ethyl)-N-(2-hydroxyethyl)-N-methyl-2-morpholino-4-oxo-4H-chromene-6-carboxamide;

8-((1S)-1-((3,5-difluorophenyl)(methyl)amino)ethyl)-6-(4-hydroxypiperidine-1-carbonyl)-2-morpholino-4H-chromen-4-one;

8-((1S)-1-(3,5-difluorophenylamino)ethyl)-N,N-dimethyl-2-((R)-2-methylmorpholino)-4-oxo-4H-chromene-6-carboxamide;

8-((1S)-1-(3,5-difluorophenylamino)ethyl)-N,N-dimethyl-2-((S)-2-methylmorpholino)-4-oxo-4H-chromene-6-carboxamide;

8-((1S)-1-((3,5-difluorophenyl)(methyl)amino)ethyl)-N,N-dimethyl-2-((R)-2-methylmorpholino)-4-oxo-4H-chromene-6-carboxamide;

8-((1S)-1-((3,5-difluorophenyl)(methyl)amino)ethyl)-N-(2-hydroxyethyl)-N-methyl-2-((R)-2-methylmorpholino)-4-oxo-4H-chromene-6-carboxamide;

8-((1S)-1-((3,5-difluorophenyl)(methyl)amino)ethyl)-6-(4-hydroxypiperidine-1-carbonyl)-2-((R)-2-methylmorpholino)-4H-chromen-4-one; and 8-((1S)-1-(3,5-difluorophenylamino)ethyl)-N,N-dimethyl-2-((S)-3-methylmorpholino)-4-oxo-4H-chromene-6-carboxamide; or a pharmaceutically-acceptable salt thereof.

According to a further aspect of the invention, a particular compound of the invention is the compound of Example 3.06b; or a pharmaceutically-acceptable salt thereof.

According to a further aspect of the invention, a particular compound of the invention is (−)-8-(1-(3,5-difluorophenylamino)ethyl)-N,N-dimethyl-2-morpholino-4-oxo-4H-chromene-6-carboxamide; or a pharmaceutically-acceptable salt thereof, where the (−)- in the chemical name signifies the optical rotation measured using the conditions described in Example 3.06b.

According to a further aspect of the invention, a particular compound of the invention is 8-((1R)-1-(3,5-difluorophenylamino)ethyl)-N,N-dimethyl-2-morpholino-4-oxo-4H-chromene-6-carboxamide; or a pharmaceutically-acceptable salt thereof.

According to a further aspect of the invention, a particular compound of the invention is 8-((1S)-1-(3,5-difluorophenylamino)ethyl)-N,N-dimethyl-2-morpholino-4-oxo-4H-chromene-6-carboxamide; or a pharmaceutically-acceptable salt thereof.

According to a further aspect of the invention, a particular compound of the invention is the compound of Example 3.13b; or a pharmaceutically-acceptable salt thereof.

According to a further aspect of the invention, a particular compound of the invention is (−)-N,N-dimethyl-2-morpholino-4-oxo-8-(1-(2,3,5-trifluorophenylamino)ethyl)-4H-chromene-6-carboxamide; or a pharmaceutically-acceptable salt thereof, where the (−)- in the chemical name signifies the optical rotation measured using the conditions described in Example 3.13b.

According to a further aspect of the invention, a particular compound of the invention is N,N-dimethyl-2-morpholino-4-oxo-8-((1R)-1-(2,3,5-trifluorophenylamino)ethyl)-4H-chromene-6-carboxamide; or a pharmaceutically-acceptable salt thereof.

According to a further aspect of the invention, a particular compound of the invention is N,N-dimethyl-2-morpholino-4-oxo-8-((1S)-1-(2,3,5-trifluorophenylamino)ethyl)-4H-chromene-6-carboxamide; or a pharmaceutically-acceptable salt thereof.

Another aspect of the present invention provides a process for preparing a compound of the Formula I, or a pharmaceutically-acceptable salt thereof. A suitable process is illustrated by the following representative process variants in which, unless otherwise stated, $R^1$, $R^2$, $R^3$, $R^4$, $R^5$, $R^6$, $R^7$, $R^8$, n and $R^9$ have any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

Suitable process variants include, for example, the following: —

(a) The reaction, conveniently in the presence of a suitable activating reagent, of a compound of the Formula II

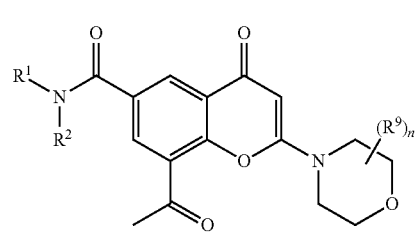

II wherein $R^1$, $R^2$, n and $R^9$ have any of the meanings defined hereinbefore except that any functional group present is protected if necessary, with an amine derivative of the Formula III:

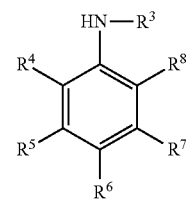

III wherein $R^3$ is H and $R^4$, $R^5$, $R^6$, $R^7$ and $R^8$ have any of the meanings defined hereinbefore except that any functional group is protected if necessary, in the presence of a suitable base, to provide an intermediate compound, of the Formula IV:

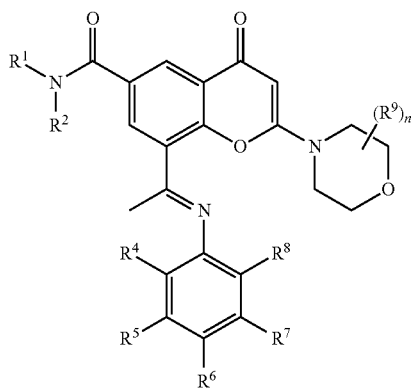

IV which is then reduced by a suitable reducing agent, to form a compound of the Formula I, whereafter any protecting group that is present is removed.

A suitable activating reagent for the reaction includes, for example, a Lewis acid such as tin (IV) tetrachloride, aluminium (III) trichloride or titanium(IV) tetrachloride. Conveniently, the suitable catalyst is titanium(IV) tetrachloride.

Conveniently, the reaction is conducted in the presence of a suitable base such as an organic base such as pyridine, 4-dimethylaminopyridine, triethylamine or N-methyl morpholine. Conveniently, the suitable base is triethylamine.

The reaction is conveniently carried out in the presence of a suitable solvent or diluent such as for example, N,N-dimethylformamide, tetrahydrofuran, 1,4-dioxane, 1,2-dimethoxyethane, benzene, toluene, xylene, halogenated solvents such as dichloromethane, chloroform or carbon tetrachloride and at a temperature in the range, for example −50° C. to 100° C., preferably in the range 0° C. to 30° C.

A suitable reducing agent is a metal borohydride such as for example sodium cyanotrihydroborate. The reduction reaction is conveniently carried out in the presence of a suitable solvent or diluent, such as for example an alcohol such as methanol or ethanol or a mixture of solvents containing alcohols, generally in the presence of a weak acid such as acetic acid. The reaction is conveniently carried out at a temperature in the range, for example, 0° C. to 30° C.

Compounds of the Formula II may, for example, be prepared by a cross coupling reaction of a compound of the Formula V:

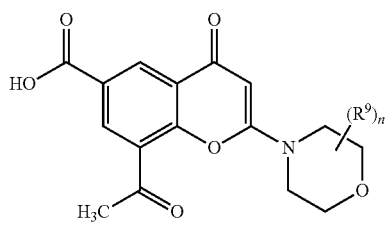

V wherein n and $R^9$ has any of the meanings defined hereinbefore except that any functional group present is protected if necessary, with an amine compound of the Formula VI:

VI wherein $R^1$ and $R^2$ has any of the meanings defined hereinbefore, in the presence of a suitable coupling agent such as, for example, TSTU (2-(2,5-dioxopyrrolidin-1-yl)-1,1,3,3-tetramethylisouronium tetrafluoroborate), whereafter any protecting group that is present is removed.

The reaction is conveniently carried out in the presence of a suitable base. A suitable base is, for example, an organic amine base such as, for example, pyridine, 2,6-lutidine, collidine, 4-dimethylaminopyridine, triethylamine, N-methylmorpholine, diazabicyclo[5.4.0]undec-7-ene, diisopropylethyl amine, or, for example, an alkali or alkaline earth metal carbonate, for example sodium carbonate, potassium carbonate or calcium carbonate.

The reaction is conveniently carried out in the presence of a suitable inert solvent or diluent such as for example, N,N-dimethylformamide, tetrahydrofuran, 1,4-dioxane, 1,2-dimethoxyethane, benzene, toluene, xylene, methanol ethanol, halogenated solvents such as dichloromethane, chloroform or carbon tetrachloride and at a temperature in the range, for example −50° C. to 100° C., preferably in the range 0° C. to 30° C.

Compounds of the Formula III may be obtained by conventional procedures or are commercially available, known in the literature, or they can be prepared by standard processes known in the art.

Compounds of the Formula V may be obtained by analogous procedures to those described in Example 1.00 herein, where the method for preparing the starting material 8-acetyl-N-(2-(dimethylamino)ethyl)-2-morpholino-4-oxo-4H-chromene-6-carboxamide is given. In particular, compounds of the Formulae V may be obtained by procedures in accordance with the following scheme:

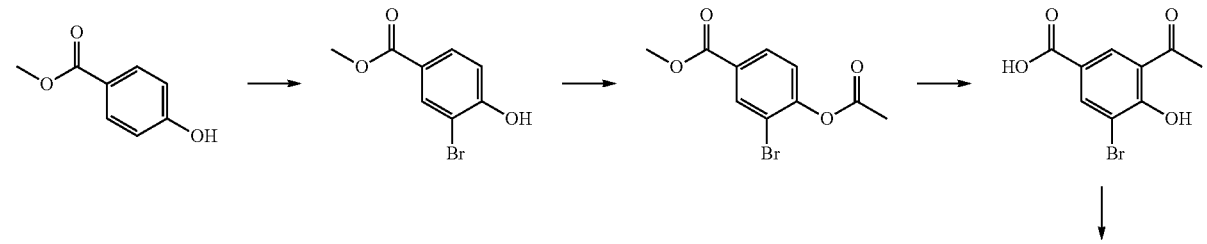

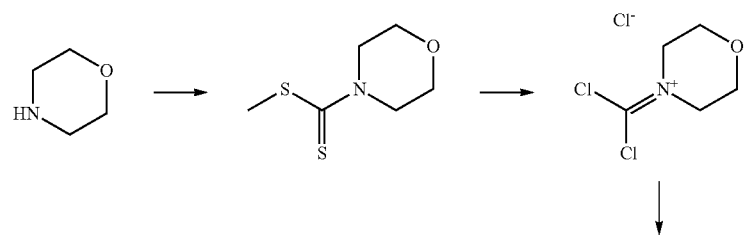

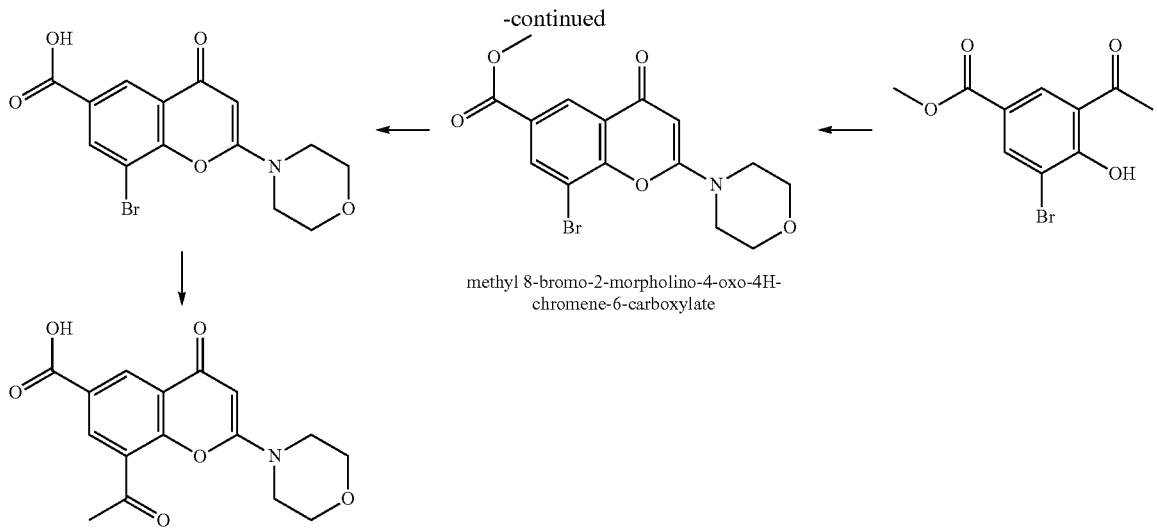

methyl 8-bromo-2-morpholino-4-oxo-4H-chromene-6-carboxylate

For example, compounds of the Formula V may, be prepared by reaction of a compound of the Formula VII:

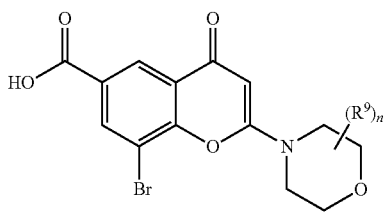

VII wherein n and $R^9$ has any of the meanings defined hereinbefore except that any functional group present is protected if necessary, with a suitable stannane such as, for example, tributyl(1-ethoxyvinyl)stannane under Stille type conditions (for further details of such conditions see for example: 'Metal-Catalyzed Cross-Coupling Reactions', Second Edition, Edited by Armin Meijere, Francois Diederich, Wiley-VCH, 2004, Volume 1, p125), whereafter any protecting group that is present is removed.

A suitable catalyst for the reaction includes, for example, a metallic catalyst such as a palladium(0), palladium(II) for example tetrakis(triphenylphosphine)palladium(0), palladium(II) chloride, palladium(II) bromide, bis(triphenylphosphine)palladium(II) chloride, [1,1'-bis(diphenylphosphino)ferrocene]dichloropalladium(II), tris(dibenzilideneacetone)dipalladium. Optionally, the catalyst can be formed in-situ by the reaction of one or more of the above catalysts with a trialkylphosphine, such as, for example, tri-N-butylphosphine or tricyclohexylphosphine.

The reaction is conveniently carried out in the presence of a suitable solvent or diluent such as for example, N,N-dimethylformamide, tetrahydrofuran, 1,4-dioxane, 1,2-dimethoxyethane, benzene, toluene, xylene and at a temperature in the range, for example 20° C. to 150° C., preferably in the range 60° C. to 120° C.

Compounds of the Formula VII may, for example, be prepared by reaction of a compound of the Formula VIII:

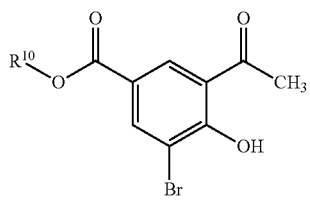

VIII wherein $R^{10}$ is (1-6C)alkyl, conveniently methyl or ethyl, with a compound of the Formula IX:

IX wherein n and $R^9$ have any of the meanings defined hereinbefore, in the presence of a suitable activating agent such as, for example, a Lewis acid, such as for example boron trifluoride-diethyl etherate, to provide a compound, of the Formula VIIIa:

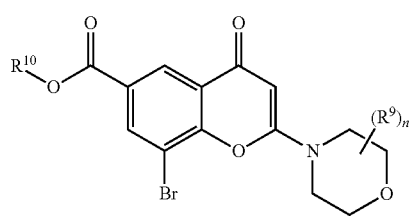

VIIIa whereafter a saponifcation reaction can be used to form the compound of the Formula VII.

Reaction of the compounds of the Formula VIII with those of the Formula IX is conveniently carried out in the presence of a suitable solvent or diluent such as for example, N,N-dimethylformamide, tetrahydrofuran, 1,4-dioxane, 1,2-dimethoxyethane, benzene, toluene, xylene, halogenated solvents such as dichloromethane, chloroform or carbon tetrachloride and at a temperature in the range, for example 20° C. to 150° C., preferably in the range 60° C. to 120° C.

The saponification reaction can be conducted for example by treatment with an alkali or alkaline earth metal hydroxide such as lithium, potassium or sodium hydroxide in a suitable solvent such as for example, methanol or a mixture of ethanol and water or a water miscible solvent, such as for example tetrahydrofuran or dioxane, at a temperature in the range, for example 0° C. to −100° C., preferably in the range 20-40° C.

Compounds of the Formula VIII have been described in the literature (Ger. Offen, DE 4318756, 1994 and Aust. J. Chem. 2003, 56, 1099), or they can be prepared by standard processes known in the art.

Compounds of the Formula VIIIa may alternatively be obtained by procedures in accordance with the following scheme, which has been described in more detail in Example 1.00 herein, where the method for preparing methyl 8-bromo-2-morpholino-4-oxo-4H-chromene-6-carboxylate using such a method is provided:

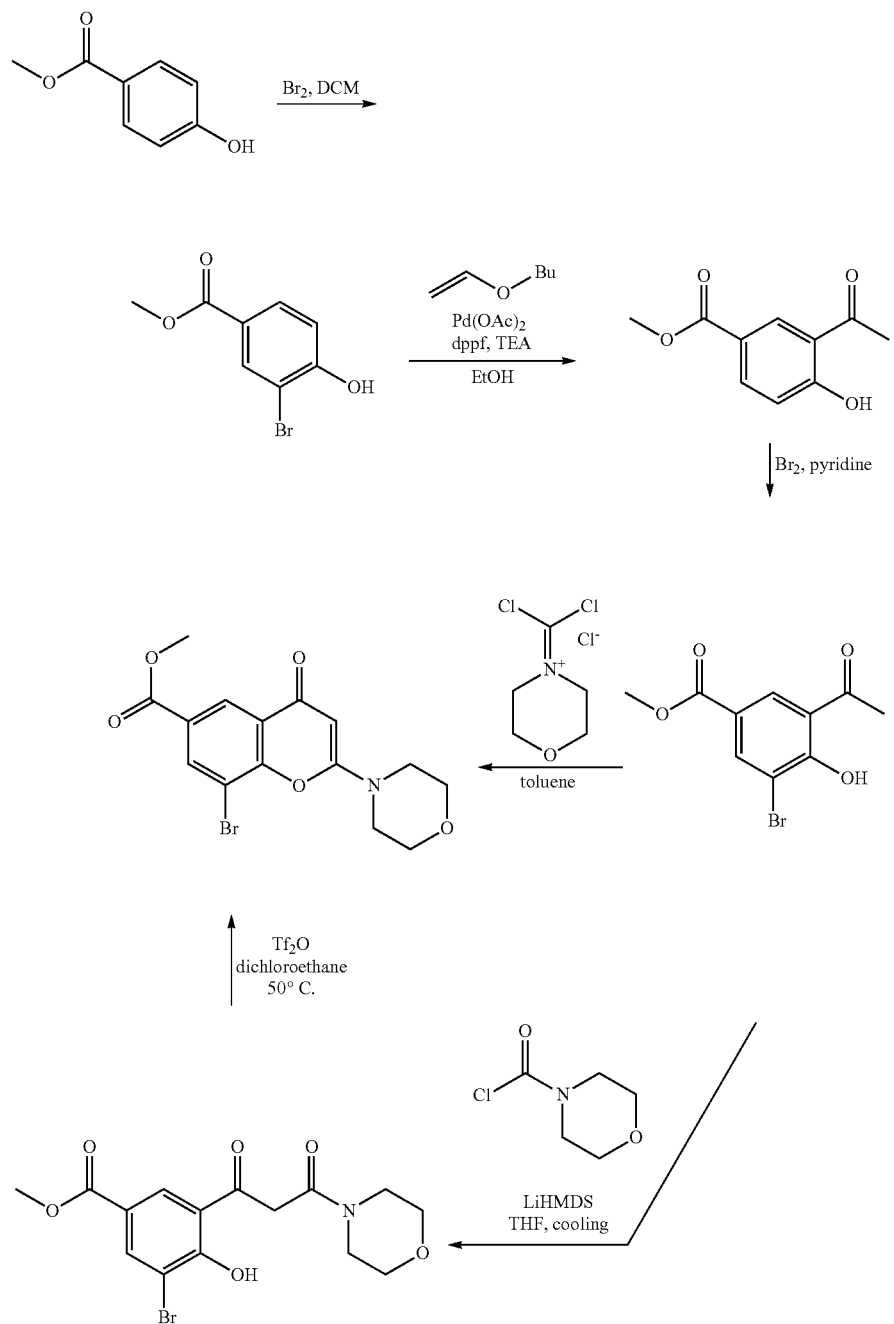

where, DCM is dichloromethane, LiHMDS is Lithium bis(trimethyl silyl)amide, EtOH is ethanol, Dppf is 1,1'-bis(diphenylphosphino)ferrocene, TEA is triethylamine, THF is tetrahydrofuran and Tf₂O is Trifluoromethanesulfonic anhydride.

For example, compounds of the Formula VIIIa may, be prepared by reaction of a compound of the Formula VIII:

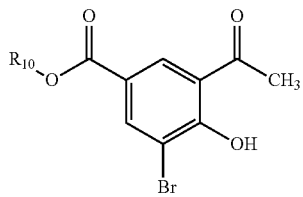

VIII wherein R¹⁰ is (1-6C)alkyl, conveniently methyl or ethyl, with a compound of the Formula IXa:

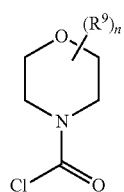

IXa wherein n and R⁹ have any of the meanings defined hereinbefore, in the presence of a suitable activating agent such as, for example, a strong base, such as for example Lithium bis(trimethyl silyl)amide, to provide a compound, of the Formulae VIIIb:

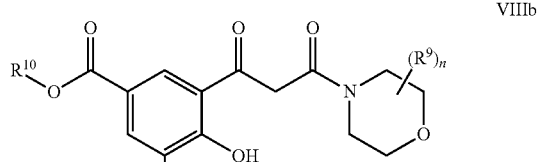

VIIIb whereafter a ring-closing reaction can be performed to form the compound of the Formula VIIIa.

Reaction of the compounds of the Formula VIII with those of the Formula IXa is conveniently carried out in the presence of a suitable solvent or diluent such as for example, tetrahydrofuran, 1,4-dioxane, 1,2-dimethoxyethane, benzene, toluene or xylene and at a temperature in the range, for example −100° C. to ambient temperature, preferably in the range −80° C. to 20° C.

The ring-closing reaction to convert a compound of the Formula VIIIb into a compound of the Formula VIIIa can be conducted for example by treatment with a dehydrating agent, such as for example trifluoromethanesulfonic anhydride, in a suitable solvent such as for example dichloroethane at a temperature in the range, for example 0° C. to −100° C., conveniently in the range 20-60° C.

Alternatively, the Compound of the Formula VIIIa may be prepared in accordance with the following scheme, which has been described in more detail in Example 9.0 herein, which describes the preparation of methyl 8-bromo-2-((R)-2-methylmorpholino)-4-oxo-4H-chromene-6-carboxylate:

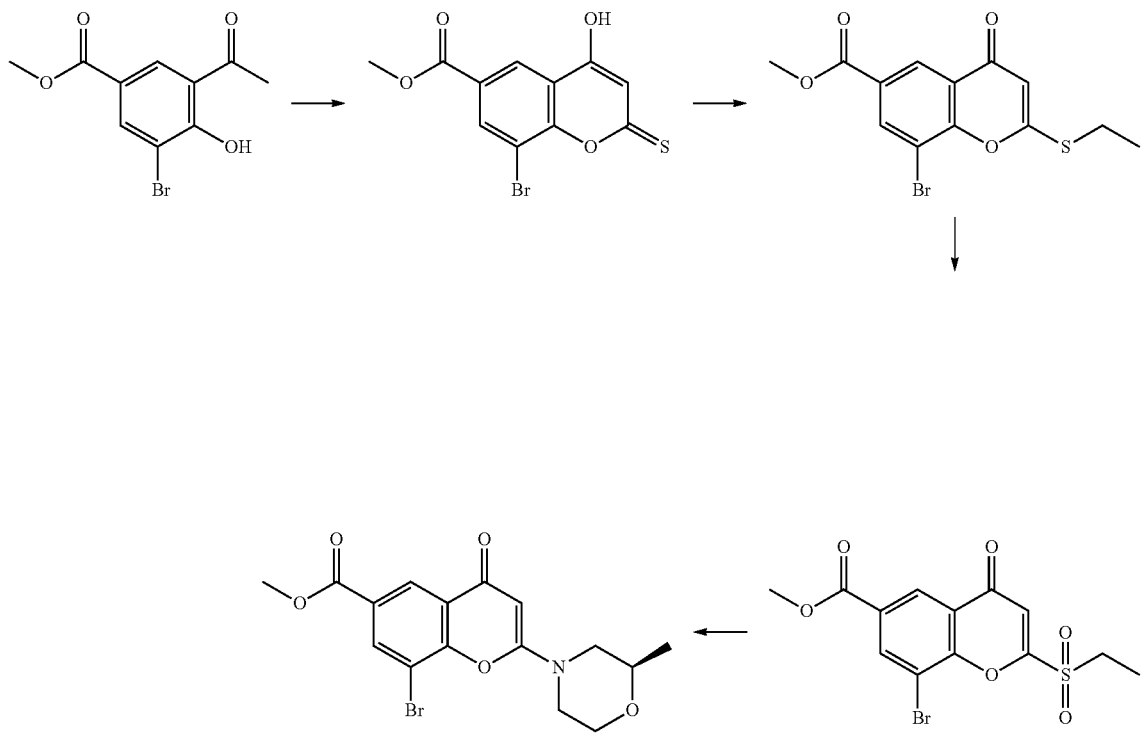

Alternatively, Compounds of the Formula II may, for example, be prepared by reaction of a compound of the Formula XVI:

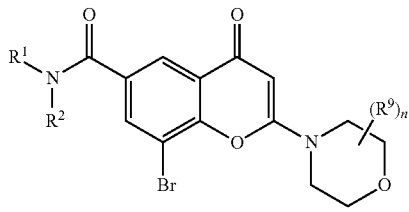

wherein $R^1$, $R^2$, n and $R^9$ have any of the meanings defined hereinbefore except that any functional group present is protected if necessary, with a suitable stannane such as, for example, tributyl(1-ethoxyvinyl)stannane under Stille type conditions (for further details of such conditions see for example: 'Metal-Catalyzed Cross-Coupling Reactions', Second Edition, Edited by Armin Meijere, Francois Diederich, Wiley-VCH, 2004, Volume 1, p125), whereafter any protecting group that is present is removed.

A suitable catalyst for the Stille reaction includes, for example, a metallic catalyst such as a palladium(0), palladium(II) for example tetrakis(triphenylphosphine)palladium (0), palladium(II) chloride, palladium(II) bromide, bis(triphenylphosphine)palladium(II) chloride, [1,1'-bis(diphenylphosphino)ferrocene]dichloropalladium(II), tris(dibenzilideneacetone)dipalladium. Optionally, the catalyst can be formed in-situ by the reaction of one or more of the above catalysts with a trialkylphosphine, such as, for example, tri-N-butylphosphine or tricyclohexylphosphine.

The reaction is conveniently carried out in the presence of a suitable solvent or diluent such as for example, N,N-dimethylformamide, tetrahydrofuran, 1,4-dioxane, 1,2-dimethoxyethane, benzene, toluene, xylene and at a temperature in the range, for example 20° C. to 150° C., conveniently in the range 60° C. to 120° C.

Alternatively, Compounds of the Formula II may, for example, be prepared by reaction of a compound of the Formula XVI:

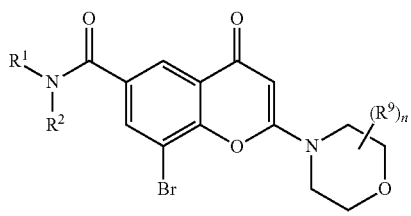

wherein $R^1$, $R^2$, n and $R^9$ have any of the meanings defined hereinbefore except that any functional group present is protected if necessary, with a suitable alkene such as for example, (1-vinyloxy)butane under Heck type conditions whereafter any protecting group that is present is removed.

A suitable catalyst for the Heck reaction includes, for example, a metallic catalyst such as a palladium(0), palladium(II) for example tetrakis(triphenylphosphine)palladium (0), palladium(II) chloride, palladium(II) bromide, bis(triphenylphosphine)palladium(II) chloride, [1,1'-bis(diphenylphosphino)ferrocene]dichloropalladium(II), tris(dibenzilideneacetone)dipalladium; Optionally, the catalyst can be formed in-situ by the reaction of one or more of the above catalysts with a trialkylphosphine, such as, for example, tri-N-butylphosphine or tricyclohexylphosphine.

Conveniently, the catalyst is palladium (II) acetate in the presence of bis(1,3-diphenylphosphino)propane.

The reaction is conveniently carried out in the presence of a suitable solvent or diluent such as for example, N,N-dimethylformamide, tetrahydrofuran, 1,4-dioxane, 1,2-dimethoxyethane, benzene, toluene, xylene or alcohols and at a temperature in the range, for example 20° C. to 150° C. Conveniently ethyleneglycol is used and the reaction is conducted at a temperature of between 90-130° C.

An example of a process scheme that may be used for the synthesis of a compound of the Formula XVI, such as for example 8-bromo-N,N-dimethyl-2-(morpholin-4-yl)-4-oxo-4H-chromene-6-carboxamide, is the following:

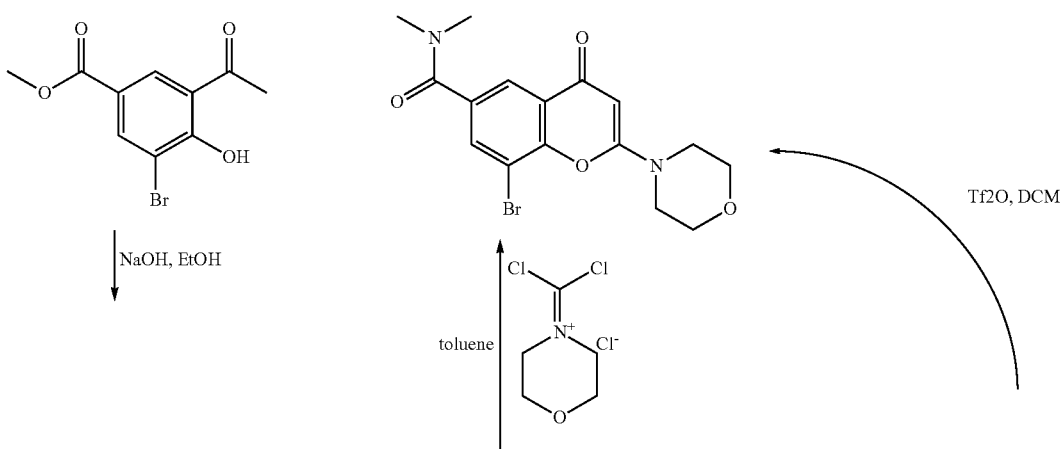

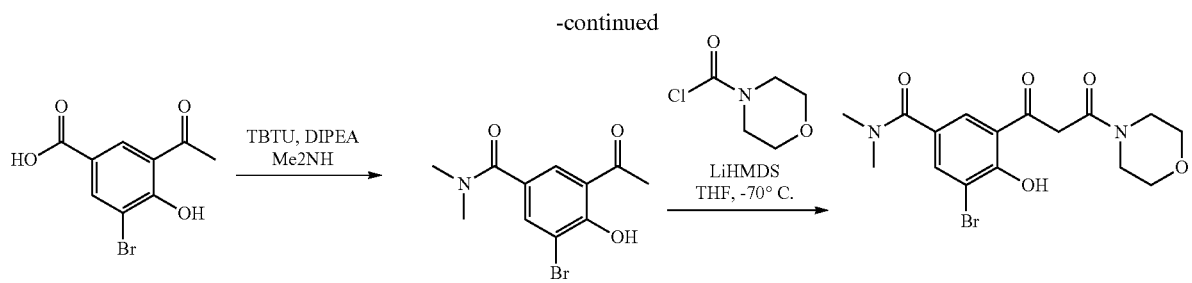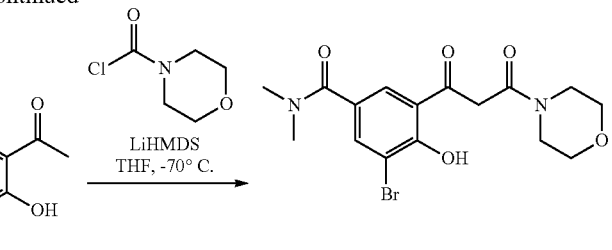

where, DCM is dichloromethane, LiHMDS is Lithium bis(trimethyl silyl)amide, EtOH is ethanol, DIPEA is diisopropylethylamine, THF is tetrahydrofuran, Tf$_2$O is Trifluoromethanesulfonic anhydride and TBTU is 2-(1H-benzo[d][1,2,3]triazol-1-yl)-1,1,3,3-tetramethylisouronium tetrafluoroborate.

(b) The cross coupling reaction, conveniently in the presence of a suitable catalyst as defined hereinbefore, of a compound of the Formula X:

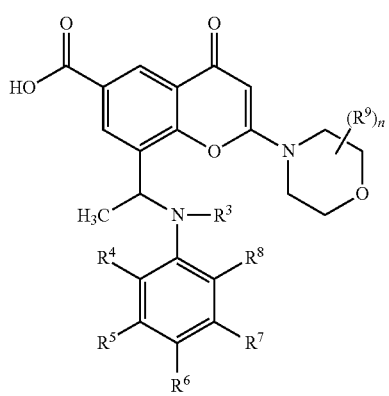

X wherein $R^3$, $R^4$, $R^5$, $R^6$, $R^7$ and $R^8$, n and $R^9$ have any of the meanings defined hereinbefore except that any functional group present is protected if necessary, conveniently in the presence of a suitable base, with an amine of the Formula VI:

VI wherein $R^1$ and $R^2$ have any of the meanings defined hereinbefore except that any functional group is protected if necessary, in the presence of a suitable coupling agent such as, for example, TSTU (2-(2,5-dioxopyrrolidin-1-yl)-1,1,3,3-tetramethylisouronium tetrafluoroborate) or TBTU (2-(1H-benzo[d][1,2,3]triazol-1-yl)-1,1,3,3-tetramethylisouronium tetrafluoroborate), whereafter any protecting group that is present is removed.

The reaction is conveniently carried out in the presence of a suitable base. A suitable base is, for example, an organic amine base such as, for example, pyridine, 2,6-lutidine, collidine, 4-dimethylaminopyridine, triethylamine, N-methylmorpholine, diazabicyclo[5.4.0]undec-7-ene, diisopropylethyl amine, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent such as for example, N,N-dimethylformamide, N-methylpyrrolidone, tetrahydrofuran, 1,4-dioxane, 1,2-dimethoxyethane, benzene, toluene, xylene, methanol ethanol, halogenated solvents such as dichloromethane, chloroform or carbon tetrachloride and at a temperature in the range, for example −50° C. to 100° C., preferably in the range 0° C. to 30° C.

Compounds of the Formula X may, for example, be prepared by a saponification reaction, of a compound of the Formula Xa:

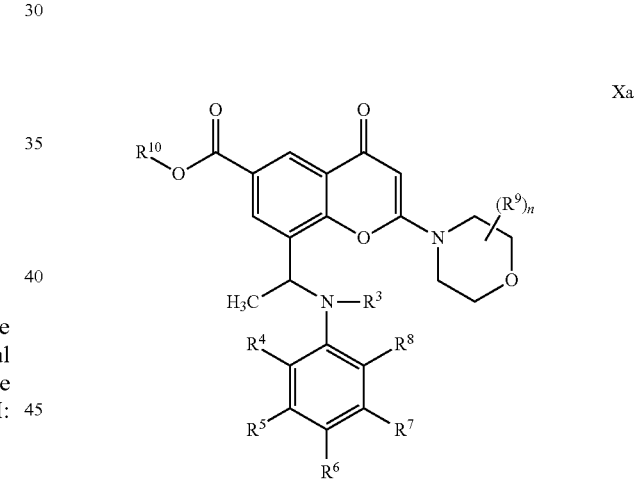

Xa wherein $R^3$, $R^4$, $R^5$, $R^6$, $R^7$, $R^8$ n and $R^9$ has any of the meanings defined hereinbefore and $R^{10}$ is (1-6C)alkyl, conveniently methyl or ethyl.

The saponification reaction can be conducted for example by treatment of a compound of Formula Xa with an alkali or alkaline earth metal hydroxide such as lithium, potassium or sodium hydroxide in a suitable solvent such as for example a mixture of ethanol and water or a water miscible solvent, such as for example tetrahydrofuran or dioxane, at a temperature in the range, for example 0° C. to −100° C., preferably in the range 20-40° C.

Compounds of the Formula Xa may, for example, be prepared by the reaction, conveniently in the presence of a suitable catalyst as defined hereinbefore, of a compound of the Formula XI:

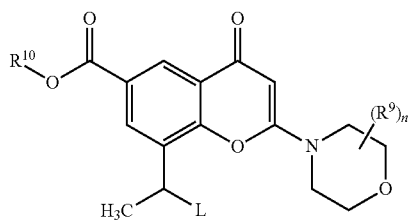

XI wherein n and $R^9$ has any of the meanings defined hereinbefore, $R^{10}$ is (1-6C)alkyl, conveniently methyl or ethyl, and L is a displaceable group, with an amine derivative of the Formula III

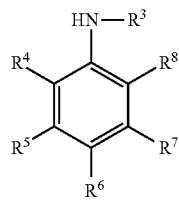

III wherein $R^3$, $R^4$, $R^5$, $R^6$, $R^7$ and $R^8$ has any of the meanings defined hereinbefore, whereafter any protecting group that is present is removed.

A suitable displaceable group L is, for example, a halogeno group such as a chloro, bromo, iodo group, trifluoromethanesulphonyl or methanesulphonyl. Conveniently, the displaceable group L is bromo.

The reaction is conveniently carried out in the presence of a suitable inert solvent or diluent such as for example, N,N-dimethylformamide, tetrahydrofuran, 1,4-dioxane, 1,2-dimethoxyethane, benzene, toluene, xylene, methanol ethanol, halogenated solvents such as dichloromethane, chloroform or carbon tetrachloride and at a temperature in the range, for example −50° C. to 100° C., preferably in the range 0° C. to 30° C.

Compounds of the Formulae XI may be obtained by analogous procedures to those described in the Example 2.00 herein, where the method for preparing the starting material 8-(1-(3-chloro-2-fluorophenylamino)ethyl)-2-morpholino-4-oxo-4H-chromene-6-carboxylic acid is given. In particular, compounds of the Formulae XI may be obtained by procedures in accordance with the following scheme:

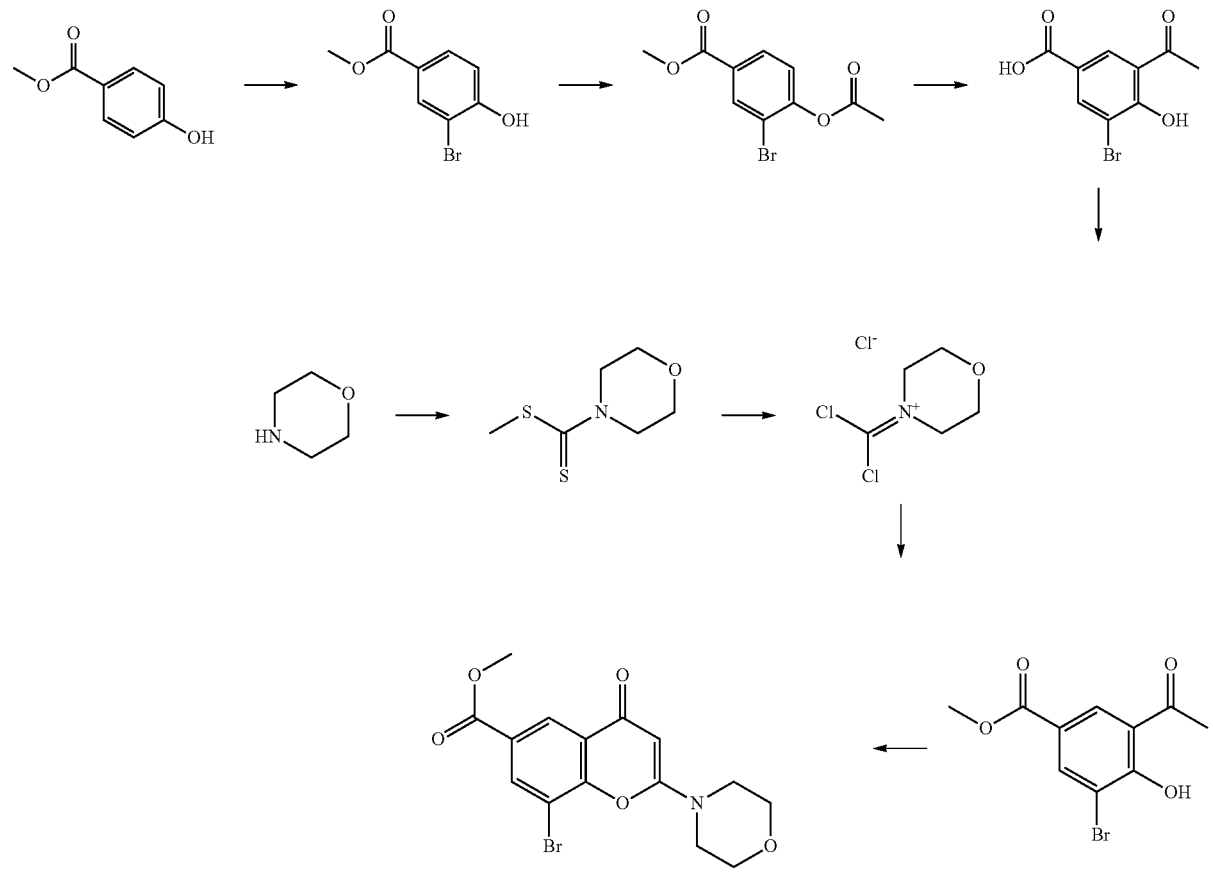

methyl 8-bromo-2-morpholino-4-oxo-4H-chromene-6-carboxylate

-continued

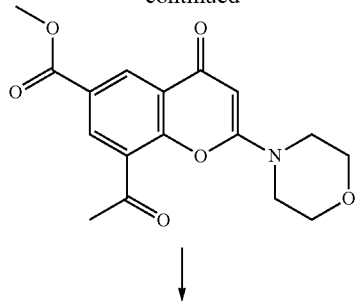

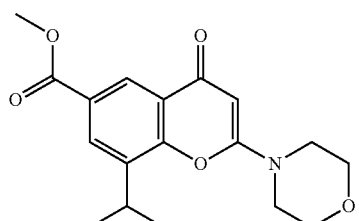

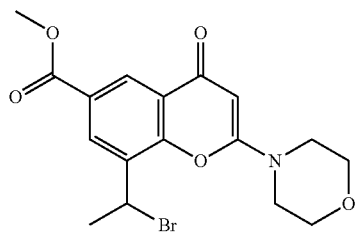

For example, compounds of the Formula XI may, be prepared by reaction of a compound of the Formula XII:

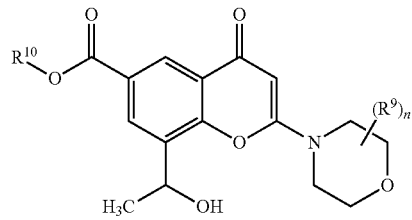

wherein n and $R^9$ has any of the meanings and $R^{10}$ is (1-6C) alkyl, conveniently methyl or ethyl, with an agent such as a halogenating agent, for example a brominating agent, such as for example phosphorus tribromide.

The reaction is conveniently carried out in the presence of a suitable inert solvent or diluent such as for example, N,N-dimethylformamide, tetrahydrofuran, 1,4-dioxane, 1,2-dimethoxyethane, benzene, toluene, xylene, halogenated solvents such as DCM, chloroform or carbon tetrachloride and at a temperature in the range, for example −50° C. to 100° C., preferably in the range 0° C. to 30° C.

Compounds of the Formula XII may, for example, be prepared by reaction of a compound of the Formula XIII:

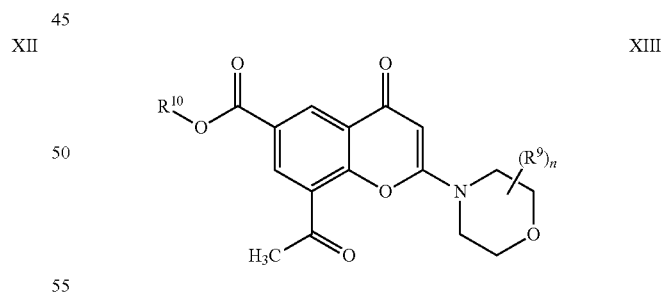

wherein n and $R^9$ has any of the meanings and $R^{10}$ is (1-6C) alkyl, conveniently methyl or ethyl, with a reducing agent such as a hydride, for example a borohydride derived reagent, such as sodium borohydride.

The reaction is conveniently carried out in the presence of a suitable solvent or diluent such as for example alcohols (methanol, ethanol) or a mixture of solvents containing alcohols and at a temperature in the range, for example −50° C. to 50° C., preferably in the range 0° C. to 20° C.

Compounds of the Formula XIII may be obtained by coupling compounds of the Formula VIIIa with a suitable stannane such as, for example, tributyl(1-ethoxyvinyl)stannane under Stille type conditions using conditions reported in process variant (a). Alternatively, Compounds of the Formula XIII may be obtained by coupling compounds of the Formula VIIIa with a suitable alkene such as for example, (1-vinyloxy) butane under Heck type conditions (see conditions reported in process variant (a)).

(c) The reaction, conveniently in the presence of a suitable catalyst as defined hereinbefore in process variant (b) above, of a compound of the Formula XIV:

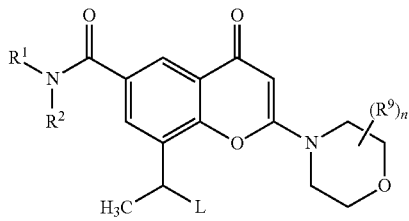

XIV wherein $R^1$, $R^2$, n and $R^9$ have any of the meanings defined hereinbefore except that any functional group present is protected if necessary and L is a displaceable group, with an amine derivative of the Formula III

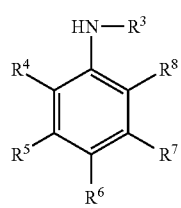

III wherein $R^3$, $R^4$, $R^5$, $R^6$, $R^7$ and $R^8$ has any of the meanings defined hereinbefore, whereafter any protecting group that is present is removed.

A suitable displaceable group L is, for example, a halogeno group such as a chloro, bromo, iodo group, a methanesulphonyl or a trifluoromethanesulphonyl group. Conveniently, the displaceable group L is bromo.

The reaction is conveniently carried out in the presence of a suitable inert solvent or diluent such as for example, N,N-dimethylformamide, N-methylpyrrolidone, tetrahydrofuran, 1,4-dioxane, 1,2-dimethoxyethane, benzene, toluene, xylene, methanol ethanol, halogenated solvents such as dichloromethane, chloroform or carbon tetrachloride and at a temperature in the range, for example −50° C. to 100° C., preferably in the range 0° C. to 50° C. Conveniently, the suitable inert solvent is N,N-dimethylformamide.

Compounds of the Formula XIV may, for example, be prepared by the reaction, conveniently in the presence of a suitable catalyst as defined hereinbefore, of a compound of the Formula XV:

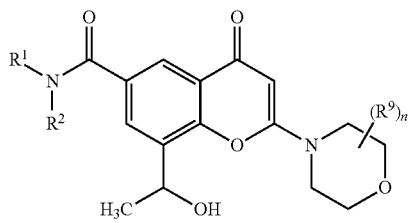

XV wherein $R^1$, $R^2$, n and $R^9$ has any of the meanings defined hereinbefore, with an agent such as a halogenating agent, for example a brominating agent, such as for example phosphorus tribromide. The reaction is conveniently carried out in the presence of a suitable inert solvent or diluent such as for example, N,N-dimethylformamide, tetrahydrofuran, 1,4-dioxane, 1,2-dimethoxyethane, benzene, toluene, xylene, halogenated solvents such as dichloromethane, chloroform or carbon tetrachloride and at a temperature in the range, for example −50° C. to 100° C., preferably in the range 0° C. to 30° C.

Compounds of the Formula XV may, for example, be prepared by a cross coupling reaction, conveniently in the presence of a suitable catalyst as defined hereinbefore in process variant (b) above, of a compound of the Formula XVa:

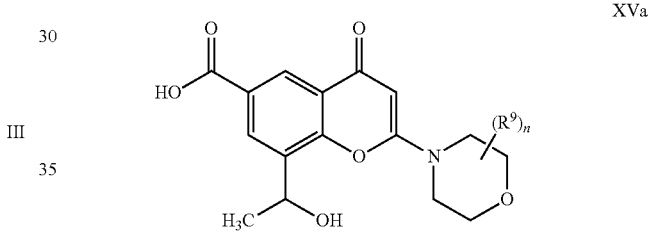

XVa wherein n and $R^9$ have any of the meanings defined hereinbefore except that any functional group present is protected if necessary, conveniently in the presence of a suitable base, with an amine of the Formula VI:

VI wherein $R^1$ and $R^2$ have any of the meanings defined hereinbefore except that any functional group is protected if necessary, in the presence of a suitable coupling agent such as, for example, TSTU (2-(2,5-dioxopyrrolidin-1-yl)-1,1,3,3-tetramethylisouronium tetrafluoroborate) or TBTU (2-(1H-benzo[d][1,2,3]triazol-1-yl)-1,1,3,3-tetramethylisouronium tetrafluoroborate), whereafter any protecting group that is present is removed.

The reaction is conveniently carried out in the presence of a suitable base. A suitable base is, for example, an organic amine base such as, for example, pyridine, 2,6-lutidine, collidine, 4-dimethylaminopyridine, triethylamine, N-methylmorpholine, diazabicyclo[5.4.0]undec-7-ene, diisopropylethyl amine, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent such as for example, N,N-dimethylformamide, N-methylpyrrolidone, tetrahydrofuran, 1,4-dioxane, 1,2-dimethoxyethane, benzene, toluene, xylene, methanol ethanol, halogenated solvents such as dichloromethane, chloroform or carbon tetrachloride and at a temperature in the range, for example −50° C. to 100° C., preferably in the range 0° C. to 30° C.

Compounds of the Formula XVa may, for example, be prepared by a saponification reaction, of a compound of the Formula XII:

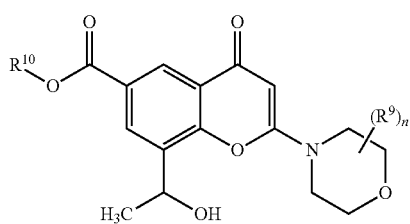

XII wherein n and $R^9$ has any of the meanings and $R^{10}$ is (1-6C) alkyl, conveniently methyl or ethyl.

The saponification reaction can be conducted for example by treatment of a compound of Formula XII with an alkali or alkaline earth metal hydroxide such as lithium, potassium or sodium hydroxide in a suitable solvent such as for example methanol, or a mixture of ethanol and water or a water miscible solvent, such as for example tetrahydrofuran or dioxane, at a temperature in the range, for example 0° C. to −100° C., preferably in the range 20-40° C.

Alternatively, compounds of the Formula XV may, for example, be prepared a reduction reaction of a compound of the Formula II, where a suitable reducing agent is employed, such as for example a metal borohydride such as for example sodium borohydride. The reaction is conveniently carried out in the presence of a suitable solvent or diluent, such as for example an alcohol such as methanol or ethanol or a mixture of solvents containing alcohols, generally in the presence of a weak acid such as acetic acid. The reaction is conveniently carried out at a temperature in the range, for example, 0° C. to 30° C.

(d) The reaction of a compound of the Formula XVII:

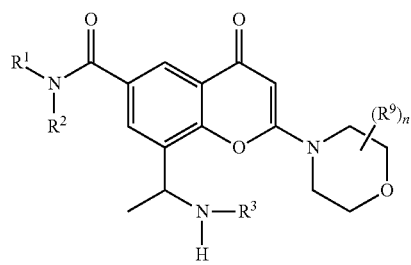

XVII wherein $R^1$, $R^2$, $R^3$, n and $R^9$ have any of the meanings defined hereinbefore except that any functional group present is protected, with compound of the Formula IIIa

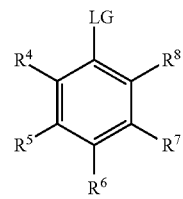

IIIa wherein $R^4$, $R^5$, $R^6$, $R^7$ and $R^8$ has any of the meanings defined hereinbefore and LG is a suitable leaving group, such as for example, a halogeno group such as a chloro, bromo, iodo group (conveniently bromo or iodo), whereafter any protecting group that is present is removed.

Suitable reactions of this type are described as palladium type coupling Buchwald reactions in 'Metal-Catalyzed Cross-Coupling Reactions', Second Edition, Edited by Armin Meijere, Francois Diederich, Wiley-VCH, 2004, Volume 1, p699).

Alternatively, compounds of the Formula I can be prepared by Chan-Lam coupling type reactions, in which a compound of the Formula XVII is reacted with a compound of the Formula IIIb:

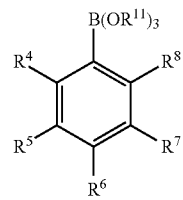

IIIb wherein, $R^{11}$ is (1-3C)alkyl or H. Such a reaction is conveniently catalysed by a copper source, such as for example copper (II) acetate in DCM and is carried out by way of exposure to atmospheric oxygen at ambient temperature (Tetrahedron Letters, 1998, 2933).

Compounds of the Formula XVII may, for example, be prepared by a reductive amination reaction of a compound of the Formula II:

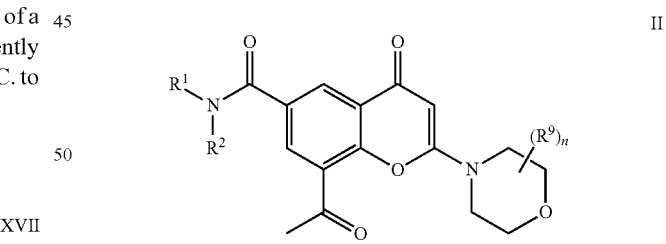

II wherein $R^1$, $R^2$, n and $R^9$ have any of the meanings defined hereinbefore except that any functional group present is protected if necessary, with an amine of the Formula $R_3NH_2$ or an equivalent, wherein $R^3$ has any of the meanings defined hereinbefore, in the presence of a reducing agent, whereafter any protecting group that is present is removed.

Where the compound of the Formula I is a single optically active enantiomer (chiral centre being the carbon atom to which the groups methyl and —N-phenyl$(R^4)(R^5)(R^6)(R^7)(R^8)$ are attached), analogous procedures to those outlined in the following scheme could be utilised to prepare compounds of the Formula XVII (for more details of a particular example of this, see Example 8.00 herein):

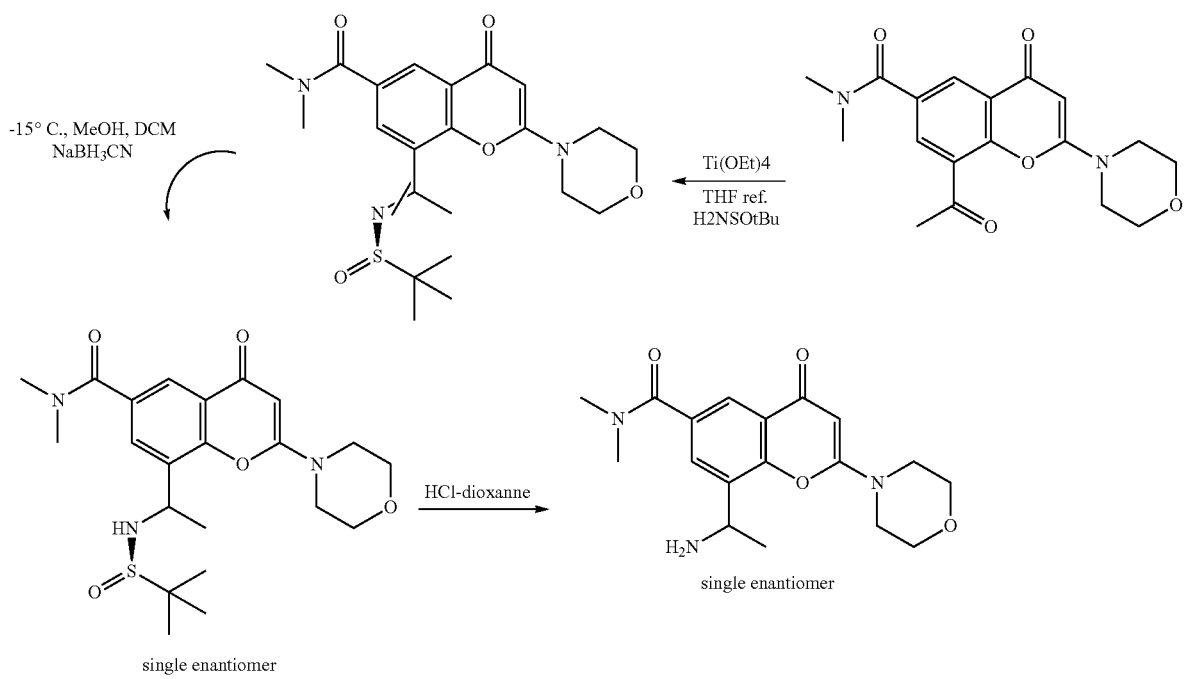

where, Ti(OEt)$_4$ is titanium (IV) tetraethoxide, (R)—H2NSOtBu is (R)-2-methylpropane-2-sulfinamide, DCM is dichloromethane, MeOH is methanol and THF is tetrahydrofuran.

For example, a single optically active enantiomer of the Formula XVII may, be prepared by a reaction of a compound of the Formula II with a chiral equivalent of R$_3$NH$_2$ such as an chiral sulfinamide for example, (R)-2-methylpropane-2-sulfinamide, to give a corresponding imine. This reaction is conveniently carried out in the presence of a Lewis acid such as titanium (IV) tetraethoxide The reaction is conveniently carried out in the presence of a suitable inert solvent or diluent such as for example, N,N-dimethylformamide, tetrahydrofuran, 1,4-dioxane, 1,2-dimethoxyethane, benzene, toluene, xylene, halogenated solvents such as dichloromethane, chloroform or carbon tetrachloride and at a temperature in the range, for example −50° C. to 100° C., preferably in the range 0° C. to 30° C.

Reduction of the corresponding imine is then performed using a reducing agent such as a borohydride, for example, sodium cyanoborohydride, whereafter any protecting group that is present is removed. The reaction is conveniently carried out in the presence of a weak acid. A suitable weak acid is, for example, acetic acid. The reaction is conveniently carried out in the presence of an alcohol such as methanol or ethanol, or a mixture of an alcohol and an suitable inert solvent or diluent such as for example, N,N-dimethylformamide, tetrahydrofuran, 1,4-dioxane, 1,2-dimethoxyethane, benzene, toluene, xylene, halogenated solvents such as dichloromethane, chloroform or carbon tetrachloride and at a temperature in the range, for example −50° C. to 20° C., preferably around −15° C.

It is to be understood that other permutations of the process steps in the process variants described above are also possible. For example, a Compound of Formula I could be prepared using analogous procedures to those descrived in process variants (a) to (d), but wherein the final step in the procedure is the introduction of the morpholine-(R$^9$)$_n$ group.

It is to be understood that any compound of Formula I obtained by any of the processes described hereinbefore can be converted into another compound of the Formula I if required. For example, a compound of the Formula I wherein R$^3$ is H can be converted into a compound of the Formula I in which R$^3$ is (1-3C)alkyl by alkylation with an alkylating agent. For example, where R$^3$ is methyl, a suitable alkylating agent such as dimethyl sulphate or methyl iodide could be used. The reaction can be perfomed in the presence of a strong base, such as for example sodium bis(trimethylsikyl)amide optionally in the presence of a suitable crown-ether (for example 1,4,7,10,13-pentaoxacyclopentadecane, also known as 15-crown-5 for sodium) at low temperature (−78° C. to 0° C.) in an inert solvent such as for example THF.

When a pharmaceutically-acceptable salt of a chromenone derivative of the Formula I is required, for example an acid-addition salt, it may be obtained by, for example, reaction of said chromenone derivative with a suitable acid.

When a pharmaceutically-acceptable pro-drug of a chromenone derivative of the Formula I is required, it may be obtained using a conventional procedure. For example, an in vivo cleavable ester of a chromenone derivative of the Formula I may be obtained by, for example, reaction of a compound of the Formula I containing a carboxy group with a pharmaceutically-acceptable alcohol or by reaction of a compound of the Formula I containing a hydroxy group with a pharmaceutically-acceptable carboxylic acid. For example, an in vivo cleavable amide of a chromenone derivative of the Formula I may be obtained by, for example, reaction of a compound of the Formula I containing a carboxy group with a pharmaceutically-acceptable amine or by reaction of a compound of the Formula I containing an amino group with a pharmaceutically-acceptable carboxylic acid.

It will also be appreciated by the person skilled in the organic synthetic arts that certain of the ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents, acylation of substituents, amidation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that, in some of the reactions mentioned hereinbefore, it may be necessary or desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain of the intermediates (for example, compounds of the Formulae II, IV, V, VII, VIIIa, VIIIb, X, Xa, XI, XII, XIII, XIV, XV, XVa, XVI, XVII) defined herein are novel and these are provided as a further feature of the invention. For example, compounds of the Formula VIIIa (wherein n, $R^9$ and $R^{10}$ have any of the meanings defined hereinbefore) may be useful as intermediates in the preparation of particular compounds of the invention:

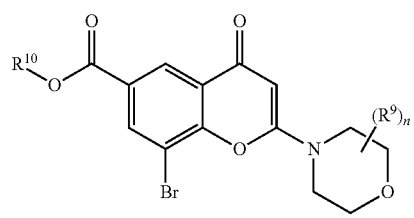

VIIIa

Furthermore, the following compound may be useful as an intermediate in the preparation of particular compounds of the invention:

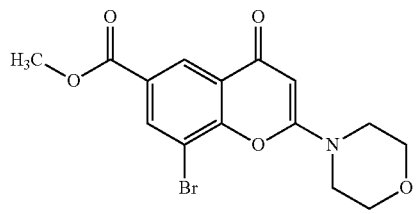 [SMILES: COC(=O)c1cc(Br)c2oc(N3CCOCC3)cc(=O)c2c1]

methyl 8-bromo-2-morpholin-4-yl-4-oxo-4H-chromene-6-carboxylate

Biological Assays

The following assays can be used to measure the effects of the compounds of the present invention as inhibitors of PI3 kinase enzymes, as inhibitors in vitro of phospho AKT (ser473) in MAD-MB-468 cells, as inhibitors in vivo of phospho AKT (ser473) in Swiss athymic nu/nu mice, and as inhibitors in vivo of tumour growth in Swiss athymic nu/nu mice translaplanted with the human prostatic adenocarcinoma cell line, PC3.

(a) In Vitro Enzyme Inhibition Assay

The inhibition of PI3Kβ, PI3Kα, PI3Kγ and PI3Kδ was evaluated in a Kinase Glo based enzyme activity assay using human recombinant enzymes. The assay measures depletion of ATP after incubation with enzyme, PIP2 and ATP plus compound. ATP at the end of the reaction is detected by addition of Kinase Glo reagent, in this the Ultra Glo™ luciferase (Promega) uses the ATP as a substrate to catalyze the mono-oxygenation of luciferin and the generation of light. A direct relationship exists between the luminescence measured with the Kinase-Glo Plus Reagent and the amount of ATP remaining in a completed kinase reaction and luminescence is inversely related to kinase activity. Twelve different compound concentrations were tested and raw data from the inhibition of PI3Kb, PI3Kα, PI3Kγ and PI3Kδ was plotted versus inhibitor concentration.

Method Details:

Compounds in 100% DMSO were added to assay plates by acoustic dispensing. PI3Kβ was added in a Tris buffer (50 mM Tris pH7.4, 0.05% CHAPS, 2.1 mM DTT, and 10 mM $MgCl_2$) and allowed to preincubate with compound for 20 minutes prior to addition of substrate solution containing PIP2 and ATP. The enzyme reaction was stopped after 80 minutes by the addition of Kinase Glo detection solution. Plates were left for 30 minutes at room temperature then read on a Pherastar Instrument (Luminescence ATP 384 program) setting gain on max well. The final concentration of DMSO, ATP and PIP2 in the assay were, 1%, 8 µM, and 80 µM respectively.

Data Analysis $IC_{50}$ values were calculated using a log curve fitting to a non-linear regression package, fitting raw data to inhibitor concentration. The $IC_{50}$ value is the concentration of test compound that inhibited 50% of enzyme activity.

(b) Protocol for Detection of Phospho AKT (ser473) in MAD-MB-468 Cells

MDA-MB-468 cells (human breast adenocarcinoma ATCC HTB 132) are seeded into Greiner 384 well black flat-bottomed plates by automated cell culture robot (Selec T). Cells can also be maintained manually and seeded into plates using multidrop or Wellmate. Cells seeded at 1500 cell/well in 40 µl of DMEN containing 10% FCS and 1% glutamine. Cell plates are incubated for 18 hours in a 37° C. incubator.

Compounds are dosed onto cells using an Echo acoustic dispenser, which dispenses nl quantities of compound or DMSO. Compounds are dosed in a 12 point concentration range from 30 µM top dose, 28 compounds are dosed on one plate. There are 17 DMSO only positive control wells per plate, and 16 negative control well which have been dosed with a concentration of reference compound that will knock-out the pAKT signal.

Plates are incubated at 37° C. for 2 hours, cells are the fixed by the addition of 10 µl of a 3.7% Formaldehyde solution in a fume cupboard using a Wellmate.

After 30 minutes to allow for fixation, the fixative and media are removed and the plates washed with Proclin PBS/A using Tecan PW384 plate washer in a fume cupboard.

Wells are blocked and permeabilised with the addition of 40 µl of PBS containing 0.5% Tween20 and 1% marvel using a Wellmate and incubated for 60 minutes at room temperature.

Permeabilisation and blocking buffer removed using Tecan PW384 plate washer, then 20 µl primary antibody solution added using a Wellmate. The primary antibody solution is a 1:500 dilution of Rabbit anti-phospho AKT Ser 473 (Cell signalling technologies catalogue number #3787) in PBS/T containing 1% marvel (dried milk powder) and incubated overnight at 4° C.

Plates are washed using a Tecan PW384 plate washer three times with Phosphate Buffered Saline+0.05% (v/v) Polysorbate20 and Proclin300 (Supelco). 20 µl of secondary antibody solution is then added to each well using a Wellmate and incubated for 1 hour at Room Temp. The secondary antibody solution is a 1:1000 dilution of Alexa Fluor 488 anti-Rabbit (Molecular Probes cat no A11008) diluted in Phosphate Buffered Saline+0.05% (v/v) Polysorbate20 containing 1% marvel. Plates are washed three times as before then 20 µl PBS added to each well and plates sealed with black plate sealer.

The plates are read on an Acumen reader as soon as possible. Using this system $IC_{50}$ values can be generated and quality of plates determined by control wells. Reference compounds are run each time to monitor assay performance.

(c) Protocol for Detection of Phospho AKT (ser473) in Swiss Athymic nu/nu Mice

Swiss athymic nu/nu mice can be transplanted s.c with human prostatic adenocarcinoma cell line PC3 (ATCC CRL1435) to determine anti-tumour activity of PI3 kinase inhibitors. On day 0, $1\times10^6$ cells in 50% Matrigel™ (BD Biosciences #354234) are injected s.c. on the left flank of the animals. Animals are randomised into required group sizes (typically 5 per treatment group) when tumours reach a volume of ~400-600 $mm^3$ and treatment commences. Tumours are taken at termination and flash frozen in liquid nitrogen and stored at −80° C. until analysis.

1 ml of lysis buffer plus phosphatase inhibitors Sigma #P2850, Sigma #P5726 (diluted 1:100) and protease inhibitors Sigma #P8340 (diluted 1:200) is added to each tumour in a Fastprep tube. The tumours are homogenised for 1 minute on the Fastprep machine and then left on ice for 10 minutes. Samples are spun for 10 minutes at 13,000 rpm in a chilled centrifuge. Cleared lysates are then taken into fresh tubes and 5 µl used for a protein determination assay. All tumour samples are diluted to same concentration so that 15 µg is run per lane on a 4-15% NuPAGE Bis-Tris gels (Invitrogen) for 90 minutes at 140 Volts. The samples are randomised so that gel effects are minimised. After blotting onto Nitrocellulose membranes they are blocked for one hour then incubated overnight with a 1:500 dilution of antibody to either total AKT (CST # 9272) or phospho AKT-ser 473 (CST # 9271). Blots are washed three times in PBST before incubation for one hour at room temperature with a 1:2,000 dilution of anti-rabbit secondary HRP-linked antibody (CST # 7074). Block and antibody incubation buffer is 5% dried milk powder in PBS with 0.05% Polysorbate. Blots are washed three times in PBS/T then visualised using Pierce West Dura ECL kit and the ChemiGenius. Bands are quantified and a ratio of phospho to total signal is obtained for each sample. The controls are averaged and each treatment sample is normalised to the averaged control value.

(d) Protocol for Detection of Tumour Growth Inhibition in Human Prostatic Adenocarcinoma Cell Line PC3 Transplanted Swiss Athymic nu/nu Mice Swiss athymic nu/nu mice can be transplanted s.c with the human prostatic adenocarcinoma cell line PC3 (ATCC CRL1435) to determine anti-tumour activity of PI3 kinase inhibitors. On day 0, $1\times10^6$ cells in 50% Matrigel (BDM) are injected s.c. on the left flank of the animals. Animals are randomised into groups of 10-15 when tumours reach a volume of ~200-300 $mm^3$ and treatment commences. Animals are dosed for 2-4 weeks by peroral, intravenous or intraperitoneal routes with compound (and optionally a cyp inhibitor such as 1-aminobenzotriazole) in a suitable vehicle at defined doses. Tumours are usually measured twice weekly by caliper and volume of tumours calculated using elliptical formula (pi/6×width×width×length).

Although the pharmacological properties of the compounds of the Formula I vary with structural change as expected, in general activity possessed by compounds of the Formula I may be demonstrated at the following concentrations or doses in one or more of the above tests (a) and (b): —

Test (a): —IC$_{50}$ versus PI3Kβ in the range, for example, 1 nM-25 µM;

Test (b): —IC$_{50}$ versus cellular phospho AKT (ser473) in MAD-MB-468 cells, in the range, for example, 1 nM-25 µM;

Conveniently, particular compounds of the invention possess activity at the following concentrations or doses in one or more of the above tests (a) and (b): —

Test (a): —IC$_{50}$ versus PI3Kβ in the range, for example, 1 nM-10 µM;

Test (b): —IC$_{50}$ versus cellular phospho AKT (ser473) in MAD-MB-468 cells, in the range, for example, 1 nM-20 µM;

Conveniently, particular compounds of the invention possess activity at the following concentrations or doses in one or more of the above tests (a), (b), (c) and (d): —

Test (a): —IC$_{50}$ versus PI3Kβ in the range, for example, 1 nM-10 µM;

Test (b): —IC$_{50}$ versus cellular phospho AKT (ser473) in MAD-MB-468 cells, in the range, for example, 1 nM-20 µM;

Test (c): —>50% inhibition of in vivo phospho AKT (ser473) in the range, for example, 1-200 mg/kg/day;

Test (d): —xenograft activity in the range, for example, 1-200 mg/kg/day.

For example, the chromenone compound disclosed as Example 1.00 possesses activity in Test (a) with an IC$_{50}$ versus PI3Kβ of approximately 2 nM; and activity in Test (b) with an IC$_{50}$ versus cellular cellular phospho AKT (ser473) in MAD-MB-468 cells of approximately 9 nM.

For example, the chromenone compound disclosed as Example 2.05 possesses activity in Test (a) with an IC$_{50}$ versus PI3Kβ of approximately 5 nM; and activity in Test (b) with an IC$_{50}$ versus cellular cellular phospho AKT (ser473) in MAD-MB-468 cells of approximately 17 nM.

For example, the chromenone compound disclosed as Example 3.03 possesses activity in Test (a) with an IC$_{50}$ versus PI3Kβ of approximately 9 nM; and activity in Test (b) with an IC$_{50}$ versus cellular cellular phospho AKT (ser473) in MAD-MB-468 cells of approximately 35 (37) nM. The value given in brackets is a mean IC$_{50}$ value calculated from a larger number of replicates than were used to calculate the first value quoted for the given Example compound.

For example, the chromenone compound disclosed as Example 3.04 possesses activity in Test (a) with an IC$_{50}$ versus PI3Kβ of approximately 11 nM; and activity in Test (b) with an IC$_{50}$ versus cellular cellular phospho AKT (ser473) in MAD-MB-468 cells of approximately 12 nM.

For example, the chromenone compound disclosed as Example 3.06 possesses activity in Test (a) with an IC$_{50}$ versus PI3Kβ of approximately 6 nM; and activity in Test (b) with an IC$_{50}$ versus cellular cellular phospho AKT (ser473) in MAD-MB-468 cells of approximately 9 nM.

For example, the chromenone compound disclosed as Example 3.06a possesses activity in Test (a) with an IC$_{50}$ versus PI3Kβ of approximately 3.7 µM; and activity in Test (b) with an IC$_{50}$ versus cellular cellular phospho AKT (ser473) in MAD-MB-468 cells of approximately 13.5 µM.

For example, the chromenone compound disclosed as Example 3.06b possesses activity in Test (a) with an IC$_{50}$ versus PI3Kβ of approximately 2 nM; and activity in Test (b) with an IC$_{50}$ versus cellular cellular phospho AKT (ser473) in MAD-MB-468 cells of approximately 5 (3) nM. The value given in brackets is a mean IC$_{50}$ value calculated from a larger number of replicates than were used to calculate the first value quoted for the given Example compound.

For example, the chromenone compound disclosed as Example 3.07 possesses activity in Test (a) with an IC$_{50}$ versus PI3Kβ of approximately 29 nM; and activity in Test (b) with an IC$_{50}$ versus cellular cellular phospho AKT (ser473) in MAD-MB-468 cells of approximately 0.58 µM.

For example, the chromenone compound disclosed as Example 3.11 possesses activity in Test (a) with an IC$_{50}$ versus PI3Kβ of approximately 4 nM; and activity in Test (b) with an IC$_{50}$ versus cellular cellular phospho AKT (ser473) in MAD-MB-468 cells of approximately 27 nM.

For example, the chromenone compound disclosed as Example 4.02 possesses activity in Test (a) with an IC$_{50}$ versus PI3Kβ of approximately 4 nM; and activity in Test (b) with an IC$_{50}$ versus cellular cellular phospho AKT (ser473) in MAD-MB-468 cells of approximately 1 (2) nM. The value given in brackets is a mean IC$_{50}$ value calculated from a larger number of replicates than were used to calculate the first value quoted for the given Example compound.

For example, the chromenone compound disclosed as Example 3.13a possesses activity in Test (a) with an IC$_{50}$ versus PI3Kβ of approximately 4.5 µM; and activity in Test (b) with an IC$_{50}$ versus cellular cellular phospho AKT (ser473) in MAD-MB-468 cells of approximately 4.3 µM.

For example, the chromenone compound disclosed as Example 5.0a possesses activity in Test (a) with an IC$_{50}$ versus PI3Kβ of approximately 5 nM; and activity in Test (b) with an IC$_{50}$ versus cellular cellular phospho AKT (ser473) in MAD-MB-468 cells of approximately 15 nM.

For example, the chromenone compounds disclosed within the Examples possess activity in Test (a) at the levels illustrated in Table A.

TABLE A

| Example number | PI3Kβ inhibition, IC$_{50}$ (µM) |
| --- | --- |
| 1.00 | 0.002 |
| 1.01 | 0.001 |
| 1.02 | 0.002 |
| 2.00 | 0.009 |
| 2.01 | 0.007 |
| 2.02 | 0.007 |
| 2.03 | 0.006 |
| 2.04 | 0.004 |
| 2.05 | 0.005 |
| 2.06 | 0.006 |
| 2.07 | 0.005 |
| 2.08 | 0.007 |
| 3.00 | 0.007 |
| 3.01 | 0.006 |
| 3.02 | 0.011 |
| 3.03 | 0.009 |
| 3.03a | 0.649 |
| 3.03b | 0.003 |
| 3.04 | 0.011 |
| 3.04a | 2.249 |
| 3.04b | 0.003 |
| 3.05 | 0.006 |
| 3.06 | 0.006 |
| 3.06a | 3.695 |
| 3.06b | 0.002 |
| 3.07 | 0.029 |
| 3.08 | 0.011 |
| 3.09 | 0.004 |
| 3.10 | 0.004 |
| 3.11 | 0.004 |
| 3.12 | 0.007 (0.005)* |
| 3.13 | 0.006 |
| 3.13a | 4.537 |
| 3.13b | 0.004 |
| 3.14 | 0.004 |
| 3.15 | 0.01 |
| 3.16 | 0.005 |

TABLE A-continued

| Example number | PI3Kβ inhibition, IC$_{50}$ (μM) |
|---|---|
| 3.17 | 0.006 |
| 3.18 | 0.01 |
| 3.19 | 0.005 |
| 3.20 | 0.005 |
| 3.21 | 0.114 |
| 3.22 | 0.004 |
| 3.23 | 0.013 |
| 3.24 | 0.006 |
| 3.25 | 0.212 |
| 3.26 | 0.004 |
| 3.27 | 0.009 |
| 3.28 | 0.004 |
| 3.29 | 0.005 |
| 3.30 | 0.004 |
| 3.31 | 0.006 |
| 3.32 | 0.008 |
| 3.33 | 0.005 |
| 3.34 | 0.004 |
| 3.35 | 0.031 |
| 3.36 | 0.024 |
| 3.37 | 0.012 |
| 3.38 | 0.017 |
| 3.39 | 0.021 |
| 3.40 | 0.043 |
| 3.41 | 0.014 |
| 4.01 | 0.004 |
| 4.02 | 0.004 |
| 4.03 | 0.004 |
| 4.04 | 0.004 |
| 4.05 | 0.008 |
| 4.06 | 0.004 |
| 4.07 | 0.004 |
| 4.08 | 0.005 |
| 4.09 | 0.003 |
| 4.10 | 0.005 |
| 4.11 | 0.002 |
| 4.12 | 0.004 |
| 4.13 | 0.009 |
| 4.14 | 0.004 |
| 4.15 | 0.004 |
| 4.16 | 0.009 |
| 4.17 | 0.005 |
| 4.18 | 0.004 |
| 4.19 | 0.023 |
| 4.20 | 0.005 |
| 4.21 | 0.004 |
| 4.22 | 0.004 |
| 4.23 | 0.003 |
| 4.24 | 0.004 |
| 4.25 | 0.005 |
| 4.26 | 0.004 |
| 5.0a | 0.005 |
| 5.0b | 1.236 |
| 5.01 | 0.008 |
| 5.02 | 0.007 |
| 5.03 | 0.007 |
| 6.0 | 0.005 |
| 7.0 | 0.011 |
| 7.0a | 3.381 |
| 7.0b | 0.005 |
| 7.01a | 0.008 |
| 7.01b | 4.315 |
| 7.02 | 0.004 |
| 8.0 | 0.003 |
| 8.01 | 0.005 |
| 8.02 | 0.002 |
| 9.0 | 0.005 |
| 9.01 | 0.004 |
| 9.01a | 17.900 |
| 9.01b | 0.003 |
| 9.02 | 0.011 |
| 9.02a | 22.671 |
| 9.02b | 0.007 |
| 9.03 | 0.064 |
| 10.01 | 0.012 |
| 10.02 | 0.011 |
| 10.03 | 0.009 |
| 11.00 | 0.021 |

*this is a mean IC$_{50}$ value calculated from a larger number of replicates than were used to calculate the first value quoted for the given Example compound.

According to a further aspect of the invention there is provided a pharmaceutical composition, which comprises a chromenone derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing) or as a suppository for rectal dosing.

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the disease state, the age and sex of the animal or patient and the route of administration, according to well known principles of medicine.

In using a compound of the Formula I for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form. Typically, unit dosage forms will contain about 10 mg to 0.5 g of a compound of this invention.

As stated above, it is known that PI 3-kinase enzymes contribute to tumourigenesis by one or more of the effects of mediating proliferation of cancer and other cells, mediating angiogenic events and mediating the motility, migration and invasiveness of cancer cells. We have found that the chromenone derivatives of the present invention possess potent anti-tumour activity which it is believed is obtained by way of inhibition of one or more of the Class I PI 3-kinase enzymes (such as the Class Ia PI 3-kinase enzymes and/or the Class Ib PI 3-kinase enzyme) that are involved in the signal transduction steps which lead to the proliferation and survival of tumour cells and the invasiveness and migratory ability of metastasising tumour cells.

Accordingly, the derivatives of the present invention are of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the chromenone derivatives of the present invention are of value as anti-proliferative and anti-invasive agents in the containment and/or treatment of solid tumour disease. Particularly, the compounds of the present invention are expected to be useful in the prevention or treatment of those tumours which are sensitive to inhibition of one or more of the multiple PI 3-kinase enzymes such as the Class Ia PI 3-kinase enzymes and the Class Ib PI 3-kinase enzyme that are involved in the signal transduction steps which lead to the proliferation and survival of tumour cells and the migratory ability and invasiveness of metastasising tumour cells. Further, the compounds of the present invention are expected to be useful in the prevention or treatment of those tumours which are mediated alone or in part by inhibition of PI 3-kinase enzymes such as the Class Ia PI 3-kinase enzymes and the Class Ib PI 3-kinase enzyme, i.e. the compounds may be used to produce a PI 3-kinase enzyme inhibitory effect in a warm blooded animal in need of such treatment.

As stated hereinbefore, inhibitors of PI 3-kinase enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including acute lymphoctic leukaemia (ALL) and chronic myelogenous leukaemia (CML)], multiple myeloma and lymphomas.

According to a further aspect of the invention there is provided a chromenone derivative of the Formula I, or a pharmaceutically acceptable salt thereof, as defined hereinbefore for use as a medicament in a warm-blooded animal such as man.

According to a further aspect of the invention, there is provided a chromenone derivative of the Formula I, or a pharmaceutically acceptable salt thereof, as defined hereinbefore for use in the production of an anti-proliferative effect in a warm-blooded animal such as man.

According to a further feature of this aspect of the invention there is provided a chromenone derivative of the Formula I, or a pharmaceutically acceptable salt thereof, as defined hereinbefore for use in a warm-blooded animal such as man as an anti-invasive agent in the containment and/or treatment of solid tumour disease.

According to a further aspect of the invention, there is provided the use of a chromenone derivative of the Formula I, or a pharmaceutically acceptable salt thereof, as defined hereinbefore for the production of an anti-proliferative effect in a warm-blooded animal such as man.

According to a further feature of this aspect of the invention there is provided the use of a chromenone derivative of the Formula I, or a pharmaceutically acceptable salt thereof, as defined hereinbefore in the manufacture of a medicament for use in the production of an anti-proliferative effect in a warm-blooded animal such as man.

According to a further feature of this aspect of the invention there is provided the use of a chromenone derivative of the Formula I, or a pharmaceutically acceptable salt thereof, as defined hereinbefore in the manufacture of a medicament for use in a warm-blooded animal such as man as an anti-invasive agent in the containment and/or treatment of solid tumour disease.

According to a further feature of this aspect of the invention there is provided a method for producing an anti-proliferative effect in a warm blooded animal, such as man, in need of such treatment which comprises administering to said animal an effective amount of a chromenone derivative of the Formula I, or a pharmaceutically acceptable salt thereof, as defined hereinbefore.

According to a further feature of this aspect of the invention there is provided a method for producing an anti-invasive effect by the containment and/or treatment of solid tumour disease in a warm blooded animal, such as man, in need of such treatment which comprises administering to said animal an effective amount of a chromenone derivative of the Formula I, or a pharmaceutically acceptable salt thereof, solvate or pro-drug, as defined hereinbefore.

According to a further aspect of the invention, there is provided a chromenone derivative of the Formula I, or a pharmaceutically acceptable salt thereof, as defined hereinbefore for use in the prevention or treatment of cancer in a warm blooded animal such as man.

According to a further aspect of the invention there is provided the use of a chromenone e derivative of the Formula I, or a pharmaceutically acceptable salt thereof, as defined hereinbefore in the manufacture of a medicament for use in the prevention or treatment of cancer in a warm blooded animal such as man.

According to a further feature of this aspect of the invention there is provided a method for the prevention or treatment of cancer in a warm blooded animal, such as man, in need of such treatment which comprises administering to said animal an effective amount of a chromenone derivative of the Formula I, or a pharmaceutically acceptable salt thereof, as defined hereinbefore.

According to a further aspect of the invention there is provided the use of a chromenone e derivative of the Formula I, or a pharmaceutically acceptable salt thereof, as defined hereinbefore in the manufacture of a medicament for use in the prevention or treatment of solid tumour disease in a warm blooded animal such as man.

According to a further feature of this aspect of the invention there is provided a method for the prevention or treatment of solid tumour disease in a warm blooded animal, such as man, in need of such treatment which comprises administering to said animal an effective amount of a chromenone derivative of the Formula I, or a pharmaceutically acceptable salt thereof, as defined hereinbefore.

According to a further aspect of the invention there is provided a chromenone derivative of the Formula I, or a pharmaceutically acceptable salt thereof, as defined hereinbefore for use in the prevention or treatment of those tumours which are sensitive to inhibition of PI 3-kinase enzymes (such as the Class Ia enzymes and/or the Class Ib PI 3-kinase enzyme) that are involved in the signal transduction steps which lead to the proliferation, survival, invasiveness and migratory ability of tumour cells.

According to a further feature of this aspect of the invention there is provided the use of a chromenone derivative of the Formula I, or a pharmaceutically acceptable salt thereof, as defined hereinbefore in the manufacture of a medicament for use in the prevention or treatment of those tumours which are sensitive to inhibition of PI 3-kinase enzymes (such as the Class Ia enzymes and/or the Class Ib PI 3-kinase enzyme) that are involved in the signal transduction steps which lead to the proliferation, survival, invasiveness and migratory ability of tumour cells.

According to a further feature of this aspect of the invention there is provided a method for the prevention or treatment of those tumours which are sensitive to inhibition of PI 3-kinase enzymes (such as the Class Ia enzymes and/or the Class Ib PI 3-kinase enzyme) that are involved in the signal transduction steps which lead to the proliferation, survival, invasiveness and migratory ability of tumour cells which comprises administering to said animal an effective amount of a chromenone derivative of the Formula I, or a pharmaceutically acceptable salt thereof, as defined hereinbefore.

According to a further aspect of the invention there is provided a chromenone derivative of the Formula I, or a pharmaceutically acceptable salt thereof, as defined hereinbefore for use in providing a PI 3-kinase enzyme inhibitory effect (such as a Class Ia PI 3-kinase enzyme or Class Ib PI 3-kinase enzyme inhibitory effect).

According to a further feature of this aspect of the invention there is provided the use of a chromenone derivative of the Formula I, or a pharmaceutically acceptable salt thereof, as defined hereinbefore in the manufacture of a medicament for use in providing a PI 3-kinase enzyme inhibitory effect (such as a Class Ia PI 3-kinase enzyme or Class Ib PI 3-kinase enzyme inhibitory effect).

According to a further aspect of the invention there is also provided a method for providing a PI 3-kinase enzyme inhibitory effect (such as a Class Ia PI 3-kinase enzyme or Class Ib PI 3-kinase enzyme inhibitory effect) which comprises administering an effective amount of a chromenone derivative of the Formula I, or a pharmaceutically acceptable salt thereof, as defined hereinbefore.

As stated hereinbefore, certain compounds of the present invention, possess substantially better potency against Class Ia PI 3-kinase enzymes than against the Class Ib PI 3-kinase enzyme or against EGF receptor tyrosine kinase, VEGF receptor tyrosine kinase or Src non-receptor tyrosine kinase enzymes. Such compounds possess sufficient potency against Class Ia PI 3-kinase enzymes that they may be used in an amount sufficient to inhibit Class Ia PI 3-kinase enzymes whilst demonstrating little activity against the Class Ib PI 3-kinase enzyme or against EGF receptor tyrosine kinase, VEGF receptor tyrosine kinase or Src non-receptor tyrosine kinase enzymes. Such compounds are likely to be useful for the selective inhibition of Class Ia PI 3-kinase enzymes and are likely to be useful for the effective treatment of, for example Class Ia PI 3-kinase enzyme driven tumours.

According to this aspect of the invention there is provided a chromenone derivative of the Formula I, or a pharmaceutically acceptable salt thereof, as defined hereinbefore for use in providing a selective Class Ia PI 3-kinase enzyme inhibitory effect.

According to a further feature of this aspect of the invention there is provided the use of a chromenone derivative of the Formula I, or a pharmaceutically acceptable salt thereof, as defined hereinbefore in the manufacture of a medicament for use in providing a selective Class Ia PI 3-kinase enzyme inhibitory effect.

According to a further aspect of the invention there is also provided a method for providing a selective Class Ia PI 3-kinase enzyme inhibitory effect which comprises administering an effective amount of a chromenone derivative of the Formula I, or a pharmaceutically acceptable salt thereof, as defined hereinbefore.

By "a selective Class Ia PI 3-kinase enzyme inhibitory effect" is meant that the chromenone derivatives of the Formula I are more potent against Class Ia PI 3-kinase enzymes than against other kinase enzymes. In particular, some of the compounds according to the invention are more potent against Class Ia PI 3-kinase enzymes than against other kinases such as receptor or non-receptor tyrosine kinases or serine/threonine kinases. For example a selective Class Ia PI 3-kinase enzyme inhibitor according to the invention is at least 5 times more potent, conveniently at least 10 times more potent, more conveniently at least 100 times more potent, against Class Ia PI 3-kinase enzymes than against other kinases.

According to a further feature of the invention there is provided a chromenone derivative of the Formula I, or a pharmaceutically acceptable salt thereof, as defined hereinbefore for use in the treatment of cancer of the breast, colorectum, lung (including small cell lung cancer, non-small cell lung cancer and bronchioalveolar cancer) and prostate.

According to a further feature of this aspect of the invention there is provided a chromenone derivative of the Formula I, or a pharmaceutically acceptable salt thereof, as defined hereinbefore for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of this aspect of the invention there is provided the use of a chromenone derivative of the Formula I, or a pharmaceutically acceptable salt thereof, as defined hereinbefore in the manufacture of a medicament for use in the treatment of cancer of the breast, colorectum, lung (including small cell lung cancer, non-small cell lung cancer and bronchioalveolar cancer) and prostate.

According to a further feature of this aspect of the invention there is provided the use of a chromenone derivative of the Formula I, or a pharmaceutically acceptable salt thereof, as defined hereinbefore in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of this aspect of the invention there is provided a method for treating cancer of the breast, colorectum, lung (including small cell lung cancer, non-small cell lung cancer and bronchioalveolar cancer) and prostate in a warm blooded animal such as man that is in need of such treatment which comprises administering an effective amount of a chromenone derivative of the Formula I, or a pharmaceutically acceptable salt thereof, as defined hereinbefore.

According to a further feature of this aspect of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas in a warm blooded animal such as man that is in need of such treatment which comprises administering an effective amount of a chromenone derivative of the Formula I, or a pharmaceutically acceptable salt thereof, as defined hereinbefore.

As stated hereinbefore, the in vivo effects of a compound of the Formula I may be exerted in part by one or more metabolites that are formed within the human or animal body after administration of a compound of the Formula I.

Particular compounds of the invention possess better potency against PI 3-kinase β than against other class I PI 3-kinase isoforms such as α, γ and δ.

The present invention therefore also contemplates a method for inhibiting phosphoinositide 3-kinase β in a patient, comprising administering to a patient an amount of the compound of formula (I), or a pharmaceutically acceptable salt thereof, effective in inhibiting the phosphoinositide 3-kinase β in the patient.

The compound of formula (I), or a pharmaceutically acceptable salt thereof, being an inhibitor of PI 3-kinase, also has potential therapeutic uses in a variety of other disease states. For example, PI 3-kinase plays an important role in promoting smooth muscle proliferation in the vascular tree, i.e. vascular smooth muscle cells, Thyberg, 1998, *European Journal of Cell Biology* 76(1):33-42, and in the lungs (airway smooth muscle cells), Krymskaya, V. P., *BioDrugs,* 2007. 21(2): 85-95. Excessive proliferation of vascular smooth muscle cells plays an important role in the formation of atherosclerotic plaques and in the development of neointimal hyperplasia following invasive vascular procedures, Scwartz et al., 1984, *Progress in Cardiovascular Disease* 26:355-372; Clowes et al., 1978, *Laboratory Investigations* 39:141-150. Moreover, excessive proliferation of airway smooth muscle cells leads to the development of COPD in the setting of asthma and chronic bronchitis Inhibitors of PI 3-kinase activity therefore may be used to prevent vascular restenosis, atherosclerosis, and COPD.

PI 3-kinases also play an important role in regulating tumor cells and in the propensity of these cells to undergo apoptosis growth (Sellers et al., 1999, *The Journal of Clinical Investigation* 104:1655-1661). Additionally, uncontrolled regulation of the PI 3-kinase lipid products PI(3,4,5)$P_3$ and PI(3,4)$P_2$ by the lipid phosphatase PTEN plays an important role in progression of a number of malignant tumors in humans (Leevers et al., 1999, *Current Opinion in Cell Biology* 11:219-225). A specific role for the phosphoinositide 3-kinase β (PI3Kβ) isoform has been described in these types of cancers (Jia S et al., 2008, *Nature* 454(7205):776-9; Wee et al., 2008, *PNAS* 105(35):13057-62). Therefore, the compound of formula (I), or a pharmaceutically acceptable salt thereof, being an inhibitor of PI 3-kinase, may be used to treat neoplasms in humans.

PI 3-kinase also plays an important role in leukocyte function (Fuller et al., 1999, *The Journal of Immunology* 162(11): 6337-6340; Eder et al., 1998, *The Journal of Biological Chemistry* 273(43):28025-31) and lymphocyte function (Vicente-Manzanares et al., 1999, *The Journal of Immunology* 163(7):4001-4012). For example, leukocyte adhesion to inflamed endothelium involves activation of endogenous leukocyte integrins by a PI 3-kinase-dependent signaling process. Furthermore, oxidative burst (Nishioka et al., 1998, *FEBS Letters* 441(1):63-66 and Condliffe, A. M., et al., *Blood,* 2005. 106(4):1432-40) and cytoskeletal reorganization (Kirsch et al., 1999, *Proceedings National Academy of Sciences USA* 96(11):6211-6216) in neutrophils appears to involve PI 3-kinase signaling. Neutrophil migration and directional movement are also dependent on PI 3-kinase activity (Camps, M., et al., Nat Med, 2005. 11(9): p. 936-43 and Sadhu, C., et al., *J Immunol,* 2003. 170(5): 2647-54). Thus, inhibitors of PI 3-kinase may be useful in reducing leukocyte adhesion and activation at sites of inflammation and therefore may be used to treat acute and/or chronic inflammatory disorders. PI 3-kinase also plays an important role in lymphocyte proliferation and activation, Fruman et al., 1999, *Science* 283 (5400): 393-397. Given the important role of lymphocytes in auto-immune diseases, an inhibitor of PI 3-kinase activity may be used in the treatment of such disorders.

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents: —

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib ($AMN_{107}$); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

According to this aspect of the invention there is provided a combination suitable for use in the treatment of cancer comprising a compound of formula I as defined hereinbefore or a pharmaceutically acceptable salt thereof and any one of the anti tumour agents listed under (i)-(ix) above.

Therefore in a further aspect of the invention there is provided a compound of formula (I) or a pharmaceutically acceptable salt thereof in combination with an anti-tumour agent selected from one listed under (i)-(ix) herein above.

In a further aspect of the invention there is provided a combination suitable for use in the treatment of cancer comprising a compound of formula I as defined hereinbefore or a pharmaceutically acceptable salt thereof and any one of the anti tumour agents listed under (i) above.

In a further aspect of the invention there is provided a combination suitable for use in the treatment of cancer comprising a compound of formula I as defined hereinbefore or a pharmaceutically acceptable salt thereof and a taxoid, such as for example taxol or taxotere, conveniently taxotere.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of formula (I) or a pharmaceutically aceeptable salt thereof in combination with an anti-tumour agent selected from one listed under (i)-(ix) herein above, in association with a pharmaceutically acceptable diluent or carrier.

According to a further aspect of the invention there is provided a pharmaceutical composition which comprises a compound of formula (I) or a pharmaceutically acceptable salt thereof in combination with an anti-tumour agent selected from one listed under (i)-(ix) herein above, in association with a pharmaceutically acceptable diluent or carrier for use in treating cancer.

According to another feature of the invention there is provided the use of a compound of the formula (I) or a pharmaceutically aceeptable salt thereof in combination with an anti-tumour agent selected from one listed under (i)-(ix) herein above, in the manufacture of a medicament for use in cancer in a warm-blooded animal, such as man.

Therefore in an additional feature of the invention, there is provided a method of treating cancer in a warm-blooded animal, such as man, in need of such treatment which comprises administering to said animal an effective amount of a compound of formula (I) or a pharmaceutically aceeptable salt thereof in combination with an anti-tumour agent selected from one listed under (i)-(ix) herein above.

According to a further aspect of the present invention there is provided a kit comprising a compound of formula (I) or a pharmaceutically aceeptable salt thereof in combination with an anti-tumour agent selected from one listed under (i)-(ix) herein above.

According to a further aspect of the present invention there is provided a kit comprising:
a) a compound of formula (I) or a pharmaceutically acceptable salt thereof in a first unit dosage form;
b) an anti-tumour agent selected from one listed under (i)-(ix) herein above; in a second unit dosage form; and
c) container means for containing said first and second dosage forms.

Although the compounds of the Formula I are primarily of value as therapeutic agents for use in warm-blooded animals (including man), they are also useful whenever it is required to inhibit the effects of Class I PI 3-kinase enzyme, particularly a Class Ia PI 3-kinase enzymes and/or Class Ib PI 3-kinase enzyme, more particularly a Class Ia PI 3-kinase enzymes, which includes PI 3-kinase β. Thus, they are useful as pharmacological standards for use in the development of new biological tests and in the search for new pharmacological agents.

The invention will now be illustrated in the following Examples in which, generally:
(i) operations were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment in vacuo and work-up procedures were carried out after removal of residual solids by filtration;

(iii) Flash chromatography purifications were performed on an automated Armen Glider Flash: Spot II Ultimate (Armen Instrument, Saint-Ave, France) using prepacked Merck normal phase Si60 silica cartridges (granulometry: 15-40 or 40-63 μm) obtained from Merck, Darmstad, Germany;

(iv) preparative chromatography was performed on a Waters instrument (600/2700 or 2525) fitted with a ZMD or ZQ ESCi mass spectrometers and a Waters X-Terra or a Waters X-Bridge or a Waters SunFire reverse-phase column (C-18, 5 microns silica, 19 mm diameter, 100 mm length, flow rate of 40 mL/minute) using decreasingly polar mixtures of water (containing 0.2% ammonium carbonate) and acetonitrile as eluent;

(v) yields, where present, are not necessarily the maximum attainable;

(vi) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;

(vii) in general, end-products of the Formula I were also characterised by mass spectroscopy following liquid chromatography (LCMS); LCMS was carried out using an Waters Alliance HT (2790 & 2795) fitted with a Waters ZQ ESCi or ZMD ESCi mass spectrometer and an X Bridge 5 μm C-18 column (2.1×50 mm) at a flow rate of 2.4 mL/min, using a solvent system of 95% A+5% C to 95% B+5% C over 4 minutes, where A=water, B=methanol, C=1:1 methanol:water (containing 0.2% ammonium carbonate);

(viii) intermediates were not generally fully characterised and purity was assessed by thin layer chromatographic, mass spectral, HPLC and/or NMR analysis;

(ix) X-ray powder diffraction spectra were determined (using a Bruker D4 Analytical Instrument) by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm antiscatter slit and a 9.55 mm detector slit. The sample was exposed for 0.03 seconds per 0.00570° 2-theta increment (continuous scan mode) over the range 2 degrees to 40 degrees 2-theta in theta-theta mode. The running time was 3 minutes and 36 seconds. The instrument was equipped with a Position sensitive detector (Lynxeye). Control and data capture was by means of a Dell Optiplex 686 NT 4.0 Workstation operating with Diffrac+software. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values;

(x) Differential Scanning calorimetry was perfomed using a TA Instruments Q1000 DSC instrument. Typically less than 5 mg of material contained in a standard aluminium pan fitted with a lid was heated over the temperature range 25° C. to 300° C. at a constant heating rate of 10° C. per minute. A purge gas using nitrogen was used at a flow rate of 50 mL per minute; and (xi) the following abbreviations have been used: —

| | |
|---|---|
| aq. | aqueous |
| $CDCl_3$ | deutero-chloroform |
| CHCl3 | chloroform |
| DCM | dichloromethane |
| DEA | diethyl amine |
| DIPEA | N-ethyl-N-isopropylpropan-2-amine |
| DMF | N,N-dimethylformamide |
| DMSO | dimethyl sulphoxide |
| DSC | Differential Scanning Calorimetry |
| DTAD | (E)-di-tert-butyl diazene-1,2-dicarboxylate |
| EDCI | 1-(3-dimethylaminopropyl)-3-ethylcarbodiimide hydrochloride |
| Ether | diethyl ether |
| % ee | % enantiomeric excess |
| HOPO | 2-hydroxy-pyridine n-oxide |
| IPA | isopropyl alcohol |
| MeCN | acetonitrile |
| MeOH | methanol |
| MTBE | methyl tert-butyl ether |
| NMP | 1-methyl-2-pyrrolidone |
| sat. | saturated |
| sol. | solution |
| THF | tetrahydrofuran |
| TEA | triethyl amine |
| TBTU | 2-(1H-benzo[d][1,2,3]triazol-1-yl)-1,1,3,3-tetramethylisouronium tetrafluoroborate |
| TSTU | 2-(2,5-dioxopyrrolidin-1-yl)-1,1,3,3-tetramethylisouronium tetrafluoroborate. |

EXAMPLE 1.00

N-(2-(dimethylamino)ethyl)-8-(1-(4-fluorophenylamino)ethyl)-2-morpholino-4-oxo-4H-chromene-6-carboxamide

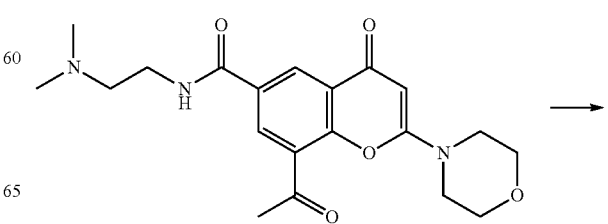

-continued

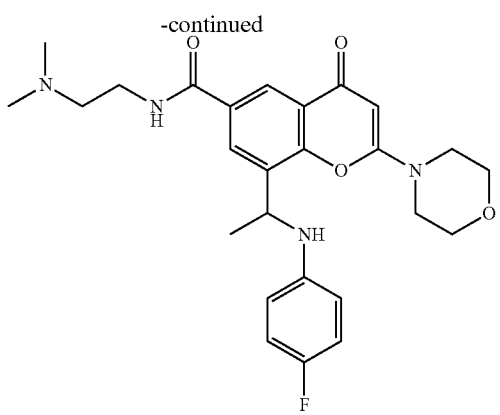

Titanium(IV) chloride (0.129 mL, 0.13 mmol) was added to a stirred suspension of 8-acetyl-N-(2-(dimethylamino)ethyl)-2-morpholino-4-oxo-4H-chromene-6-carboxamide (100 mg, 0.26 mmol), 4-fluoroaniline (0.042 mL, 0.44 mmol) and triethylamine (0.108 mL, 0.77 mmol) in DCM (2 mL) under nitrogen at 10° C. The resulting solution was stirred at 23° C. for 2 days. A saturated solution of sodium carbonate was added and extracted with DCM. The organic phase was washed with water, brine, dried over magnesium sulfate, and concentrated to afford the crude imine. The imine was diluted with DCM and MeOH, and acetic acid (0.030 mL, 0.52 mmol) and sodium cyanotrihydroborate (32.4 mg, 0.52 mmol) were added. The resulting solution was stirred at room temperature for 30 min. A solution of sodium carbonate was added and extracted with DCM. The organic phase was washed with water, brine, dried over magnesium sulfate, and concentrated to dryness. The crude product was purified by flash chromatography on silica gel eluting with 5% methanol in DCM followed by 5% methanolic ammonia (7 N) in DCM. The solvent was evaporated to dryness and a second purification was done on a preparative HPLC using a Waters X-Terra reverse-phase column (C-18, 5 microns silica, 19 mm diameter, 100 mm length, flow rate of 40 mL/minute) and decreasingly polar mixtures of water (containing 0.2% ammonium carbonate) and acetonitrile as eluent. The fractions containing the desired compound were evaporated to dryness to give a white solid which was triturated in MTBE then dried under vacuum to afford N-(2-(dimethylamino)ethyl)-8-(1-(4-fluorophenylamino)ethyl)-2-morpholino-4-oxo-4H-chromene-6-carboxamide (73.0 mg, 58.6%). Mass Spectrum: M+H$^+$ 483. NMR Spectrum: (CDCl$_3$) 1.60 (d, 3H), 2.25 (s, 6H), 2.50 (t, 2H), 3.45-3.58 (m, 6H), 3.79-3.89 (m, 4H), 4.02 (bs, 1H), 4.88-4.98 (m, 1H), 5.56 (s, 1H), 6.40 (dd, 2H), 6.81 (dd, 2H), 6.91 (bs, 1H), 8.27 (d, 1H), 8.34 (d, 1H).

The 8-acetyl-N-(2-(dimethylamino)ethyl)-2-morpholino-4-oxo-4H-chromene-6-carboxamide used as starting material was made as follows: —

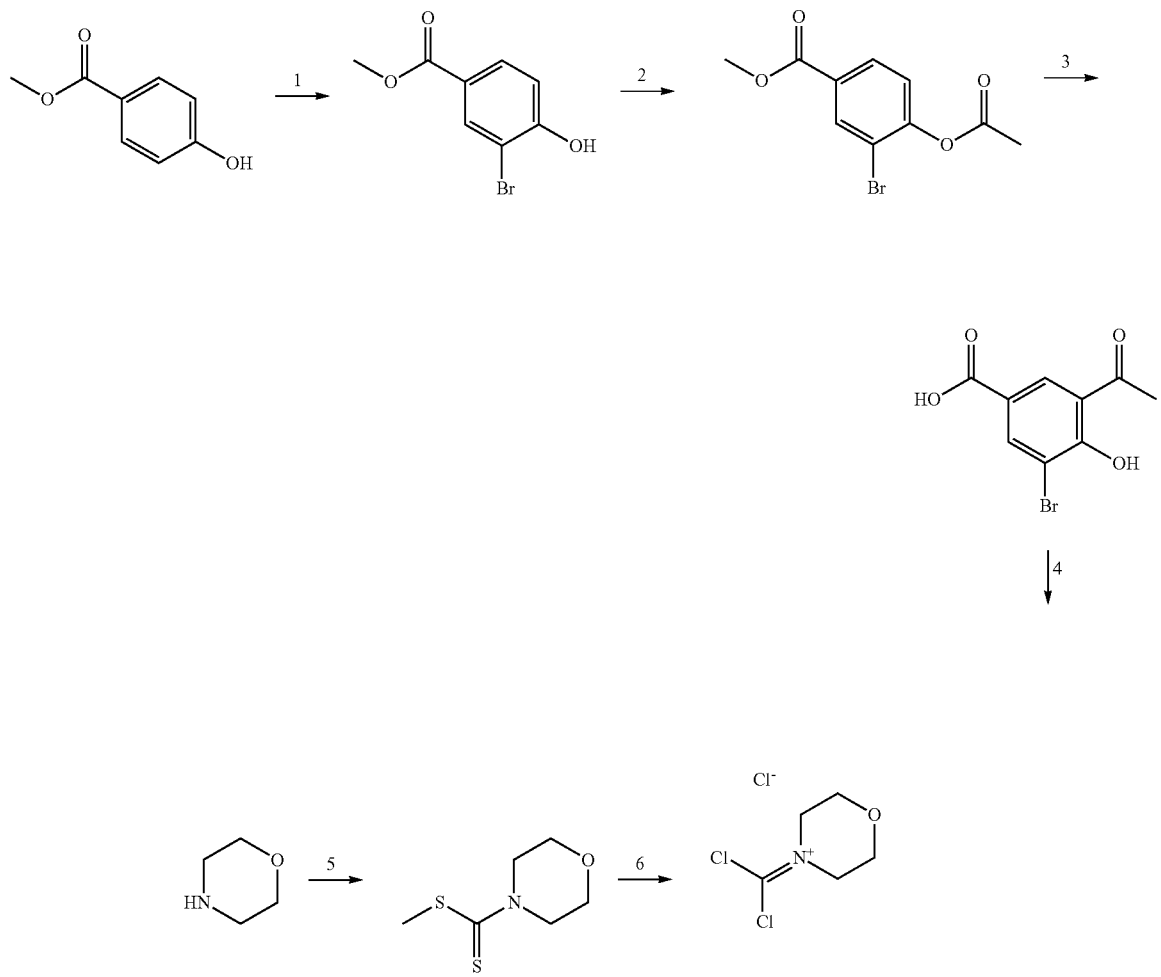

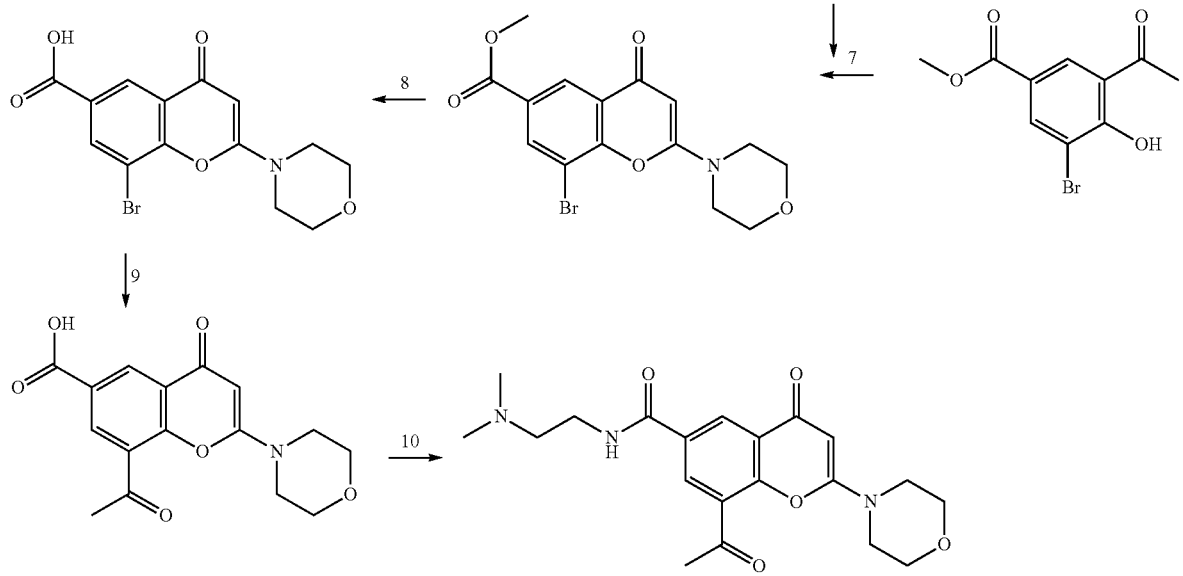

Step 1

To a stirred suspension of methyl 4-hydroxybenzoate (180 g, 1183 mmol) in DCM (3 L) was added dropwise bromine (64 mL, 1242 mmol) under nitrogen and at 0° C. and the reaction mixture was left to stir at room temperature for 36 hrs. A solution of sodium thiosulfate (500 mL of a 10% solution) was then added while keeping the temperature around 15° C. followed by addition of MeOH (250 mL). The organic layer was washed with water, then brine, dried over magnesium sulfate, filtered and concentrated to dryness to afford methyl 3-bromo-4-hydroxybenzoate (290 g) as a white solid. Mass Spectrum: [M–H]⁻ 229.

Step 2

To a stirred suspension of methyl 3-bromo-4-hydroxybenzoate (270 g, 1168 mmol) in DCM (1.5 L) was added pyridine (150 mL). Acetyl chloride (87 mL, 1227 mmol) was then added dropwise at room temperature and under nitrogen. The mixture was left to stir for 2 hrs at room temperature. Water (1 L) was then added followed by HCl 2N until pH 1. The organic layer was then washed with water, brine, dried over magnesium sulfate, filtered and evaporated to dryness to afford methyl 4-acetoxy-3-bromobenzoate (300 g, 94%) as a white powder. NMR Spectrum: (DMSOd₆) 2.34 (s, 3H), 3.87 (s, 3H), 7.47 (d, 1H), 8.01 (dd, 1H), 8.20 (d, 1H).

Step 3

To methyl 4-acetoxy-3-bromobenzoate (150 g, 549.3 mmol) was added aluminum trichloride (220 g, 1647.9 mmol) and the mixture was heated at 140° C. in the absence of solvent for 3 h. Upon cooling to room temperature the solid was crushed and cautiously added to water (1.5 L) with stirring. HCl (250 mL of 12N) was then added and stirring was maintained for 30 mins. The solid obtained was collected by filtration, washed with water (2×2 L) and dried overnight to afford 3-acetyl-5-bromo-4-hydroxybenzoic acid (120 g, 84%) as a yellow powder. Mass Spectrum: [M–H]⁻ 258.

Step 4

To a stirred suspension of 3-acetyl-5-bromo-4-hydroxybenzoic acid (240 g, 926 mmol) in MeOH (2 L) was added dropwise sulfurous dichloride (68 mL, 926.5 mmol) under nitrogen and the mixture was heated at 80° C. for 3 h. The reaction mixture was cooled to room temperature concentrated, diluted with DCM. The organic layer was washed with brine, dried over magnesium sulfate, filtered and concentrated to afford a crude compound, which was purified on silica, eluting with 70% of DCM in petroleum ether. The solvents were evaporated to dryness to afford methyl 3-acetyl-5-bromo-4-hydroxybenzoate (108 g, 42.7%) as a white powder. Mass Spectrum: [M–H]⁻ 229.

Step 5

To a stirred solution of morpholine (201 mL, 2295 mmol) in water (2 L) was added carbon disulfide (0.138 L, 2295.67 mmol) under nitrogen. Sodium hydroxide (96 g, 2410 mmol in solution in 1 L of water) was then added dropwise. The resulting mixture was stirred at room temperature for 1 h, then cooled to 5° C. with an ice bath and dimethyl sulfate (217 mL, 2295 mmol) was added dropwise. The mixture was stirred 1 hr at room temperature, the obtained solid was collected by filtration, washed with water (2×μL) and dried under vacuum over phosphorus pentoxide at 50° C. to give methyl morpholine-4-carbodithioate (360 g, 88%). NMR Spectrum: (CDCl₃): 2.68 (s, 3H), 3.71-3.84 (m, 4H), 4.02 (bs, 2H), 4.30 (bs, 2H).

Step 6

Chlorine gas (455 g, 6417 mmol) was bubbled through a solution of methyl morpholine-4-carbodithioate (170 g, 959 mmol) in DCM (1.5 L) over a 2 hrs period, while keeping the temperature around 10-15° C. Once the chlorine addition was completed, stirring was maintained for an additional 1.5 hr while a precipitation occurred. Nitrogen was then passed through the mixture for 30 min. The solid was collected by filtration under nitrogen, washed with DCM and stored under nitrogen in the fridge. There was thus obtained 4-(dichloromethylene)morpholin-4-ium chloride (180 g, 92%) as a white hygroscopic solid.

Step 7

To a stirred solution methyl 3-acetyl-5-bromo-4-hydroxybenzoate (106 g, 388 mmol) in toluene (1 L) was added dropwise (diethyloxonio)trifluoroborate (0.201 L, 1630 mmol), under nitrogen. The resulting solution was left to stir overnight at room temperature, then 4-(dichloromethylene)morpholin-4-ium chloride (143 g, 698 mmol) was added and mixture heated at 90° C. for 12 h. Upon cooling to room temperature, diethyl ether (1.5 L) was added and the solid was collected by filtration. This solid was then suspended in MeOH (1 L) and the mixture was heated at 50° C. for 2 h.

Upon cooling to room temperature, the solid was collected by filtration then solubilized in DCM (1 L) and washed with water and a saturated solution of sodium bicarbonate. The organic layer was dried over magnesium sulfate, filtered and evaporated to dryness to afford methyl 8-bromo-2-morpholino-4-oxo-4H-chromene-6-carboxylate (68.0 g, 47.6%) as an off-white solid. Mass Spectrum: M+H+ 368. This intermediate can also be prepared by an alternative route (see below)

Step 8

Sodium hydroxide (4.35 mL, 8.69 mmol) was added to a stirred suspension of methyl 8-bromo-2-morpholino-4-oxo-4H-chromene-6-carboxylate (1.6 g, 4.35 mmol) dissolved in MeOH (30 mL). The resulting suspension was stirred at 23° C. for 16 hrs. The mixture was diluted with water and the pH adjusted to 3 with HCl 2N. The precipitate was collected by filtration, washed with water and dried over phosphorus pentoxide overnight to give 8-bromo-2-morpholino-4-oxo-4H-chromene-6-carboxylic acid (1.30 g, 84%) as a beige solid. Mass Spectrum: M+H+ 356

Step 9

Bis(triphenylphosphine) palladium (II) chloride (12.78 mg, 0.02 mmol) was added to a stirred mixture of 8-bromo-2-morpholino-4-oxo-4H-chromene-6-carboxylic acid (215 mg, 0.61 mmol) and tributyl(1-ethoxyvinyl)stannane (0.226 mL, 0.67 mmol) in 1,4-dioxane (5 mL) and the mixture was purged with nitrogen. The resulting mixture was stirred at 100° C. for 3 hrs. HCl2N (0.5 mL) was added and the reaction mixture was stirred at 50° C. for 25 minutes then allowed to cool to room temperature and concentrated under vacuum. The product was diluted with diethyl ether and pentane to afford a solid, which was collected by filtration and washed with ether/pentane to give 8-acetyl-2-morpholino-4-oxo-4H-chromene-6-carboxylic acid (200 mg, 104%) as a beige solid. Mass Spectrum: M+H+ 318.

Step 10

To a suspension of 8-acetyl-2-morpholino-4-oxo-4H-chromene-6-carboxylic acid (470 mg, 1.48 mmol) in DCM (10 mL) at room temperature, were added to DIPEA (0.284 mL, 1.63 mmol) and TSTU (491 mg, 1.63 mmol). The mixture was stirred for 15 minutes, N1,N1-dimethylethane-1,2-diamine (0.171 mL, 1.56 mmol) was added stirring was maintained for an additional hour. The mixture was adsorbed on silica gel and purified by flash chromatography on silica gel eluting with 5 to 10% methanol in DCM then with 10% methanolic ammonia (7 N) in DCM. The solvent was evaporated to dryness to afford 8-acetyl-N-(2-(dimethylamino) ethyl)-2-morpholino-4-oxo-4H-chromene-6-carboxamide (352 mg, 61.3%) as a beige solid. Mass Spectrum: M+H+ 388.

Alternative route to prepare methyl 8-bromo-2-morpholino-4-oxo-4H-chromene-6-carboxylate:

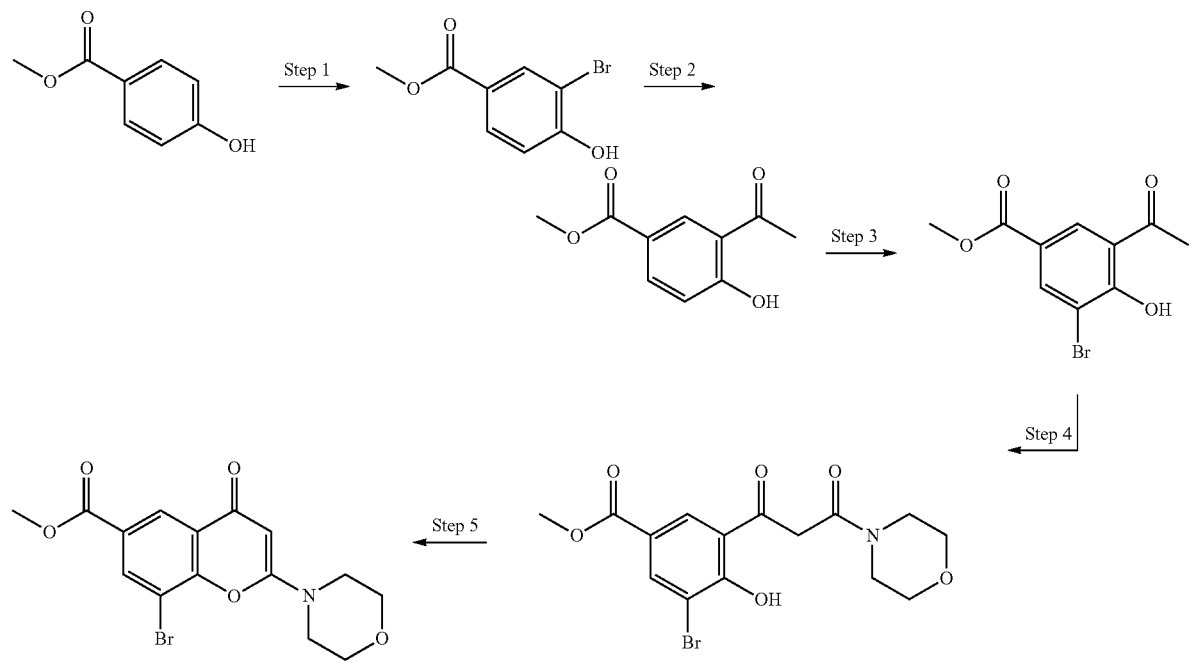

Step 1

Dibromine (0.185 L, 3614.92 mmol) was added dropwise a stirred suspension of methyl 4-hydroxybenzoate (500 g, 3286 mmol) in DCM (4 L) at 0° C. under N2. The mixture was left to stir for 24 hrs at RT under N2 (need to trap HBr). A solution of sodium metabisulfite (62.5 g, 329 mmol) in 2 L of water was then added, while keeping the temperature around 15° C., followed by 500 mL of MeOH. The organic layer was washed with water, brine, dried over magnesium sulfate, filtered and concentrated to dryness to afford methyl 3-bromo-4-hydroxybenzoate (710 g, 94%) as a white solid. NMR Spectrum (CDCl3): 3.89 (s, 3H), 5.95 (s, 1H), 7.05 (d, 1H), 7.92 (dd, 1H), 8.19 (d, 1H).

Step 2

To a degassed solution of methyl 3-bromo-4-hydroxybenzoate (350 g, 1514.87 mmol) in ethanol (3 L) were added triethylamine (0.528 L, 3787.17 mmol), 1-(vinyloxy)butane (0.588 L, 4544.60 mmol), 1,1'-bis(diphenylphosphino)ferrocene (33.1 g, 60.6 mmol) and diacetoxypalladium (8.50 g, 37.9 mmol) under nitrogen. The mixture was heated at 70° C. overnight. The reaction was cooled down, filtered and the filtrate concentrated. The resulting solid was solubilized with DCM (2 L) and HCl 4N (1.14 L, 4544 mmol) was added under stirring. Stirring was maintained for 2 hrs, the organic phase was separated, dried over magnesium sulfate, filtered and concentrated to afford a solid which was stirred in diethyl ether (5 L) for 2 hrs. The solid was filtered off and the filtrate concentrated to dryness to afford methyl 3-acetyl-4-hydroxybenzoate (240 g, 82%) as a beige powder.

Mass spectrum: [M–H]⁻ 193.

Step 3

To a stirred solution of methyl 3-acetyl-4-hydroxybenzoate (240 g, 1236 mmol) in DCM (2 L) was added pyridine (0.400 L, 4944 mmol) followed by a dropwise addition of dibromine (0.070 L, 1360 mmol) at 0° C. The reaction mixture was stirred at RT for 2 hrs then cooled to 5° C. and HCl 4N (0.927 L, 3708 mmol) was added dropwise. The organic phase was separated, dried over magnesium sulfate, filtered and concentrated to afford a brown solid which was stirred in ether/petroleum ether (1:1, 1 L) for 1 hr. The solid was collected by filtration and dried to afford methyl 3-acetyl-5-bromo-4-hydroxybenzoate (270 g, 80%) as a beige powder.

Step 4

To a solution of lithium bis(trimethylsilyl)amide (1.41 L, 1406 mmol) at –65° C. under nitrogen was added dropwise methyl 3-acetyl-5-bromo-4-hydroxybenzoate (120 g, 439 mmol) in THF (1.2 L). The solution was allowed to warm to 0° C., and maintained at this temperature for 1 hr. The solution was cooled back to –65° C. and morpholine-4-carbonyl chloride (0.055 L, 483 mmol) was added. The mixture was stirred at RT for 2 hrs then cooled to –30° C., DCM (1.5 L) and water (1 L) were added followed by dropwise addition of HCl 6N (500 mL) then HCl2N (300 mL) until pH 7, the aqueous solution was extracted with DCM (3×). The combined extracts were dried over magnesium sulfate and evaporated. The crude product was triturated in MTBE to obtain methyl 3-bromo-4-hydroxy-5-(3-morpholino-3-oxopropanoyl)benzoate (153 g, 90%) as a beige solid. Mass Spectrum: M+H⁺ 388.

Step 5

Trifluoromethanesulfonic anhydride (0.755 L, 4487 mmol) was added to a stirred solution of methyl 3-bromo-4-hydroxy-5-(3-morpholino-3-oxopropanoyl)benzoate (433 g, 1122 mmol, pooled material from several batches) dissolved in 1,2-dichloroethane (1 L) at RT under nitrogen (exotherm). The resulting solution was stirred at 50° C. overnight. The mixture was partially evaporated, and the residue was diluted with MeOH (1.6 L) at 0° C. (exotherm) and stirred for 1 hr at RT. The solvent was evaporated again and the residue was diluted in DCM, quenched with a saturated aqueous solution of sodium carbonate and extracted with DCM. The combined organic phases were washed with brine, dried over magnesium sulfate and concentrated to afford the crude product. The crude was triturated under MTBE (2×), ethyl acetate (1×) and MTBE (1×). The solid was dried to afford methyl 8-bromo-2-morpholino-4-oxo-4H-chromene-6-carboxylate (208 g, 50%) as a beige solid. Mass Spectrum: M+H⁺ 370.

EXAMPLE 1.01

N-(2-(dimethylamino)ethyl)-8-(1-(3-fluorophenylamino)ethyl)-2-morpholino-4-oxo-4H-chromene-6-carboxamide

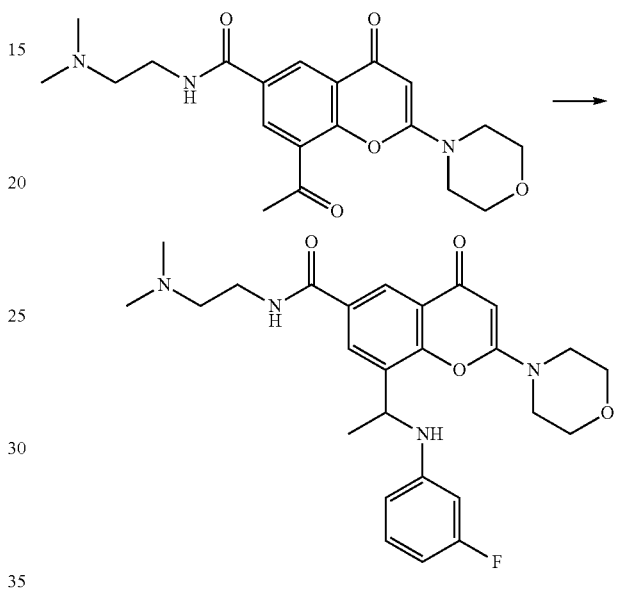

N-(2-(dimethylamino)ethyl)-8-(1-(3-fluorophenylamino) ethyl)-2-morpholino-4-oxo-4H-chromene-6-carboxamide was prepared using an analogous procedure to that described in Example 1.00 (28.0 mg, 18.7%). Mass Spectrum: M+H⁺ 483. NMR Spectrum: (CDCl₃) 1.62 (d, 3H), 2.27 (s, 6H), 2.52 (t, 2H), 3.44-3.58 (m, 6H), 3.78-3.89 (m, 4H), 4.55 (bs, 1H), 4.92-5.02 (m, 1H), 5.56 (s, 1H), 6.14 (ddd, 1H), 7.27 (dd, 1H), 7.36 (ddd, 1H), 6.95 (bs, 1H), 7.03 (dd, 1H), 8.28 (d, 1H), 8.35 (d, 1H).

EXAMPLE 1.02

N-(2-(dimethylamino)ethyl)-2-morpholino-4-oxo-8-(1-(phenylamino)ethyl)-4H-chromene-6-carboxamide

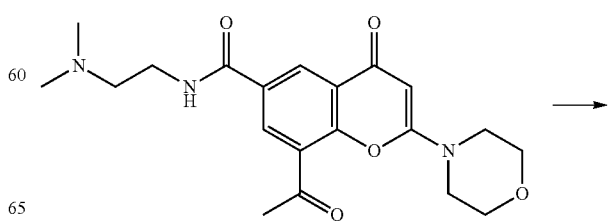

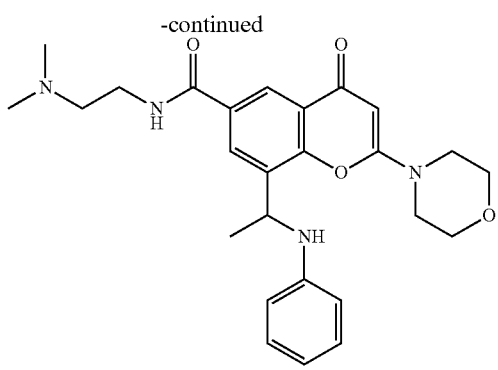

N-(2-(dimethylamino)ethyl)-2-morpholino-4-oxo-8-(1-(phenylamino)ethyl)-4H-chromene-6-carboxamide was prepared using an analogous procedure to that described in Example 1.00 (36.0 mg, 25%). Mass Spectrum: M+H⁺ 465. NMR Spectrum: (CDCl₃) 1.62 (d, 3H), 2.25 (s, 6H), 2.49 (t, 2H), 3.44-3.57 (m, 6H), 3.75-3.86 (m, 4H), 4.09 (d, 1H), 4.95-5.05 (m, 1H), 5.56 (s, 1H), 6.58 (d, 2H), 6.68 (t, 1H), 6.90 (bs, 1H), 7.11 (dd, 2H), 8.30 (d, 1H), 8.34 (d, 1H).

EXAMPLE 2.00

8-(1-(3-chloro-2-fluorophenylamino)ethyl)-N-(2-(dimethylamino)ethyl)-2-morpholino-4-oxo-4H-chromene-6-carboxamide

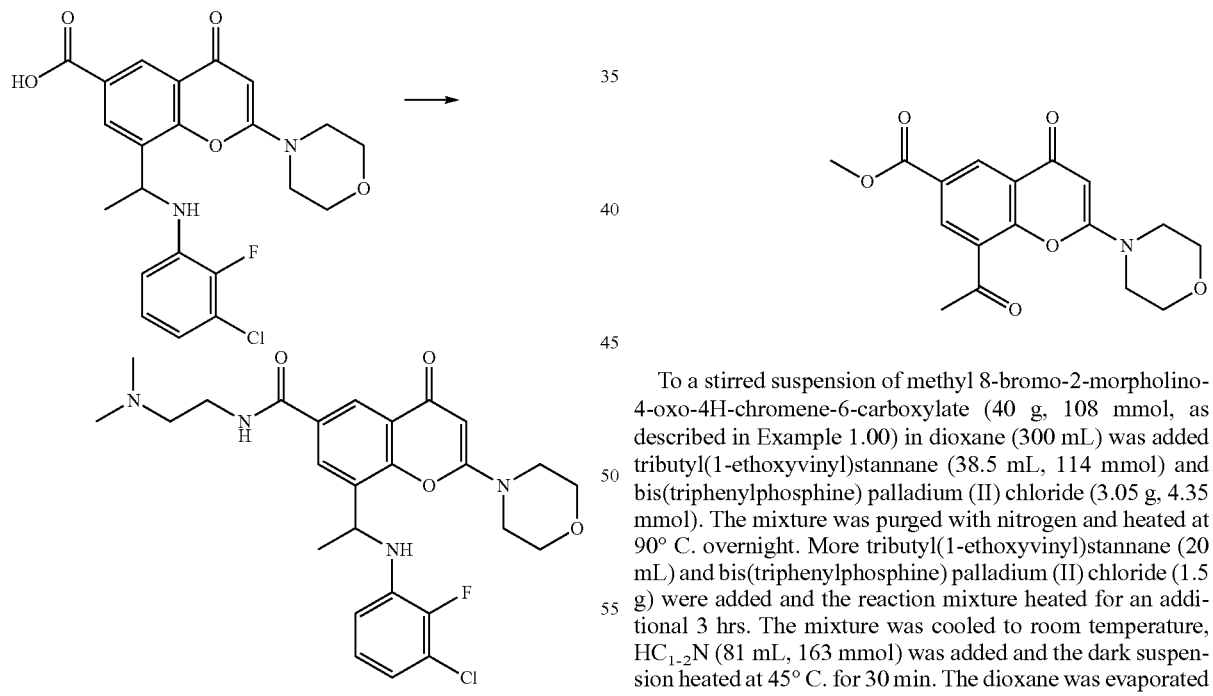

2-(1H-benzo[d][1,2,3]triazol-1-yl)-1,1,3,3-tetramethylisouronium tetrafluoroborate (73.3 mg, 0.23 mmol) was added to a stirred solution of 8-(1-(3-chloro-2-fluorophenylamino)ethyl)-2-morpholino-4-oxo-4H-chromene-6-carboxylic acid (85 mg, 0.19 mmol), 4-methylmorpholine (0.052 mL, 0.48 mmol) and N1,N1-dimethylethane-1,2-m diamine (0.025 mL, 0.23 mmol) dissolved in NMP (1.2 mL) at room temperature. The resulting solution was stirred for 2 hrs. The reaction mixture was purified by preparative HPLC using a Waters SunFire reverse-phase column (C-18, 5 microns silica, 19 mm diameter, 100 mm length, flow rate of 40 mL/minute) and decreasingly polar mixtures of water (containing 0.2% ammonium carbonate) and acetonitrile as eluent. The fractions containing the desired compound were evaporated, triturated with diethyl ether and dried to afford 8-(1-(3-chloro-2-fluorophenylamino)ethyl)-N-(2-(dimethylamino)ethyl)-2-morpholino-4-oxo-4H-chromene-6-carboxamide (59.2 mg, 60.2%) as a white solid. Mass Spectrum: M+H⁺ 517. NMR Spectrum: (DMSOd₆) 1.57 (d, 3H), 2.15 (s, 6H), 2.37 (t, 2H), 3.26-3.34 (m partially hidden by H2O, 2H), 3.50-3.62 (m, 4H), 3.70-3.79 (m, 4H), 5.03-5.12 (m, 1H), 5.61 (s, 1H), 6.34 (dd, 1H), 6.49 (d, 1H), 6.64 (ddd, 1H), 6.82 (d, 1H), 8.10 (d, 1H), 8.32 (d, 1H), 8.61 (t, 1H).

The 8-(1-(3-chloro-2-fluorophenylamino)ethyl)-2-morpholino-4-oxo-4H-chromene-6-carboxylic acid used as starting material was made as follows:—

To a stirred suspension of methyl 8-bromo-2-morpholino-4-oxo-4H-chromene-6-carboxylate (40 g, 108 mmol, as described in Example 1.00) in dioxane (300 mL) was added tributyl(1-ethoxyvinyl)stannane (38.5 mL, 114 mmol) and bis(triphenylphosphine) palladium (II) chloride (3.05 g, 4.35 mmol). The mixture was purged with nitrogen and heated at 90° C. overnight. More tributyl(1-ethoxyvinyl)stannane (20 mL) and bis(triphenylphosphine) palladium (II) chloride (1.5 g) were added and the reaction mixture heated for an additional 3 hrs. The mixture was cooled to room temperature, HC₁₋₂N (81 mL, 163 mmol) was added and the dark suspension heated at 45° C. for 30 min. The dioxane was evaporated under vacuum, the residue was dissolved in DCM and a saturated solution of sodium bicarbonate was added until pH 4. The organic layer was washed with brine, dried over magnesium sulfate, filtered and concentrated to afford a crude compound which was triturated in diethylether, filtered and dried to afford methyl 8-acetyl-2-morpholino-4-oxo-4H-chromene-6-carboxylate (25.0 g, 69.5%) as an off-white solid.

Mass Spectrum: M+H⁺ 332.

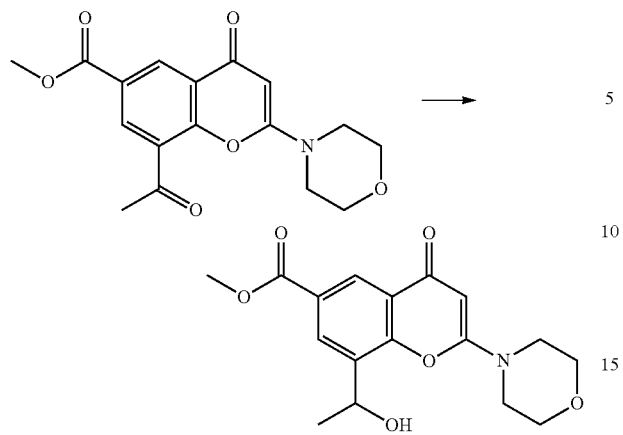

Sodium tetrahydroborate (82 mg, 2.16 mmol) was added to a solution of methyl 8-acetyl-2-morpholino-4-oxo-4H-chromene-6-carboxylate (650 mg, 1.96 mmol) in methanol (20 mL) and DCM (10 mL) at −10° C. After 15 min of stirring at −10° C., the reaction mixture was quenched with water (25 mL). The volatiles were removed and the aqueous layer extracted twice with DCM. The combined organics phases were washed with brine, dried over magnesium sulfate and concentrated. The residue was triturated with diethylether and the solid collected by filtration to give methyl 8-(1-hydroxyethyl)-2-morpholino-4-oxo-4H-chromene-6-carboxylate (500 mg, 76%) as a brown solid, which used for the next step without further purification. Mass Spectrum: M+H$^+$ 334.

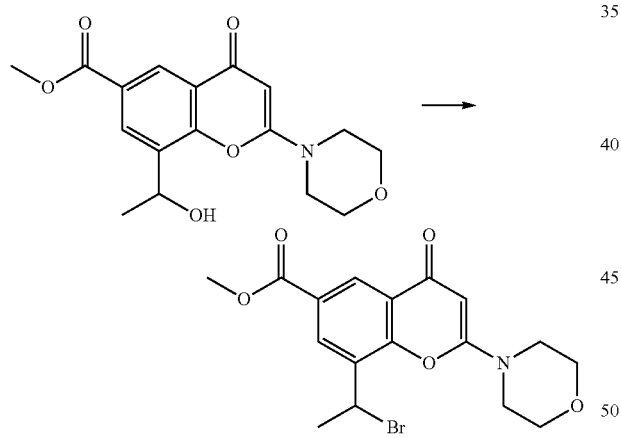

Tribromophosphine (1.65 mL, 1.65 mmol) was added to a stirred suspension of methyl 8-(1-hydroxyethyl)-2-morpholino-4-oxo-4H-chromene-6-carboxylate (500 mg, 1.50 mmol) in DCM (10 mL) in an ice bath under nitrogen. The resulting solution was stirred at room temperature for 24 hrs. The reaction was incomplete and further tribromophosphine (0.300 mL, 0.30 mmol) was added and the reaction mixture stirred for an additional 12 hrs. The solvent was evaporated, the residue was suspended in water and ice and a sodium carbonate solution was carefully added until pH 6. The precipitate was collected by filtration, washed with water then with diethylether and dried to afford methyl 8-(1-bromoethyl)-2-morpholino-4-oxo-4H-chromene-6-carboxylate (470 mg, 79%) as a dark beige solid. Mass Spectrum: M+H$^+$ 398.

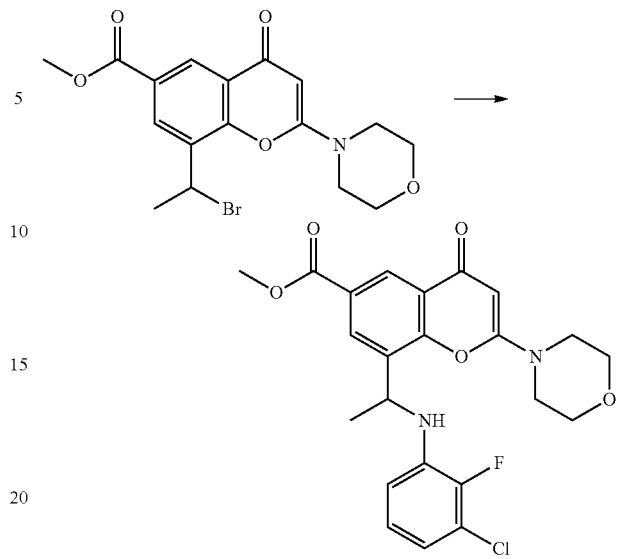

3-chloro-2-fluoroaniline (0.239 mL, 2.17 mmol) was added to a stirred suspension of methyl 8-(1-bromoethyl)-2-morpholino-4-oxo-4H-chromene-6-carboxylate (215 mg, 0.54 mmol) dissolved in DCM (3 mL) at room temperature. The resulting suspension was stirred for 16 hrs then the temperature was increased to 50° C. for 16 hrs. The crude product was purified by flash chromatography on silica gel eluting with 5% methanol in DCM. The solvent was evaporated to dryness to afford methyl 8-(1-(3-chloro-2-fluorophenylamino)ethyl)-2-morpholino-4-oxo-4H-chromene-6-carboxylate (206 mg, 82%) as a white solid. Mass Spectrum: M+H$^+$ 461.

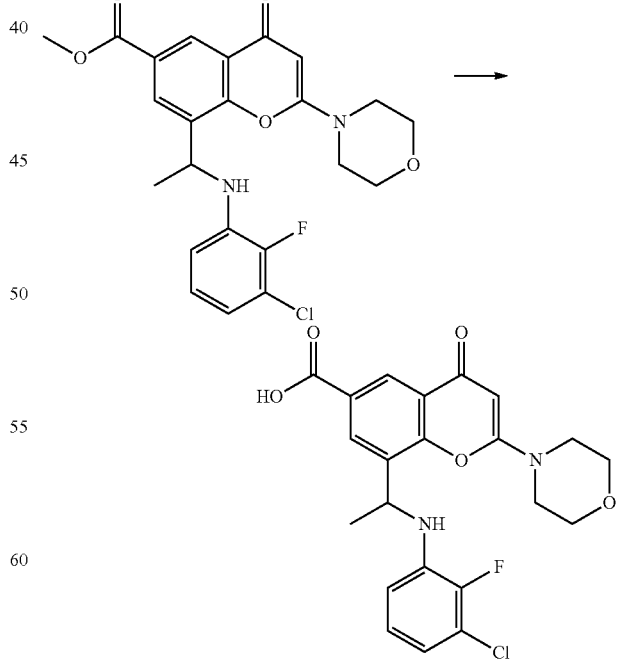

Sodium hydroxide (0.217 mL, 0.43 mmol) was added to a stirred solution of methyl 8-(1-(3-chloro-2-fluorophenylamino)ethyl)-2-morpholino-4-oxo-4H-chromene-6-carboxylate (200 mg, 0.43 mmol) dissolved in MeOH (2 mL). The resulting solution was stirred at room temperature for 16 hrs. THF was added and the resulting solution was stirred at 50° C. for 8 hrs. The pH was adjusted to 3 with HCl 2N, the solvent was removed under vacuum and the residue diluted with H2O. The solid was collected by filtration, washed with water and dried to give 8-(1-(3-chloro-2-fluorophenylamino)ethyl)-2-morpholino-4-oxo-4H-chromene-6-carboxylic acid (171 mg, 88%) as a white solid. Mass Spectrum: M+H⁺ 447.

EXAMPLE 2.01

8-(1-(4-fluorophenylamino)ethyl)-N,N-dimethyl-2-morpholino-4-oxo-4H-chromene-6-carboxamide

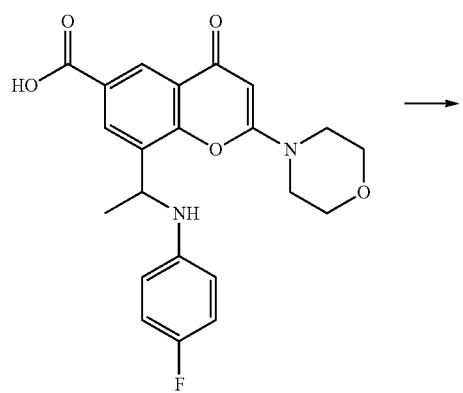

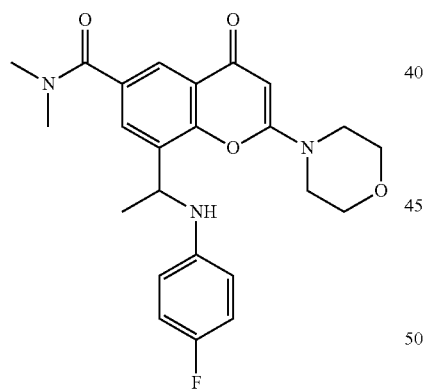

8-(1-(4-fluorophenylamino)ethyl)-2-morpholino-4-oxo-4H-chromene-6-carboxylic acid (82 mg, 0.20 mmol) was reacted with dimethylamine (0.119 mL, 0.24 mmol) using a procedure similar to the one described in Example 2.00 to afford 8-(1-(4-fluorophenylamino)ethyl)-N,N-dimethyl-2-morpholino-4-oxo-4H-chromene-6-carboxamide (53 mg, 60.7%) as a white solid. Mass Spectrum: M+H⁺ 440.

NMR Spectrum: (DMSOd₆) 1.50 (d, 3H), 2.66 (s, 3H), 2.92 (s, 3H), 3.50-3.65 (m, 4H), 3.70-3.81 (m, 4H), 4.92-5.02 (m, 1H), 5.60 (s, 1H), 6.27 (d, 1H), 6.46 (dd, 2H), 6.84 (dd, 2H), 7.56 (d, 1H), 7.77 (d, 1H).

The 8-(1-(4-fluorophenylamino)ethyl)-2-morpholino-4-oxo-4H-chromene-6-carboxylic acid used as starting material was made using a procedure similar to the one described in Example 2.00. Mass Spectrum: M+H⁺ 413.

EXAMPLE 2.02

N-(2-(dimethylamino)ethyl)-8-(1-(4-fluorophenylamino)ethyl)-N-methyl-2-morpholino-4-oxo-4H-chromene-6-carboxamide

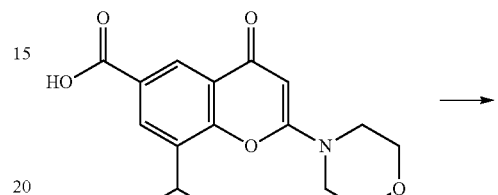

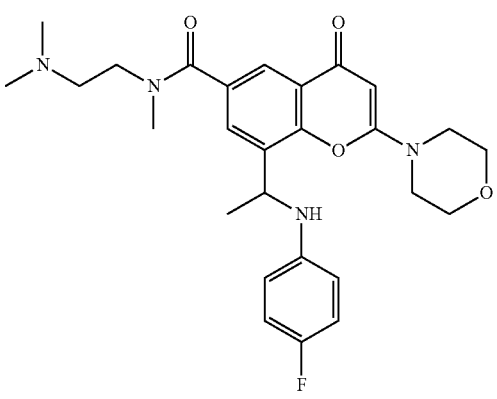

8-(1-(4-fluorophenylamino)ethyl)-2-morpholino-4-oxo-4H-chromene-6-carboxylic acid (80 mg, 0.19 mmol) was reacted with N1,N1,N2-trimethylethane-1,2-diamine (0.030 mL, 0.23 mmol) using a procedure similar to the one described in Example 2.00 to afford N-(2-(dimethylamino)ethyl)-8-(1-(4-fluorophenylamino)ethyl)-N-methyl-2-morpholino-4-oxo-4H-chromene-6-carboxamide (15.0 mg, 15.6%) as a white solid. Mass Spectrum: M+H⁺ 497. NMR Spectrum: (DMSOd₆) 1.49 (d, 3H), 1.74 (bs, 3H), 2.01 (bs, 1H), 2.18 (s, 3H), 2.66 (bs, 1.5H), 2.89 (bs, 2H), 3.05 (bs, 1.5H), 3.47 (bs, 1H), 3.50-3.64 (m, 4H), 3.71-3.79 (m, 4H), 4.93-5.01 (m, 1H), 5.59 (s, 1H), 6.29 (bs, 1H), 6.46 (dd, 2H), 6.84 (dd, 2H), 6.54 (d, 1H), 6.73 (d, 1H).

EXAMPLE 2.03

8-(1-(3-chloro-4-fluorophenylamino)ethyl)-6-(4-hydroxypiperidine-1-carbonyl)-2-morpholino-4H-chromen-4-one

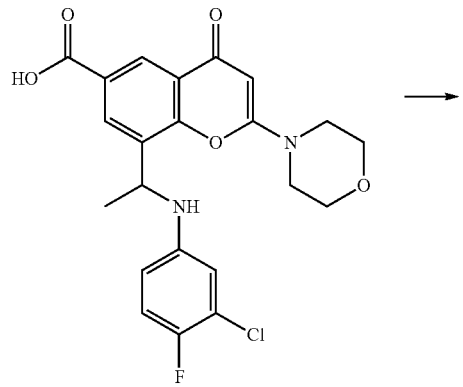

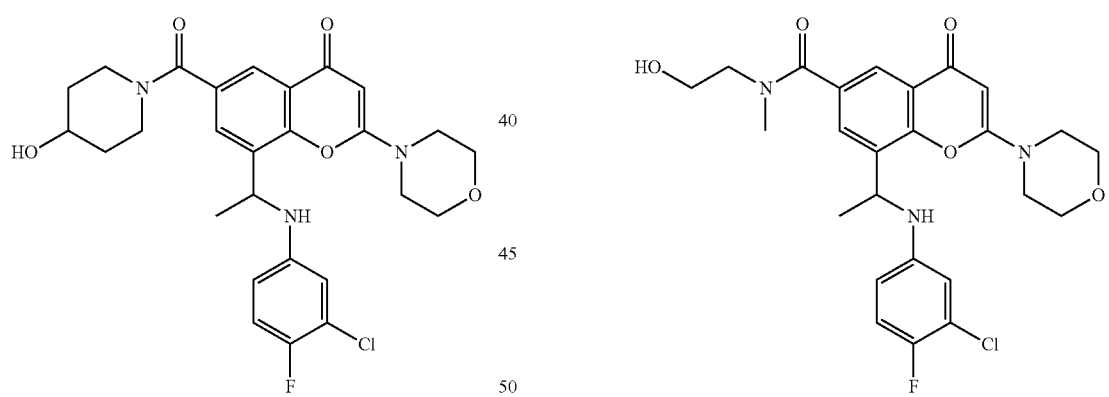

8-(1-(3-chloro-4-fluorophenylamino)ethyl)-2-morpholino-4-oxo-4H-chromene-6-carboxylic acid (125 mg, 0.28 mmol) was reacted with piperidin-4-ol (34.0 mg, 0.34 mmol) using a procedure similar to the one described in Example 2.00 to afford 8-(1-(3-chloro-4-fluorophenylamino)ethyl)-6-(4-hydroxypiperidine-1-carbonyl)-2-morpholino-4H-chromen-4-one (110 mg, 74.2%) as a white solid. Mass Spectrum: M+H$^+$ 530. NMR Spectrum: (DMSOd$_6$) at 323° K: 1.24 (bs, 2H), 1.51 (d, 3H), 2.99 (bs, 2H), 3.30 (bs, 2H), 3.37 (bs, 2H), 3.49-3.63 (m, 4H), 3.63-3.72 (m, 1H), 3.72-3.82 (m, 4H), 4.62 (d, 1H), 4.92-5.02 (m, 1H), 5.56 (s, 1H), 6.36-6.46 (m, 2H), 6.59 (dd, 1H), 7.01 (dd, 1H), 7.51 (d, 1H), 7.76 (d, 1H).

The 8-(1-(3-chloro-4-fluorophenylamino)ethyl)-2-morpholino-4-oxo-4H-chromene-6-carboxylic acid used as starting material was made using a procedure similar to the one described in Example 2.00. Mass Spectrum: M+H$^+$ 447.

EXAMPLE 2.04

8-(1-(3-chloro-4-fluorophenylamino)ethyl)-N-(2-hydroxyethyl)-N-methyl-2-morpholino-4-oxo-4H-chromene-6-carboxamide 8-(1-(3-chloro-4-fluorophenylamino)ethyl)-2-morpholino-4-oxo-4H-chromene-6-carboxylic acid (78 mg, 0.17 mmol) was reacted with 2-(methylamino)ethanol (0.017 mL, 0.21 mmol) using a procedure similar to the one described in Example 2.00 to give 8-(1-(3-chloro-4-fluorophenylamino)ethyl)-N-(2-hydroxyethyl)-N-methyl-2-morpholino-4-oxo-4H-chromene-6-carboxamide (60.0 mg, 68.2%) as a white solid. Mass Spectrum: M+H$^+$ 504. NMR Spectrum: (DMSOd$_6$) at 323° K: 1.51 (d, 3H), 2.82 (bs, 1.5H), 2.90 (bs, 1.5H), 3.42 (bs, 4H), 3.49-3.63 (m, 4H), 3.69-3.79 (m, 4H), 4.60 (bs, 1H), 4.92-5.01 (m, 1H), 5.56 (s, 1H), 6.37 (dd, 1H), 6.42 (ddd, 1H), 6.61 (dd, 1H), 7.02 (dd, 1H), 7.57 (d, 1H), 7.80 (d, 1H).

The 8-(1-(3-chloro-4-fluorophenylamino)ethyl)-2-morpholino-4-oxo-4H-chromene-6-carboxylic acid used as starting material was made using a procedure similar to the one described in Example 2.0. Mass Spectrum: M+H+ 447.

EXAMPLE 2.05

8-(1-(3-chloro-2-fluorophenylamino)ethyl)-N-(2-hydroxyethyl)-N-methyl-2-morpholino-4-oxo-4H-chromene-6-carboxamide

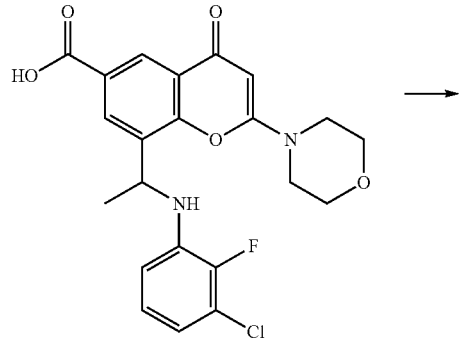

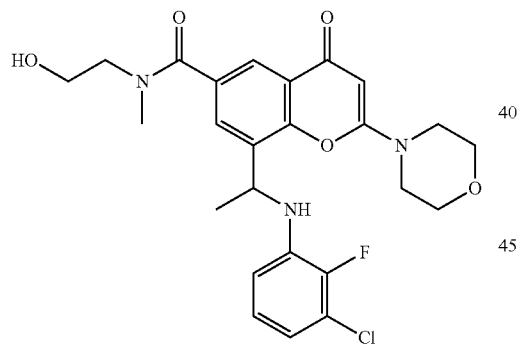

8-(1-(3-chloro-2-fluorophenylamino)ethyl)-2-morpholino-4-oxo-4H-chromene-6-carboxylic acid (130 mg, 0.29 mmol) was reacted with 2-(methylamino)ethanol (0.028 mL, 0.35 mmol) using a procedure similar to the one described in Example 2.00 to afford 8-(1-s (3-chloro-2-fluorophenylamino)ethyl)-N-(2-hydroxyethyl)-N-methyl-2-morpholino-4-oxo-4H-chromene-6-carboxamide (65.0 mg, 44.3%) as a white solid. Mass Spectrum: M+H+ 504. NMR Spectrum: (DMSOd6) 1.57 (d, 3H), 2.76 (s, 1.5H), 2.94 (s, 1.5H), 3.07 (bs, 1H), 3.27 (bs, 1H), 3.45 (bs, 1H), 3.51-3.64 (m, 5H), 3.70-3.78 (m, 4H), 4.69 (bs, 0.5H), 4.78 (ns, 0.5H), 5.08 (bs, 1H), 5.60 (s, 1H), 6.33-6.47 (bs, 2H), 6.65 (ddd, 1H), 6.83 (dd, 1H), 7.60 (bs, 0.5H), 7.61 (bs, 0.5H), 7.79 (bs, 0.5H), 7.81 (bs, 0.5H).

The 8-(1-(3-chloro-2-fluorophenylamino)ethyl)-2-morpholino-4-oxo-4H-chromene-6-carboxylic acid used as starting material was made using a procedure similar to the one described in Example 2.00. Mass Spectrum: M+H+ 447.

EXAMPLE 2.06

8-(1-(3-chloro-2-fluorophenylamino)ethyl)-6-(4-hydroxypiperidine-1-carbonyl)-2-morpholino-4H-chromen-4-one

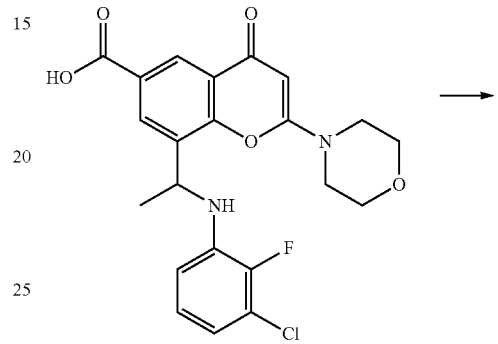

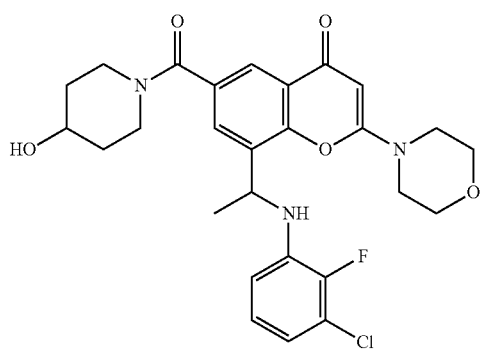

8-(1-(3-chloro-2-fluorophenylamino)ethyl)-2-morpholino-4-oxo-4H-chromene-6-carboxylic acid (130 mg, 0.29 mmol) was reacted with piperidin-4-ol (35.3 mg, 0.35 mmol) using a procedure similar to the one described in Example 2.00 to give 8-(1-(3-chloro-2-fluorophenylamino)ethyl)-6-(4-hydroxypiperidine-1-carbonyl)-2-morpholino-4H-chromen-4-one (101 mg, 65.5%) as a white solid. Mass Spectrum: M+H+ 530. NMR Spectrum: (DMSOd6) at 323° K: 1.24 (bs, 2H), 1.62 (d, 3H), 1.63 (bs, 2H), 2.99 (bs, 2H), 3.19 (bs partially hidden by H2O, 2H), 3.49-3.63 (m, 4H), 3.65-3.72 (m, 1H), 3.72-3.78 (m, 4H), 4.62 (d, 1H), 5.04-5.13

(m, 1H), 5.56 (s, 1H), 6.28 (d, 1H), 6.33 (dd, 1H), 6.64 (ddd, 1H), 6.82 (ddd, 1H), 7.57 (d, 1H), 7.77 (d, 1H).

EXAMPLE 2.07

8-(1-(3,5-difluorophenylamino)ethyl)-6-(morpholine-4-carbonyl)-2-morpholino-4H-chromen-4-one

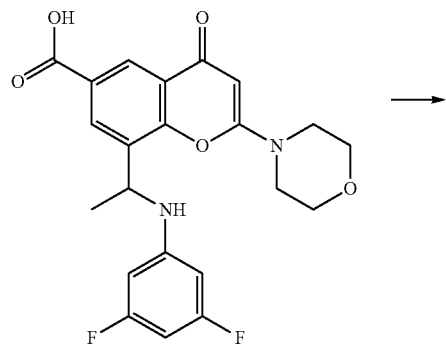

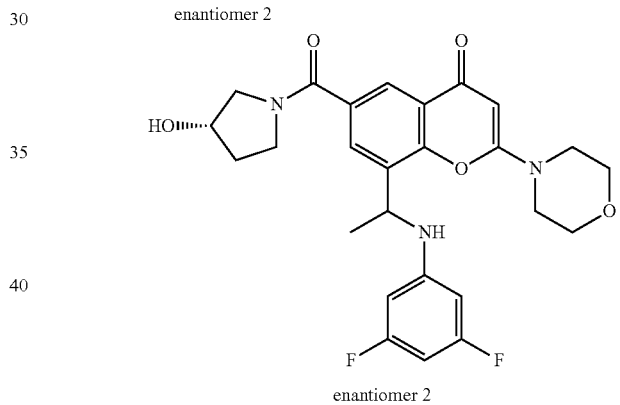

TSTU (84 mg, 0.28 mmol) at 25° C., was added to 8-(1-(3,5-difluorophenylamino)ethyl)-2-morpholino-4-oxo-4H-chromene-6-carboxylic acid (100 mg, 0.14 mmol) and DIPEA (0.049 mL, 0.28 mmol) dissolved in DCM (1 mL). The resulting solution was stirred at 25° C. for 2 hrs. Morpholine (0.037 mL, 0.42 mmol) was then added, the resulting solution was stirred at 25° C. for 30 minutes then concentrated. The crude was diluted with 1 mL of DMA and purified by preparative HPLC using a Waters X-Bridge reverse-phase column (C-18, 5 microns silica, 19 mm diameter, 100 mm length, flow rate of 40 mL/minute) and decreasingly polar mixtures of water (containing 0.2% ammonium carbonate) and acetonitrile as eluent. The fractions containing the desired compound were evaporated to dryness, triturated in diethyl ether and collected by filtration to afford 8-(1-(3,5-difluorophenylamino)ethyl)-6-(morpholine-4-carbonyl)-2-morpholino-4H-chromen-4-one (63.0 mg, 90%) as a yellow solid. Mass Spectrum: M+H⁺ 500. NMR Spectrum: (DMSOd₆) 1.53 (d, 3H), 3.11 (bs, 2H), 3.37-3.71 (m, 10H), 3.71-3.80 (m, 4H), 4.98-5.07 (m, 1H), 5.62 (s, 1H), 6.15 (dd, 2H), 6.25 (ddd, 1H), 6.97 (d, 1H), 7.51 (d, 1H), 7.82 (d, 1H).

The 8-(1-(3,5-difluorophenylamino)ethyl)-2-morpholino-4-oxo-4H-chromene-6-carboxylic acid used as starting material was made using a procedure similar to the one described in Example 2.00.

EXAMPLE 2.08

8-(1-(3,5-difluorophenylamino)ethyl)-6-((S)-3-hydroxypyrrolidine-1-carbonyl)-2-morpholino-4H-chromen-4-one (enantiomer 2)

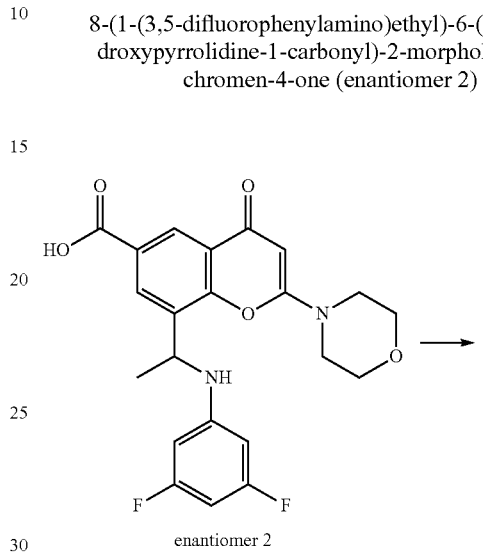

EDCI (102 mg, 0.53 mmol) was added in one portion to 8-(1-(3,5-difluorophenylamino)ethyl)-2-morpholino-4-oxo-4H-chromene-6-carboxylic acid (200 mg, 0.35 mmol, enantiomer 2 ([α]$^D_{20°}$-102°, described as a starting material in Example 7.0a), (S)-pyrrolidin-3-ol (0.043 mL, 0.53 mmol) and HOPO (47.1 mg, 0.42 mmol) dissolved in DCM (2 mL) in a screwcap vial. The resulting solution was stirred at RT for 5 min then 50° C. for 30 min. More EDCI (~50 mg) was added to complete the reaction. The solution was washed with a 10% aq. citric acid solution, water, brine and dried over magnesium sulfate. The solvent was evaporated and the crude product purified by flash chromatography on silica gel (40 g) eluting with 0 to 10% MeOH in DCM. The solvent was evaporated to dryness to afford 8-(1-(3,5-difluorophenylamino)ethyl)-6-((S)-3-hydroxypyrrolidine-1-carbonyl)-2-morpholino-4H-chromen-4-one (95%) as a off-white foam. Mass Spectrum: M+H⁺ 500. NMR Spectrum (CDCl₃): 1.60 (d, 3H), 1.89-2.11 (m, 1H), 2.54 (bs, 0.5H), 2.81 (bs, 0.5H), 3.29-3.43 (m, 2H), 3.51 (bs, 4H), 3.64-3.78 (m, 2H), 3.79-3.91 (m, 5H), 4.42 (bs, 0.5H), 4.54 (bs, 0.5H), 4.59 (bs, 0.5H), 4.70 (bs, 0.5H), 4.87-4.95 (m, 1H), 5.54 (bs, 1H), 5.89-6.01 (m, 2H), 6.09 (dd, 1H), 7.85 (s, 0.5H), 7.87 (s, 0.5H), 8.18 (bs, 0.5H), 8.25 (bs, 0.5H).

EXAMPLE 3.00

N-(2-(dimethylamino)ethyl)-8-(1-((4-fluorophenyl)(methyl)amino)ethyl)-2-morpholino-4-oxo-4H-chromene-6-carboxamide

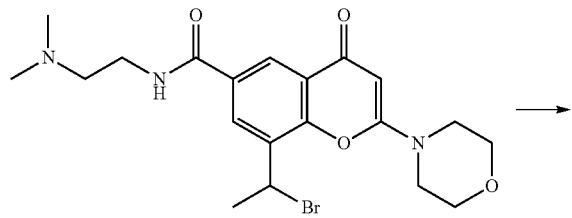

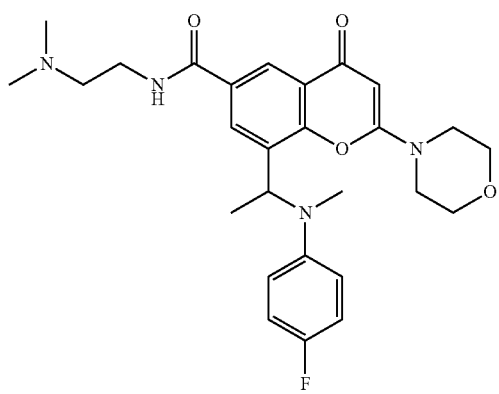

A solution of 8-(1-bromoethyl)-N-(2-(dimethylamino)ethyl)-2-morpholino-4-oxo-4H-chromene-6-carboxamide hydrobromide (85 mg, 0.16 mmol) and 4-fluoro-N-methylaniline (0.077 mL, 0.64 mmol) in NMP (1 mL) was stirred at room temperature for 4 h then at 45° C. for 1 h. The reaction mixture was allowed to cool to room temperature and purified by preparative HPLC using a Waters X-Bridge reverse-phase column (C-18, 5 microns silica, 19 mm diameter, 100 mm length, flow rate of 40 mL/minute) and decreasingly polar mixtures of water (containing 0.2% ammonium carbonate) and acetonitrile as eluent. The fractions containing the desired compound were evaporated to dryness. The residue was triturated in diethyl ether, collected by filtration and dried to afford N-(2-(dimethylamino)ethyl)-8-(1-((4-fluorophenyl)(methyl)amino)ethyl)-2-morpholino-4-oxo-4H-chromene-6-carboxamide (42.0 mg, 53.1%) as a white solid. Mass Spectrum: M+H$^+$ 497. NMR Spectrum: (CDCl$_3$) 1.66 (d, 3H), 2.33 (s, 6H), 2.33 (bs, 2H), 2.60 (bs, 2H), 2.61 (s, 3H), 3.09-3.24 (m, 4H), 3.44-3.57 (m, 4H), 3.57-3.66 (m, 2H), 5.36 (q, 1H), 5.48 (s, 1H), 6.75 (dd, 2H), 6.77 (dd, 2H), 7.14 (bs, 1H), 8.33 (s, 1H), 8.44 (s, 1H).

The 8-(1-bromoethyl)-N-(2-(dimethylamino)ethyl)-2-morpholino-4-oxo-4H-chromene-6-carboxamide hydrobromide used as starting material was made as follows: —

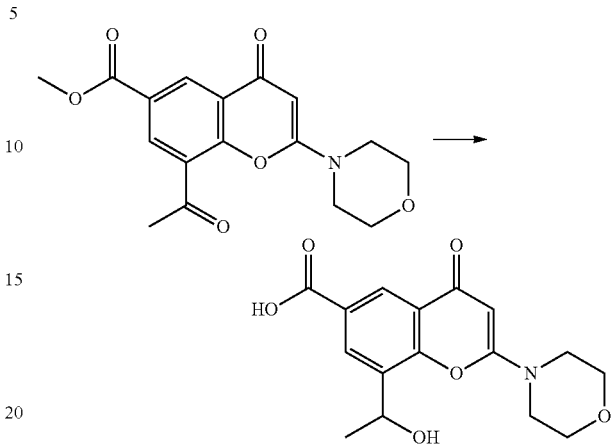

To a suspension of methyl 8-acetyl-2-morpholino-4-oxo-4H-chromene-6-carboxylate (193 mg, 0.41 mmol, as described in Example 2.00) in methanol (2 mL) was added at −15° C. sodium tetrahydroborate (15.4 mg, 0.41 mmol). The resulting suspension was stirred at −15° C. for 20 minutes. The reaction mixture was quenched with a 2N aqueous NaOH solution (0.408 mL, 0.82 mmol) and allowed to warm to room temperature for 1 hr. More NaOH (0.408 mL, 0.82 mmol) was added and stirring was maitained for another 15 min. HCl (0.917 mL, 1.83 mmol) was added to adjust pH to 2-3. The resulting precipitate was diluted with a about 1 mL of water, collected by filtration, washed with ethyl acetate, diethyl ether and dried to a constant weight to afford 8-(1-hydroxyethyl)-2-morpholino-4-oxo-4H-chromene-6-carboxylic acid (122 mg, 94%) as a orange solid which was used without further purification. Mass Spectrum: M+H$^+$ 320.

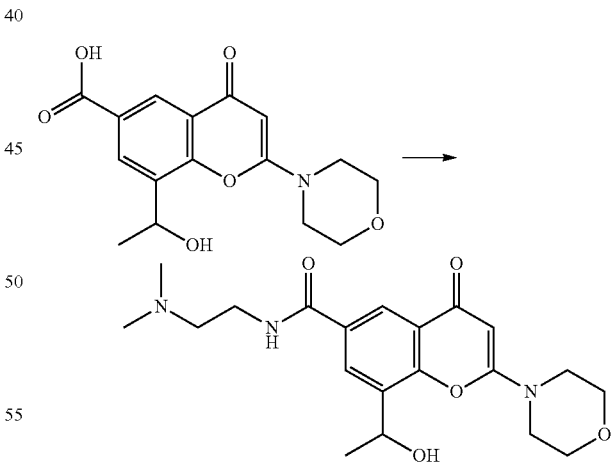

TSTU (104 mg, 0.34 mmol) at 25° C., was added portionwise to 8-(1-hydroxyethyl)-2-morpholino-4-oxo-4H-chromene-6-carboxylic acid (110 mg, 0.34 mmol) and DIPEA (0.066 mL, 0.38 mmol) suspended in DCM (1 mL) under nitrogen. The resulting mixture was stirred at 25° C. for 1.5 hrs. N1,N1-dimethylethane-1,2-diamine (0.038 mL, 0.34 mmol) was then added and the mixture stirred at 25° C. for 30 minutes. The mixture was poured onto a silica gel column and purified by flash chromatography eluting with 5% methanolic ammonia (7 N) in DCM. The solvent was evaporated to dryness, the residue was triturated in diethyl ether, collected by filtration and dried to afford N-(2-(dimethylamino)ethyl)-8-(1-hydroxyethyl)-2-morpholino-4-oxo-4H-chromene-6-carboxamide (80 mg, 0.205 mmol, 59.6%) as a off-white solid. Mass Spectrum: M+H$^+$ 390.

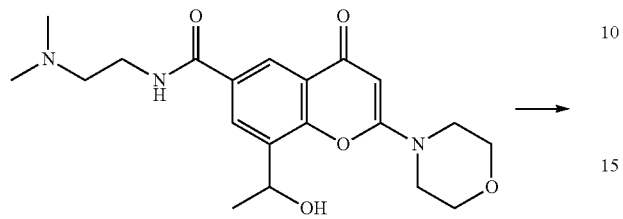

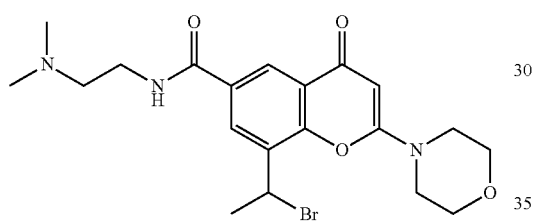

A solution of tribromophosphine 1M in DCM (0.154 mL, 0.15 mmol) at 25° C., was added dropwise to N-(2-(dimethylamino)ethyl)-8-(1-hydroxyethyl)-2-morpholino-4-oxo-4H-chromene-6-carboxamide (60 mg, 0.15 mmol) suspended in DCM (1 mL). This suspension was stirred at 25° C. for 4 days. The resulting precipitate was collected by filtration, washed with diethyl ether and dried to afford 8-(1-bromoethyl)-N-(2-(dimethylamino)ethyl)-2-morpholino-4-oxo-4H-chromene-6-carboxamide hydrobromide (98 mg, >100%) as a white solid, which was used without further purification. Mass Spectrum: M+H$^+$ 454.

EXAMPLE 3.01

8-(1-((3,4-difluorophenyl)(methyl)amino)ethyl)-N-(2-(dimethylamino)ethyl)-2-morpholino-4-oxo-4H-chromene-6-carboxamide

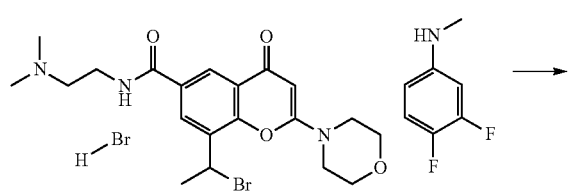

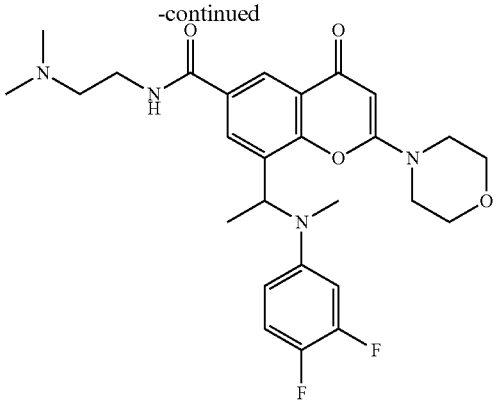

3,4-difluoro-N-methylaniline (161 mg, 1.13 mmol) was reacted with 8-(1-bromoethyl)-N-(2-(dimethylamino)ethyl)-2-morpholino-4-oxo-4H-chromene-6-carboxamide hydrobromide (150 mg, 0.28 mmol) using a procedure similar to the one described in Example 3.00 to give 8-(1-((3,4-difluorophenyl)(methyl)amino)ethyl)-N-(2-(dimethylamino)ethyl)-2-morpholino-4-oxo-4H-chromene-6-carboxamide (66.0 mg, 45.6%). Mass Spectrum: M+H$^+$ 515. NMR Spectrum: (DMSOd$_6$) 1.56 (d, 3H), 2.18 (s, 6H), 2.41 (t, 2H), 2.63 (s, 3H), 3.21-3.28 (m, 2H), 3.34-3.41 (m partially hidden by H2O, 4H), 3.41-3.49 (m, 2H), 3.49-3.56 (m, 2H), 5.53 (q, 1H), 5.55 (s, 1H), 6.61 (d, 1H), 6.87 (ddd, 1H), 7.24 (dd, 1H), 8.09 (d, 1H), 8.43 (d, 1H), 8.74 (t, 1H).

EXAMPLE 3.02

N-(2-(dimethylamino)ethyl)-8-(1-((4-fluorophenyl)(methyl)amino)ethyl)-N-methyl-2-morpholino-4-oxo-4H-chromene-6-carboxamide

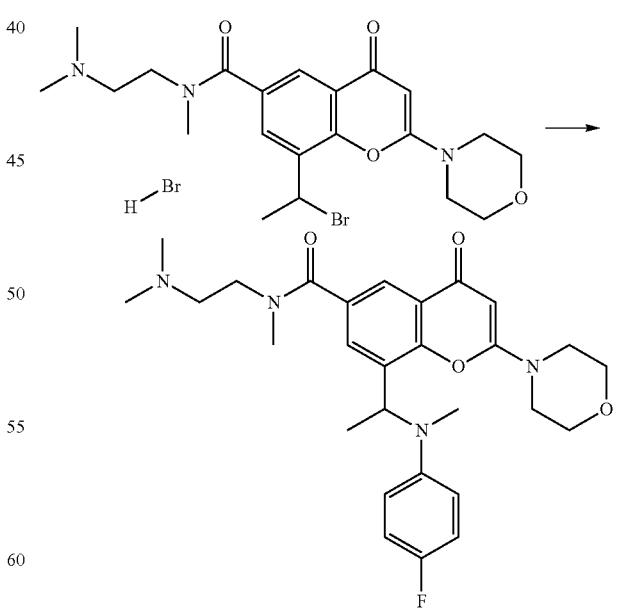

4-fluoro-N-methylaniline (82 mg, 0.66 mmol) was reacted with 8-(1-bromoethyl)-N-(2-(dimethylamino)ethyl)-N-methyl-2-morpholino-4-oxo-4H-chromene-6-carboxamide hydrobromide (90 mg, 0.16 mmol) using a procedure similar to the one described in example 3.00 to give N-(2-(dimethylamino)ethyl)-8-(1-((4-fluorophenyl)(methyl)amino)ethyl)-N-methyl-2-morpholino-4-oxo-4H-chromene-6-carboxamide (39.0 mg, 46.4%) as a white solid. Mass Spectrum: M+H$^+$ 511. NMR Spectrum: (DMSOd$_6$) at 323° K: 1.55 (d, 3H), 2.04 (bs, 6H), 2.40 (bs, 2H), 2.68 (s, 3H), 2.93 (s, 3H), 3.22-3.36 (m, 4H), 3.37 (bs, 2H), 3.44-3.58 (m, 4H), 5.45 (q, 1H), 5.50 (s, 1H), 6.82 (dd, 2H), 7.01 (dd, 2H), 7.56 (d, 1H), 7.83 (d, 1H).

The 8-(1-bromoethyl)-N-(2-(dimethylamino)ethyl)-N-methyl-2-morpholino-4-oxo-4H-chromene-6-carboxamide hydrobromide used as starting material was made using a procedure similar to the one described for the starting material in Example 3.00 except that N1,N1,N2-trimethylethane-1,2-diamine was used instead of N1,N1-dimethylethane-1,2-diamine.

EXAMPLE 3.03

8-(1-(3,4-difluorophenylamino)ethyl)-N,N-dimethyl-2-morpholino-4-oxo-4H-chromene-6-carboxamide

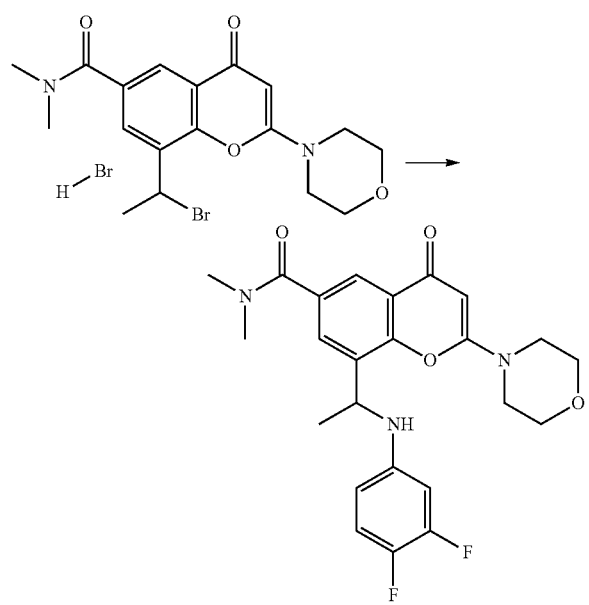

3,4-difluoroaniline (0.105 mL, 1.06 mmol) was reacted with 8-(1-bromoethyl)-N,N-dimethyl-2-morpholino-4-oxo-4H-chromene-6-carboxamide hydrobromide (130 mg, 0.27 mmol) using a procedure similar to the one described in Example 3.00 to give 8-(1-(3,4-difluorophenylamino)ethyl)-N,N-dimethyl-2-morpholino-4-oxo-4H-chromene-6-carboxamide (35.0 mg, 28.8%) as a white solid. Mass Spectrum: M+H$^+$ 458. NMR Spectrum: (DMSOd$_6$) 1.50 (d, 3H), 2.70 (s, 3H), 2.94 (s, 3H), 3.50-3.63 (m, 4H), 3.71-3.79 (m, 4H), 4.92-5.01 (m, 1H), 5.60 (s, 1H), 6.25 (d, 1H), 6.46 (ddd, 1H), 6.54 (d, 1H), 7.05 (dd, 1H), 7.54 (d, 1H), 7.78 (d, 1H).

A larger batch of the above racemic compound was resolved by chiral preparative HPLC using the following conditions:

| Column | CelluCoat 250 × 50 10 μm |
| Eluent | Heptane/EtOH/TEA 50/50/0.1 |
| Oven Temperature | Ambient |
| Flow | 118 mL/min |
| Wavelength | 300 nm |
| Sample Conc | 50 mg/ml Heptane/EtOH 1/1 |
| Injection amount | 600 mg |

2.19 g of racemic compound was separated using the above conditions to give: First eluting enantiomer 1100 mg (Example 3.03a) [α]$^D_{20°}$: +119° (99.1% ee) in MeCN Second eluting enantiomer 1090 mg (Example 3.03b) [α]$^D_{20°}$: −120° (99.3% ee) in MeCN The 8-(1-bromoethyl)-N,N-dimethyl-2-morpholino-4-oxo-4H-chromene-6-carboxamide hydrobromide used as starting material was made as follows:

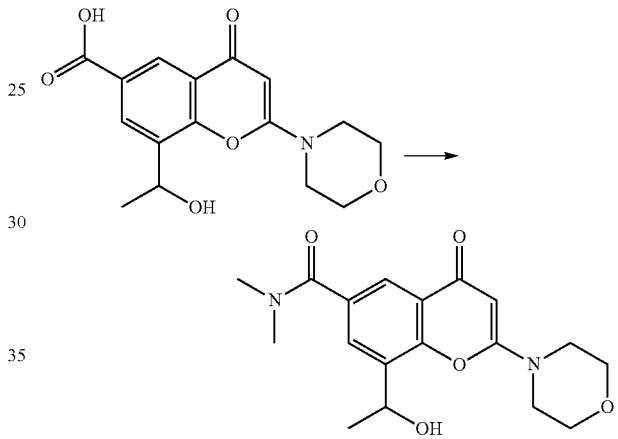

TSTU (108 mg, 0.36 mmol) was added portionwise to 8-(1-hydroxyethyl)-2-morpholino-4-oxo-4H-chromene-6-carboxylic acid (115 mg, 0.36 mmol, as described in Example 3.00) and DIPEA (0.069 mL, 0.40 mmol) suspended in DCM (1 mL) at 25° C. under nitrogen. The resulting mixture was stirred at 25° C. for 1.5 hrs. Dimethylamine (0.180 ml, 0.36 mmol) was then added and stirring was maintained for an additional 30 min. The mixture was poured onto a silica gel column and purified by flash chromatography eluting with 5% methanolic ammonia (7 N) in dichloromethane. The solvent was evaporated to dryness. The residue was triturated in diethyl ether, collected by filtration and dried to afford 8-(1-hydroxyethyl)-N,N-dimethyl-2-morpholino-4-oxo-4H-chromene-6-carboxamide (123 mg, 0.355 mmol, 99%) as a off-white solid. Mass Spectrum: M+H$^+$ 347.

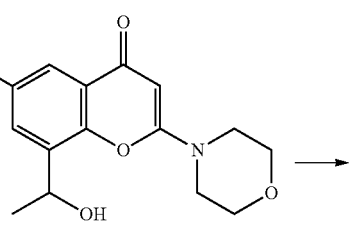

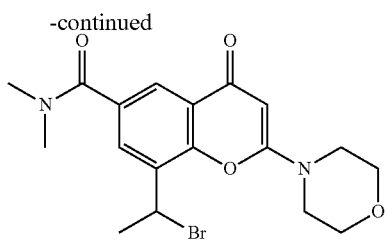

A solution of tribromophosphine 1M in CH2Cl2 (0.346 mL, 0.35 mmol) at 25° C., was added dropwise to 8-(1-hydroxyethyl)-N,N-dimethyl-2-morpholino-4-oxo-4H-chromene-6-carboxamide (120 mg, 0.35 mmol) suspended in DCM (1 mL). The resulting suspension was stirred at 25° C. for 4 days. The resulting gum was triturated in ether to give a precipitate which was collected by filtration, washed with ether and dried to a constant weight to afford 8-(1-bromoethyl)-N,N-dimethyl-2-morpholino-4-oxo-4H-chromene-6-carboxamide hydrobromide (140 mg, 82%) as a white solid, which was used without further purification. Mass Spectrum: M+H$^+$ 409.

EXAMPLE 3.04

8-(1-(3-chloro-2-fluorophenylamino)ethyl)-N,N-dimethyl-2-morpholino-4-oxo-4H-chromene-6-carboxamide

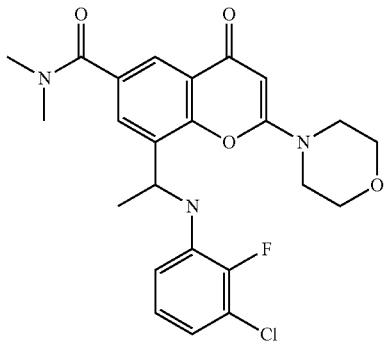 [SMILES: CC(Nc1cccc(Cl)c1F)c1cc(C(=O)N(C)C)cc2c(=O)cc(N3CCOCC3)oc12]

3-chloro-2-fluoroaniline (0.179 mL, 1.63 mmol) was reacted with 8-(1-bromoethyl)-N,N-dimethyl-2-morpholino-4-oxo-4H-chromene-6-carboxamide hydrobromide (200 mg, 0.41 mmol, as described in Example 3.03) using a procedure similar to the one described in Example 3.00 to give 8-(1-(3-chloro-2-fluorophenylamino)ethyl)-N,N-dimethyl-2-morpholino-4-oxo-4H-chromene-6-carboxamide (121 mg, 62.6%) as a white solid. Mass Spectrum: M+H$^+$ 474. NMR Spectrum: (DMSOd$_6$) 1.58 (d, 3H), 2.70 (s, 3H), 2.94 (s, 3H), 3.50-3.64 (m, 4H), 3.70-3.80 (m, 4H), 5.05-5.15 (m, 1H), 5.60 (m, 1H), 6.37 (dd, 1H), 6.44 (d, 1H), 6.65 (ddd, 1H), 6.83 (dd, 1H), 7.60 (d, 1H), 7.78 (d, 1H).

A larger batch of the above racemic compound was resolved by chiral preparative HPLC using the following conditions:

| Column | Chiralpak IC 21 × 250 mm, 5 μm |
| --- | --- |
| Eluent | DCM/isopropanol 1:1 |
| Oven Temperature | Ambient |
| Flow | 20 mL/min |
| Wavelength | 220 nm |
| Sample Conc | 50 mg/mL in DCM/MeOH 1:1 |
| Injection | 100 mg |

1.8 g of racemic compound was separated using the above conditions to give:

First eluting enantiomer 741 mg (Example 3.04a) [α]$^D_{20°}$: +159° (>98% ee) in MeCN Second eluting enantiomer 622 mg (Example 3.04b) [α]$^D_{20°}$: −159° (>98% ee) in MeCN

EXAMPLE 3.05

8-(1-(3-chloro-4-fluorophenylamino)ethyl)-N,N-dimethyl-2-morpholino-4-oxo-4H-chromene-6-carboxamide

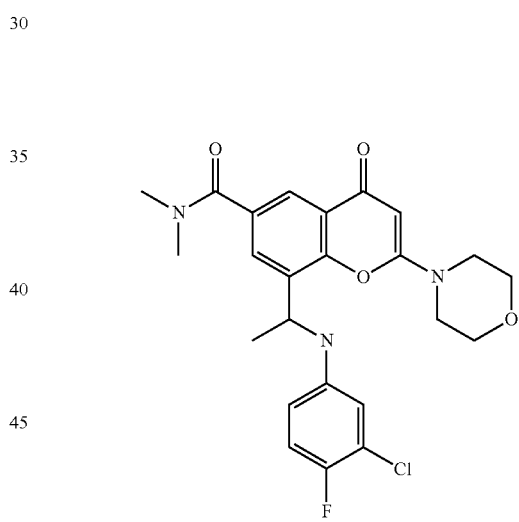

3-chloro-4-fluoroaniline (238 mg, 1.63 mmol) was reacted with 8-(1-bromoethyl)-N,N-dimethyl-2-morpholino-4-oxo-4H-chromene-6-carboxamide hydrobromide (200 mg, 0.41 mmol, as described in Example 3.03) to give 8-(1-(3-chloro-4-fluorophenylamino)ethyl)-N,N-dimethyl-2-morpholino-4-oxo-4H-chromene-6-carboxamide (122 mg, 63.1%) as a white solid. Mass Spectrum: M+H$^+$ 474. NMR Spectrum: (DMSOd$_6$) 1.51 (d, 3H), 2.70 (s, 3H), 2.94 (s, 3H), 3.50-3.64

(m, 4H), 3.69-3.81 (m, 4H), 4.94-5.05 (m, 1H), 5.60 (m, 1H), 6.47 (ddd, 1H), 6.52 (d, 1H), 6.67 (dd, 1H), 7.05 (dd, 1H), 7.55 (d, 1H), 7.79 (d, 1H).

EXAMPLE 3.06

8-(1-(3,5-difluorophenylamino)ethyl)-N,N-dimethyl-2-morpholino-4-oxo-4H-chromene-6-carboxamide

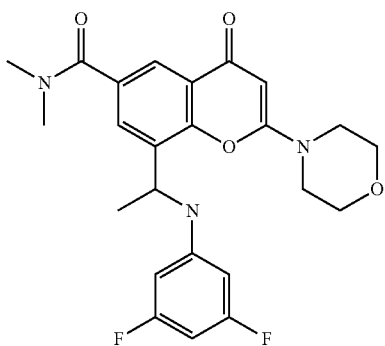 [SMILES: CC(Nc1cc(F)cc(F)c1)c1cc(C(=O)N(C)C)cc2c(=O)cc(N3CCOCC3)oc12]

To a suspension of 8-(1-bromoethyl)-N,N-dimethyl-2-morpholino-4-oxo-4H-chromene-6-carboxamide hydrobromide (3.63 g, 7.41 mmol, as described in Example 3.03) in DMF (35 mL) under nitrogen was added 3,5-difluoroaniline (3.82 g, 29.62 mmol). The resulting yellow solution was stirred at 50° C. for 5 hrs. The reaction mixture was concentrated to dryness, then purified by flash chromatography on silica gel eluting with 1 to 7% methanol in DCM. The solvent was evaporated to dryness to afford 8-(1-(3,5-difluorophenylamino)ethyl)-N,N-dimethyl-2-morpholino-4-oxo-4H-chromene-6-carboxamide (2.32 g, 68.5%) as a pale yellow solid. Mass Spectrum: M+H+ 458. NMR Spectrum: (DMSOd$_6$) 1.52 (d, 3H), 2.74 (s, 3H), 2.95 (s, 3H), 3.50-3.64 (m, 4H), 3.70-3.79 (m, 4H), 4.97-5.05 (m, 1H), 5.60 (m, 1H), 6.15 (dd, 2H), 6.22 (tt, 1H), 6.96 (d, 1H), 7.54 (d, 1H), 7.81 (d, 1H).

This racemic compound was resolved by chiral preparative HPLC using the following conditions:
Instrument Gilson Prep (200 mL heads)
Column Merck 50 mm 20 nm Chiralpak IC
Eluent MeCN/MeOH/DEA 90/10/0.2
Oven Temperature Ambient
Flow 60 mL/min
Wavelength 254 nm
Sample Conc 12 mg/mL in MeCN/MeOH/DEA 90/10/0.5
Injection volume 30 mL
Run Time 50 min
First eluting enantiomer (r.t: 10.8 min) 0.820 g (Example 3.06a) $[\alpha]^D_{20}$=+121.8° in EtOH.
Second eluting enantiomer (r.t: 15.4 min) 0.923 g (Example 3.06b) $[\alpha]^D_{20}$=−122.6° in EtOH.
Retention times (r.t.) are from analytical HPLC post chiral separation (1 mL/min, 20 μm Chiralpak AD MeCN/MeOH/DEA 90/10/0.5).

The Second eluting enantiomer (Example 3.06b) was crystallized in ethanol, before drying under ambient conditions to yield Form A material. This form was determined to be crystalline by XRPD (see Figure A) and had the following characteristic X-Ray Powder Diffraction peaks:

| Angle 2-Theta (2θ) | Intensity % |
|---|---|
| 7.9 | 100.0 |
| 16.7 | 9.2 |
| 20.3 | 8.0 |
| 19.3 | 7.7 |
| 13.2 | 7.3 |
| 7.2 | 6.8 |
| 19.5 | 6.4 |
| 17.9 | 5.8 |
| 23.0 | 5.8 |
| 5.0 | 5.5 |

DSC analysis of Form A was also carried out (Figure B) and showed an initial event with an onset at 125.8° C. and a peak at 129.2° C., followed by an exothermic event before a melt with an onset of 223.8° C. and a peak at 226.7° C.

Form B material was produced by slurrying Form A material in acetonitrile, ethylacetate or methanol. With each of the given solvents approximately 20 mg of the original material was placed in a vial with a magnetic flea, and approximately 2 ml of solvent added, the vial was then sealed tightly with a cap and left to stir on a magnetic stirrer plate. After 3 days, the sample was removed from the plate, the cap taken off and the slurry left to dry under ambient conditions before it was analysed by XRPD and DSC. This form (Form B) was determined to be crystalline by XRPD (Figure C) and seen to be different to Form A. This form had the following characteristic X-Ray Powder Diffraction peaks:

| Angle 2-Theta (2θ) | Intensity % |
|---|---|
| 20.7 | 100 |
| 13.8 | 54.7 |
| 21.5 | 50.8 |
| 19.6 | 36.6 |
| 12.8 | 35.7 |
| 15.4 | 24.9 |
| 10.7 | 20.5 |
| 8.5 | 19.7 |
| 22.4 | 18.9 |

DSC analysis (Figure D) showed that the Form B material had a melting point of 225.8° C. (onset).

EXAMPLE 3.07

8-(1-((4-fluorophenyl)(methyl)amino)ethyl)-N,N-dimethyl-2-morpholino-4-oxo-4H-chromene-6-carboxamide

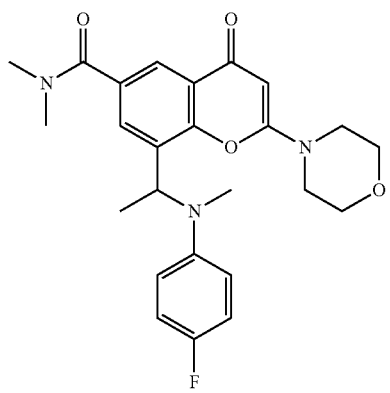 [SMILES: CC(c1cc(C(=O)N(C)C)cc2c(=O)cc(N3CCOCC3)oc12)N(C)c1ccc(F)cc1]

4-fluoro-N-methylaniline (204 mg, 1.63 mmol) was reacted with 8-(1-bromoethyl)-N,N-dimethyl-2-morpholino-4-oxo-4H-chromene-6-carboxamide hydrobromide (200 mg, 0.41 mmol, as described in Example 3.03), using an analgous procedure to that described in Example 3.00, to afford 8-(1-((4-fluorophenyl)(methyl)amino)ethyl)-N,N-dimethyl-2-morpholino-4-oxo-4H-chromene-6-carboxamide (96 mg, 51.9%) as a white solid. Mass Spectrum: M+H$^+$ 454. NMR Spectrum: (DMSOd$_6$) 1.55 (d, 3H), 2.65 (s, 3H), 2.89 (s, 3H), 3.00 (s, 3H), 3.20-3.27 (m, 2H), 3.27-3.33 (m partially hidden by H2O, 2H), 3.42-3.48 (ms, 2H), 3.48-3.56 (m, 2H), 5.48 (q, 1H), 5.54 (s, 1H), 6.83 (dd, 2H), 7.04 (dd, 1H), 7.65 (d, 2H), 7.86 (d, 1H).

EXAMPLE 3.08

8-(1-((3-chloro-4-fluorophenyl)(methyl)amino)ethyl)-N,N-dimethyl-2-morpholino-4-oxo-4H-chromene-6-carboxamide

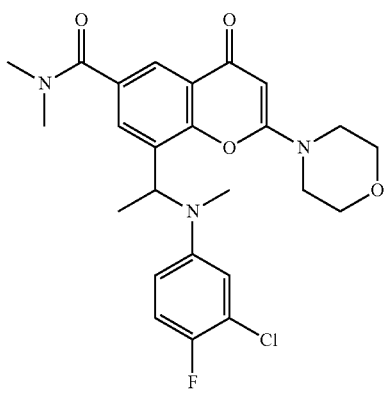 [SMILES: CC(c1cc(C(=O)N(C)C)cc2c(=O)cc(N3CCOCC3)oc12)N(C)c1ccc(F)c(Cl)c1]

3-chloro-4-fluoro-N-methylaniline (260 mg, 1.63 mmol) was reacted with 8-(1-bromoethyl)-N,N-dimethyl-2-morpholino-4-oxo-4H-chromene-6-carboxamide hydrobromide (200 mg, 0.41 mmol, as described in Example 3.03), using an analgous procedure to that described in Example 3.00, to afford 8-(1-((3-chloro-4-fluorophenyl) (methypamino) ethyl)-N,N-dimethyl-2-morpholino-4-oxo-4H-chromene-6-carboxamide (107 mg, 53.7%) as a white solid. Mass Spectrum: M+H$^+$ 488. NMR Spectrum: (DMSOd$_6$) 1.55 (d, 3H), 2.63 (s, 3H), 2.91 (s, 3H), 3.01 (s, 3H), 3.20-3.29 (m, 2H), 3.30-3.37 (m partially hidden by H2O, 2H), 3.42-3.49 (ms, 2H), 3.49-3.57 (m, 2H), 5.54 (s, 1H), 5.55 (q, 1H), 6.79 (dd, 1H), 6.98 (dd, 1H), 7.23 (dd, 1H), 7.68 (d, 1H), 7.87 (d, 1H).

EXAMPLES 3.09-3.13

For preparation of the compounds of Examples 3.09 to 3.13 (shown in Table I), the appropriate aniline (1.20 mmol) and 8-(1-bromoethyl)-N,N-dimethyl-2-morpholino-4-oxo-4H-chromene-6-carboxamide hydrobromide (0.123 g, 0.3 mmol) were suspended in NMP (1.0 mL) and sealed into a tube. The reaction was purged with argon and heated at 75° C. over a period of 15 hrs. The reaction mixture was purified by preparative HPLC using a Waters X-Bridge reverse-phase column (C-18, 5 microns silica, 19 mm diameter, 100 mm length, flow rate of 40 mL/minute) and decreasingly polar mixtures of water (containing 0.2% ammonium carbonate and acetonitrile as eluent. The fractions containing the desired compound were evaporated to dryness.

TABLE I

| Ex. | Structure | Reagent Name | Product | Product Mass (g) | Yield (%) | MH+ |
|---|---|---|---|---|---|---|
| 3.09 | 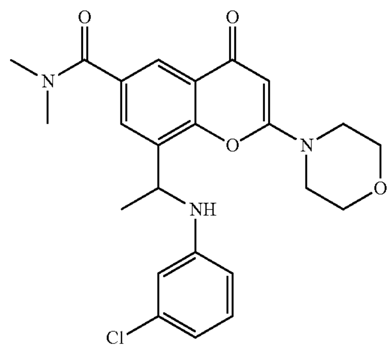 [SMILES: CC(Nc1cccc(Cl)c1)c1cc(C(=O)N(C)C)cc2c(=O)cc(N3CCOCC3)oc12] | 3-chloroaniline | 8-(1-(3-chlorophenylamino)ethyl)-N,N-dimethyl-2-morpholino-4-oxo-4H-chromene-6-carboxamide | 0.068 | 49.7 | 456 |
| 3.10 | 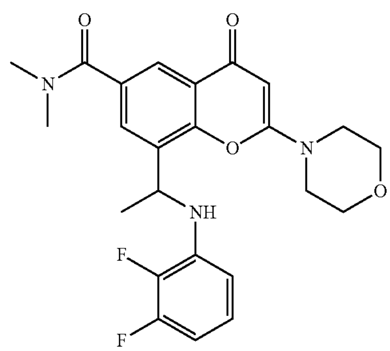 [SMILES: CC(Nc1cccc(F)c1F)c1cc(C(=O)N(C)C)cc2c(=O)cc(N3CCOCC3)oc12] | 2,3-difluoroaniline | 8-(1-(2,3-difluorophenylamino)ethyl)-N,N-dimethyl-2-morpholino-4-oxo-4H-chromene-6-carboxamide | 0.059 | 43.0 | 458 |
| 3.11 | 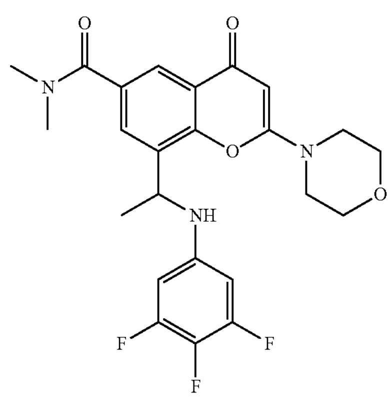 [SMILES: CC(Nc1cc(F)c(F)c(F)c1)c1cc(C(=O)N(C)C)cc2c(=O)cc(N3CCOCC3)oc12] | 3,4,5-trifluoroaniline | N,N-dimethyl-2-morpholino-4-oxo-8-(1-(3,4,5-trifluorophenylamino)ethyl)-4H-chromene-6-carboxamide | 0.074 | 51.9 | 476 |
| 3.12 | 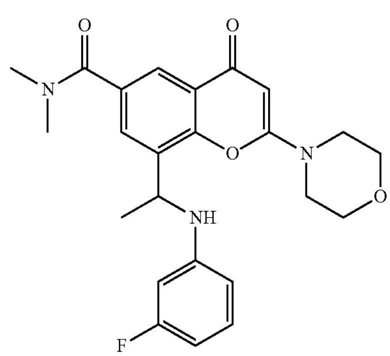 [SMILES: CC(Nc1cccc(F)c1)c1cc(C(=O)N(C)C)cc2c(=O)cc(N3CCOCC3)oc12] | 3-fluoroaniline | 8-(1-(3-fluorophenylamino)ethyl)-N,N-dimethyl-2-morpholino-4-oxo-4H-chromene-6-carboxamide | 0.094 | 71.3 | 440 |

TABLE I-continued

| Ex. | Structure | Reagent Name | Product | Product Mass (g) | Yield (%) | MH+ |
|---|---|---|---|---|---|---|
| 3.13 | 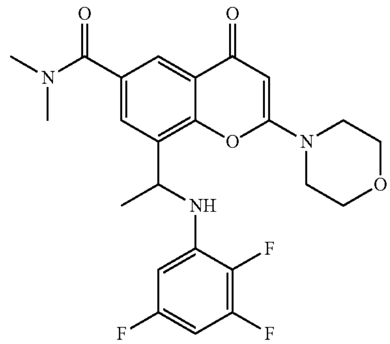 [SMILES: CC(Nc1cc(F)cc(F)c1F)c1cc(C(=O)N(C)C)cc2c(=O)cc(N3CCOCC3)oc12] | 2,3,5-trifluoroaniline | N,N-dimethyl-2-morpholine-4-oxo-8-(1-(2,3,5-trifluorophenylamino)ethyl)-4H-chromene-6-carboxamide | 0.049 | 74 | 476 |

Notes
Further characterising data for the products is given below.

EXAMPLE 3.09

NMR Spectrum: (CDCl$_3$) 1.62 (d, 3H), 2.85 (s, 3H), 3.06 (s, 3H), 3.42-3.55 (m, 4H), 3.76-3.77 (m, 4H), 4.14 (d, 1H), 4.90-5.00 (m, 1H), 5.54 (s, 1H), 6.34 (dd, 1H), 6.45 (dd, 1H), 6.64 (dd, 1H), 7.01 (dd, 1H), 7.71 (d, 1H), 8.12 (d, 1H).

EXAMPLE 3.10

NMR Spectrum: (CDCl$_3$) 1.67 (d, 3H), 2.86 (s, 3H), 3.07 (s, 3H), 3.44-3.57 (m, 4H), 3.79-3.88 (m, 4H), 4.38 (bs, 1H), 4.94-5.02 (m, 1H), 5.55 (s, 1H), 6.08 (dd, 1H), 6.48 (dd, 1H), 6.74 (dd, 1H), 7.71 (d, 1H), 8.12 (d, 1H).

EXAMPLE 3.11

NMR Spectrum: (CDCl$_3$) 1.56 (d, 3H), 2.91 (s, 3H), 3.07 (s, 3H), 3.45-3.59 (m, 4H), 3.78-3.92 (m, 4H), 4.39 (d, 1H), 4.77-4.88 (m, 1H), 5.55 (s, 1H), 6.01 (dd, 2H), 7.70 (d, 1H), 8.12 (d, 1H).

EXAMPLE 3.12

NMR Spectrum: (CDCl$_3$) 1.60 (d, 3H), 2.85 (s, 3H), 3.06 (s, 3H), 3.45-3.55 (m, 4H), 3.76-3.87 (m, 4H), 4.22 (d, 1H), 4.89-4.99 (m, 1H), 5.55 (s, 1H), 6.13 (ddd, 1H), 6.26 (dd, 1H), 6.36 (ddd, 1H), 7.04 (dd, 1H), 7.73 (d, 1H), 8.11 (d, 1H).

EXAMPLE 3.13

NMR Spectrum: (CDCl$_3$): 1.67 (d, 3H), 2.92 (s, 3H), 3.09 (s, 3H), 3.46-3.58 (m, 4H), 3.81-3.90 (m, 4H), 4.53 (bs, 1H), 4.88-4.96 (m, 1H), 5.56 (s, 1H), 5.80-5.88 (m, 1H), 6.17-6.27 (m, 1H), 7.71 (d, 1H), 8.13 (d, 1H).

A larger batch of this compound was prepared and the enantiomers separated as follows:

| | |
|---|---|
| Instrument | Kronlab |
| Column | Amicon 100 mm Chiralpak IC 20 µm |
| Eluent | DCM/EtOH/HOAc/TEA 50/50/0.2/0.1 |
| Oven Temperature | Ambient |
| Flow | 350 ml/min |
| Wavelength | 254 nm |
| Sample Conc | 4.0 g/100 ml in DCM/EtOH 50/50 |
| Injection volume | 50 mL |
| Run Time | 20 min |

4.2 g of the compound of Example 3.13 was chromatographed in 2 injections using the above conditions. Each enantiomer was dissolved in MeOH and added onto an SCX column. The column was flushed with MeOH then the product eluted with 7M ammonia in MeOH. The solvents were evaporated, giving a glass which was slurried with MTBE (75 mL) for 48 hrs until it had all turned into a white powdery solid. This was collected by filtration, washed with MTBE and dried under vacuum at 50° C.

First eluted enantiomer: 2.0 g isolated $[\alpha]^D_{20°}$: +50° in DCM (enantiomer 1) Example 3.13a.

Second eluted enantiomer: 1.9 g isolated $[\alpha]^D_{20°}$: −50° in DCM (enantiomer 2) Example 3.13b.

The Second eluting enantiomer (Example 3.13b) was crystallized in DCM, before drying under ambient conditions to yield Form A material. This form was determined to be crystalline by XRPD (see Figure E) and had the following characteristic X-Ray Powder Diffraction peaks:

| Angle 2-Theta (2θ) | Intensity % |
|---|---|
| 20.0 | 100.0 |
| 18.0 | 80.2 |
| 14.0 | 62.0 |
| 19.4 | 51.8 |
| 23.2 | 29.7 |
| 23.8 | 29.4 |
| 10.8 | 28.4 |
| 19.1 | 28.2 |
| 11.2 | 24.4 |
| 27.8 | 21.8 |

DSC analysis of Form A was also carried out (Figure F) and showed that this material had a melting point of 156.0° C. (onset).

Form B material was produced by slurrying Form A material in a water/methanol mixture. Approximately 20 mg of the original material was placed in a vial with a magnetic flea, and approximately 100 mcL of methanol and 2 mL of water added, the vial was then sealed tightly with a cap and left to stir on a magnetic stirrer plate. After 3 days, the sample was removed from the plate, the cap taken off and the slurry left to dry under ambient conditions before it was analysed by XRPD and DSC. This form (Form B) was determined to be crystalline by XRPD (Figure G) and seen to be different to Form A. The form had the following characteristic X-Ray Powder Diffraction peaks:

| Angle 2-Theta (2θ) | Intensity % |
|---|---|
| 6.2 | 100.0 |
| 7.0 | 20.4 |
| 10.3 | 10.0 |
| 22.4 | 8.3 |
| 15.9 | 7.7 |
| 20.4 | 7.5 |
| 27.2 | 6.9 |
| 12.4 | 6.6 |
| 18.7 | 6.3 |
| 12.8 | 6.3 |

This material had an onset of desolvation at 98.6° C. (onset) (see Figure H) and thermogravemetirc analysis showed the material to have a mass loss consistent with a 1:1 methanol solvate (Figure I).

EXAMPLE 3.14

8-(1-(3-chloro-5-fluorophenylamino)ethyl)-N,N-dimethyl-2-morpholino-4-oxo-4H-chromene-6-carboxamide

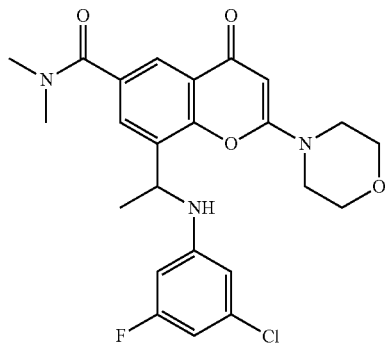

3-chloro-5-fluoroaniline (0.074 mL, 0.73 mmol) was reacted with 8-(1-bromoethyl)-N,N-dimethyl-2-morpholino-4-oxo-4H-chromene-6-carboxamide hydrobromide (0.09 g, 0.18 mmol)) using an analogous procedure to the one described in Example 3.03 to give 8-(1-(3-chloro-5-fluorophenylamino)ethyl)-N,N-dimethyl-2-morpholino-4-oxo-4H-chromene-6-carboxamide (0.065 g, 75%) as a white solid. Mass Spectrum: M+H+ 474. NMR Spectrum (CDCl₃): 1.61 (d, 3H), 2.90 (bs, 3H), 3.09 (bs, 3H), 3.46-3.55 (m, 4H), 3.80-3.88 (m, 4H), 4.35 (d, 1H), 4.88-4.96 (m, 1H), 5.56 (s, 1H), 6.03 (ddd, 1H), 6.27 (dd, 1H), 6.39 (ddd, 1H), 7.70 (d, 1H), 8.12 (d, 1H).

EXAMPLE 3.15

8-(1-(2,5-difluorophenylamino)ethyl)-N,N-dimethyl-2-morpholino-4-oxo-4H-chromene-6-carboxamide

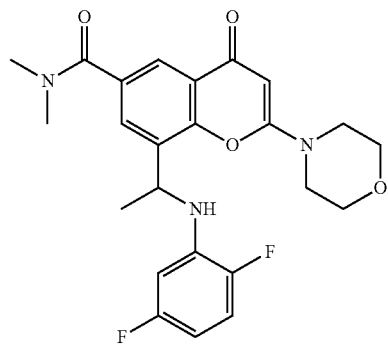 [SMILES: CC(Nc1cc(F)ccc1F)c1cc(C(=O)N(C)C)cc2c(=O)cc(N3CCOCC3)oc12]

2,5-difluoroaniline (0.074 mL, 0.73 mmol) was reacted with 8-(1-bromoethyl)-N,N-dimethyl-2-morpholino-4-oxo-4H-chromene-6-carboxamide hydrobromide (0.09 g, 0.18 mmol) using an analogous procedure to the one described in Example 3.03 to give 8-(1-(2,5-difluorophenylamino)ethyl)-N,N-dimethyl-2-morpholino-4-oxo-4H-chromene-6-carboxamide (0.055 g, 66%) as a white solid. Mass Spectrum: M+H+ 458. NMR Spectrum (DMSOd6): 1.57 (d, 3H), 2.72 (bs, 3H), 2.94 (bs, 3H), 3.51-3.64 (m, 4H), 3.71-3.78 (m, 4H), 5.02-5.11 (m, 1H), 5.61 (s, 1H), 6.19-1.33 (m, 2H), 6.43 (d, 1H), 7.01-7.09 (m, 1H), 7.60 (d, 1H), 7.79 (d, 1H).

EXAMPLE 3.16

8-(1-(3-fluoro-5-methylphenylamino)ethyl)-N,N-dimethyl-2-morpholino-4-oxo-4H-chromene-6-carboxamide

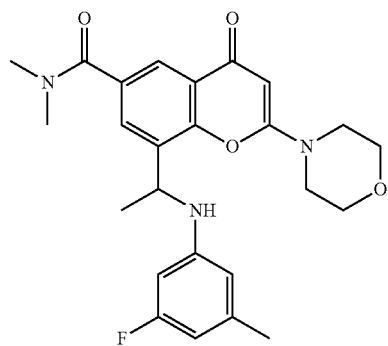

3-fluoro-5-methylaniline (0.091 mL, 0.82 mmol) was reacted with 8-(1-bromoethyl)-N,N-dimethyl-2-morpholino-4-oxo-4H-chromene-6-carboxamide hydrobromide (0.1 g, 0.20 mmol) using an analogous procedure to the one described in Example 3.03 to give 8-(1-(3-fluoro-5-methylphenylamino)ethyl)-N,N-dimethyl-2-morpholino-4-oxo-4H-chromene-6-carboxamide (0.053 g, 57%) as a white solid. Mass Spectrum: M+H+ 454.

NMR Spectrum (CDCl₃): 1.60 (d, 3H), 2.20 (s, 3H), 2.87 (bs, 3H), 3.07 (bs, 3H), 3.45-3.54 (m, 4H), 3.79-3.85 (m, 4H), 4.11 (d, 1H), 4.90-4.97 (m, 1H), 5.55 (s, 1H), 5.92 (ddd, 1H), 6.12 (s, 1H), 6.20 (d, 1H), 7.73 (d, 1H), 8.12 (d, 1H).

EXAMPLE 3.17

8-(1-(3-cyano-5-fluorophenylamino)ethyl)-N,N-dimethyl-2-morpholino-4-oxo-4H-chromene-6-carboxamide

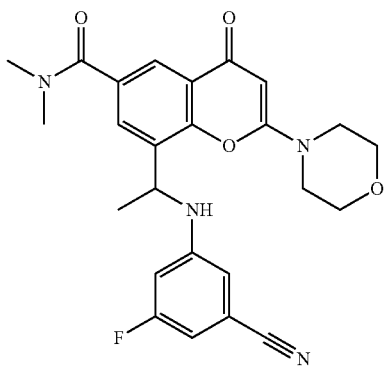

3-amino-5-fluorobenzonitrile (0.111 g, 0.82 mmol) was reacted with 8-(1-bromoethyl)-N,N-dimethyl-2-morpholino-4-oxo-4H-chromene-6-carboxamide hydrobromide (0.1 g, 0.20 mmol) using an analogous procedure to the one described in Example 3.03 to give 8-(1-(3-cyano-5-fluorophenylamino)ethyl)-N,N-dimethyl-2-morpholino-4-oxo-4H-chromene-6-carboxamide (0.052 g, 55%) as a white solid. Mass Spectrum: M+H⁺ 465.

NMR Spectrum (CDCl₃): 1.62 (d, 3H), 2.92 (bs, 3H), 3.08 (bs, 3H), 3.45-3.58 (m, 4H), 3.82-3.91 (m, 4H), 4.61 (d, 1H), 4.88-4.97 (m, 1H), 5.57 (s, 1H), 6.36 (ddd, 1H), 6.49 (dd, 1H), 6.65 (ddd, 1H), 7.70 (d, 1H), 8.14 (d, 1H).

EXAMPLE 3.18

8-(1-(3-cyanophenylamino)ethyl)-N,N-dimethyl-2-morpholino-4-oxo-4H-chromene-6-carboxamide

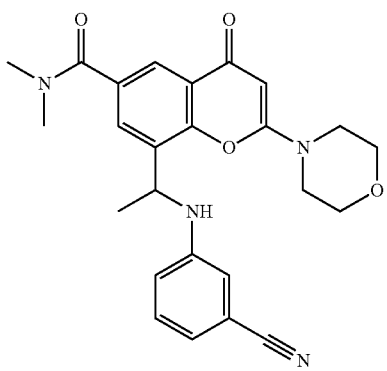

3-aminobenzonitrile (96 mg, 0.82 mmol) was reacted with 8-(1-bromoethyl)-N,N-dimethyl-2-morpholino-4-oxo-4H-chromene-6-carboxamide hydrobromide (0.1 g, 0.20 mmol) using an analogous procedure to the one described in Example 3.03 to give 8-(1-(3-cyanophenylamino)ethyl)-N,N-dimethyl-2-morpholino-4-oxo-4H-chromene-6-carboxamide (44 mg, 48%) as a white solid. Mass Spectrum: M+H⁺ 447.

NMR Spectrum (CDCl₃): 1.63 (d, 3H), 2.88 (bs, 3H), 3.07 (bs, 3H), 3.45-3.58 (m, 4H), 3.81-3.88 (m, 4H), 4.35 (d, 1H), 4.91-4.99 (m, 1H), 5.57 (s, 1H), 6.64 (s, 1H), 6.70 (dd, 1H), 6.96 (d, 1H), 7.19 (dd, 1H), 7.71 (d, 1H), 8.13 (d, 1H).

EXAMPLE 3.19

8-(1-(2,3-dichlorophenylamino)ethyl)-N,N-dimethyl-2-morpholino-4-oxo-4H-chromene-6-carboxamide

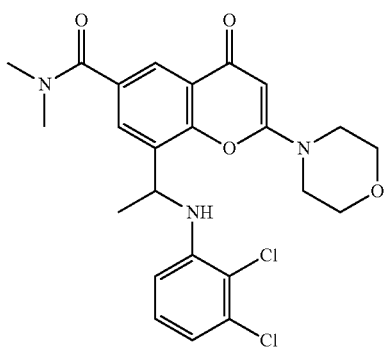

2,3-dichloroaniline (0.097 mL, 0.82 mmol) was reacted with 8-(1-bromoethyl)-N,N-dimethyl-2-morpholino-4-oxo-4H-chromene-6-carboxamide hydrobromide (0.1 g, 0.20 mmol) using an analogous procedure to the one described in Example 3.03 to give 8-(1-(2,3-dichlorophenylamino)ethyl)-N,N-dimethyl-2-morpholino-4-oxo-4H-chromene-6-carboxamide (51 mg, 51%) as a white solid. Mass Spectrum: M+H⁺ 490.

NMR Spectrum (CDCl₃): 1.69 (d, 3H), 2.85 (s, 3H), 3.07 (s, 3H), 3.47-3.56 (m, 4H), 3.79-3.88 (m, 4H), 4.86 (d, 1H), 4.93-5.02 (m, 1H), 5.56 (s, 1H), 6.19 (d, 1H), 6.78 (dd, 1H), 6.89 (dd, 1H), 7.66 (d, 1H), 8.12 (d, 1H).

EXAMPLE 3.20

8-(1-(3-ethynylphenylamino)ethyl)-N,N-dimethyl-2-morpholino-4-oxo-4H-chromene-6-carboxamide

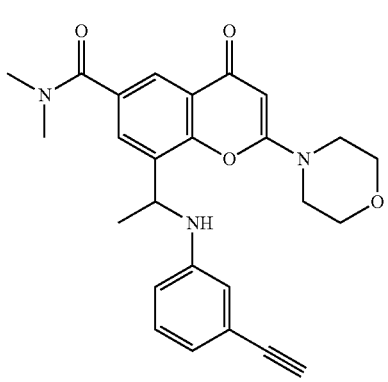

3-ethynylaniline (0.083 mL, 0.73 mmol) was reacted with 8-(1-bromoethyl)-N,N-dimethyl-2-morpholino-4-oxo-4H-chromene-6-carboxamide hydrobromide (0.09 g, 0.18 mmol) using an analogous procedure to the one described in Example 3.03 to give 8-(1-(3-ethynylphenylamino)ethyl)-N,N-dimethyl-2-morpholino-4-oxo-4H-chromene-6-carboxamide (52 mg, 64%) as a white solid. Mass Spectrum: M+H$^+$ 446.

NMR Spectrum (DMSOd6): 1.52 (d, 3H), 2.68 (bs, 3H), 2.93 (bs, 3H), 3.50-3.64 (m, 4H), 3.69-3.79 (m, 4H), 3.99 (s, 1H), 4.98-5.06 (m, 1H), 5.60 (s, 1H), 6.46-6.54 (m, 2H), 6.57-6.63 (m, 2H), 7.00 (dd, 1H), 7.56 (d, 1H), 7.78 (d, 1H).

EXAMPLE 3.21

8-(1-(5-cyano-2-methylphenylamino)ethyl)-N,N-dimethyl-2-morpholino-4-oxo-4H-chromene-6-carboxamide

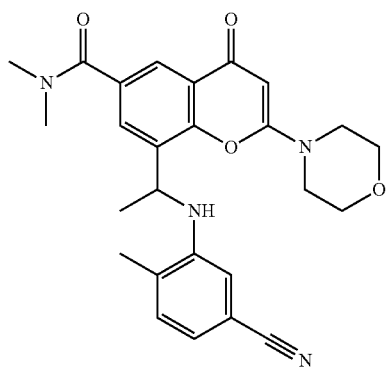 [SMILES: Cc1ccc(C#N)cc1NC(C)c1cc(C(=O)N(C)C)cc2c(=O)cc(N3CCOCC3)oc12]

3-amino-4-methylbenzonitrile (108 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(5-cyano-2-methylphenylamino)ethyl)-N,N-dimethyl-2-morpholino-4-oxo-4H-chromene-6-carboxamide (50 mg, 53%) as a white solid. Mass Spectrum: M+H$^+$ 461.

NMR Spectrum (DMSOd6): 1.62 (d, 3H), 2.30 (s, 3H), 2.69 (bs, 3H), 2.93 (bs, 3H), 3.51-3.64 (m, 4H), 3.70-3.80 (m, 4H), 5.00-5.08 (m, 1H), 5.56 (d, 1H), 5.61 (s, 1H), 5.96 (dd, 1H), 6.24 (ddd, 1H), 6.96 (dd, 1H), 7.58 (d, 1H), 7.79 (d, 1H).

EXAMPLE 3.22

8-(1-(5-fluoro-2-methylphenylamino)ethyl)-N,N-dimethyl-2-morpholino-4-oxo-4H-chromene-6-carboxamide

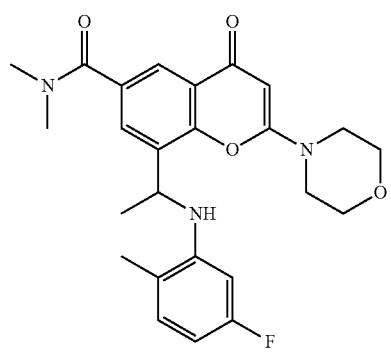 [SMILES: Cc1ccc(F)cc1NC(C)c1cc(C(=O)N(C)C)cc2c(=O)cc(N3CCOCC3)oc12]

5-fluoro-2-methylaniline (102 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(5-fluoro-2-methylphenylamino)ethyl)-N,N-dimethyl-2-morpholino-4-oxo-4H-chromene-6-carboxamide (56 mg, 61%) as a white solid. Mass Spectrum: M+H$^+$ 454. NMR Spectrum (DMSOd6): 1.60 (d, 3H), 2.20 (s, 3H), 2.69 (bs, 3H), 2.93 (bs, 3H), 3.53-3.65 (m, 4H), 3.72-3.80 (m, 4H), 5.08-5.18 (m, 1H), 5.62 (s, 1H), 5.73 (d, 1H), 6.52 (d, 1H), 6.92 (dd, 1H), 7.18 (dd, 1H), 7.58 (d, 1H), 7.80 (d, 1H).

EXAMPLE 3.23

8-(1-(3-cyano-5-methylphenylamino)ethyl)-N,N-dimethyl-2-morpholino-4-oxo-4H-chromene-6-carboxamide

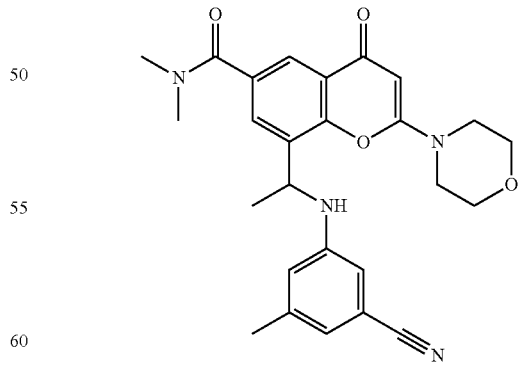

3-amino-5-methylbenzonitrile (108 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure similar to the one described in Example 3.03 to give 8-(1-(3-cyano-5-methylphenylamino)ethyl)-N,N-dimethyl-2-morpholino-4-oxo-4H-chromene-6-carboxamide (45 mg, 48%) as a white solid. Mass Spectrum: M+H⁺ 461.

NMR Spectrum (DMSOd6): 1.53 (d, 3H), 2.16 (s, 3H), 2.71 (bs, 3H), 2.94 (bs, 3H), 3.51-3.64 (m, 4H), 3.69-3.80 (m, 4H), 5.00-5.10 (m, 1H), 5.61 (s, 1H), 6.60 (s, 1H), 6.67 (s, 1H), 6.73 (d, 1H), 6.74 (s, 1H), 7.54 (d, 1H), 7.79 (d, 1H).

EXAMPLE 3.24

8-(1-(5-fluoro-2-methoxyphenylamino)ethyl)-N,N-dimethyl-2-morpholino-4-oxo-4H-chromene-6-carboxamide

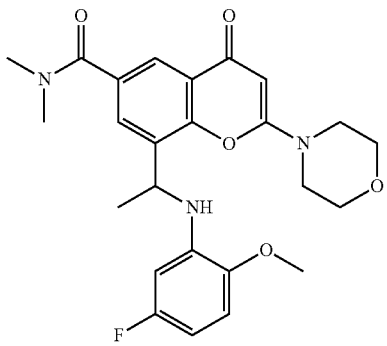 [SMILES: COc1ccc(F)cc1NC(C)c1cc(C(=O)N(C)C)cc2c(=O)cc(N3CCOCC3)oc12]

5-fluoro-2-methoxyaniline (115 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(5-fluoro-2-methoxyphenylamino)ethyl)-N,N-dimethyl-2-morpholino-4-oxo-4H-chromene-6-carboxamide (54 mg, 56%) as a white solid. Mass Spectrum: M+H⁺ 470. NMR Spectrum (DMSOd6): 1.58 (d, 3H), 2.71 (bs, 3H), 2.94 (bs, 3H), 3.51-3.64 (m, 4H), 3.70-3.78 (m, 4H), 3.82 (s, 3H), 4.97-5.06 (m, 1H), 5.61 (s, 1H), 6.60 (s, 1H), 6.67 (s, 1H), 6.73 (d, 1H), 6.74 (s, 1H), 7.54 (d, 1H), 7.79 (d, 1H).

EXAMPLE 3.25

8-(1-(5-cyano-2-methoxyphenylamino)ethyl)-N,N-dimethyl-2-morpholino-4-oxo-4H-chromene-6-carboxamide

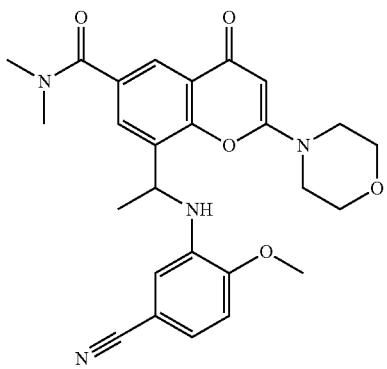 [SMILES: COc1ccc(C#N)cc1NC(C)c1cc(C(=O)N(C)C)cc2c(=O)cc(N3CCOCC3)oc12]

3-amino-4-methoxybenzonitrile (121 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(5-cyano-2-methoxyphenylamino)ethyl)-N,N-dimethyl-2-morpholino-4-oxo-4H-chromene-6-carboxamide (50 mg, 51%) as a white solid. Mass Spectrum: M+H⁺ 477.

NMR Spectrum (DMSOd6): 1.60 (d, 3H), 2.72 (bs, 3H), 2.94 (bs, 3H), 3.51-3.65 (m, 4H), 3.71-3.80 (m, 4H), 3.92 (s, 3H), 5.05-5.13 (m, 1H), 5.61 (s, 1H), 5.86 (d, 1H), 6.57 (d, 1H), 6.98 (d, 1H), 7.03 (dd, 1H), 7.57 (d, 1H), 7.79 (d, 1H).

EXAMPLE 3.26

8-(1-(2-chloro-5-fluorophenylamino)ethyl)-N,N-dimethyl-2-morpholino-4-oxo-4H-chromene-6-carboxamide

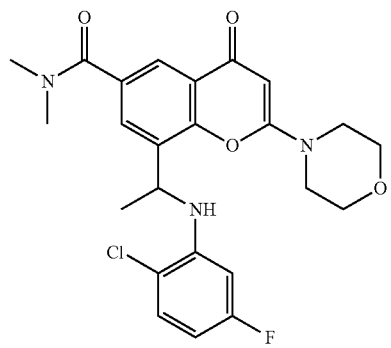 [SMILES: CC(Nc1cc(F)ccc1Cl)c1cc(C(=O)N(C)C)cc2c(=O)cc(N3CCOCC3)oc12]

2-chloro-5-fluoroaniline (119 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(2-chloro-5-fluorophenylamino)ethyl)-N,N-dimethyl-2-morpholino-4-oxo-4H-chromene-6-carboxamide (45 mg, 47%) as a white solid. Mass Spectrum: M+H⁺ 474. NMR Spectrum (DMSOd6): 1.62 (d, 3H), 2.74 (bs, 3H), 2.94 (bs, 3H), 3.51-3.65 (m, 4H), 3.69-3.79 (m, 4H), 5.06-5.16 (m, 1H), 5.61 (s, 1H), 5.99 (d, 1H), 6.27 (dd, 1H), 6.40 (ddd, 1H), 7.30 (dd, 1H), 7.59 (d, 1H), 7.80 (d, 1H).

EXAMPLE 3.27

N,N-dimethyl-2-morpholino-4-oxo-8-(1-(2,3,6-trifluorophenylamino)ethyl)-4H-chromene-6-carboxamide

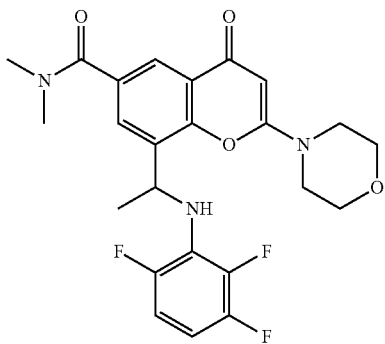

2,3,6-trifluoroaniline (0.086 mL, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give N,N-dimethyl-2-morpholino-4-oxo-8-(1-(2,3,6-trifluorophenylamino)ethyl)-4H-chromene-6-carboxamide (42 mg, 43%) as a white solid. Mass Spectrum: M+H+ 476. NMR Spectrum (DMSOd6): 1.56 (d, 3H), 2.75 (bs, 3H), 2.97 (bs, 3H), 3.50-3.59 (m, 4H), 3.69-3.80 (m, 4H), 5.38-5.47 (m, 1H), 5.57 (s, 1H), 6.05 (d, 1H), 6.60-6.70 (m, 1H), 6.86-6.96 (m, 1H), 7.73 (d, 1H), 7.76 (d, 1H).

EXAMPLE 3.28

8-(1-(5-chloro-2-methylphenylamino)ethyl)-N,N-dimethyl-2-morpholino-4-oxo-4H-chromene-6-carboxamide

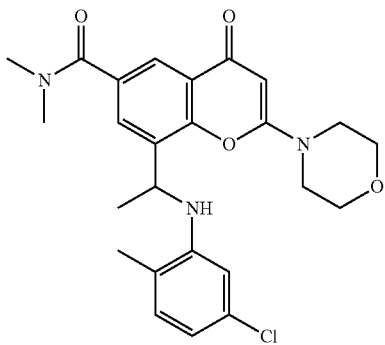 [SMILES: Cc1ccc(Cl)cc1NC(C)c1cc(C(=O)N(C)C)cc2c(=O)cc(N3CCOCC3)oc12]

5-chloro-2-methylaniline (0.098 mL, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(5-chloro-2-methylphenylamino)ethyl)-N,N-dimethyl-2-morpholino-4-oxo-4H-chromene-6-carboxamide (56 mg, 58%) as a white solid. Mass Spectrum: M+H+ 470. NMR Spectrum (DMSOd6): 1.61 (d, 3H), 2.21 (s, 3H), 2.71 (bs, 3H), 2.93 (bs, 3H), 3.52-3.65 (m, 4H), 3.70-3.80 (m, 4H), 5.03-5.11 (m, 1H), 5.55 (d, 1H), 5.62 (s, 1H), 6.19 (d, 1H), 6.49 (dd, 1H), 6.97 (d, 1H), 7.62 (d, 1H), 7.79 (d, 1H).

EXAMPLE 3.29

8-(1-(3-cyano-2-methylphenylamino)ethyl)-N,N-dimethyl-2-morpholino-4-oxo-4H-chromene-6-carboxamide

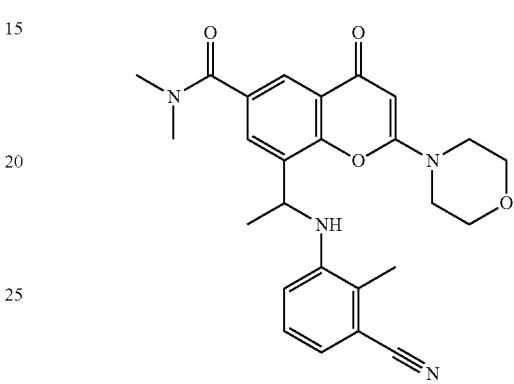

3-amino-2-methylbenzonitrile (108 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(3-cyano-2-methylphenylamino)ethyl)-N,N-dimethyl-2-morpholino-4-oxo-4H-chromene-6-carboxamide (52 mg, 55%) as a white solid. Mass Spectrum: M+H+ 461.

NMR Spectrum (DMSOd6): 1.61 (d, 3H), 2.45 (s, 3H), 2.65 (bs, 3H), 2.92 (bs, 3H), 3.50-3.64 (m, 4H), 3.70-3.79 (m, 4H), 5.05-5.14 (m, 1H), 5.61 (s, 1H), 5.81 (d, 1H), 6.46 (d, 1H), 6.92 (d, 1H), 7.02 (dd, 1H), 7.56 (d, 1H), 7.78 (d, 1H).

EXAMPLE 3.30

8-(1-(3-fluoro-5-methoxyphenylamino)ethyl)-N,N-dimethyl-2-morpholino-4-oxo-4H-chromene-6-carboxamide

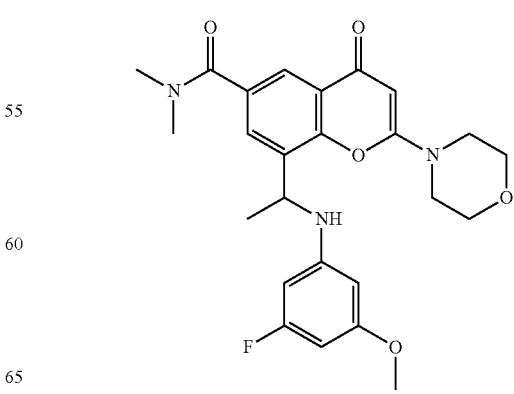

3-fluoro-5-methoxyaniline (115 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(3-fluoro-5-methoxyphenylamino)ethyl)-N,N-dimethyl-2-morpholino-4-oxo-4H-chromene-6-carboxamide (60 mg, 63%) as a white solid. Mass Spectrum: M+H$^+$ 470. NMR Spectrum (DMSOd6): 1.50 (d, 3H), 2.74 (bs, 3H), 2.94 (bs, 3H), 3.50-3.63 (m, 4H), 3.61 (s, 3H), 3.68-3.79 (m, 4H), 4.94-5.03 (m, 1H), 5.60 (s, 1H), 5.87 (dd, 1H), 5.88 (s, 1H), 5.93 (ddd, 1H), 6.63 (d, 1H), 7.57 (d, 1H), 7.79 (d, 1H).

EXAMPLE 3.31

8-(1-(3-fluoro-2-methoxyphenylamino)ethyl)-N,N-dimethyl-2-morpholino-4-oxo-4H-chromene-6-carboxamide

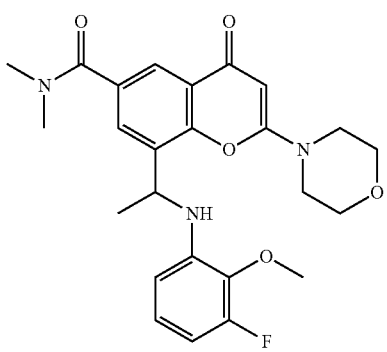 [SMILES: COc1c(F)cccc1NC(C)c1cc(C(=O)N(C)C)cc2c(=O)cc(N3CCOCC3)oc12]

3-fluoro-2-methoxyaniline (115 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(3-fluoro-2-methoxyphenylamino)ethyl)-N,N-dimethyl-2-morpholino-4-oxo-4H-chromene-6-carboxamide (57 mg, 60%) as a white solid. Mass Spectrum: M+H$^+$ 470. NMR Spectrum (DMSOd6): 1.59 (d, 3H), 2.70 (bs, 3H), 2.93 (bs, 3H), 3.50-3.63 (m, 4H), 3.71-3.79 (m, 4H), 3.83 (s, 3H), 5.02-5.11 (m, 1H), 5.60 (s, 1H), 5.95 (d, 1H), 6.11 (d, 1H), 6.39 (dd, 1H), 6.72 (ddd, 1H), 7.59 (d, 1H), 7.78 (d, 1H).

EXAMPLE 3.32

8-(1-(3-chloro-2,6-difluorophenylamino)ethyl)-N,N-dimethyl-2-morpholino-4-oxo-4H-chromene-6-carboxamide

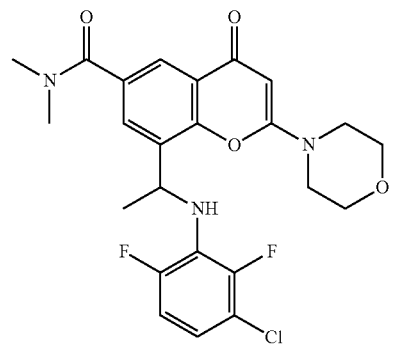 [SMILES: CC(Nc1c(F)ccc(Cl)c1F)c1cc(C(=O)N(C)C)cc2c(=O)cc(N3CCOCC3)oc12]

3-chloro-2,6-difluoroaniline (133 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(3-chloro-2,6-difluorophenylamino)ethyl)-N,N-dimethyl-2-morpholino-4-oxo-4H-chromene-6-carboxamide (47 mg, 47%) as a white solid. Mass Spectrum: M+H$^+$ 492. NMR Spectrum (DMSOd6): 1.56 (d, 3H), 2.74 (bs, 3H), 2.97 (bs, 3H), 3.50-3.58 (m, 4H), 3.70-3.80 (m, 4H), 5.37-5.46 (m, 1H), 5.57 (s, 1H), 5.99 (d, 1H), 6.81 (ddd, 1H), 6.94 (ddd, 1H), 7.72 (d, 1H), 7.76 (d, 1H).

EXAMPLE 3.33

8-(1-(3,5-dichlorophenylamino)ethyl)-N,N-dimethyl-2-morpholino-4-oxo-4H-chromene-6-carboxamide

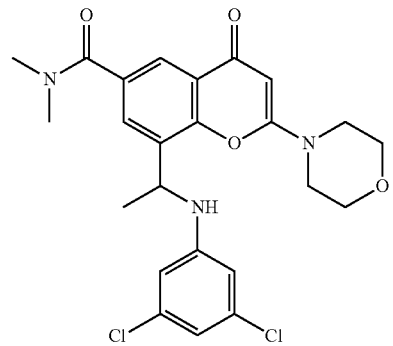 [SMILES: CC(Nc1cc(Cl)cc(Cl)c1)c1cc(C(=O)N(C)C)cc2c(=O)cc(N3CCOCC3)oc12]

3,5-dichloroaniline (132 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(3,5-dichlorophenylamino)ethyl)-

N,N-dimethyl-2-morpholino-4-oxo-4H-chromene-6-carboxamide (75 mg, 75%) as a white solid. Mass Spectrum: M+H⁺ 490. NMR Spectrum (DMSOd6): 1.52 (d, 3H), 2.75 (bs, 3H), 2.95 (bs, 3H), 3.51-3.63 (m, 4H), 3.70-3.78 (m, 4H), 5.01-5.09 (m, 1H), 5.61 (s, 1H), 6.50 (s, 2H), 6.61 (s, 1H), 6.91 (d, 1H), 7.54 (d, 1H), 7.81 (d, 1H)

EXAMPLE 3.34

8-(1-(3-ethynyl-5-fluorophenylamino)ethyl)-N,N-dimethyl-2-morpholino-4-oxo-4H-chromene-6-carboxamide

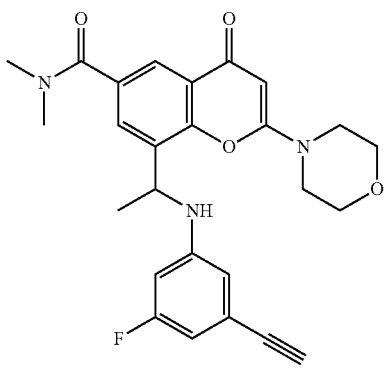 [SMILES: C#Cc1cc(F)cc(NC(C)c2cc(C(=O)N(C)C)cc3c(=O)cc(N4CCOCC4)oc23)c1]

3-ethynyl-5-fluoroaniline (165 mg, 1.22 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(3-ethynyl-5-fluorophenylamino)ethyl)-N,N-dimethyl-2-morpholino-4-oxo-4H-chromene-6-carboxamide (80 mg, 56%) as a white solid. Mass Spectrum: M+H⁺ 464. NMR Spectrum (DMSOd6): 1.52 (d, 3H), 2.72 (bs, 3H), 2.94 (bs, 3H), 3.50-3.63 (m, 4H), 3.69-3.78 (m, 4H), 4.12 (s, 1H), 4.98-5.07 (m, 1H), 5.66 (s, 1H), 6.31 (d, 1H), 6.40 (d, 1H), 6.46 (s, 1H), 6.81 (d, 1H), 7.54 (d, 1H), 7.80 (d, 1H).

EXAMPLE 3.35

8-(1-(2-cyano-5-fluorophenylamino)ethyl)-N,N-dimethyl-2-morpholino-4-oxo-4H-chromene-6-carboxamide

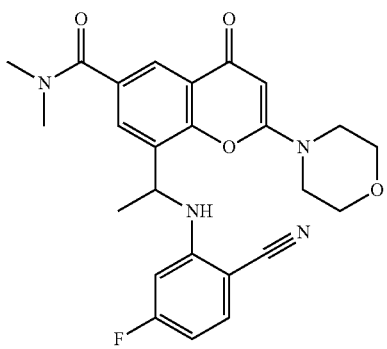 [SMILES: CC(Nc1cc(F)ccc1C#N)c1cc(C(=O)N(C)C)cc2c(=O)cc(N3CCOCC3)oc12]

2-amino-4-fluorobenzonitrile (111 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03 to give 8-(1-(2-cyano-5-fluorophenylamino)ethyl)-N,N-dimethyl-2-morpholino-4-oxo-4H-chromene-6-carboxamide (40 mg, 42%) as a white solid. Mass Spectrum: M+H⁺ 465.

NMR Spectrum (DMSOd6): 1.62 (d, 3H), 2.76 (bs, 3H), 2.96 (bs, 3H), 3.49-3.64 (m, 4H), 3.67-3.79 (m, 4H), 5.12-5.22 (m, 1H), 5.61 (s, 1H), 6.35 (dd, 1H), 6.52 (ddd, 1H), 6.88 (d, 1H), 7.61 (dd, 1H), 7.68 (d, 1H), 7.82 (d, 1H).

EXAMPLE 3.36

8-(1-(2-cyano-3-fluorophenylamino)ethyl)-N,N-dimethyl-2-morpholino-4-oxo-4H-chromene-6-carboxamide

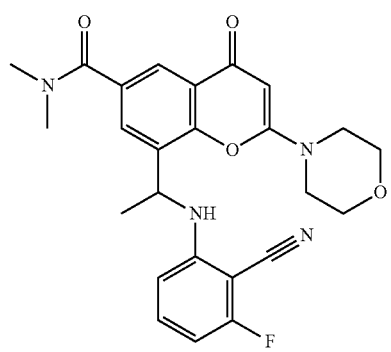 [SMILES: CC(Nc1cccc(F)c1C#N)c1cc(C(=O)N(C)C)cc2c(=O)cc(N3CCOCC3)oc12]

2-amino-6-fluorobenzonitrile (111 mg, 0.82 mmol) was reacted with 8-(1-bromoethyl)-N,N-dimethyl-2-morpholino-4-oxo-4H-chromene-6-carboxamide hydrobromide (100 mg, 0.20 mmol) using an analogous procedure to the one described in Example 3.03. The crude product was purified by flash chromatography on silica gel eluting with 0 to 10% MeOH in DCM. The solvent was evaporated to dryness. The resulting oil was crystallised from ethyl acetate to give 8-(1-(2-cyano-3-fluorophenylamino)ethyl)-N,N-dimethyl-2-morpholino-4-oxo-4H-chromene-6-carboxamide (45.0 mg, 64.3%) as a white solid. Mass Spectrum: M+H⁺ 465. NMR Spectrum (DMSOd6): 1.61 (d, 3H), 2.74 (bs, 3H), 2.95 (bs, 3H), 3.49-3.62 (m, 4H), 3.69-3.77 (m, 4H), 5.17-5.26 (m, 1H), 5.61 (s, 1H), 6.33 (d, 1H), 6.56 (dd, 1H), 6.99 (d, 1H), 7.32 (dd, 1H), 7.69 (d, 1H), 7.81 (d, 1H).

EXAMPLE 3.37

8-(1-((3-chloro-5-fluorophenyl)(methyl)amino) ethyl)-N,N-dimethyl-2-morpholino-4-oxo-4H-chromene-6-carboxamide

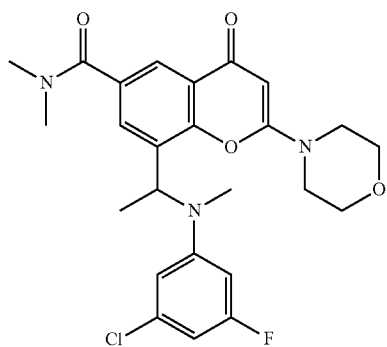 [SMILES: CC(c1cc(C(=O)N(C)C)cc2c(=O)cc(N3CCOCC3)oc12)N(C)c1cc(F)cc(Cl)c1]

3-chloro-5-fluoro-N-methylaniline (195 mg, 1.22 mmol) was reacted with 8-(1-bromoethyl)-N,N-dimethyl-2-morpholino-4-oxo-4H-chromene-6-carboxamide hydrobromide (150 mg, 0.31 mmol) using an analogous procedure to the one described in Example 3.03 to give 8-(1-((3-chloro-5-fluorophenyl)(methyl)amino)ethyl)-N,N-dimethyl-2-morpholino-4-oxo-4H-chromene-6-carboxamide (38 mg, 25%) as a white solid. Mass Spectrum: M+H⁺ 488. NMR Spectrum (DMSOd6): 1.55 (d, 3H), 2.61 (s, 3H), 2.93 (bs, 3H), 3.01 (bs, 3H), 3.20-3.27 (m, 2H), 3.33-3.37 (m partially hidden by H2O, 2H), 3.42-3.48 (m, 2H), 3.49-3.55 (m, 2H), 5.55 (s, 1H), 5.61 (q, 1H), 6.61 (d, 1H), 6.66 (d, 1H), 6.75 (s, 1H), 7.71 (d, 1H), 7.89 (d, 1H).

EXAMPLE 3.38

N,N-dimethyl-8-(1-(methyl(3,4,5-trifluorophenyl) amino)ethyl)-2-morpholino-4-oxo-4H-chromene-6-carboxamide

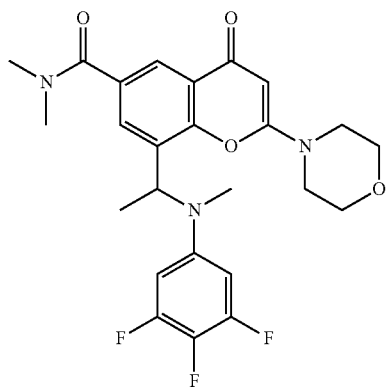 [SMILES: CC(c1cc(C(=O)N(C)C)cc2c(=O)cc(N3CCOCC3)oc12)N(C)c1cc(F)c(F)c(F)c1]

3,4,5-trifluoro-N-methylaniline (197 mg, 1.22 mmol) was reacted with 8-(1-bromoethyl)-N,N-dimethyl-2-morpholino-4-oxo-4H-chromene-6-carboxamide hydrobromide (150 mg, 0.31 mmol) using an analogous procedure to the one described in Example 3.03 to give N,N-dimethyl-8-(1-(methyl(3,4,5-trifluorophenyl)amino)ethyl)-2-morpholino-4-oxo-4H-chromene-6-carboxamide (54.0 mg, 36.1%) as a white solid. Mass Spectrum: M+H⁺ 490.

NMR Spectrum (DMSOd6): 1.54 (d, 3H), 2.62 (s, 3H), 2.91 (bs, 3H), 3.00 (bs, 3H), 3.24-3.31 (m partially hidden by H2O, 2H), 3.33-3.42 (m partially hidden by H2O, 2H), 3.45-3.52 (m, 2H), 3.52-3.60 (m, 2H), 5.55 q, 1H), 5.56 (s, 1H), 6.73 (d, 1H), 6.75 (d, 1H), 7.67 (d, 1H), 7.89 (d, 1H).

EXAMPLE 3.39

N,N-dimethyl-8-(1-(methyl(2,3,5-trifluorophenyl) amino)ethyl)-2-morpholino-4-oxo-4H-chromene-6-carboxamide

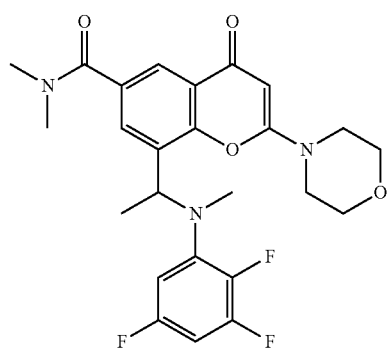 [SMILES: CC(c1cc(C(=O)N(C)C)cc2c(=O)cc(N3CCOCC3)oc12)N(C)c1cc(F)cc(F)c1F]

2,3,5-trifluoro-N-methylaniline (197 mg, 1.22 mmol) was reacted with 8-(1-bromoethyl)-N,N-dimethyl-2-morpholino-4-oxo-4H-chromene-6-carboxamide hydrobromide (150 mg, 0.31 mmol) using an analogous procedure to the one described in Example 3.03 to give N,N-dimethyl-8-(1-(methyl(2,3,5-trifluorophenyl)amino)ethyl)-2-morpholino-4-oxo-4H-chromene-6-carboxamide (12 mg, 8%) as a white solid. Mass Spectrum: M+H⁺ 490.

NMR Spectrum (DMSOd6): 1.63 (d, 3H), 2.67 (s, 3H), 2.92 (bs, 3H), 3.02 (bs, 3H), 3.18-3.26 (m, 2H), 3.22-3.37 (m partially hidden by H2O, 2H), 3.49-3.56 (m, 2H), 3.56-3.63

(m, 2H), 5.38 (q, 1H), 5.53 (s, 1H), 6.68-6.75 (m, 1H), 6.88-6.96 (m, 1H), 7.78 (d, 1H), 7.86 (d, 1H).

EXAMPLE 3.40

N,N-dimethyl-8-(1-(methyl(phenyl)amino)ethyl)-2-morpholino-4-oxo-4H-chromene-6-carboxamide

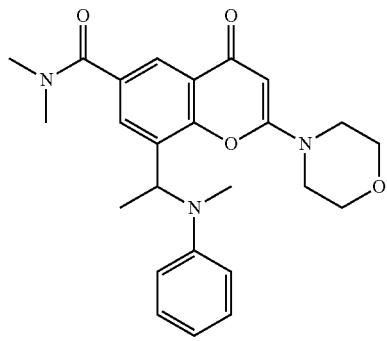 [SMILES: CC(c1cc(C(=O)N(C)C)cc2c(=O)cc(N3CCOCC3)oc12)N(C)c1ccccc1]

N-methylaniline (153 mg, 1.43 mmol) was reacted with 8-(1-bromoethyl)-N,N-dimethyl-2-morpholino-4-oxo-4H-chromene-6-carboxamide hydrobromide (175 mg, 0.36 mmol) using an analogous procedure to the one described in Example 3.03 to give N,N-dimethyl-8-(1-(methyl(phenyl)amino)ethyl)-2-morpholino-4-oxo-4H-chromene-6-carboxamide (57 mg, 37%) as a white solid. Mass Spectrum: M+H$^+$ 436. NMR Spectrum (DMSOd6): 1.57 (d, 3H), 2.65 (s, 3H), 2.90 (bs, 3H), 3.00 (bs, 3H), 3.16-3.22 (m, 2H), 3.23-3.31 (m partially hidden by H2O, 2H), 3.36-3.42 (m, 2H), 3.42-3.49 (m, 2H), 5.52 (s, 1H), 5.55 (q, 1H), 6.66 (t, 1H), 6.84 (d, 2H), 7.19 (t, 2H), 7.67 (d, 1H), 7.87 (d, 1H).

EXAMPLE 3.41

8-(1-((3-ethynyl-5-fluorophenyl)(methyl)amino)ethyl)-N,N-dimethyl-2-morpholino-4-oxo-4H-chromene-6-carboxamide

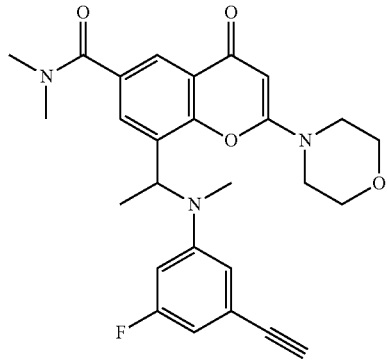 [SMILES: C#Cc1cc(F)cc(N(C)C(C)c2cc(C(=O)N(C)C)cc3c(=O)cc(N4CCOCC4)oc23)c1]

8-(1-bromoethyl)-N,N-dimethyl-2-morpholino-4-oxo-4H-chromene-6-carboxamide (185 mg, 0.37 mmol), N,N-diethylaniline (174 µl, 1.10 mmol) and 3-ethynyl-5-fluoro-N-methylaniline (60 mg, 0.40 mmol) in DMF (1043 µl) were stirred at 50° C. for 2 days. Purification was done using an analogous procedure to the one described in Example 3.03 to give 8-(1-((3-ethynyl-5-fluorophenyl)(methyl)amino)ethyl)-N,N-dimethyl-2-morpholino-4-oxo-4H-chromene-6-carboxamide (60 mg, 34%) as a white solid. Mass Spectrum: M+H$^+$ 478. NMR Spectrum (DMSOd6): 1.55 (d, 3H), 2.62 (s, 3H), 2.92 (bs, 3H), 3.01 (bs, 3H), 3.18-3.27 (m, 2H), 3.28-3.33 (m partially hidden by H2O, 2H), 3.40-3.48 (m, 2H), 3.48-3.57 (m, 2H), 4.21 (s, 1H), 5.54 (q, 1H), 5.62 (s, 1H), 6.52 (d, 1H), 6.73 (d, 1H), 6.80 (s, 1H), 7.72 (d, 1H), 7.89 (d, 1H).

EXAMPLES 4.01-4.26

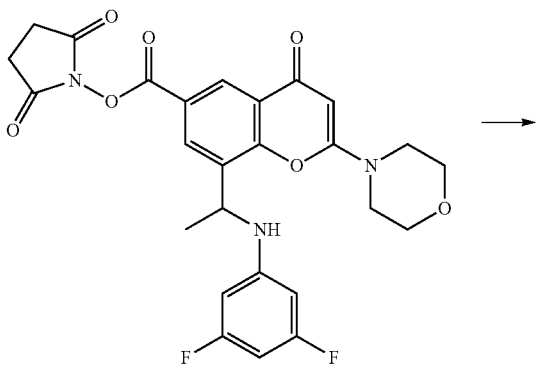

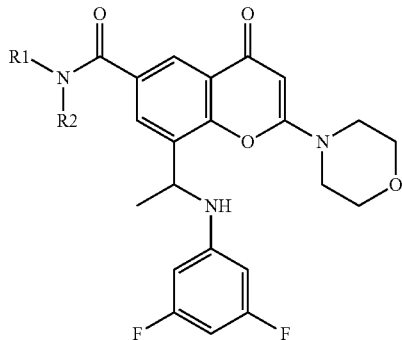

0.17 mmole of a previously prepared solution of 2,5-dioxopyrrolidin-1-yl 8-(1-(3,5-difluorophenylamino)ethyl)-2-morpholino-4-oxo-4H-chromene-6-carboxylate was introduced into 26 vials, each containing the appropriate amine (0.51 mmol) for each Example compound (as shown under the column named 'Reagent Name' in Table II). The resulting solution was stirred at 35° C. for 2 hrs, concentrated to dryness and diluted with DMF (1.5 mL). The reaction mixture was purified by preparative HPLC using a Waters X-Bridge reverse-phase column (C-18, 5 microns silica, 19 mm diameter, 100 mm length, flow rate of 40 mL/minute) and decreasingly polar mixtures of water (containing 0.2% ammonium carbonate) and acetonitrile as eluent. The fractions containing the desired compound were evaporated to dryness to afford the desired product.

TABLE II

| EX. | Structure | Reagent Name | Product | Product Mass (g) | Yield (%) | MH+ |
|---|---|---|---|---|---|---|
| 4.01 | 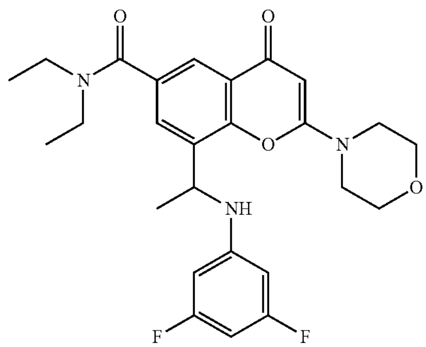 [SMILES: CCN(CC)C(=O)c1cc(C(C)Nc2cc(F)cc(F)c2)c2oc(N3CCOCC3)cc(=O)c2c1] | diethylamine | 8-(1-(3,5-difluorophenylamino)ethyl)-N,N-diethyl-2-morpholino-4-oxo-4H-chromene-6-carboxamide | 46 | 56.2 | 486 |
| 4.02 | 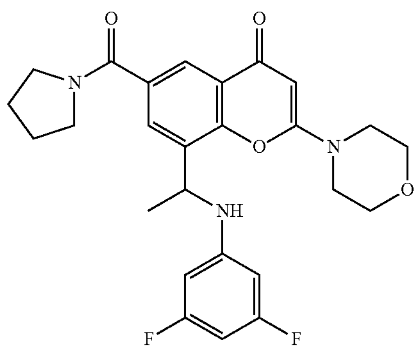 [SMILES: CC(Nc1cc(F)cc(F)c1)c1cc(C(=O)N2CCCC2)cc2c(=O)cc(N3CCOCC3)oc12] | pyrrolidine | 8-(1-(3,5-difluorophenylamino)ethyl)-2-morpholino-6-(pyrrolidine-1-carbonyl)-4H-chromen-4-one | 54 | 65.1 | 484 |
| 4.03 | 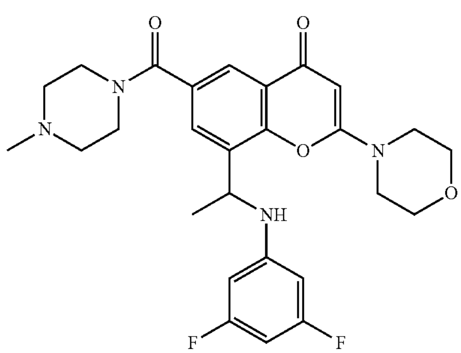 [SMILES: CC(Nc1cc(F)cc(F)c1)c1cc(C(=O)N2CCN(C)CC2)cc2c(=O)cc(N3CCOCC3)oc12] | 1-methyl piperazine | 8-(1-(3,5-difluorophenylamino)ethyl)-6-(4-methylpiperazine-1-carbonyl)-2-morpholino-4H-chromen-4-one | 60 | 68.3 | 513 |
| 4.04 | 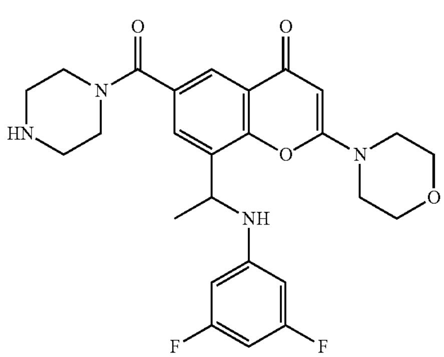 [SMILES: CC(Nc1cc(F)cc(F)c1)c1cc(C(=O)N2CCNCC2)cc2c(=O)cc(N3CCOCC3)oc12] | tert-butyl piperazine-1-carboxylate (2 steps) | 8-(1-(3,5-difluorophenylamino)ethyl)-2-morpholino-6-(piperazine-1-carbonyl)-4H-chromen-4-one | 39 | 46.0 | 499 |

TABLE II-continued

| EX. | Structure | Reagent Name | Product | Product Mass (g) | Yield (%) | MH+ |
|---|---|---|---|---|---|---|
| 4.05 | 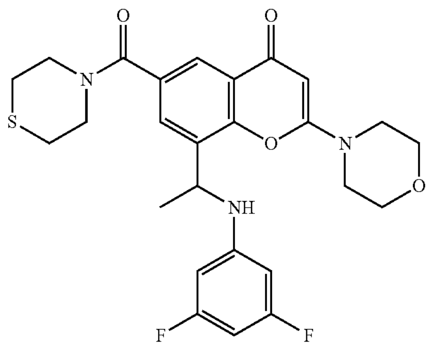 [SMILES: CC(Nc1cc(F)cc(F)c1)c1cc(C(=O)N2CCSCC2)cc2c(=O)cc(N3CCOCC3)oc12] | thiomorpholine | 8-(1-(3,5-difluorophenylamino)ethyl)-2-morpholino-6-(thiomorpholine-4-carbonyl)-4H-chromen-4-one | 52 | 58.6 | 516 |
| 4.06 | 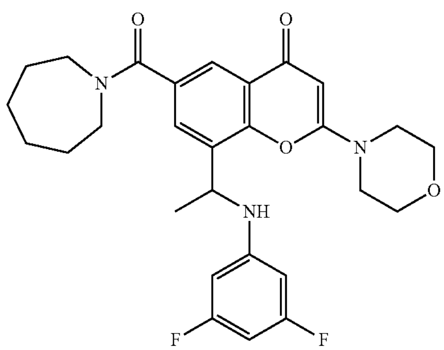 | azepane | 6-(azepane-1-carbonyl)-8-(1-(3,5-difluorophenylamino)ethyl)-2-morpholino-4H-chromen-4-one | 56 | 64.1 | 512 |
| 4.07 | 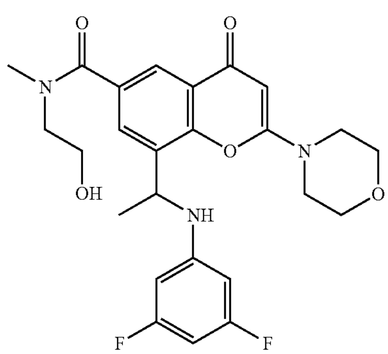 [SMILES: CC(Nc1cc(F)cc(F)c1)c1cc(C(=O)N(C)CCO)cc2c(=O)cc(N3CCOCC3)oc12] | 2-(methylamino)ethanol | 8-(1-(3,5-difluorophenylamino)ethyl)-N-(2-hydroxyethyl)-N-methyl-2-morpholino-4-oxo-4H-chromene-6-carboxamide | 52 | 62.5 | 488 |
| 4.08 | 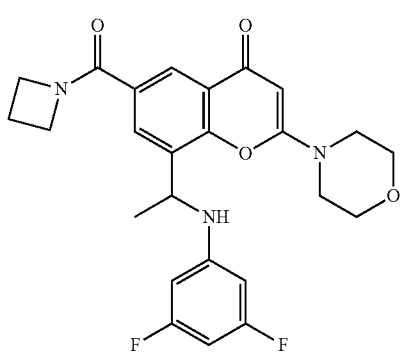 [SMILES: CC(Nc1cc(F)cc(F)c1)c1cc(C(=O)N2CCC2)cc2c(=O)cc(N3CCOCC3)oc12] | azetidine | 6-(azetidine-1-carbonyl)-8-(1-(3,5-difluorophenylamino)ethyl)-2-morpholino-4H-chromen-4-one | 48 | 59.8 | 470 |

TABLE II-continued

| EX. | Structure | Reagent Name | Product | Product Mass (g) | Yield (%) | MH+ |
|---|---|---|---|---|---|---|
| 4.09 | 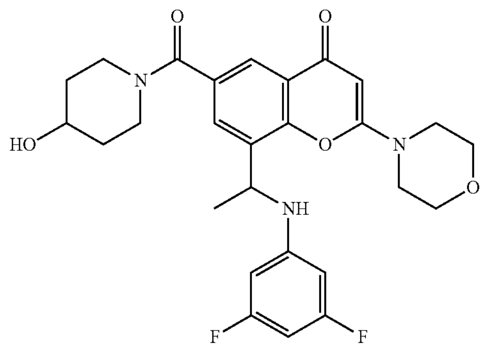 [SMILES: CC(Nc1cc(F)cc(F)c1)c1cc(C(=O)N2CCC(O)CC2)cc2c(=O)cc(N3CCOCC3)oc12] | piperidin-4-ol | 8-(1-(3,5-difluorophenylamino)ethyl)-6-(4-hydroxypiperidine-1-carbonyl)-2-morpholino-4H-chromen-4-one | 55 | 63.3 | 514 |
| 4.10 | 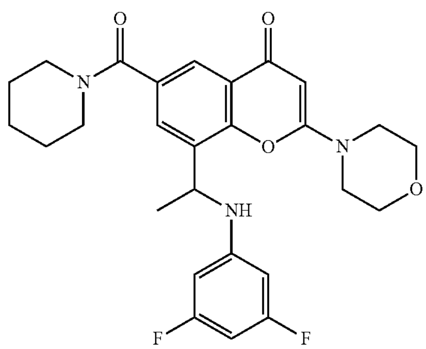 [SMILES: CC(Nc1cc(F)cc(F)c1)c1cc(C(=O)N2CCCCC2)cc2c(=O)cc(N3CCOCC3)oc12] | piperidine | 8-(1-(3,5-difluorophenylamino)ethyl)-2-morpholino-6-(piperidine-1-carbonyl)-4H-chromen-4-one | 51 | 60.3 | 498 |
| 4.11 | 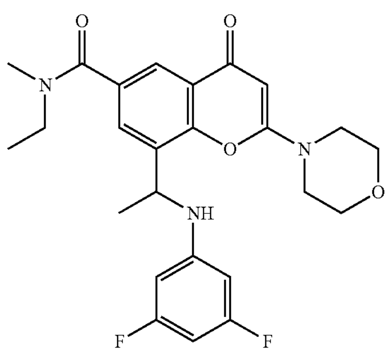 [SMILES: CCN(C)C(=O)c1cc(C(C)Nc2cc(F)cc(F)c2)c2oc(N3CCOCC3)cc(=O)c2c1] | N-methyl ethanamine | 8-(1-(3,5-difluorophenylamino)ethyl)-N-ethyl-N-methyl-2-morpholino-4-oxo-4H-chromene-6-carboxamide | 51 | 63.9 | 472 |
| 4.12 | 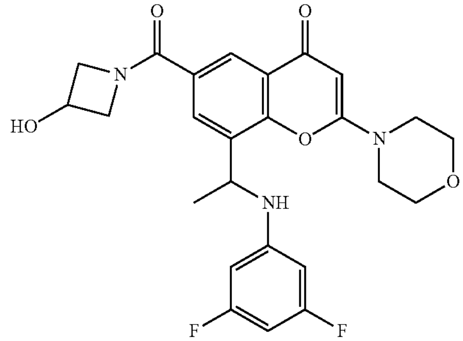 [SMILES: CC(Nc1cc(F)cc(F)c1)c1cc(C(=O)N2CC(O)C2)cc2c(=O)cc(N3CCOCC3)oc12] | azetidin-3-ol hydrochloride | 8-(1-(3,5-difluorophenylamino)ethyl)-6-(3-hydroxyazetidine-1-carbonyl)-2-morpholino-4H-chromen-4-one | 50 | 60.9 | 486 |

TABLE II-continued

| EX. | Structure | Reagent Name | Product | Product Mass (g) | Yield (%) | MH+ |
|---|---|---|---|---|---|---|
| 4.13 | 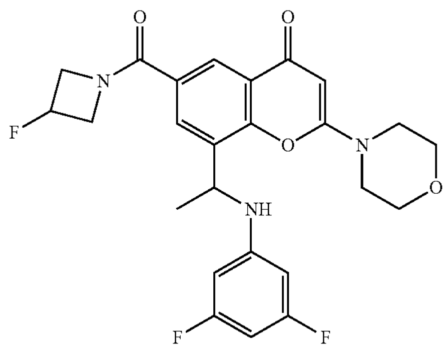 [SMILES: CC(Nc1cc(F)cc(F)c1)c1cc(C(=O)N2CC(F)C2)cc2c(=O)cc(N3CCOCC3)oc12] | 3-fluoroazetidine hydrochloride | 8-(1-(3,5-difluorophenylamino)ethyl)-6-(3-fluoroazetidine-1-carbonyl)-2-morpholino-4H-chromen-4-one | 49 | 58.9 | 488 |
| 4.14 | 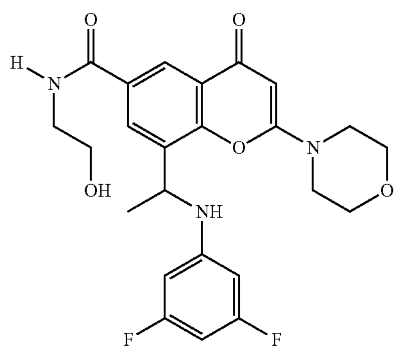 [SMILES: CC(Nc1cc(F)cc(F)c1)c1cc(C(=O)NCCO)cc2c(=O)cc(N3CCOCC3)oc12] | 2-aminoethanol | 8-(1-(3,5-difluorophenylamino)ethyl)-N-(2-hydroxyethyl)-2-morpholino-4-oxo-4H-chromene-6-carboxamide | 49 | 61.0 | 474 |
| 4.15 | 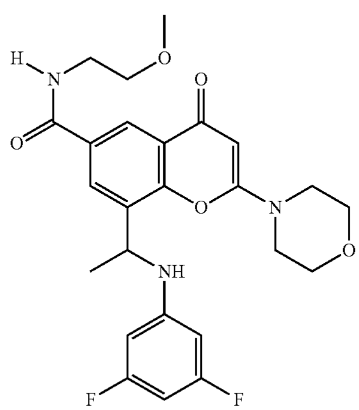 | 2-methoxy-ethanamine | 8-(1-(3,5-difluorophenylamino)ethyl)-N-(2-methoxyethyl)-2-morpholino-4-oxo-4H-chromene-6-carboxamide | 53 | 63.5 | 488 |
| 4.16 | 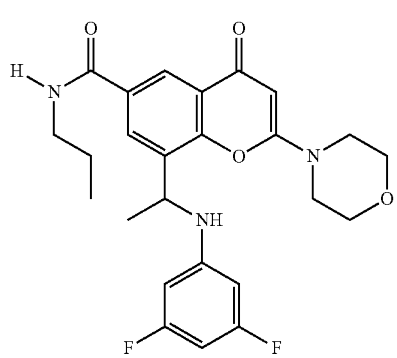 [SMILES: CCCNC(=O)c1cc(C(C)Nc2cc(F)cc(F)c2)c2oc(N3CCOCC3)cc(=O)c2c1] | propan-1-amine | 8-(1-(3,5-difluorophenylamino)ethyl)-2-morpholino-4-oxo-N-propyl-4H-chromene-6-carboxamide | 44 | 54 | 472 |

TABLE II-continued

| EX. | Structure | | Reagent Name | Product | Product Mass (g) | Yield (%) | MH+ |
|---|---|---|---|---|---|---|---|
| 4.17 | 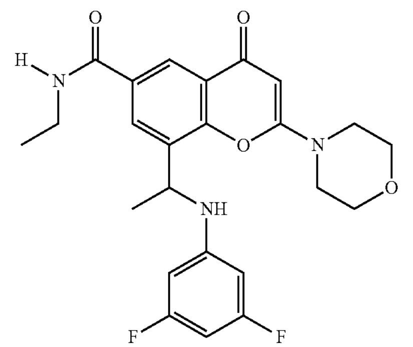 [SMILES: CCNC(=O)c1cc(C(C)Nc2cc(F)cc(F)c2)c2oc(N3CCOCC3)cc(=O)c2c1] | | ethanamine hydrochloride | 8-(1-(3,5-difluorophenylamino)ethyl)-N-ethyl-2-morpholino-4-oxo-4H-chromene-6-carboxamide | 33 | 42 | 458 |
| 4.18 | 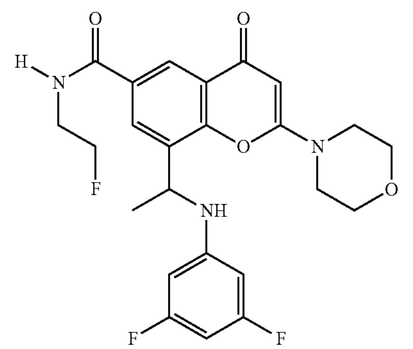 [SMILES: CC(Nc1cc(F)cc(F)c1)c1cc(C(=O)NCCF)cc2c(=O)cc(N3CCOCC3)oc12] | | 2-fluoro-ethanamine hydrochloride | 8-(1-(3,5-difluorophenylamino)ethyl)-N-(2-fluoroethyl)-2-morpholino-4-oxo-4H-chromene-6-carboxamide | 43 | 53.3 | 476 |
| 4.19 | 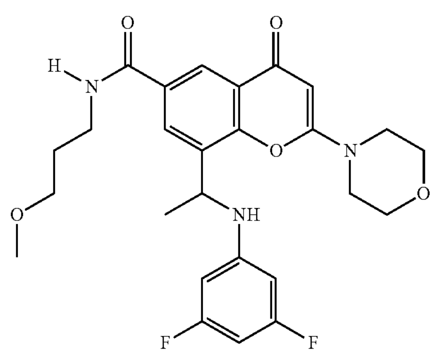 [SMILES: COCCCNC(=O)c1cc(C(C)Nc2cc(F)cc(F)c2)c2oc(N3CCOCC3)cc(=O)c2c1] | | 3-methoxy propan-1-amine | 8-(1-(3,5-difluorophenylamino)ethyl)-N-(3-methoxypropyl)-2-morpholino-4-oxo-4H-chromene-6-carboxamide | 40 | 46.5 | 502 |
| 4.20 | 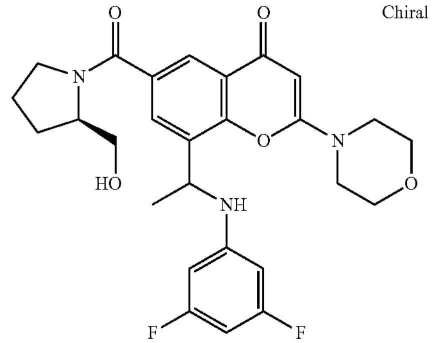 [SMILES: CC(Nc1cc(F)cc(F)c1)c1cc(C(=O)N2CCC[C@@H]2CO)cc2c(=O)cc(N3CCOCC3)oc12] | Chiral | (R)-pyrrolidin-2-ylmethanol | 8-(1-(3,5-difluorophenylamino)ethyl)-6-((R)-2-(hydroxymethyl)pyrrolidine-1-carbonyl)-2-morpholino-4H-chromen-4-one | 53 | 60.7 | 514 |

TABLE II-continued

| EX. | Structure | Reagent Name | Product | Product Mass (g) | Yield (%) | MH+ |
|---|---|---|---|---|---|---|
| 4.21 | Chiral | (S)-pyrrolidin-2-ylmethanol | 8-(1-(3,5-difluorophenylamino)ethyl)-6-((S)-2-(hydroxymethyl)pyrrolidine-1-carbonyl)-2-morpholino-4H-chromen-4-one | 52 | 59.3 | 514 |
| 4.22 | 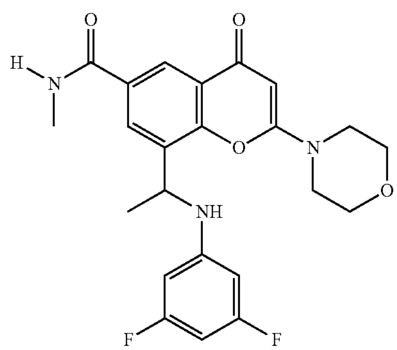 [SMILES: CNC(=O)c1cc(C(C)Nc2cc(F)cc(F)c2)c2oc(N3CCOCC3)cc(=O)c2c1] | methanamine | 8-(1-(3,5-difluorophenylamino)ethyl)-N-methyl-2-morpholino-4-oxo-4H-chromene-6-carboxamide | 22 | 29.5 | 444 |
| 4.23 | 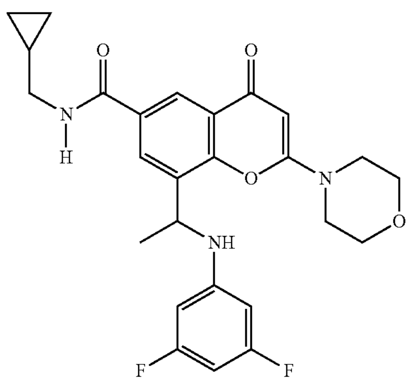 [SMILES: CC(Nc1cc(F)cc(F)c1)c1cc(C(=O)NCC2CC2)cc2c(=O)cc(N3CCOCC3)oc12] | cyclopropyl-methanamine | N-(cyclopropylmethyl)-8-(1-(3,5-difluorophenylamino)ethyl)-2-morpholino-4-oxo-4H-chromene-6-carboxamide | 53 | 63.8 | 484 |
| 4.24 | 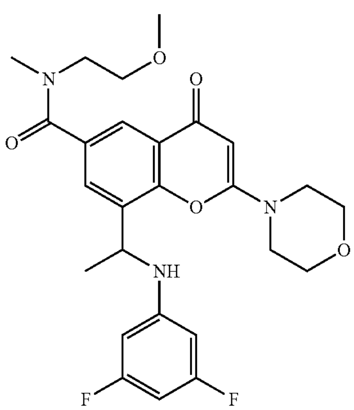 [SMILES: COCCN(C)C(=O)c1cc(C(C)Nc2cc(F)cc(F)c2)c2oc(N3CCOCC3)cc(=O)c2c1] | 2-methoxy-N-methyl ethanamine | 8-(1-(3,5-difluorophenylamino)ethyl)-N-(2-methoxyethyl)-N-methyl-2-morpholino-4-oxo-4H-chromene-6-carboxamide | 53 | 62.4 | 502 |

TABLE II-continued

| EX. | Structure | Reagent Name | Product | Product Mass (g) | Yield (%) | MH+ |
|---|---|---|---|---|---|---|
| 4.25 | 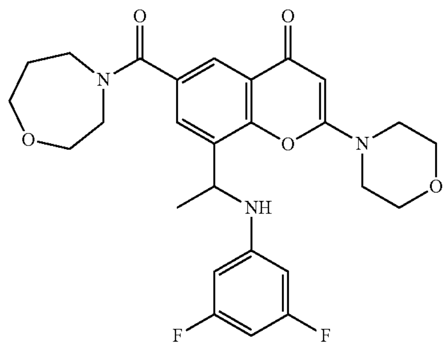 [SMILES: CC(Nc1cc(F)cc(F)c1)c1cc(C(=O)N2CCCOCC2)cc2c(=O)cc(N3CCOCC3)oc12] | 1,4-oxazepane hydrochloride | 8-(1-(3,5-difluorophenylamino)ethyl)-2-morpholino-6-(1,4-oxazepane-4-carbonyl)-4H-chromen-4-one | 49 | 56.3 | 514 |
| 4.26 | 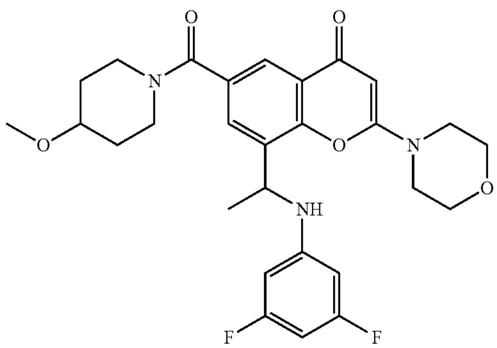 [SMILES: COC1CCN(C(=O)c2cc(C(C)Nc3cc(F)cc(F)c3)c3oc(N4CCOCC4)cc(=O)c3c2)CC1] | 4-methoxy piperidine | 8-(1-(3,5-difluorophenylamino)ethyl)-6-(4-methoxypiperidine-1-carbonyl)-2-morpholino-4H-chromen-4-one | 58 | 64.9 | 528 |

Notes
Further characterising data for the products is given below.

EXAMPLE 4.01

NMR Spectrum: (DMSOd$_6$) at 353° K: 1.01 (t, 6H), 1.56 (d, 3H), 3.25 (bs, 4H), 3.52-3.65 (m, 4H), 3.73-3.81 (m, 4H), 4.98-5.06 (m, 1H), 5.55 (s, 1H), 6.11-6.22 (m, 3H), 6.72 (d, 1H), 7.54 (d, 1H), 7.78 (d, 1H).

EXAMPLE 4.02

NMR Spectrum: (DMSOd$_6$) at 323° K: 1.52 (d, 3H), 1.66-1.78 (m, 2H), 1.78-1.91 (m, 2H), 3.07-3.23 (m, 2H), 3.37-3.49 (m partially hidden by H2O, 2H), 3.51-3.64 (m, 4H), 3.69-3.81 (m, 4H), 4.98-5.08 (m, 1H), 5.61 (s, 1H), 6.16 (dd, 2H), 6.24 (ddd, 1H), 6.97 (d, 1H), 7.67 (d, 1H), 7.93 (d, 1H).

EXAMPLE 4.03

NMR Spectrum: (DMSOd$_6$) 1.52 (d, 3H), 1.93 (bs, 1H), 2.08 (bs, 1H), 2.14 (s, 3H), 2.41 (bs, 2H), 3.05 (bs, 2H), 3.50-3.64 (m, 5H), 3.68 (bs, 1H), 3.72-3.80 (ms, 4H), 4.98-5.06 (m, 1H), 5.62 (s, 1H), 6.15 (dd, 2H), 6.25 (ddd, 1H), 6.98 (d, 1H), 7.46 (d, 1H), 7.78 (d, 1H).

EXAMPLE 4.04

NMR Spectrum: (DMSOd$_6$) 1.52 (d, 3H), 2.43 (bs, 2H), 2.69 (bs, 2H), 3.00 (bs, 2H), 3.46 (bs partially hidden by H2O, 2H), 3.50-3.65 (m, 5H), 3.70-3.79 (m, 4H), 4.97-5.05 (m, 1H), 5.61 (s, 1H), 6.14 (dd, 2H), 6.24 (ddd, 1H), 6.98 (d, 1H), 7.47 (d, 1H), 7.78 (d, 1H).

The removal of the tert-butyl-carboxylate protecting group was done as follows: The crude solution was washed with a 10% solution of citric acid (pH~4), water, dried over magnesium sulfate and concentrated. HCl (4N in dioxane; 1066 µl, 4.27 mmol) was added and the mixture was stirred at room temperature for 30 minutes. The volatils were removed under vacuum and the residue dissolved into a 10% methanolic ammonia in DCM (5 mL). The insolubles were removed by filtration, the filtrate was concentrated and the crude product was purified by preparative HPLC as described above.

EXAMPLE 4.05

NMR Spectrum: (DMSOd$_6$) 1.52 (d, 3H), 2.32 (bs, 2H), 2.66 (bs, 2H), 3.45 (bs partially hidden by H2O, 1H), 3.50-3.64 (m, 5H), 3.68 (bs, 1H), 3.70-3.81 (m, 4H), 3.96 (bs, 1H), 4.96-5.06 (m, 1H), 5.61 (s, 1H), 6.14 (dd, 2H), 6.25 (ddd, 1H), 6.96 (d, 1H), 7.51 (d, 1H), 7.80 (d, 1H).

EXAMPLE 4.06

NMR Spectrum: (DMSOd$_6$) 1.11-1.22 (m, 1H), 1.22-1.32 (m, 1H), 1.32-1.43 (m, 2H), 1.44-1.55 (m, 2H), 1.52 (d, 3H), 1.62-1.73 (m, 2H), 3.03-3.12 (m, 2H), 3.37-3.45 (m partially hidden by H2O, 1H), 3.51-3.70 (m, 5H), 3.71-3.79 (m, 4H), 4.97-5.06 (m, 1H), 5.61 (s, 1H), 6.14 (dd, 2H), 6.23 (ddd, 1H), 6.98 (d, 1H), 7.45 (d, 1H), 7.73 (d, 1H).

EXAMPLE 4.07

NMR Spectrum: (DMSOd$_6$) at 323° K: 1.54 (d, 3H), 2.90 (bs, 3H), 3.20 (bs partially hidden by H2O, 2H), 3.47 (bs, 2H), 3.51-3.64 (m, 4H), 3.71-3.79 (m, 4H), 4.61 (bs, 1H), 4.97-

5.05 (m, 1H), 5.58 (s, 1H), 6.15 (dd, 2H), 6.20 (ddd, 1H), 6.83 (d, 1H), 7.58 (d, 1H), 7.84 (d, 1H).

EXAMPLE 4.08

NMR Spectrum: (DMSOd$_6$) 1.51 (d, 3H), 2.17-2.28 (m, 2H), 3.49-3.64 (m, 4H), 3.70-3.79 (m, 4H), 3.97-4.09 (m, 2H), 4.09-4.20 (m, 2H), 4.97-5.06 (m, 1H), 5.62 (s, 1H), 6.15 (dd, 2H), 6.23 (ddd, 1H), 7.04 (d, 1H), 7.79 (d, 1H), 8.03 (d, 1H).

EXAMPLE 4.09

NMR Spectrum: (DMSOd$_6$) at 323° K: 1.27 (bs, 2H), 1.54 (d, 3H), 1.64 (bs, 2H), 3.04 (bs, 2H), 3.49 (bs, 1H), 3.52-3.62 (m, 4H), 3.63 (bs, 1H), 3.66-3.74 (bs, 1H), 3.72-3.80 (m, 4H), 4.66 (d, 1H), 4.97-5.05 (m, 1H), 5.58 (s, 1H), 6.15 (dd, 2H), 6.20 (ddd, 1H), 6.86 (d, 1H), 7.53 (d, 1H), 7.80 (d, 1H).

EXAMPLE 4.10

NMR Spectrum: (DMSOd$_6$) at 323° K: 1.39 (bs, 4H), 1.54 (d, 3H), 1.54-4.64 (m, 2H), 3.31 (bs partially hidden by H2O, 4H), 3.49-3.66 (m, 4H), 3.68-3.84 (m, 4H), 4.96-5.07 (m, 1H), 5.58 (s, 1H), 6.14 (dd, 2H), 6.20 (ddd, 1H), 6.86 (d, 1H), 7.52 (d, 1H), 7.79 (d, 1H).

EXAMPLE 4.11

NMR Spectrum: (DMSOd$_6$) at 323° K: 0.96 (bs, 3H), 1.54 (d, 3H), 2.85 (bs, 3H), 3.23 (bs partially hidden by H2O, 2H), 3.51-3.65 (m, 4H), 3.75-3.82 (m, 4H), 4.97-5.06 (m, 1H), 5.58 (s, 1H), 6.15 (dd, 2H), 6.20 (ddd, 1H), 6.86 (d, 1H), 7.54 (s, 1H), 7.79 (d, 1H).

EXAMPLE 4.12

NMR Spectrum: (DMSOd$_6$) at 323° K: 1.53 (d, 3H), 3.51-3.64 (m, 4H), 3.71-3.80 (m, 4H), 3.84 (bs, 2H), 4.19-4.32 (m, 2H), 4.43-4.52 (m, 1H), 4.97-5.06 (m, 1H), 5.59 (s, 1H), 5.63 (d, 1H), 6.16 (dd, 2H), 6.20 (ddd, 1H), 6.92 (d, 1H), 7.80 (s, 1H), 8.05 (d, 1H).

EXAMPLE 4.13

NMR Spectrum: (DMSOd$_6$) 323° K: 1.53 (d, 3H), 3.52-3.66 (m, 4H), 3.71-3.82 (m, 4H), 4.04-4.24 (m, 2H), 4.29-4.51 (m, 2H), 4.98-5.09 (m, 1H), 5.39 (ddddd, 1H), 5.59 (s, 1H), 6.17 (dd, 2H), 6.20 (ddd, 1H), 6.91 (d, 1H), 7.81 (s, 1H), 8.06 (d, 1H).

EXAMPLE 4.14

NMR Spectrum: (DMSOd$_6$) 1.53 (d, 3H), 3.27-3.33 (m, 2H), 3.47-3.52 (m, 2H), 3.52-3.63 (m, 4H), 3.70-3.79 (m, 4H), 4.73 (t, 1H), 4.96-5.04 (m, 1H), 5.62 (s, 1H), 6.15 (dd, 2H), 6.22 (ddd, 1H), 7.03 (d, 1H), 8.08 (s, 1H), 8.38 (d, 1H), 8.69 (t, 1H).

EXAMPLE 4.15

NMR Spectrum: (DMSOd$_6$) 1.52 (d, 3H), 3.26 (s, 3H), 3.35-3.42 (m partially hidden by H2O, 2H), 3.42-3.48 (m, 2H), 3.50-3.64 (m, 4H), 3.70-3.79 (m, 4H), 4.96-5.05 (m, 1H), 5.62 (s, 1H), 6.14 (dd, 2H), 6.22 (ddd, 1H), 7.03 (d, 1H), 8.07 (s, 1H), 8.37 (d, 1H), 8.78 (t, 1H).

EXAMPLE 4.16

NMR Spectrum: (DMSOd$_6$) 0.88 (t, 3H), 1.47-1.58 (m, 2H), 1.52 (d, 3H), 3.13-3.24 (m, 2H), 3.50-3.64 (m, 4H), 3.70-3.79 (m, 4H), 4.96-5.05 (m, 1H), 5.62 (s, 1H), 6.14 (dd, 2H), 6.22 (ddd, 1H), 7.03 (d, 1H), 8.07 (s, 1H), 8.36 (d, 1H), 8.73 (t, 1H).

EXAMPLE 4.17

NMR Spectrum: (DMSOd$_6$) 1.11 (t, 3H), 1.51 (d, 3H), 3.21-3.30 (m, 2H), 3.50-3.64 (m, 4H), 3.69-3.80 (m, 4H), 4.96-5.04 (m, 1H), 5.62 (s, 1H), 6.14 (dd, 2H), 6.22 (ddd, 1H), 7.03 (d, 1H), 8.07 (s, 1H), 8.35 (d, 1H), 8.74 (t, 1H).

EXAMPLE 4.18

NMR Spectrum: (DMSOd$_6$) 1.52 (d, 3H), 3.48-3.64 (m, 6H), 3.70-3.78 (m, 4H), 4.53 (dt, 2H), 4.96-5.04 (m, 1H), 5.62 (s, 1H), 6.14 (dd, 2H), 6.22 (ddd, 1H), 7.03 (d, 1H), 8.09 (d, 1H), 8.39 (d, 1H), 8.96 (t, 1H).

EXAMPLE 4.19

NMR Spectrum: (DMSOd$_6$) 1.52 (d, 3H), 1.70-1.79 (m, 2H), 3.23 (s, 3H), 3.24-3.30 (m, 2H), 3.36-3.42 (m partially hidden by H2O, 2H), 3.50-3.63 (m, 4H), 3.71-3.78 (m, 4H), 4.96-5.04 (m, 1H), 5.62 (s, 1H), 6.14 (dd, 2H), 6.22 (ddd, 1H), 7.03 (d, 1H), 8.06 (d, 1H), 8.35 (d, 1H), 8.73 (t, 1H).

EXAMPLE 4.20

NMR Spectrum: (DMSOd$_6$) 1.54 (d, 3H), 1.56-1.98 (m, 4H), 2.75-3.47 (m, 2H), 3.48-3.65 (m, 6H), 3.68-3.82 (m, 4H), 4.11 (bs, 1H), 4.76-4.86 (m, 1H), 4.95-5.07 (m, 1H), 5.61 (s, 1H), 6.15 (dd, 2H), 6.23 (ddd, 1H), 6.93-7.02 (m, 1H) 7.64 (s, 0.5H), 7.68 (s, 0.5H), 7.95 (s, 1H).

EXAMPLE 4.21

NMR Spectrum: (DMSOd$_6$) 1.54 (d, 3H), 1.56-1.98 (m, 4H), 2.75-3.47 (m, 2H), 3.48-3.65 (m, 6H), 3.68-3.82 (m, 4H), 4.11 (bs, 1H), 4.76-4.86 (m, 1H), 4.95-5.07 (m, 1H), 5.61 (s, 1H), 6.15 (dd, 2H), 6.23 (ddd, 1H), 6.93-7.02 (m, 1H) 7.64 (s, 0.5H), 7.68 (s, 0.5H), 7.95 (s, 1H).

EXAMPLE 4.22

NMR Spectrum: (DMSOd$_6$) 1.51 (d, 3H), 1.75 (d, 3H), 3.51-3.62 (m, 4H), 3.71-3.78 (m, 4H), 4.96-5.04 (m, 1H), 5.61 (s, 1H), 6.14 (dd, 2H), 6.22 (ddd, 1H), 7.03 (d, 1H), 8.07 (d, 1H), 8.33 (d, 1H), 8.67 (q, 1H).

EXAMPLE 4.23

NMR Spectrum: (DMSOd$_6$) 0.18-0.27 (m, 2H), 0.39-0.48 (m, 2H), 0.98-1.08 (m, 1H), 1.51 (d, 3H), 3.08-3.16 (m, 2H), 3.51-3.64 (m, 4H), 3.71-3.80 (m, 4H), 4.97-5.06 (m, 1H), 5.63 (s, 1H), 6.15 (dd, 2H), 6.23 (ddd, 1H), 7.05 (d, 1H), 8.09 (d, 1H), 8.38 (d, 1H), 8.86 (t, 1H).

EXAMPLE 4.24

NMR Spectrum: (DMSOd$_6$) at 323° K: 1.52 (d, 3H), 2.89 (s, 3H), 3.02-3.50 (m partially hidden by H2O, 7H), 3.50-3.68

(m, 4H), 3.71-3.80 (m, 4H), 5.01 (bs, 1H), 5.63 (s, 1H), 6.14 (dd, 2H), 6.23 (ddd, 1H), 6.98 (d, 1H), 7.52 (d, 1H), 7.78 (d, 1H).

EXAMPLE 4.25

NMR Spectrum: (DMSOd$_6$) at 323° K: 1.43 (bs, 2H), 1.55 (d, 3H), 1.87 (bs, 1H), 3.27-3.89 (m, 15H), 4.97-5.06 (m, 1H), 5.59 (s, 1H), 6.15 (dd, 2H), 6.21 (ddd, 1H), 6.87 (d, 1H), 7.54 (d, 1H), 7.80 (d, 1H).

EXAMPLE 4.26

NMR Spectrum: (DMSOd$_6$) at 323° K: 1.34 (bs, 2H), 1.51 (d, 3H), 1.72 (bs, 2H), 3.08 (bs, 2H), 3.25 (s, 3H), 3.36-3.44 (m, 1H), (m, 4H), 3.67 (bs, 2H), 3.69-3.82 (m, 4H), 4.97-5.07 (m, 1H), 5.58 (s, 1H), 6.15 (dd, 2H), 6.21 (ddd, 1H), 6.86 (d, 1H), 7.52 (d, 1H), 7.80 (d, 1H).

The 2,5-dioxopyrrolidin-1-yl 8-(1-(3,5-difluorophenylamino)ethyl)-2-morpholino-4-oxo-4H-chromene-6-carboxylate used as starting material for the prepartion of compounds of Examples 4.01-4.26 was made as follows: —

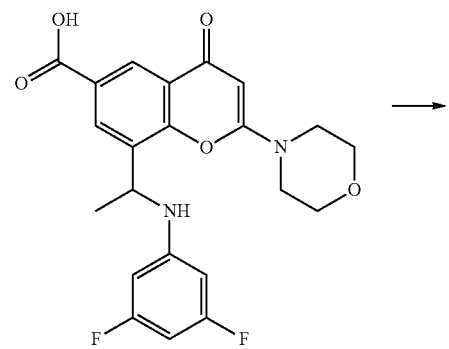

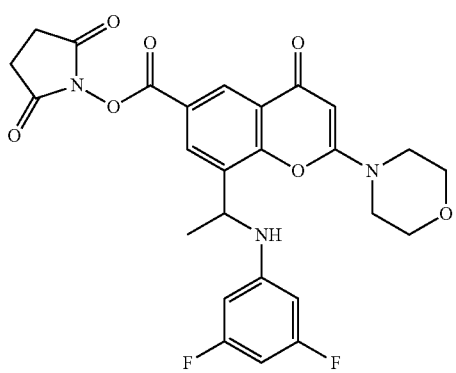

TSTU (2.098 g, 6.97 mmol) was added at room temperature to 8-(1-(3,5-difluorophenylamino)ethyl)-2-morpholino-4-oxo-4H-chromene-6-carboxylic acid (made using a procedure similar to the one described for the synthesis of 8-(1-(3-chloro-2-fluorophenylamino)ethyl)-2-morpholino-4-oxo-4H-chromene-6-carboxylic acid in Example 2.00; 2.5 g, 3.49 mmol) and DIPEA (1.214 mL, 6.97 mmol) in DCM (25 mL). The resulting solution was stirred for 2 hrs. This solution of intermediate was used as such for the next step.

EXAMPLE 5.0

8-(1-((3,5-difluorophenyl)(methyl)amino)ethyl)-N,N-dimethyl-2-morpholino-4-oxo-4H-chromene-6-carboxamide

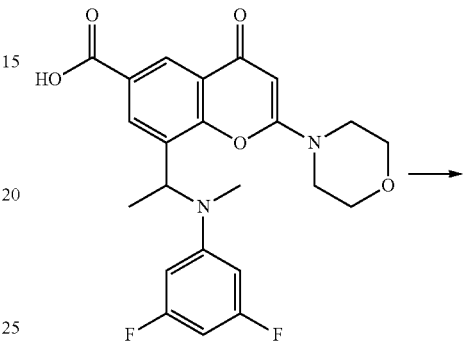

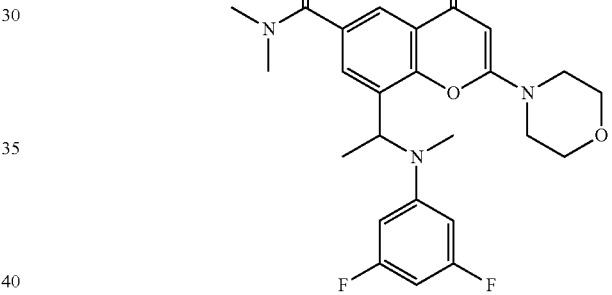

2-(2,5-dioxopyrrolidin-1-yl)-1,1,3,3-tetramethylisouronium tetrafluoroborate (2.134 g, 7.09 mmol), was added in one portion to a stirred solution of 8-(1-((3,5-difluorophenyl)(methyl)amino)ethyl)-2-morpholino-4-oxo-4H-chromene-6-carboxylic acid (2.1 g, 4.73 mmol) and N-ethyl-N-isopropylpropan-2-amine (1.646 mL, 9.45 mmol) in DCM (20 mL) at RT and stirred at RT for 90 mins. Dimethylamine (4.73 mL, 9.45 mmol) was then added and the reaction mixture was stirred at RT for 30 min. Water and DCM were added, the organic phase was washed with brine, dried over magnesium sulfate and concentrated. The crude product was purified by flash chromatography on silica gel eluting with DCM/MeCN (1:1) then 0 to 10% MeOH in DCM. The solvent was evaporated to dryness to afford a foam which crystallised from ethyl acetate (10 mL). Ether (10 mL) was added to complete the crytallisation and the white solid was collected by filtration and dried to give 8-(1-((3,5-difluorophenyl)(methyl)amino)ethyl)-N,N-dimethyl-2-morpholino-4-oxo-4H-chromene-6-carboxamide (1.65 g, 74%). Mass Spectrum: M+H$^+$ 472. NMR Spectrum (DMSOd6): 1.55 (d, 3H), 2.63 (s, 3H), 2.92 (bs, 3H), 3.01 (bs, 3H), 3.21-3.29 (m, 2H), 3.31-3.39 (m partially hidden by H2O, 2H), 3.41-3.49 (m, 2H), 3.49-3.57 (m, 2H), 5.55 (s, 1H), 5.58 (q, 1H), 6.40 (t, 1H), 6.53 (d, 2H), 7.70 (d, 1H), 7.89 (d, 1H).

This racemic compound was resolved by chiral preparative HPLC using the following conditions:

| Column | Chiralpak IA; 21 × 250 mm, 5μ |
|---|---|
| Eluent | CO2/MeOH 75:25 |
| Oven Temperature | 40° C. |
| Flow | 60 mL/min |
| Wavelength | 220 nm |
| Sample Conc | 50 mg/mL in MeOH |
| Injection | 50 mg |

1.5 g of racemic was separated using the above conditions to give:

First eluting enantiomer 0.7 g (ee>98%) (Example 5.0a) $[\alpha]^D_{20°}$: +5° in MeCN Second eluting enantiomer 0.7 g (ee>98%) (Example 5.0b) $[\alpha]^D_{20°}$: −5° in MeCN The 8-(1-((3,5-difluorophenyl)(methyl)amino)ethyl)-2-morpholino-4-oxo-4H-chromene-6-carboxylic acid used as starting material was made as follows: —

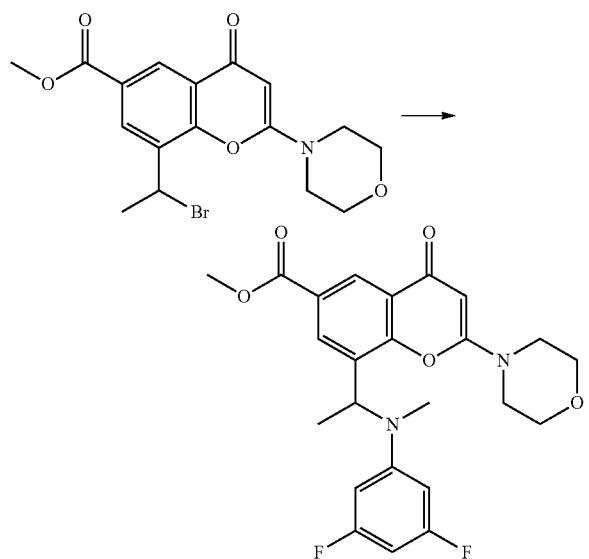

Potassium iodide (1.521 g, 9.16 mmol) was added to a suspension of methyl 8-(1-bromoethyl)-2-morpholino-4-oxo-4H-chromene-6-carboxylate (3.3 g, 8.33 mmol, as described in Example 2.00) and 3,5-difluoro-N-methylaniline (3.58 g, 24.99 mmol) in CHCl₃ (16 mL) and MeOH (4 mL). The mixture was stirred at RT over the weekend. The reaction mixture was concentrated to dryness and the resulting dark oil was triturated with diethyl ether to give a solid which was collected by filtration. This solid was suspended in water and pH was adjusted to 6-7 with 2N NaOH. The crude product was filtered and washed with ether, dried and purified by flash chromatography on silica gel eluting with 0 to 10% MeOH in DCM. The solvent was evaporated to dryness to afford methyl 8-(1-((3,5-difluorophenyl)(methyl)amino) ethyl)-2-morpholino-4-oxo-4H-chromene-6-carboxylate (3.1 g, 81%) as a white solid. Mass Spectrum: M+H+ 459.

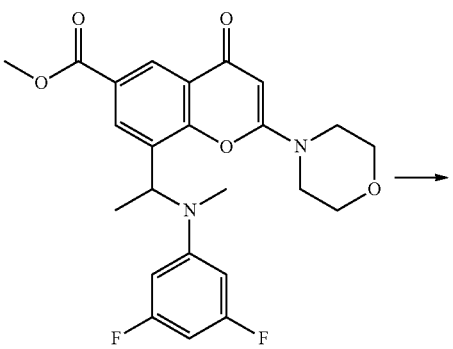

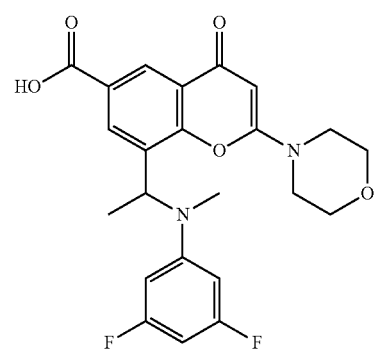

2N NaOH (6.54 mL, 13.1 mmol), was added dropwise to a stirred suspension of methyl 8-(1-((3,5-difluorophenyl)(methyl)amino)ethyl)-2-morpholino-4-oxo-4H-chromene-6-carboxylate (3 g, 6.54 mmol), in THF (30 mL)/MeOH (30 mL). The resulting solution was stirred at RT overnight. The reaction mixture was diluted with water, the pH was adjusted to 3 with a 2M aq. sol. HCl. The solvents were removed and the white precipitate was collected by filtration, washed with water and dried then washed with ethyl acetate and ether to afford 8-(1-((3,5-difluorophenyl)(methyl)amino)ethyl)-2-morpholino-4-oxo-4H-chromene-6-carboxylic acid (2.5 g, 86%) which was used without further purification. Mass Spectrum: M+H+ 445.

The compound of Example 5.0a could also be made using the following alternative method:

Lithium bis(trimethylsilyl)amide (1N in THF) (26.2 mL, 26.23 mmol) was added to a stirred solution of 8-(1-(3,5-difluorophenylamino)ethyl)-N,N-dimethyl-2-morpholino-4-oxo-4H-chromene-6-carboxamide (6 g, 13.12 mmol, prepared as described in Example 3.06b; $[\alpha]^D_{20}$=−122.6° in EtOH) dissolved in anhydrous THF (60 mL) at −60° C. under argon. The light red solution was allowed to warm to −10° C. over a period of 15 minutes then cooled down to −60° C. before addition of dimethyl sulfate (2.482 mL, 26.23 mmol). The resulting light yellow solution was allowed to warm to 0° C. and stirred for 15 minutes. The reaction mixture was cooled back to −10° C. prior to addition of a sat. aq. sol. of NH₄Cl (30 mL) followed by extraction with DCM. The crude product (7 g) was purified by flash chromatography on silica gel eluting with 0 to 15% EtOH in DCM/ethyl acetate (1/1)

then 15% EtOH in DCM. The solvent was evaporated to dryness to afford (4.2 g, 8.91 mmol, 67.9%) as an off-white foam.

EXAMPLE 5.01

8-(1-((3,5-difluorophenyl)(methyl)amino)ethyl)-6-(4-hydroxypiperidine-1-carbonyl)-2-morpholino-4H-chromen-4-one

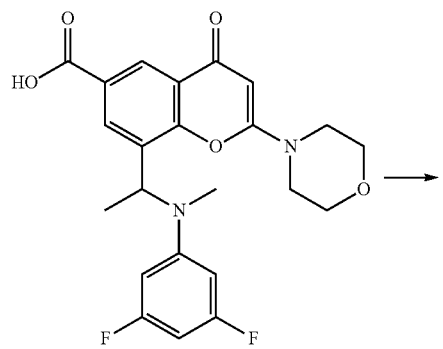

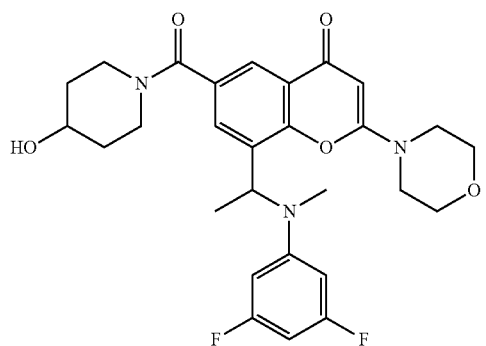

2-(1H-benzo[d][1,2,3]triazol-1-yl)-1,1,3,3-tetramethylisouronium tetrafluoroborate (113 mg, 0.35 mmol) was added to a stirred solution of 8-(1-((3,5-difluorophenyl)(methyl)amino)ethyl)-2-morpholino-4-oxo-4H-chromene-6-carboxylic acid (130 mg, 0.29 mmol), 4-methylmorpholine (0.080 mL, 0.73 mmol) and piperidin-4-ol (36 mg, 0.35 mmol) dissolved in NMP (1.2 mL). The resulting solution was stirred at 23° C. for 2 hrs. The reaction mixture was purified by preparative HPLC using a Waters SunFire system. The fractions containing the desired compound were evaporated, triturated with ether and dried to afford 8-(1-((3,5-difluorophenyl)(methyl)amino)ethyl)-6-(4-hydroxypiperidine-1-carbonyl)-2-morpholino-4H-chromen-4-one (90 mg, 58%) as a white solid. Mass Spectrum: M+H$^+$ 528. NMR Spectrum (DMSOd6 at 323° K): 1.38 (bs, 2H), 1.57 (d, 3H), 1.75 (bs, 2H), 2.66 (s, 3H), 3.23-3.30 (m, 2H), 3.30-3.38 (m, 2H), 3.61 (m, 4H), 3.65 (bs, 4H), 3.71-3.79 (m, 1H), 4.66 (d, 1H), 5.52 (s, 1H), 5.54 (q, 1H), 6.36 (t, 1H), 6.50 (d, 2H), 7.62 (d, 1H), 7.87 (d, 1H).

EXAMPLE 5.02

8-(1-((3,5-difluorophenyl)(methyl)amino)ethyl)-6-(3-hydroxypyrrolidine-1-carbonyl)-2-morpholino-4H-chromen-4-one

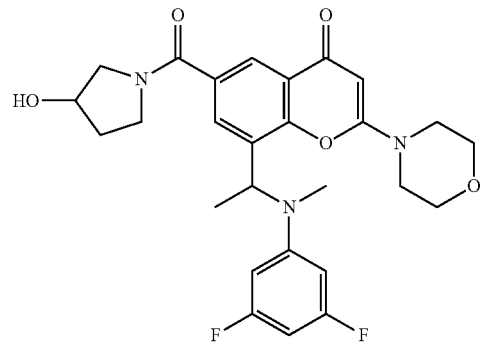 [SMILES: CC(c1cc(C(=O)N2CCC(O)C2)cc2c(=O)cc(N3CCOCC3)oc12)N(C)c1cc(F)cc(F)c1]

This compound was prepared using an analogous procedure to the one described in Example 5.01. Pyrrolidin-3-ol (0.028 mL, 0.35 mmol) was used in place of piperidin-4-ol to give 8-(1-((3,5-difluorophenyl)(methyl)amino)ethyl)-6-(3-hydroxypyrrolidine-1-carbonyl)-2-morpholino-4H-chromen-4-one (80 mg, 53%) as a white solid. Mass Spectrum: M+H$^+$ 514. NMR Spectrum (DMSOd6 at 323° K): 1.57 (d, 3H), 1.82 (bs, 1H), 1.96 (bs, 1H), 2.63 (s, 1.5H), 2.65 (s, 1.5H), 3.22-3.62 (m, 12H), 4.25 (bs, 0.5H), 4.33 (bs, 0.5H), 4.86 (bs, 0.5H), 4.92 (bs, 0.5H), 5.51 (s, 1H), 5.56 (q, 1H), 6.36 (t, 1H), 6.51 (d, 2H), 7.76 (d, 0.5H), 7.78 (bs, 0.5H), 8.02 (bs, 1H).

EXAMPLE 5.03

8-(1-((3,5-difluorophenyl)(methyl)amino)ethyl)-6-((R)-2-(hydroxymethyl)pyrrolidine-1-carbonyl)-2-morpholino-4H-chromen-4-one

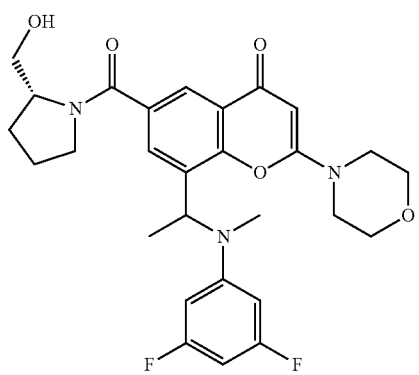 [SMILES: CC(c1cc(C(=O)N2CCC[C@@H]2CO)cc2c(=O)cc(N3CCOCC3)oc12)N(C)c1cc(F)cc(F)c1]

This compound was prepared using a procedure similar to the one described in Example 5.01. (R)-pyrrolidin-2-yl-methanol (0.035 mL, 0.35 mmol) was used in place of piperidin-4-ol to give 8-(1-((3,5-difluorophenyl)(methyl)amino)

ethyl)-6-((R)-2-(hydroxymethyl)pyrrolidin-1-carbonyl)-2-morpholino-4H-chromen-4-one (81 mg, 53%) as a white solid. Mass Spectrum: M+H⁺ 528. NMR Spectrum (DMSOd6 at 323° K): 1.57 (d, 3H), 1.72 (bs, 1H), 1.83-2.01 (m, 3H), 2.61 (s, 1.5H), 2.65 (s, 1.5H), 3.22-3.68 (m, 12H), 4.17 (bs, 1H), 4.68 (bs, 1H), 5.51 (s, 0.5H), 5.52 (s, 0.5H), 5.53-5.60 (m, 1H), 6.36 (t, 1H), 6.47-6.55 (m, 2H), 6.74 (s, 0.5H), 6.78 (s, 0.5H), 8.01 (bs, 1H).

EXAMPLE 6.0

8-(1-((3,5-difluorophenyl)(methyl)amino)ethyl)-2-morpholino-6-(pyrrolidine-1-carbonyl)-4H-chromen-4-one

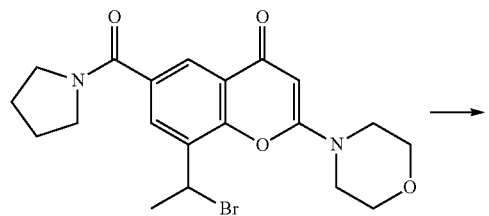

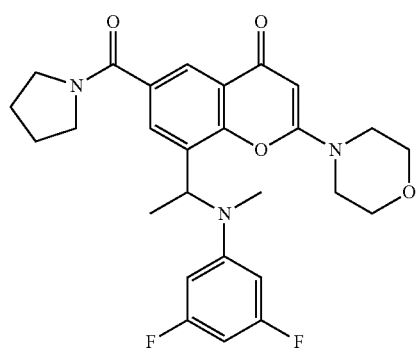

3,5-difluoro-N-methylaniline (222 mg, 1.55 mmol), 8-(1-bromoethyl)-2-morpholino-6-(pyrrolidine-1-carbonyl)-4H-chromen-4-one hydrobromide (200 mg, 0.39 mmol) and potassium iodide (64.3 mg, 0.39 mmol) in CHCl₃ (0.8 mL) and MeOH (0.2 mL) were stirred at 20° C. for 25 hrs. The reaction mixture was concentrated to dryness, diluted with DCM (30 mL), washed with water, brine, dried over magnesium sulfate and concentrated to afford the crude product. Purification was done by flash chromatography on silica gel eluting with 2 to 4% MeOH in DCM. The solvent was evaporated to dryness to afford a foam which was dissolved in acetonitrile-water and concentrated under vacuum to give 8-(1-((3,5-difluorophenyl)(methyl)amino)ethyl)-2-morpholino-6-(pyrrolidine-1-carbonyl)-4H-chromen-4-one (115 mg, 60%) as a white solid. Mass Spectrum: M+H⁺ 498. NMR Spectrum (DMSOd6): 1.56 (d, 3H), 1.78-1.93 (m, 4H), 2.62 (s, 3H), 3.23-3.29 (m, 2H), 3.35-3.56 (m, 10H), 5.55 (s, 1H), 5.59 (q, 1H), 6.40 (t, 1H), 6.53 (d, 2H), 7.79 (d, 1H), 8.01 (d, 1H).

The 8-(1-bromoethyl)-2-morpholino-6-(pyrrolidine-1-carbonyl)-4H-chromen-4-one hydrobromide used as starting material was made as follows:—

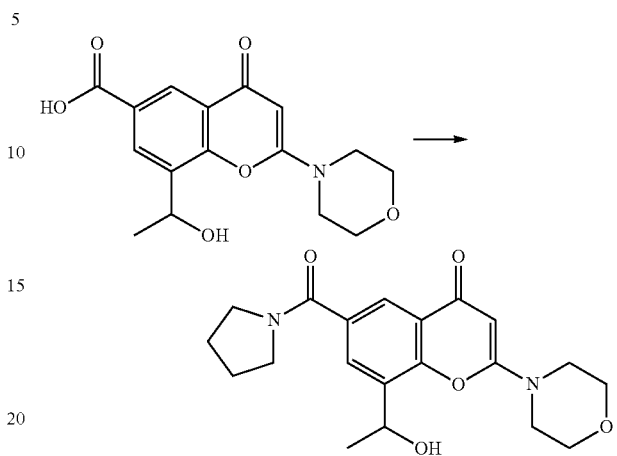

2-(2,5-dioxopyrrolidin-1-yl)-1,1,3,3-tetramethylisouronium tetrafluoroborate (3.34 g, 11.09 mmol) at 25° C. was added portionwise to 8-(1-hydroxyethyl)-2-morpholino-4-oxo-4H-chromene-6-carboxylic acid (1.77 g, 5.54 mmol) and N-ethyl-N-isopropylpropan-2-amine (2.028 mL, 11.64 mmol) suspended in DCM (15 mL) under nitrogen. The resulting mixture was stirred at 25° C. for 5 hrs. Pyrrolidine (1.388 mL, 16.63 mmol) was then added to the mixture and the resulting mixture was stirred at 25° C. overnight. The mixture was poured onto a silica gel column and purified by flash chromatography eluting with 2 to 7% methanolic ammonia (7 N) in DCM. The solvent was evaporated to dryness, the residue was triturated in ethylacetate (10 mL), collected by filtration and dried to afford 8-(1-hydroxyethyl)-2-morpholino-6-(pyrrolidine-1-carbonyl)-4H-chromen-4-one (1.66 g, 80%) as a beige solid. Mass Spectrum: M+H+ 373.

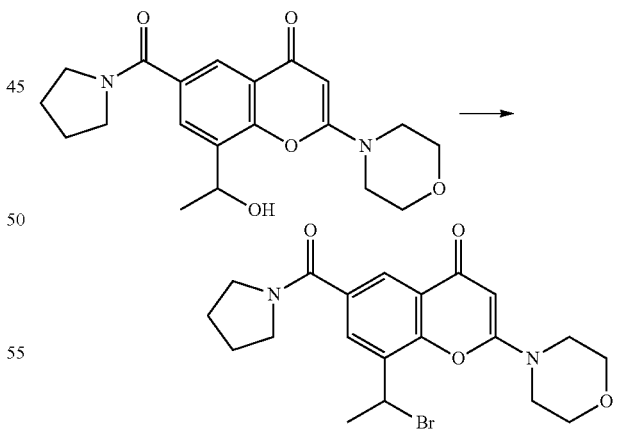

A solution of tribromophosphine (0.491 mL, 5.22 mmol) in 1,2-dichloroethane (4 mL) at 10° C., was added dropwise to 8-(1-hydroxyethyl)-2-morpholino-6-(pyrrolidine-1-carbonyl)-4H-chromen-4-one (1.62 g, 4.35 mmol) suspended in 1,2-dichloroethane (18 mL) under nitrogen. The resulting suspension was stirred at 50° C. for 1 hour. The reaction mixture was allowed to cool to RT under stirring and diluted with diethyl ether (18 mL). The precipitate was collected by filtration, washed with diethyl ether and dried to a constant weight to afford 8-(1-bromoethyl)-2-morpholino-6-(pyrrolidine-1-carbonyl)-4H-chromen-4-one (2.45 g, 100%) hydrobromide as a white solid, which was used without further purification. NMR Spectrum (DMSOd6): 1.79-1.93 (m, 4H), 2.11 (d, 3H), 3.37-3.44 (m, 2H), 3.46-3.53 (m, 2H), 3.57-3.70 (m, 4H), 3.73-3.80 (m, 4H), 5.66 (s, 1H), 5.92 (q, 1H), 7.99-8.03 (m, 2H).

EXAMPLE 7.0

8-(1-((3,5-difluorophenyl)(methyl)amino)ethyl)-N-(2-hydroxyethyl)-N-methyl-2-morpholino-4-oxo-4H-chromene-6-carboxamide 3.01 (s, 3H), 3.23-3.40 (m, 5H), 3.4-3.71 (m, 7H), 4.74 (bs, 1H), 5.52 (s, 1H), 5.57 (q, 1H), 6.38 (t, 1H), 6.53 (d, 2H), 7.74 (bs, 1H), 7.93 (s, 1H).

EXAMPLE 7.0a 8-(1-((3,5-difluorophenyl)(methyl)amino)ethyl)-N-(2-hydroxyethyl)-N-methyl-2-morpholino-4-oxo-4H-chromene-6-carboxamide (enantiomer 1)

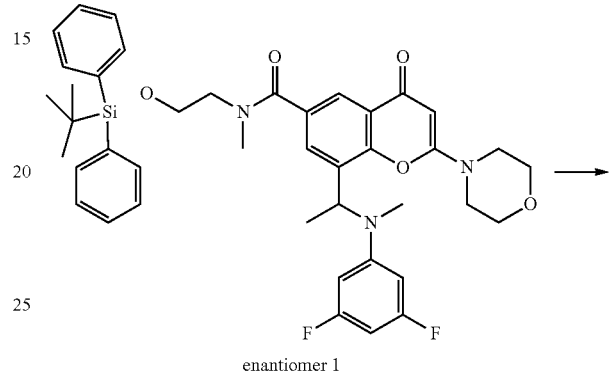

enantiomer 1

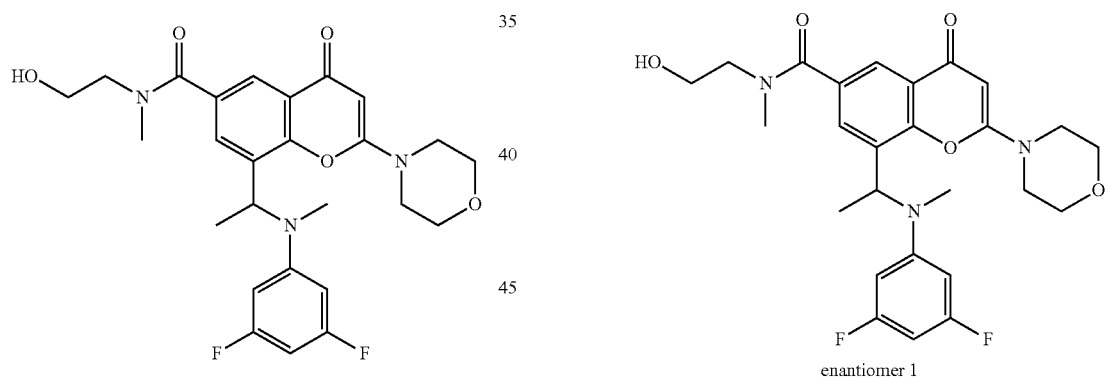

enantiomer 1

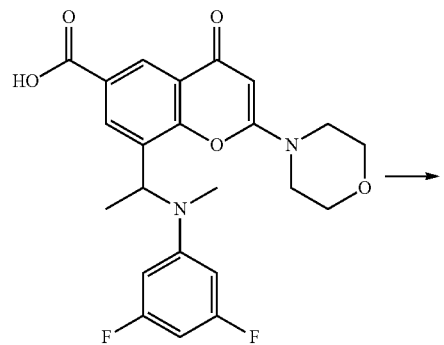

TBTU (108 mg, 0.34 mmol) was added in one portion to a stirred solution of 8-(1-((3,5-difluorophenyl)(methyl)amino)ethyl)-2-morpholino-4-oxo-4H-chromene-6-carboxylic acid (125 mg, 0.28 mmol), N-ethyl-N-isopropylpropan-2-amine (0.103 mL, 0.59 mmol) and 2-s (methylamino)ethanol (0.027 mL, 0.34 mmol) in DMF (1 mL). The resulting solution was stirred at RT for 2 hrs. The reaction mixture was filtered and purified by preparative HPLC using a reverse-phase column (C-18, 5 microns silica, 19 mm diameter, 100 mm length, flow rate of 40 mL/minute) and decreasingly polar mixtures of water (containing 0.2% ammonium carbonate) and acetonitrile as eluent. The fractions containing the desired compound were evaporated to dryness to afford 8-(1-((3,5-difluorophenyl)(methyl)amino)ethyl)-N-(2-hydroxyethyl)-N-methyl-2-morpholino-4-oxo-4H-chromene-6-carboxamide (90 mg, 64%) as a off-white solid. Mass Spectrum: M+H$^+$ 502. NMR Spectrum (DMSOd6 at 323° K): 1.58 (d, 3H), 2.65 (s, 3H), Tetrabutylammonium fluoride (0.568 mL, 0.57 mmol) was added to a stirred solution of N-(2-(tert-butyldiphenylsilyloxy)ethyl)-8-(1-((3,5-difluorophenyl)(methyl)amino)ethyl)-N-methyl-2-morpholino-4-oxo-4H-chromene-6-carboxamide enantiomer 1 (210 mg, 0.28 mmol) dissolved in THF (2 mL) at RT under nitrogen and the resulting solution stirred for 16 hrs. The mixture was evaporated to dryness, diluted with DCM and washed with water, brine, dried over magnesium sulfate, filtered and concentrated. The crude product was purified by flash chromatography on silica gel eluting with 5 to 7% MeOH in DCM. The solvent was evaporated to dryness, the gum was triturated in ether/pentane, the solid was collected by filtration and dried to give 8-(1-((3,5-difluorophenyl)(methyl)amino)ethyl)-N-(2-hydroxyethyl)-N-methyl-2-morpholino-4-oxo-4H-chromene-6-carboxamide enantiomer 1 (79 mg, 56%) as a white solid. Mass Spectrum: M+H$^+$ 502. $[\alpha]^D_{20°}$: −9° in MeCN.

The N-(2-(tert-butyldiphenylsilyloxy)ethyl)-8-(1-((3,5-difluorophenyl)(methyl)amino)ethyl)-N-methyl-2-morpholino-4-oxo-4H-chromene-6-carboxamide enantiomer 1 used as starting material was made as follows: —

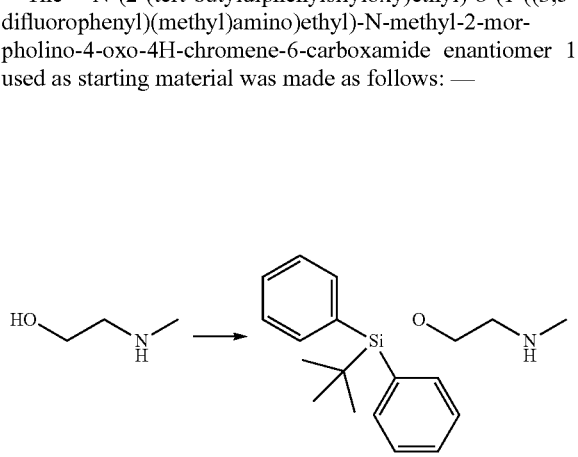

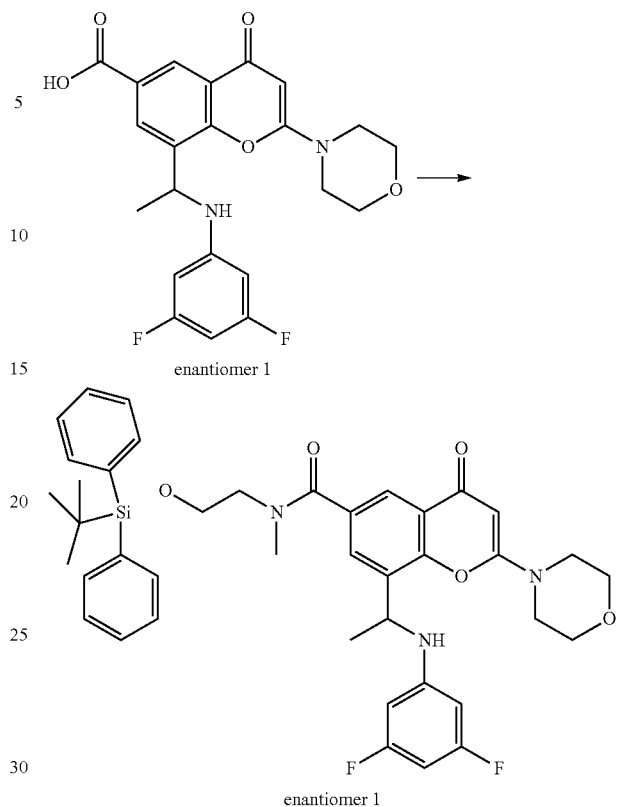

enantiomer 1 enantiomer 1

To a solution of 2-(methylamino)ethanol (2.14 mL, 26.6 mmol) in DCM (60 mL) was added triethylamine (4.1 mL, 29.3 mmol),N,N-dimethylpyridin-4-amine (1.63 g, 13.3 mmol) and tert-butylchlorodiphenylsilane (7.6 mL, 29.3 mmol). The reaction was stirred overnight at 40° C. After cooling to RT, the reaction was quenched with water (20 mL) and ether (100 mL). The organic phase was washed with water, brine, dried over magnesium sulfate and concentrated to afford the crude product which was purified by flash chromatography on silica gel eluting with 0 to 10% MeOH in DCM. The solvent was evaporated to dryness to afford 2-(tert-butyldiphenylsilyloxy)-N-methylethanamine (4.4 g, 53%) as a colorless oil. NMR Spectrum (DMSOd6): 0.99 (s, 9H), 2.27 (s, 3H), 2.63 (t, 2H), 3.68 (t, 2H), 7.40-7.49 (m, 6H), 7.60-7.65 (m, 4H).

8-(1-(3,5-difluorophenylamino)ethyl)-2-morpholino-4-oxo-4H-chromene-6-carboxylic acid was prepared as described in Example 2.00 and the two enantiomers were separated by chiral preparative HPLC using the following conditions:

| Instrument | Kronlab |
|---|---|
| Column | 100 mm Chiralpak IC 20 µm |
| Eluent | DCM/IPA/HOAC/TEA 50/50/0.2/0.1 |
| Oven Temperature | Ambient |
| Flow | 350 ml/min |
| Wavelength | 254 nm, 280 nm |
| Sample Conc | 4.5 g/100 ml in DCM/IPA 50/50 |
| Injection volume | 100 mL |
| Run Time | 40 min |

48.1 g of racemic compound was separated using the above conditions to give:

First eluting enantiomer 24 g (strength 76%) $[\alpha]^D_{20°}$: +115° in MeCN (enantiomer 1)

Second eluting enantiomer 24.1 g (strength 81%) $[\alpha]^D_{20°}$: −102° in MeCN (enantiomer 2)

1-(3-dimethylaminopropyl)-3-ethylcarbodiimide hydrochloride (135 mg, 0.71 mmol) was added in one portion to 8-(1-(3,5-difluorophenylamino)ethyl)-2-morpholino-4-oxo-4H-chromene-6-carboxylic acid (200 mg, 0.35 mmol, enantiomer 1; $[\alpha]^D_{20°}$: +115°, 2-(tert-butyldiphenylsilyloxy)-N-methylethanamine (221 mg, 0.71 mmol) and 2-hydroxypyridine N-oxide (78 mg, 0.71 mmol) dissolved in DCM (2 mL) under argon. The resulting solution was stirred at RT overnight. The solution was evaporated to dryness, water was added and product was extracted with DCM. The organic phase was washed with brine and dried over magnesium sulfate, the solvent was evaporated to afford N-(2-(tert-butyldiphenylsilyloxy)ethyl)-8-(1-(3,5-difluorophenylamino)ethyl)-N-methyl-2-morpholino-4-oxo-4H-chromene-6-carboxamide (94%) as a white solid. Mass Spectrum: M+H$^+$ 726.

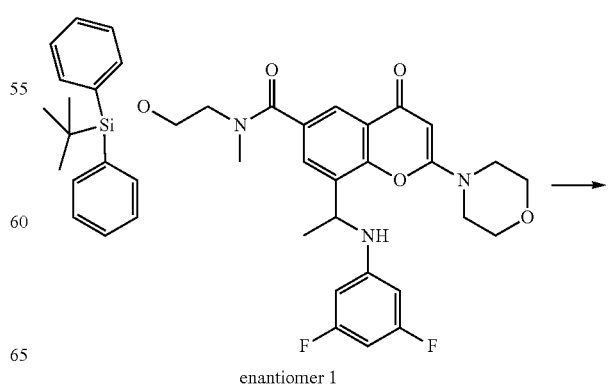

enantiomer 1

151

-continued

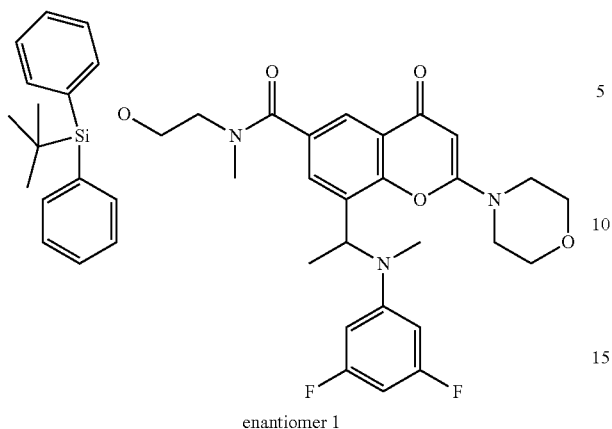

enantiomer 1

Lithium bis(trimethylsilyl)amide (0.539 mL, 0.54 mmol) was added to a stirred solution of N-(2-(tert-butyldiphenylsilyloxy)ethyl)-8-(1-(3,5-difluorophenylamino)ethyl)-N-methyl-2-morpholino-4-oxo-4H-chromene-6-carboxamide (230 mg, 0.32 mmol) dissolved in dry THF (3 mL). The solution was stirred over a period of 10 minutes at −20° C. under nitrogen. Dimethyl sulfate (0.051 mL, 0.54 mmol) was added to the mixture and the resulting suspension was left to rise to RT for 1 h30 under nitrogen. A sat. aq. sol. of NH$_4$Cl was added and the reaction mixture was extracted with DCM. The combined organic phases were washed with brine, dried over magnesium sulfate and concentrated. The crude product was diluted with DCM and purified by flash chromatography on silica gel eluting with 4% ethyl alcohol in DCM. The solvent was evaporated to dryness to afford N-(2-(tert-butyldiphenylsilyloxy)ethyl)-8-(1-((3,5-difluorophenyl)(methyl)amino)ethyl)-N-methyl-2-morpholino-4-oxo-4H-chromene-6-carboxamide enantiomer 1 (210 mg, 90%) as a white solid. Mass Spectrum: M+H$^+$ 740.

EXAMPLE 7.0b 8-(1-((3,5-difluorophenyl)(methyl)amino)ethyl)-N-(2-hydroxyethyl)-N-methyl-2-morpholino-4-oxo-4H-chromene-6-carboxamide (enantiomer 2)

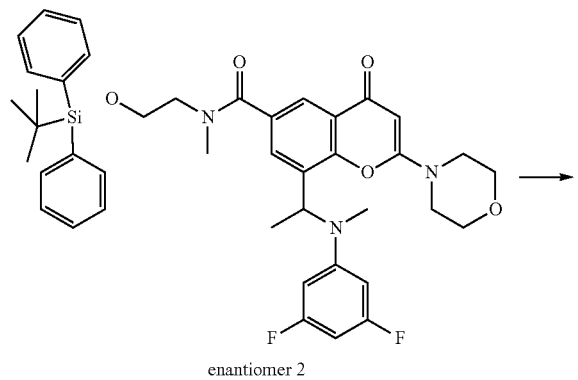

enantiomer 2

152

-continued enantiomer 2

This compound was prepared using an analogous procedure to that described for Example 7.0a but instead using enantiomer 2 of 8-(1-(3,5-difluorophenylamino)ethyl)-2-morpholino-4-oxo-4H-chromene-6-carboxylic acid ([α]$^D_{20°}$: −102°). Thus N-(2-(tert-butyldiphenylsilyloxy)ethyl)-8-(1-((3,5-difluorophenyl)(methyl)amino)ethyl)-N-methyl-2-morpholino-4-oxo-4H-chromene-6-carboxamide enantiomer 2 (1.8 g, 2.43 mmol) gave 8-(1-((3,5-difluorophenyl)(methyl)amino)ethyl)-N-(2-hydroxyethyl)-N-methyl-2-morpholino-4-oxo-4H-chromene-6-carboxamide enantiomer 2 (0.985 g, 80%) as a white solid [α]$^D_{20°}$: +10° in MeCN. Mass Spectrum: M+H$^+$ 502. NMR Spectrum (DMSOd6): 1.54 (bs, 3H), 2.61 (s, 3H), 2.96 (s, 1.5H), 3.01 (s, 1.5H), 3.20-3.30 (m, 4H), 3.41-3.58 (m, 7H), 3.65 (bs, 1H), 4.68 (bs, 1H), 5.54 (s, 1H), 5.58 (q, 1H), 6.40 (d, 2H), 6.54 (t, 1H), 7.70 (bs, 0.5H), 7.77 (bs, 0.5H), 7.90 (bs, 0.5H) 7.93 (bs, 0.5H).

EXAMPLE 7.01a 8-(1-((3,5-difluorophenyl)(methyl)amino)ethyl)-6-(4-hydroxypiperidine-1-carbonyl)-2-morpholino-4H-chromen-4-one (enantiomer 2)

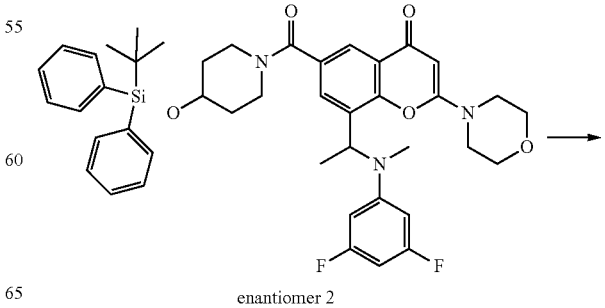

enantiomer 2

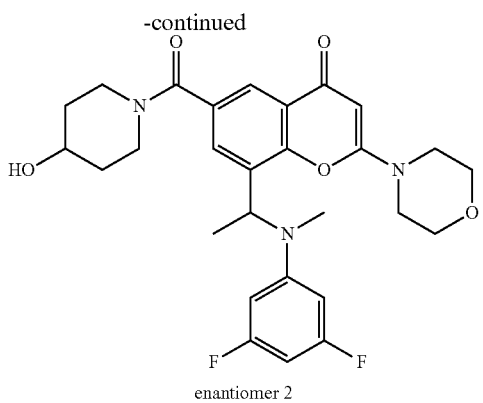

enantiomer 2

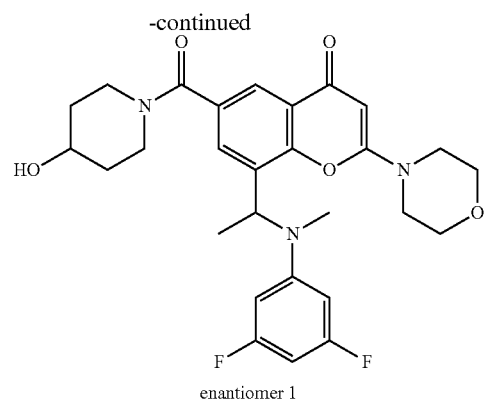

enantiomer 1

Tetrabutylammonium fluoride (1N in THF) (7.83 mL, 7.83 mmol) was added dropwise to a stirred solution of 6-(4-(tert-butyldiphenylsilyloxy)piperidine-1-carbonyl)-8-(1-((3,5-difluorophenyl)(methyl)amino)ethyl)-2-morpholino-4H-chromen-4-one (3 g, 3.92 mmol, enantiomer 2 in Example 7.0a, $[\alpha]^D_{20°}$: −102°) dissolved in THF (20 mL) at RT under nitrogen and stirred for 2 hrs. The mixture was evaporated to dryness, diluted with DCM, washed with water. The organic phase was washed with brine, dried over magnesium sulfate, filtered and concentrated. The crude product was purified by flash chromatography on silica gel (80 g) eluting with 3 to 7% MeOH in DCM. The solvent was evaporated to dryness to give a foam which was triturated in ether (2-5 mL). The resulting white solid was collected by filtration and dried to give 8-(1-((3,5-difluorophenyl)(methyl)amino)ethyl)-6-(4-hydroxypiperidine-1-carbonyl)-2-morpholino-4H-chromen-4-one enantiomer 2 (1.7 g, 82%) as a white solid. Mass Spectrum: M+H⁺ 528. $[\alpha]^D_{20°}$: +7° in MeCN.

The preparation of the racemic 8-(1-((3,5-difluorophenyl)(methyl)amino)ethyl)-6-(4-hydroxypiperidine-1-carbonyl)-2-morpholino-4H-chromen-4-one is described in Example 5.01.

The 6-(4-(tert-butyldiphenylsilyloxy)piperidine-1-carbonyl)-8-(1-((3,5-difluorophenyl)(methyl)amino)ethyl)-2-morpholino-4H-chromen-4-one enantiomer 2 used as starting material was made using an analogous procedure to the one described for the synthesis of the starting material in Example 7.0a. Mass Spectrum: M+H⁺ 766.

EXAMPLE 7.01b 8-(1-((3,5-difluorophenyl)(methyl)amino)ethyl)-6-(4-hydroxypiperidine-1-carbonyl)-2-morpholino-4H-chromen-4-one (enantiomer 1)

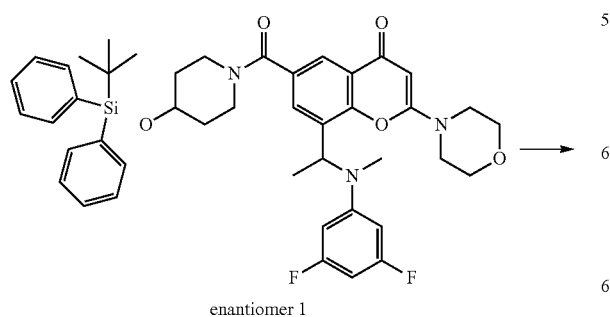

enantiomer 1

This compound was prepared using an analogous procedure to that described in Example 7.01a except that the chiral acid starting material was 8-(1-(3,5-difluorophenylamino)ethyl)-2-morpholino-4-oxo-4H-chromene-6-carboxylic acid enantiomer 1 ($[\alpha]^D_{20°}$: +115°) from Example 7.0a. There was thus obtained: 8-(1-((3,5-difluorophenyl)(methyl)amino)ethyl)-6-(4-hydroxypiperidine-1-carbonyl)-2-morpholino-4H-chromen-4-one enantiomer 1 (45 mg, 69%) as a white solid. $[\alpha]^D_{20°}$: −3° in MeCN. Mass Spectrum: M+H⁺ 528.

EXAMPLE 7.02

6-(azetidine-1-carbonyl)-8-(1-(3,5-difluorophenylamino)ethyl)-2-morpholino-4H-chromen-4-one (enantiomer 2)

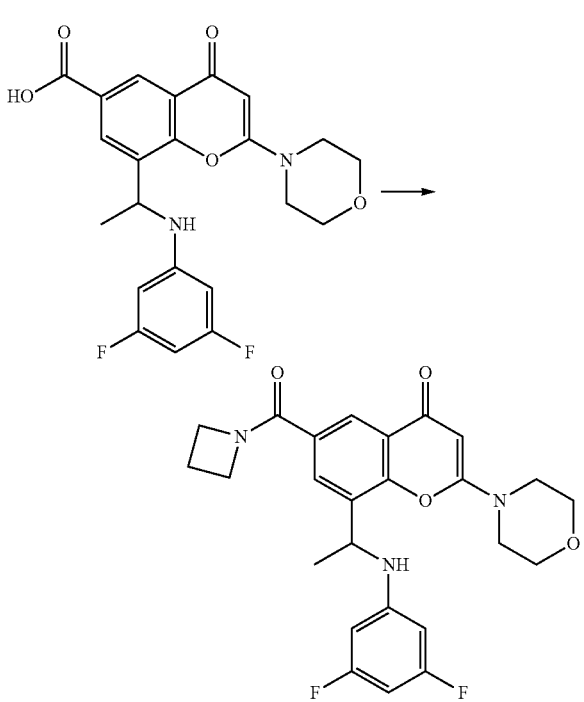

2-(2,5-dioxopyrrolidin-1-yl)-1,1,3,3-tetramethylisouronium tetrafluoroborate (409 mg, 1.36 mmol) was added portionwise to a suspension of the enantiomer 2 of 8-(1-(3,5-difluorophenylamino)ethyl)-2-morpholino-4-oxo-4H-chromene-6-carboxylic acid ($[\alpha]^D_{20°}$: −102°, enantiomer 2, see Example 7.0a) (450 mg, 1.05 mmol) and N-ethyl-N-isopropylpropan-2-amine (0.310 mL, 1.78 mmol) in DCM (5 mL) at RT under nitrogen. The resulting mixture was stirred at RT for 4 hrs. Azetidine (0.211 mL, 3.14 mmol) was then added to the mixture and stirring was maintained overnight. The mixture was diluted with DMF and concentrated to remove DCM. The reaction mixture was purified by preparative HPLC on a Waters X-Bridge system. The fractions were evaporated to dryness to afford a white solid 6-(azetidine-1-carbonyl)-8-(1-(3,5-difluorophenylamino)ethyl)-2-morpholino-4H-chromen-4-one (300 mg, 61%). Mass Spectrum: M+H+ 470. [α]$^D_{20°}$: −113° in MeCN. NMR Spectrum (DMSOd6): 1.50 (d, 3H), 2.18-2.28 (m, 2H), 3.50-3.63 (m, 4H), 3.69-3.78 (m, 4H), 3.98-4.07 (m, 2H), 4.09-4.19 (m, 2H), 4.97-5.05 (m, 1H), 5.61 (s, 1H), 6.15 (d, 2H), 6.21 (t, 1H), 7.03 (d, 1H), 7.79 (d, 1H), 8.02 (d, 1H).

EXAMPLE 8.0

8-(1-(3-chloro-5-fluorophenylamino)ethyl)-N,N-dimethyl-2-morpholino-4-oxo-4H-chromene-6-carboxamide (single enantiomer)

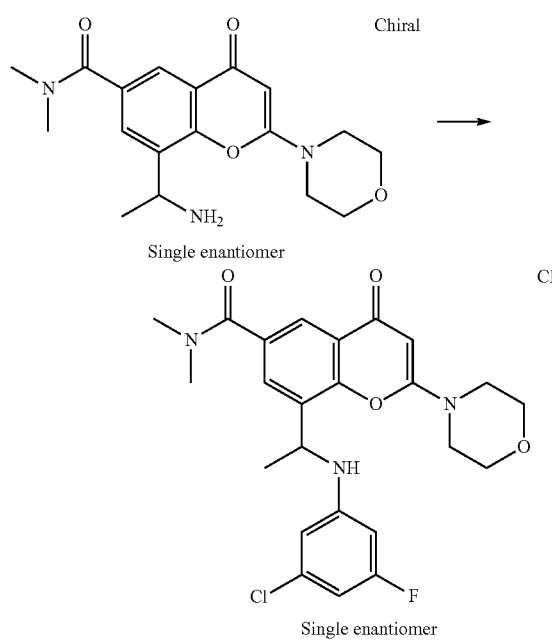

To a mixture of 8-(1-aminoethyl)-N,N-dimethyl-2-morpholino-4-oxo-4H-chromene-6-carboxamide (350 mg, 1.01 mmol, single enantiomer, [α]$^D_{20°}$: +35° in acetonitrile), cesium carbonate (1288 mg, 3.95 mmol), (9,9-dimethyl-9H-xanthene-4,5-diyl)bis(diphenylphosphine) (147 mg, 0.25 mmol) and 1-bromo-3-chloro-5-fluorobenzene (467 mg, 2.23 mmol) in degassed 1,4-dioxane (2 ml), was added tris(dibenzylideneacetone)dipalladium (70 mg, 0.08 mmol). The suspension was heated in a sealed container at 95° C. for 16 hrs. The reaction mixture was filtered through a short pad of dicalite and concentrated under reduced pressure. The crude product was purified by flash chromatography on silica gel eluting with 0 to 8% isopropanol in DCM. The solvent was evaporated to dryness, the product triturated with diethyl ether—DCM (9:1), collected by filtration and dried to afford 8-(1-(3-chloro-5-fluorophenylamino)ethyl)-N,N-dimethyl-2-morpholino-4-oxo-4H-chromene-6-carboxamide (320 mg; 67%) as a clear yellow solid. Mass Spectrum: M+H+ 474. [α]$^D_{20°}$: −138°. NMR Spectrum (DMSOd6): 1.52 (d, 3H), 2.75 (bs, 3H), 2.95 (bs, 3H), 3.49-3.63 (m, 4H), 3.70-3.79 (m, 4H), 4.98-5.07 (m, 1H), 5.60 (s, 1H), 6.23 (d, 1H), 6.42 (d, 1H), 6.43 (ddd, 1H), 6.94 (d, 1H), 7.54 (d, 1H), 7.80 (d, 1H).

The 8-(1-aminoethyl)-N,N-dimethyl-2-morpholino-4-oxo-4H-chromene-6-carboxamide (single enantiomer, [α]$^D_{20°}$: +35° in acetonitrile) used as starting material was made as follows: —

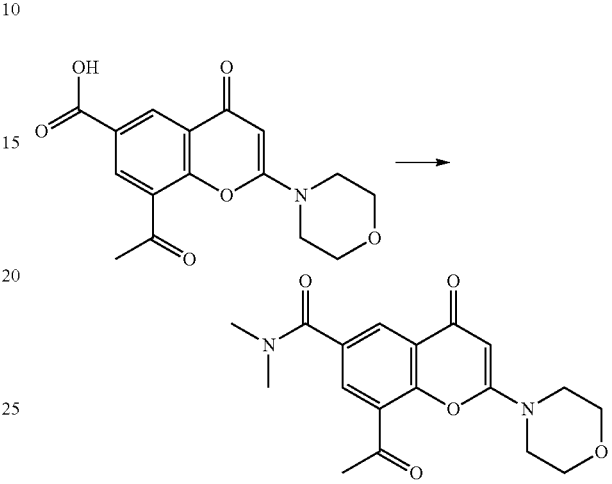

N-ethyl-N-isopropylpropan-2-amine (9.4 mL, 53.9 mmol) was added to 8-acetyl-2-morpholino-4-oxo-4H-chromene-6-carboxylic acid (5.7 g, 18 mmol) in DCM (100 mL). Five minutes later dimethylamine hydrochloride (2.9 g, 35.9 mmol) and 2-(1H-benzo[d][1,2,3]triazol-1-yl)-1,1,3,3-tetramethylisouronium tetrafluoroborate (6.92 g, 21.6 mmol) were added. The mixture was diluted with DCM, washed with NaHCO3, dried over magnesium sulfate and concentrated to afford the crude product which was purified by flash chromatography on silica gel eluting with 0 to 5% MeOH/DCM. The solvent was evaporated to dryness to afford 8-acetyl-N,N-dimethyl-2-morpholino-4-oxo-4H-chromene-6-carboxamide (2.75 g, 46%) as a yellow solid. Mass Spectrum: M+H+ 345.

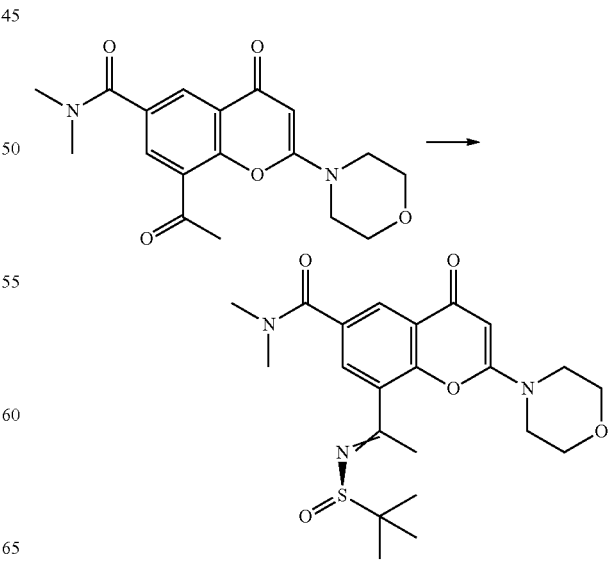

Tetraethoxytitanium (12.5 g, 46.5 mmol) was added to a stirred solution of 8-acetyl-N,N-dimethyl-2-morpholino-4-oxo-4H-chromene-6-carboxamide (4 g, 11.6 mmol) and (R)-2-methylpropane-2-sulfinamide (2.48 g, 20.4 mmol) in THF (100 mL) under nitrogen. The resulting mixture was stirred under reflux for 24 hrs. The reaction mixture was allowed to cool to RT, quenched with brine (100 ml) and diluted with ethyl acetate. The precipitate was removed by filtration over celite and washed with ethyl acetate. The phases were separated and the aqueous phase was extracted with ethyl acetate. The organic phases were combined, washed with water (twice), brine, dried over magnesium sulfate and concentrated to dryness to afford 2 g of the desired product. More product (2.8 g) was recovered from the aqueous phase by DCM extraction. The 2 batches were combined to give 8-(1-(tert-butylsulfinylimino)ethyl)-N,N-dimethyl-2-morpholino-4-oxo-4H-chromene-6-carboxamide (4.5 g, 87%) as an yellow foam, which was used in the next step without further purification. Mass Spectrum: M+H⁺ 448.

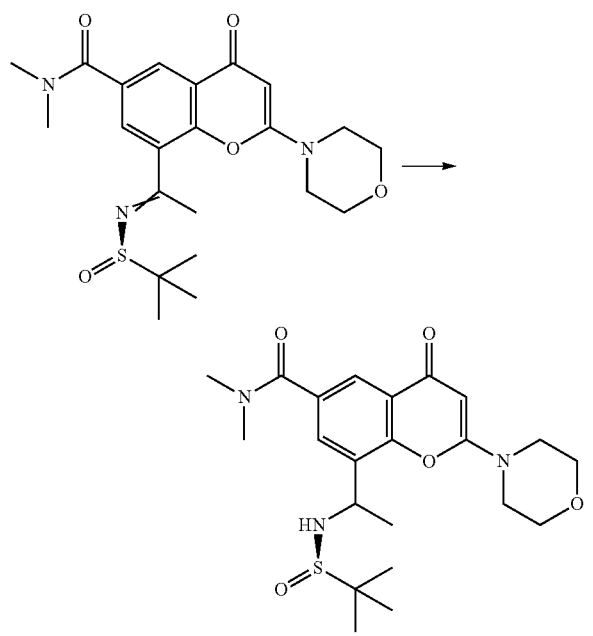

The 8-(1-(tert-butylsulfinylimino)ethyl)-N,N-dimethyl-2-morpholino-4-oxo-4H-chromene-6-carboxamide was diluted in DCM (35 mL) and MeOH (35 mL), acetic acid (4.6 mL, 80.4 mmol) and sodium cyanotrihydroborate (1.9 g, 30.2 mmol) was added at −15° C. The resulting mixture was stirred at −15° C. for 5 hrs then allowed to warm to 0° C. A sat. sol. of Na2CO3 was added at 0° C. until pH~8-9 and extracted with DCM (×2). The organic phase was washed with brine, dried over magnesium sulfate and concentrated. The crude product was purified by flash chromatography on silica gel (column SiO2, 15-40 µm-150 g Merck) eluting with 5 to 15% EtOH in DCM. The fractions containing impure product were concentrated down and repurified using the same system. The fractions containing pure 8-(1-((R)-1,1-dimethylethylsulfinamido)ethyl)-N,N-dimethyl-2-morpholino-4-oxo-4H-chromene-6-carboxamide were combined and the solvent was evaporated to dryness to afford 2.48 g, (5.52 mmol, 54.9%) as a white foam. The fractions containing a mixture of diastereoisomers were combined, concentrated and purified by preparative HPLC on a Waters X-Bridge system. The fractions containing the desired compound were evaporated to dryness to afford a further crop of 8-(1-((R)-1,1-dimethylethylsulfinamido)ethyl)-N,N-dimethyl-2-morpholino-4-oxo-4H-chromene-6-carboxamide (0.25 g, 0.556 mmol, 5.53%) as a white foam. These 2 batches (2.48 g) and (0.25 g) were combined to give 8-(1-((R)-1,1-dimethylethylsulfinamido)ethyl)-N,N-dimethyl-2-morpholino-4-oxo-4H-chromene-6-carboxamide (2.73 g, 60%, diastereomeric excess >95%). Mass Spectrum: M+H⁺ 450.

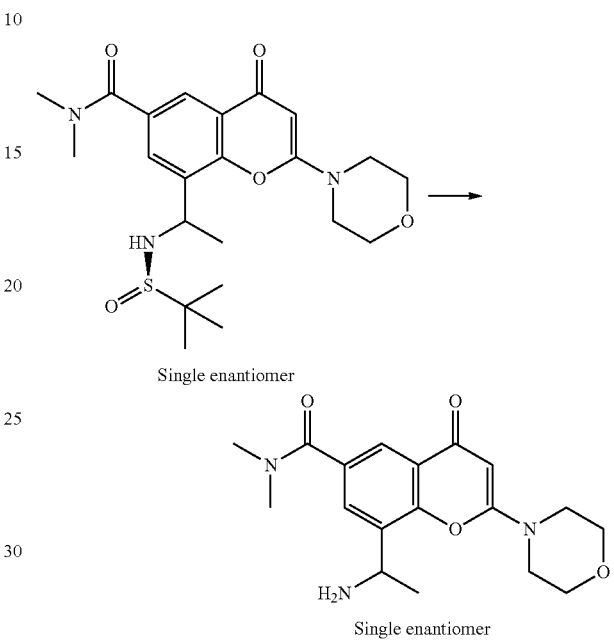

Hydrogen chloride in dioxane 4M (15 mL, 60.1 mmol) was added to 8-(1-((R)-1,1-dimethylethylsulfinamido)ethyl)-N,N-dimethyl-2-morpholino-4-oxo-4H-chromene-6-carboxamide (2.7 g, 6.0 mmol) dissolved in dioxane (40 mL). The resulting white suspension was stirred at RT for 1 hour, collected by filtration, washed with diethyl ether and dried. It was dissolved into a 5% methanolic ammonia (7 N) sol. in DCM (200 mL) and stirred for 5 minutes. The precipitate (NH4Cl) was removed by filtration and the filtrate was concentrated to dryness to afford 8-(1-aminoethyl)-N,N-dimethyl-2-morpholino-4-oxo-4H-chromene-6-carboxamide (single enantiomer, 1.85 g, 89%) as an off-white solid. Mass Spectrum: M+H⁺ 346. [α]$^D_{20°}$: +35° in acetonitrile.

EXAMPLE 8.01

8-(1-(3-cyano-5-fluorophenylamino)ethyl)-N,N-dimethyl-2-morpholino-4-oxo-4H-chromene-6-carboxamide (single enantiomer)

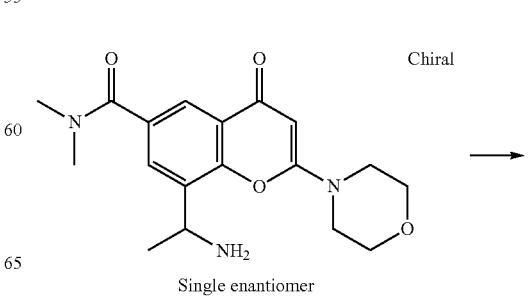

-continued

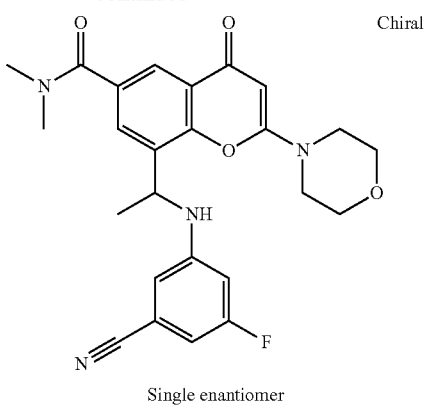

Single enantiomer 8-(1-aminoethyl)-N,N-dimethyl-2-morpholino-4-oxo-4H-chromene-6-carboxamide (300 mg, 0.87 mmol, [α]$^D_{20°}$: +35° in acetonitrile) was reacted with 3-bromo-5-fluorobenzonitrile (382 mg, 1.91 mmol) using a procedure similar to the one described in Example 8.00. Purification was done by flash chromatography on silica gel eluting with 0 to 5% MeOH in DCM followed by preparative HPLC on a Waters X-Bridge system. The fractions containing the desired compound were evaporated to dryness to afford 8-(1-(3-cyano-5-fluorophenylamino)ethyl)-N,N-dimethyl-2-morpholino-4-oxo-4H-chromene-6-carboxamide (330 mg, 82%) as a clear white solid. Mass Spectrum: M+H$^+$ 465.

[α]$^D_{20°}$: −128° in MeCN. NMR Spectrum (CDCl$_3$): 1.51 (d, 3H), 2.91 (s, 3H), 3.09 (s, 3H), 3.44-3.60 (m, 4H), 3.78-3.93 (m, 4H), 4.85-4.94 (m, 1H), 5.17 (d, 1H), 5.56 (s, 1H), 6.38 (ddd, 1H), 6.51 (s, 1H), 6.61 (d, 1H), 7.70 (d, 1H), 8.12 (d, 1H).

EXAMPLE 8.02

N,N-dimethyl-2-morpholino-4-oxo-8-(1-(3,4,5-trifluorophenylamino)ethyl)-4H-chromene-6-carboxamide (single enantiomer)

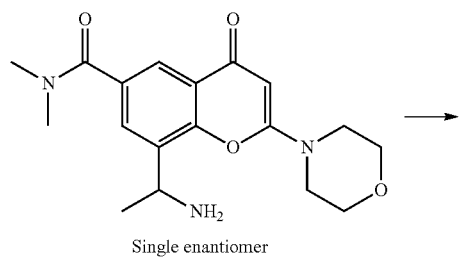

Single enantiomer

-continued

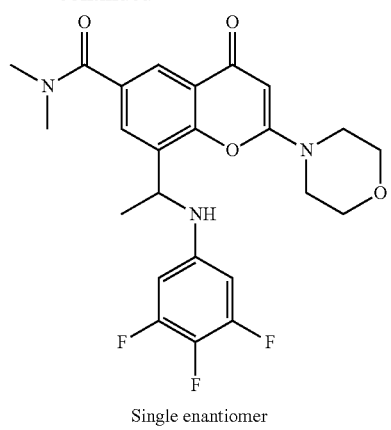

Single enantiomer 8-(1-aminoethyl)-N,N-dimethyl-2-morpholino-4-oxo-4H-chromene-6-carboxamide (232 mg, 0.67 mmol, [α]$^D_{20°}$: +35° in acetonitrile), 3,4,5-trifluorophenylboronic acid (236 mg, 1.34 mmol), diacetoxycopper hydrate (148 mg, 0.74 mmol) and molecular sieves 4A (1 g) were weighed out in a flask. Dichloroethane (4 mL) then pyridine (0.109 mL, 1.34 mmol) were added and the resulting mixture was stirred at RT for 2 days under an oxygen atmosphere. The mixture was diluted with DCM, filtered through a pad of celite, the filtrate was washed with a 0.5N NaOH aq. sol. and the aqueous phase extracted with DCM. The combined organics were dried over magnesium sulphate and concentrated down. The crude product was purified by flash chromatography on silica gel eluting with 0 to 10% MeOH in ethyl acetate/DCM (1:1). The solvent was evaporated to dryness to afford N,N-dimethyl-2-morpholino-4-oxo-8-(1-(3,4,5-trifluorophenylamino)ethyl)-4H-chromene-6-carboxamide single enantiomer (100 mg, 31%) as a white foam. Mass Spectrum: M+H 476. [α]$^D_{20°}$: −108° in MeCN. NMR Spectrum (CDCl$_3$): 1.56 (d, 3H), 2.91 (s, 3H), 3.09 (s, 3H), 3.47-3.56 (m, 4H), 3.82-3.90 (m, 4H), 4.35 (d, 1H), 4.79-4.88 (m, 1H), 5.56 (s, 1H), 6.03 (dd, 2H), 7.70 (d, 1H), 8.12 (d, 1H).

EXAMPLE 9.0

8-(1-(4-fluorophenylamino)ethyl)-N,N-dimethyl-2-((R)-2-methylmorpholino)-4-oxo-4H-chromene-6-carboxamide

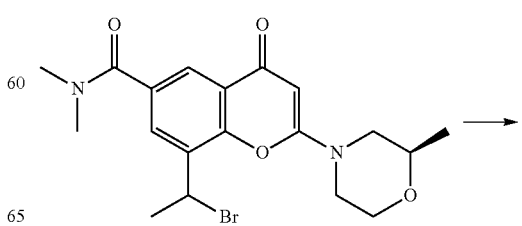

-continued

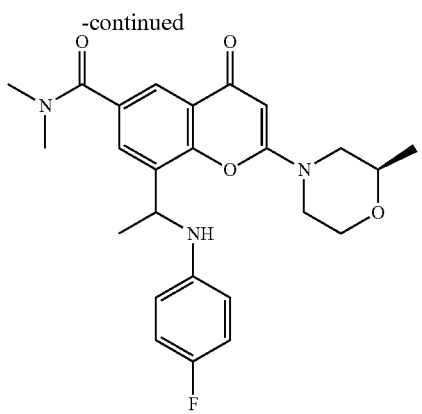

8-(1-bromoethyl)-N,N-dimethyl-2-((R)-2-methylmorpholino)-4-oxo-4H-chromene-6-carboxamide hydrobromide (150 mg, 0.30 mmol) and 4-fluoroaniline (0.113 mL, 1.19 mmol) in DMA (1 mL) were stirred at RT for 4 hrs. The reaction mixture was filtered and purified by preparative HPLC using a reverse-phase column (C-18, 5 microns silica, 19 mm diameter, 100 mm length, flow rate of 40 mL/minute) and decreasingly polar mixtures of water (containing 0.2% ammonium carbonate) and acetonitrile as eluent. A further purification was done by flash chromatography on silica gel eluting with 0 to 10% MeOH in DCM. The solvent was evaporated to dryness to afford a oil which was triturated with pentane to give 8-(1-(4-fluorophenylamino)ethyl)-N,N-dimethyl-2-((R)-2-methylmorpholino)-4-oxo-4H-chromene-6-carboxamide (80 mg, 59%) as a white solid.

NMR Spectrum (DMSOd6): 1.16 (d, 3H), 1.50 (d, 3H), 2.66 (bs, 3H), 2.81 (ddd, 1H), 2.93 (bs, 3H), 3.14 (ddd, 1H), 3.57-3.70 (m, 2H), 3.87-4.03 (m, 3H), 4.93-5.01 (m, 1H), 5.62 (s, 1H), 6.24-6.29 (m, 1H), 6.43-6.50 (m, 2H), 6.85 (t, 2H), 7.55 (d, 0.5H), 7.56 (d, 0.5H), 7.77 (d, 1H).

The 8-(1-bromoethyl)-N,N-dimethyl-2-((R)-2-methylmorpholino)-4-oxo-4H-chromene-6-carboxamide hydrobromide used as starting material was made as follows: —

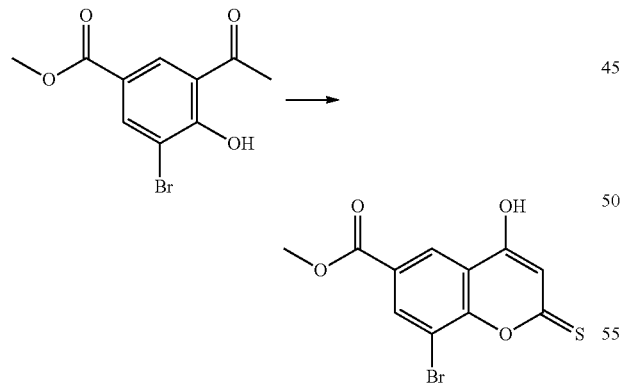

To a suspension of methyl 3-acetyl-5-bromo-4-hydroxybenzoate (75 g, 258 mmol) in THF (350 mL) at −50° C. under nitrogen was added sodium bis(trimethylsilyl)amide (1M in THF) (904 mL, 903.58 mmol) over a 15 min period. The dark solution was allowed to warm to −5-0° C. and stirred for 1 h. Carbon disulfide (24.8 mL, 413 mmol) was added in one portion to the solution at −20° C. The mixture was allowed to warm to RT and stirred for 24 hrs. The reaction mixture was cooled to −50° C., quenched slowly with a 15% aq. sol. H2SO4 (750 mL) (need to trap the H2S formed). The reaction was extracted 3 times with ethyl acetate. The organic phase was washed with brine, dried over magnesium sulfate and concentrated. This residue was triturated with DCM (500 mL), collected by filtration, washed with ether and dried under vacuum to give methyl 8-bromo-4-hydroxy-2-thioxo-2H-chromene-6-carboxylate (33.5 g, 41%) as an yellow solid. The filtrate was evaporated and the resulting dark gum was triturated with ethyl acetate (300 mL) to give a solid which was collected by filtration washed with ether and dried under vacuum to give a second batch of methyl 8-bromo-4-hydroxy-2-thioxo-2H-chromene-6-carboxylate (17.5 g, 22%) as a orange solid. Mass Spectrum: [M−H]⁻ 314 for both batches.

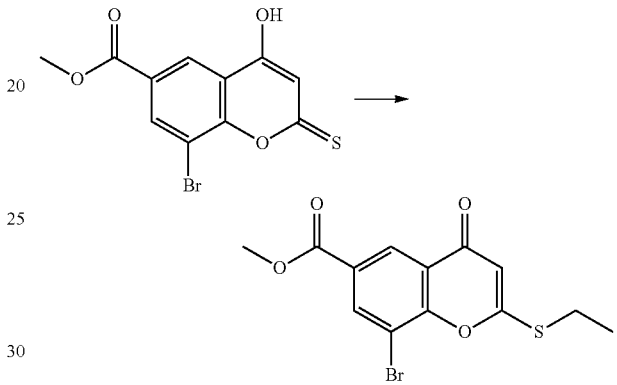

Iodoethane (2.04 mL, 25.54 mmol), was added to a stirred suspension of methyl 8-bromo-4-hydroxy-2-thioxo-2H-chromene-6-carboxylate (2.3 g, 7.30 mmol) and potassium carbonate (1.21 g, 8.76 mmol) in acetone (100 mL) under argon. The resulting mixture was stirred at 60° C. for 2 hrs. The mixture was concentrated in vacuo, and the residue was pardoned between water and DCM. The aqueous layer was extracted into DCM, and the organic extracts were combined, washed with brine, dried over magnesium sulfate and evaporated. The crude product was purified by flash chromatography on silica gel eluting with 0 to 10% ethyl acetate in DCM. The solvent was evaporated to dryness to afford methyl 8-bromo-2-(ethylthio)-4-oxo-4H-chromene-6-carboxylate (1.8 g, 72%) as an orange solid. Mass Spectrum: M+H⁺ 343.

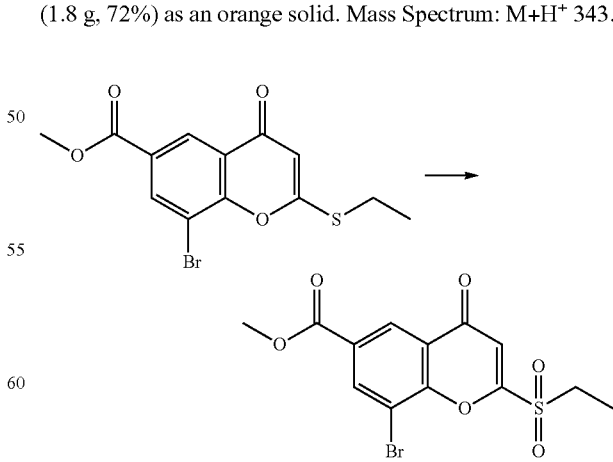

To a stirred solution of methyl 8-bromo-2-(ethylthio)-4-oxo-4H-chromene-6-carboxylate (1.8 g, 5.24 mmol) in DCM (40 mL) was added dropwise 3-chlorobenzoperoxoic acid (2.59 g, 10.49 mmol) while keeping the temperature around 20° C. with a cold bath then left to stir at RT for 2 hrs. The solution was cooled to −15° C., the solid was filtered off and rinsed with cold DCM. The filtrate was then washed with a solution of sodium sulfothioate pentahydrate (0.651 g, 2.62 mmol) in 30 mL H2O, and twice with a solution of NaHCO3. The organic was dried over magnesium sulfate and evaporated to afford methyl 8-bromo-2-(ethylsulfonyl)-4-oxo-4H-chromene-6-carboxylate (1.85 g, 94%) as a red powder consisting approximately of a 70:30 sulfone/sulfoxide mixture which was used as such for the next step.

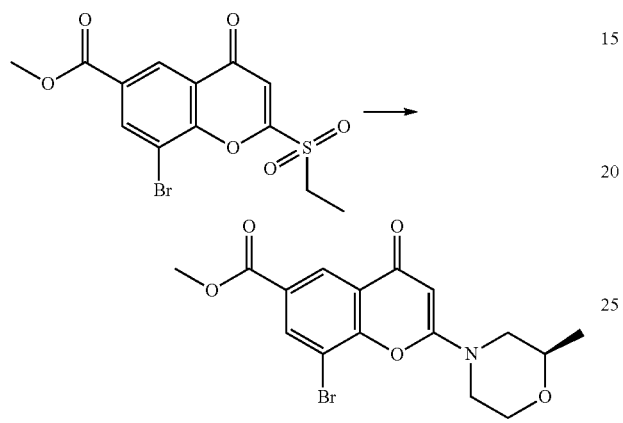

A mixture of (R)-2-methylmorpholine hydrochloride (0.436 g, 3.17 mmol) and N-ethyl-N-isopropylpropan-2-amine (1.184 mL, 6.80 mmol) in DCM (5 mL) was added dropwise to a stirred solution of methyl 8-bromo-2-(ethylsulfonyl)-4-oxo-4H-chromene-6-carboxylate (0.85 g, 2.27 mmol) in DCM (10 mL) at 10° C. under argon. The resulting solution was stirred at RT for 3 hrs. The reaction mixture was quenched with 1M HCl, the phases were separated, the organic phase was washed with brine dried over magnesium sulfate and concentrated to afford the crude product which was purified by flash chromatography on silica gel eluting with 0 to 10% MeOH in DCM. The solvent was evaporated to dryness to afford after a trituration with ether, methyl 8-bromo-2-((R)-2-methylmorpholino)-4-oxo-4H-chromene-6-carboxylate (0.760 g, 88%) as a pale yellow foam. Mass Spectrum: M+H⁺ 382. The reaction was repeated on a similar scale before proceeding to the next step.

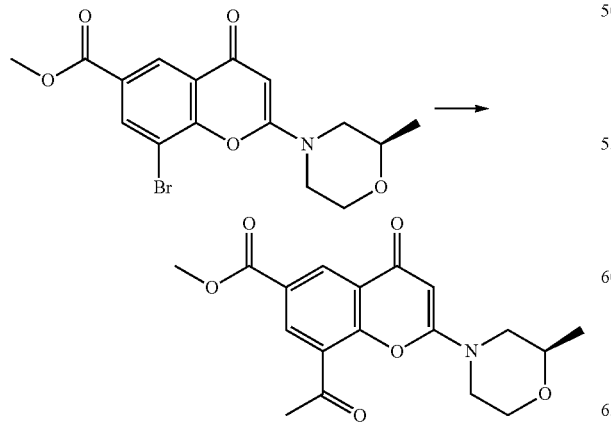

Methyl 8-bromo-2-((R)-2-methylmorpholino)-4-oxo-4H-chromene-6-carboxylate (1.45 g, 3.79 mmol), bis(triphenylphosphine) palladium(II) chloride (0.107 g, 0.15 mmol) and tributyl(1-ethoxyvinyl)stannane (1.346 mL, 3.98 mmol) in 1,4-dioxane (20 mL) were degased, purged with argon and heated to 90° C. for 4 hrs. After cooling to RT, HCl2N (1.9 mL, 3.79 mmol) was added and the mixture was left to stir for 1 h. The reaction mixture was concentrated, suspended in water, neutralised with NaHCO3 and extracted with DCM. The combined organic phases were washed with water, brine, dried over magnesium sulfate and concentrated. The crude product was triturated with n-heptane, filtered and retriturated with ether, filtered and dried to give methyl 8-acetyl-2-((R)-2-methylmorpholino)-4-oxo-4H-chromene-6-carboxylate (1.15 g, 88%) as a grey solid. Mass Spectrum: M+H⁺ 346.

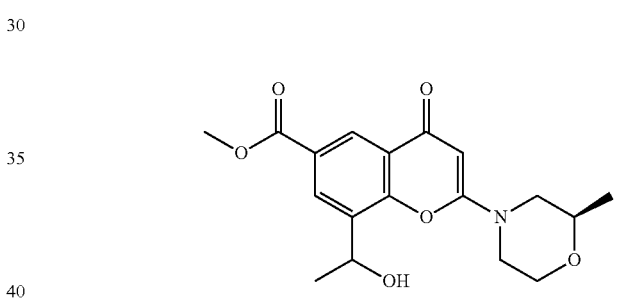

To a solution of methyl 8-acetyl-2-((R)-2-methylmorpholino)-4-oxo-4H-chromene-6-carboxylate (1.15 g, 3.33 mmol) in MeOH (20 mL)/DCM (10 mL) was added sodium tetrahydroborate (0.139 g, 3.66 mmol) at −10° C. The reaction mixture was quenched with water (50 mL) 15 min later. The volatiles were removed and the aqueous layer was extracted twice with DCM. Combined organics phases were washed with brine, dried over magnesium sulfate and concentrated. The residue was triturated with MTBE/DCM (9/1) and collected by filtration to give methyl 8-(1-hydroxyethyl)-2-((R)-2-methylmorpholino)-4-oxo-4H-chromene-6-carboxylate (1.0 g, 86%) as a grey solid, which was used in the next step without further purification. Mass Spectrum: M+H⁺ 348.

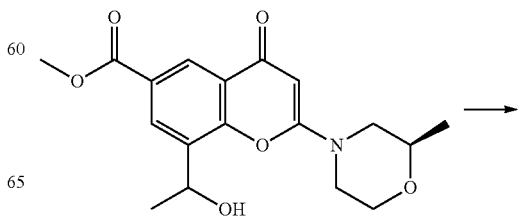

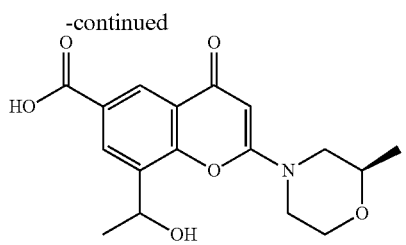

NaOH (3.56 mL, 7.11 mmol) was added to a stirred suspension of methyl 8-(1-hydroxyethyl)-2-((R)-2-methylmorpholino)-4-oxo-4H-chromene-6-carboxylate (988 mg, 2.84 mmol) in MeOH (10 mL)/water (10 mL). The resulting mixture was stirred at RT for 1 hour then acidified to pH 2-3 with a 2N aq. HCl (7.68 mL, 7.68 mmol). The resulting precipitate was collected by filtration, washed with diethyl ether and dried to afford 8-(1-hydroxyethyl)-2-((R)-2-methylmorpholino)-4-oxo-4H-chromene-6-carboxylic acid (900 mg, 95%) as a grey solid, which was used without further purification. Mass Spectrum: M+H$^+$ 334.

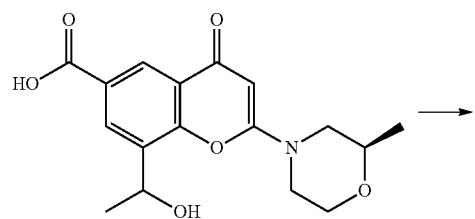

2-(2,5-dioxopyrrolidin-1-yl)-1,1,3,3-tetramethylisouronium tetrafluoroborate (2.38 g, 3.96 mmol) was added portionwise to 8-(1-hydroxyethyl)-2-((R)-2-methylmorpholino)-4-oxo-4H-chromene-6-carboxylic acid (0.88 g, 2.64 mmol) and N-ethyl-N-isopropylpropan-2-amine (1.380 mL, 7.92 mmol) suspended in DCM (15 mL) at 10° C. under nitrogen. The resulting mixture was stirred at RT for 2 hrs. Dimethylamine (3.96 mL, 7.92 mmol) was then added at 10° C. and the resulting mixture was stirred at RT overnight. The mixture was poured onto a silica gel column and purified by flash chromatography eluting with 0 to 10% methanolic ammonia (7 N) in DCM. The solvent was evaporated to dryness to afford a foam which crystallised from ethyl acetate, the solid was collected by filtration and dried to a constant weight in a vacuum oven to afford 8-(1-hydroxyethyl)-N,N-dimethyl-2-((R)-2-methylmorpholino)-4-oxo-4H-chromene-6-carboxamide (0.800 g, 84%) as a white solid. Mass Spectrum: M+H$^+$ 361.

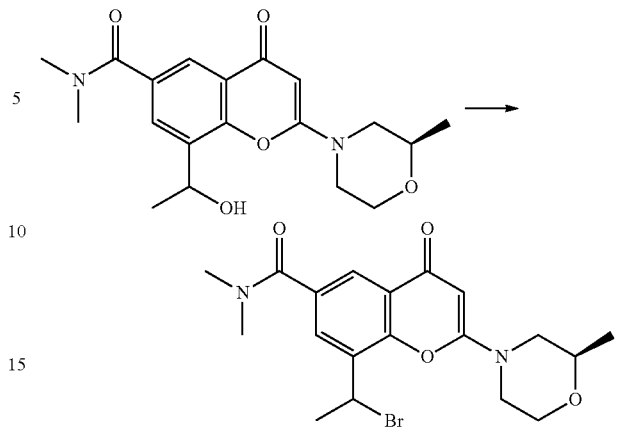

A solution of tribromophosphine (0.215 mL, 2.29 mmol) in 1,2-dichloroethane (1 mL) at 10° C. was added dropwise to 8-(1-hydroxyethyl)-N,N-dimethyl-2-((R)-2-methylmorpholino)-4-oxo-4H-chromene-6-carboxamide (750 mg, 2.08 mmol) suspended in 1,2-dichloroethane (9 mL) under nitrogen. The resulting suspension was stirred at 50° C. for 1 hour. The reaction mixture was allowed to cool to RT under stirring and diluted with diethyl ether (40 mL). The precipitate was collected by filtration, washed with diethyl ether and dried to a constant weight to afford 8-(1-bromoethyl)-N,N-dimethyl-2-((R)-2-methylmorpholino)-4-oxo-4H-chromene-6-carboxamide hydrobromide (1.3 g, 124%) as a white solid, which was used without further purification. Mass Spectrum: M+H$^+$ 424.

EXAMPLE 9.01

8-(1-(3,5-difluorophenylamino)ethyl)-N,N-dimethyl-2-((R)-2-methylmorpholino)-4-oxo-4H-chromene-6-carboxamide

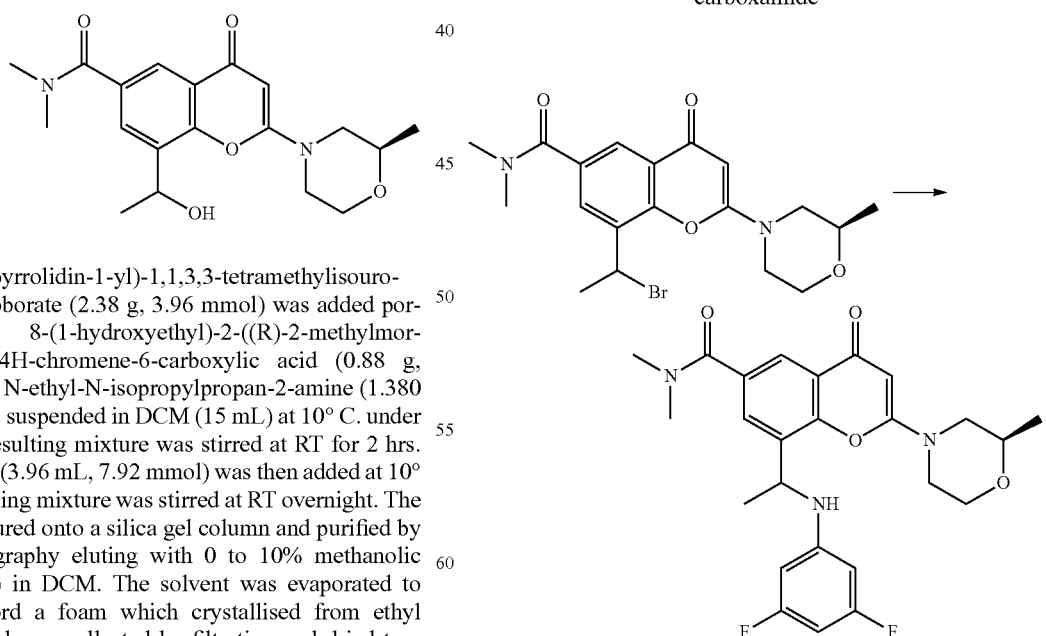

8-(1-bromoethyl)-N,N-dimethyl-2-((R)-2-methylmorpholino)-4-oxo-4H-chromene-6-carboxamide hydrobromide (1 g, 1.98 mmol) and 3,5-difluoroaniline (1.024 g, 7.93 mmol) in DMA (5 mL) were reacted as described in Example 9.0 to give 8-(1-(3,5-difluorophenylamino)ethyl)-N,N-dimethyl-2-((R)-2-methylmorpholino)-4-oxo-4H-chromene-6-carboxamide (0.550 g, 57%). Mass Spectrum: M+H⁺ 472. NMR Spectrum (DMSOd6): 1.16 (d, 3H), 1.52 (d, 3H), 2.74 (bs, 3H), 2.75-2.84 (m, 1H), 2.95 (bs, 3H), 3.08-3.16 (m, 1H), 3.56-3.68 (m, 2H), 3.86-4.04 (m, 3H), 4.97-5.08 (m, 1H), 5.62 (s, 1H), 6.12-6.19 (m, 2H), 6.22 (t, 1H), 6.93 (d, 0.5H), 6.94 (d, 0.5H), 6.54 (d, 0.5H), 6.55 (d, 0.5H), 7.81 (s, 1H).

The above mixture of diastereoisomers (495 mg) was purified by chiral preparative HPLC using the following conditions:

| Column | CelluCoat 250 × 50 10 μm |
|---|---|
| Eluent | Heptane/IPA/TEA 50/50/0.1 |
| Oven Temperature | Ambient |
| Flow | 120 mL/min |
| Wavelength | 270 nm |
| Sample Conc | 50 mg/ml EtOH/DCM 1:1 |
| Injection amount | 495 mg |

First eluting diastereoisomer 234 mg (Example 9.01a) $[\alpha]^D_{20°}$: +136° in MeCN.

Second eluting diastereoisomer 240 mg (Example 9.01b) $[\alpha]^D_{20°}$: −99° in MeCN.

EXAMPLE 9.02

8-(1-(3,5-difluorophenylamino)ethyl)-N,N-dimethyl-2-((S)-2-methylmorpholino)-4-oxo-4H-chromene-6-carboxamide

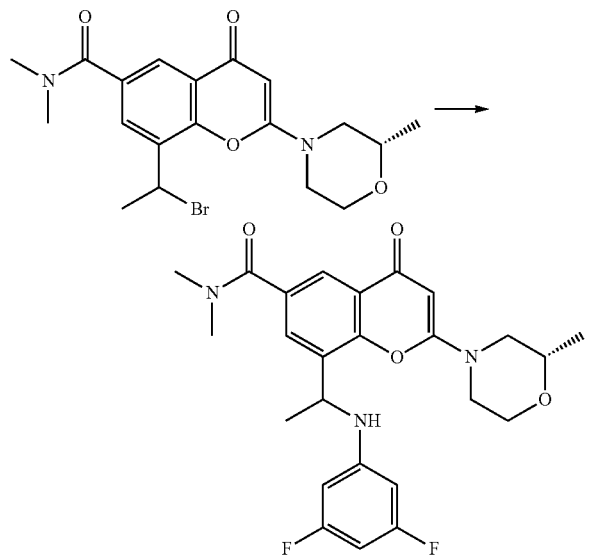

A solution of 8-(1-bromoethyl)-N,N-dimethyl-2-((S)-2-methylmorpholino)-4-oxo-4H-chromene-6-carboxamide (670 mg, 1.42 mmol) and 3,5-difluoroaniline (736 mg, 5.70 mmol) in DMA (4 mL) were stirred at 50° C. for 4 hrs then at rt over the weekend. The reaction mixture was diluted with ethyl acetate, washed with a sat. aq. sol. of sodium hydrogenocarbonate, water brine, dried over magnesium sulfate and concentrated to afford the crude product, which was purified by flash chromatography on silica gel eluting with 0 to 10% MeOH in DCM. The solvent was evaporated to dryness and the obtained foam was triturated with diethyl ether to give a white solid which was collected by filtration and dried under vacuum to give 8-(1-(3,5-difluorophenylamino)ethyl)-N,N-dimethyl-2-((S)-2-methylmorpholino)-4-oxo-4H-chromene-6-carboxamide (400 mg, 60%). Mass Spectrum: M+H⁺ 472. NMR Spectrum (CDCl₃): 1.25 (d, 3H), 1.61 (d partially hidden by H2O, 3H), 2.83 (ddd, 1H), 2.90 (bs, 3H), 3.08 (bs, 3H), 3.18 (dddd, 1H), 3.63-3.82 (m, 4H), 4.02 (ddd, 1H), 4.37 (bs, 1H), 4.88-4.97 (m, 1H), 5.55 (s, 1H), 5.97 (d, 2H), 6.13 (t, 1H), 7.72 (d, 1H), 8.12 (d, 1H).

The above mixture of diastereoisomers (370 mg) was purified by chiral preparative HPLC using the following conditions:

| Column | Chiralpak IC 20 × 250 mm, 10 μm |
|---|---|
| Eluent | DCM/IPA 6:4 |
| Oven Temperature | Ambient |
| Flow | 20 mL/min |
| Wavelength | 280 nm |
| Sample Conc | 110 mg/mL in DCM/MeOH 6:4 |
| Injection | 55 mg |

First eluting diastereomer 122 mg (Example 9.02a) $[\alpha]^D_{20°}$: +111° in MeCN Second eluting diastereomer 105 mg (Example 9.02b) $[\alpha]^D_{20°}$: −163° in MeCN

EXAMPLE 9.03

8-(1-(4-fluorophenylamino)ethyl)-N,N-dimethyl-2-((S)-2-methylmorpholino)-4-oxo-4H-chromene-6-carboxamide

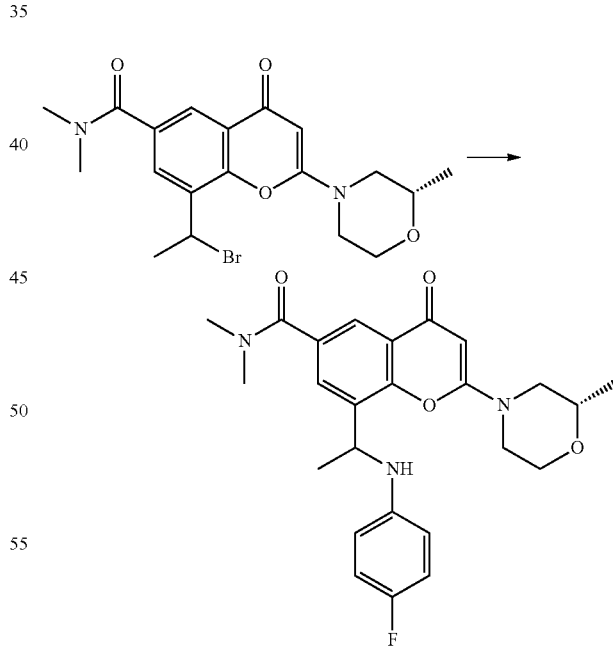

8-(1-bromoethyl)-N,N-dimethyl-2-((S)-2-methylmorpholino)-4-oxo-4H-chromene-6-carboxamide (110 mg, 0.20 mmol) and 4-fluoroaniline in DMA (1 mL) were stirred at 50° C. for 5 hrs. The reaction mixture was purified by preparative HPLC on a Waters X-Bridge system. The fractions containing the desired compound were concentrated. The obtained gum was triturated in diethyl ether and petroleum ether, the resulting solid was collected by filtration and dried to afford 8-(1-(4-fluorophenylamino)ethyl)-N,N-dimethyl-2-((S)-2-methylmorpholino)-4-oxo-4H-chromene-6-carboxamide (45 mg, 51%) as a white solid. Mass Spectrum: M+H⁺ 545. NMR Spectrum (CDCl₃): 1.25 (d, 1.5H), 1.26 (d, 1.5H), 1.61 (d, 3H), 2.77-2.88 (m, 1H), 2.83 (bs, 3H), 3.06 (bs, 3H), 3.13-3.22 (m, 1H), 3.64-3.82 (m, 4H), 3.97 (bs, 1H), 3.98-4.06 (m, 1H), 4.91 (q, 1H), 5.56 (s, 1H), 6.37-6.43 (m, 2H), 6.82 (t, 2H), 7.73 (d, 1H), 8.11 (d, 1H).

EXAMPLE 10.0

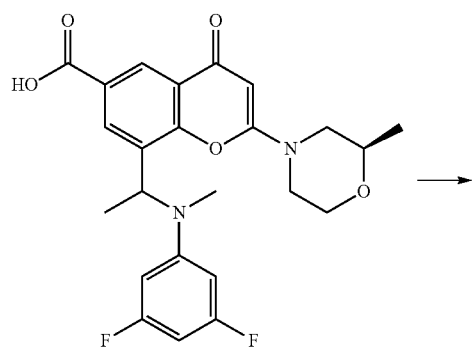

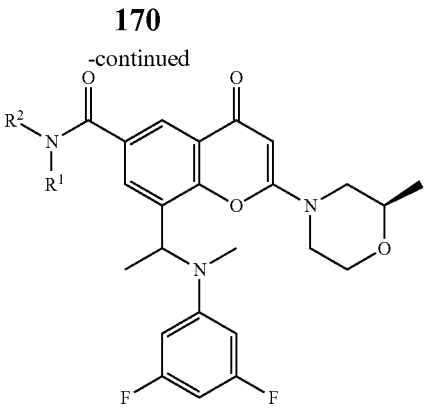

For preparation of the compounds of Examples 10.01 to 10.03 (shown in Table III), TBTU (96 mg, 0.30 mmol) was added in one portion to a stirred solution of the desired amine reagent (-, 0.30 mmol), 8-(1-((3,5-difluorophenyl)(methyl)amino)ethyl)-2-((R)-2-methylmorpholino)-4-oxo-4H-chromene-6-carboxylic acid (125 mg, 0.27 mmol) and 4-methylmorpholine (0.066 mL, 0.60 mmol) in DMF (1 mL). The resulting solution was stirred at RT overnight. The reaction mixture was filtered and purified by preparative HPLC on a Waters X-Bridge system. The fractions containing the desired compound were evaporated to dryness.

TABLE III

| Ex. | Amine reageant | Structure | Product | Prod. Mass | Yield | MH⁺ |
|---|---|---|---|---|---|---|
| 10.01 | dimethyl amine | 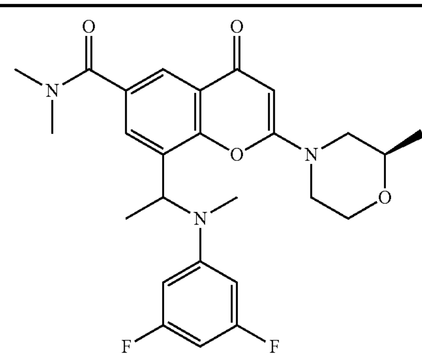 | 8-(1-((3,5-difluorophenyl)(methyl)amino)ethyl)-N,N-dimethyl-2-((R)-2-methylmorpholino)-4-oxo-4H-chromene-6-carboxamide | 83 mg | 63% | 486 |
| 10.02 | (methyl-amino) ethanol | 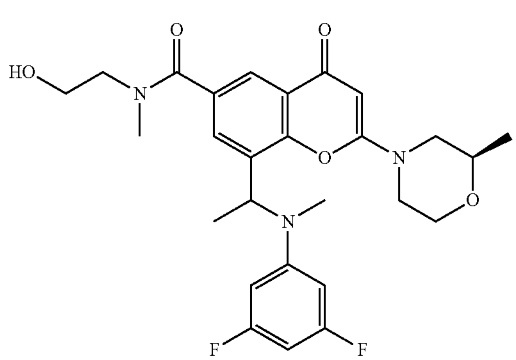 [SMILES: CC(c1cc(C(=O)N(C)CCO)cc2c(=O)cc(N3CCO[C@H](C)C3)oc12)N(C)c1cc(F)cc(F)c1] | 8-(1-((3,5-difluorophenyl)(methyl)amino)ethyl)-N-(2-hydroxyethyl)-N-methyl-2-((R)-2-methylmorpholino)-4-oxo-4H-chromene-6-carboxamide | 79 mg | 56% | 516 |

TABLE III-continued

| Ex. | Amine reageant | Structure | Product | Prod. Mass | Yield | MH+ |
|---|---|---|---|---|---|---|
| 10.03 | piperidin-4-ol | 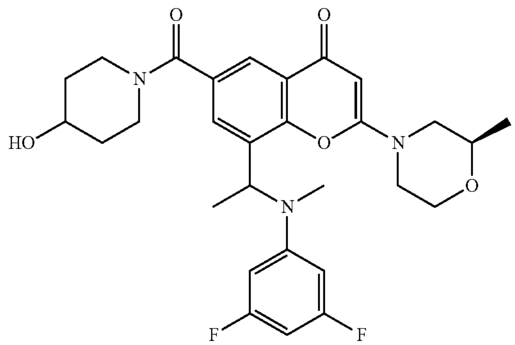 [SMILES: CC(c1cc(C(=O)N2CCC(O)CC2)cc2c(=O)cc(N3CCO[C@H](C)C3)oc12)N(C)c1cc(F)cc(F)c1] | 8-(1-((3,5-difluorophenyl)(methyl)amino)ethyl)-6-(4-hydroxypiperidine-1-carbonyl)-2-((R)-2-methylmorpholino)-4H-chromen-4-one | 85 mg | 58% | 542 |

Notes
Further characterising data for the products is given below.

EXAMPLE 10.01

DMSOd6 at 323° K: 1.01 (d, 1.5H), 1.02 (d, 1.5H), 1.57 (d, 3H), 2.63 (s, 1.5H), 2.67 (s, 1.5H), 2.65-2.71 (m, 0.5H), 2.74-2.83 (m, 0.5H), 2.98 (bs, 6H), 3.31-3.55 (m, 2H), 3.61-3.81 (m, 4H), 5.56 (s, 1H), 5.59 (q, 1H), 6.37 (t, 1H), 6.57 (d, 2H), 7.70 (s, 1H), 7.92 (s, 1H).

EXAMPLE 10.02

DMSOd6 at 323° K: 1.01 (d, 1.5H), 1.02 (d, 1.5H), 1.56 (d, 3H), 2.46-2.51 (m, 0.5H), 2.61 (s, 1.5H), 2.64 (s, 1.5H), 2.64-2.71 (m, 0.5H), 2.74-2.82 (m, 0.5H), 2.94-3.00 (m, 0.5H), 3.00 (bs, 3H), 3.27-3.90 (m, 9H), 4.74 (t, 1H), 5.55 (s, 1H), 5.59 (q, 1H), 6.37 (t, 1H), 6.55 (d, 2H), 7.74 (bs, 1H), 7.93 (s, 1H).

EXAMPLE 10.03

DMSOd6 at 323° K: 1.02 (d, 1.5H), 1.05 (d, 1.5H), 1.39 (bs, 2H), 1.58 (d, 3H), 1.79 (bs, 2H), 2.48-2.55 m partially hidden by DMSOd6, 0.5H), 2.64 (s, 1.5H), 2.66-2.71 (m, 0.5H), 2.67 (s, 1.5H), 2.76-2H), 3.63-3.81 (m, 4H), 3.84 (bs, 2H), 4.69 (d, 1H), 5.56 (s, 1H), 5.58 (q, 1H), 6.37 (t, 1H), 6.53 (d, 2H), 7.64 (bs, 1H), 7.89 (s, 1H).

EXAMPLE 11

8-(1-(3,5-difluorophenylamino)ethyl)-N,N-dimethyl-2-((S)-3-methylmorpholino)-4-oxo-4H-chromene-6-carboxamide

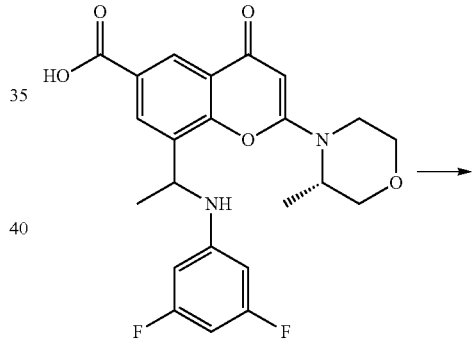

2-(1H-benzo[d][1,2,3]triazol-1-yl)-1,1,3,3-tetramethylisouronium tetrafluoroborate (55.6 mg, 0.17 mmol), was added in one portion to a stirred solution of 8-(1-(3,5-difluorophenylamino)ethyl)-2-((S)-3-methylmorpholino)-4-oxo-4H-chromene-6-carboxylic acid (70 mg, 0.16 mmol), dimethylamine (0.095 mL, 0.19 mmol) and 4-methylmorpholine (0.038 mL, 0.35 mmol) in DMF (1 mL). The resulting solution was stirred at RT for 1 hour. The reaction mixture was purified by preparative HPLC using a reverse-phase column (C-18, 5 microns silica, 19 mm diameter, 100 mm length, flow rate of 40 mL/minute) and decreasingly polar mixtures of water (containing 0.2% ammonium carbonate) and acetonitrile as eluent. The fractions containing the desired compound were evaporated to dryness to afford a residue which was triturated with Et2O, filtered and dried to give 8-(1-(3,5-difluorophenylamino)ethyl)-N,N-dimethyl-2-((S)-3-methylmorpholino)-4-oxo-4H-chromene-6-carboxamide (45 mg, 61%) as a pale orange solid. Mass Spectrum: M+H$^+$ 471. NMR Spectrum (CDCl$_3$): 1.37 (d, 1.5H), 1.41 (d, 1.5H), 1.59 (d, 1.5H), 1.60 (d, 1.5H), 2.89 (s, 1.5H), 2.91 (s, 1.5H), 3.08 (s, 3H), 3.35-3.43 (m, 1H), 3.52-3.69 (m, 2H), 3.75-3.83 (m, 2H), 3.98-4.09 (m, 2H), 4.52 (d, 1H), 4.85-4.96 (m, 1H), 5.53 (s, 1H), 5.97 (d, 2H), 6.11 (t, 1H), 7.71 (d, 0.5H), 7.73 (d, 0.5H), 8.13 (d, 1H).

The 8-(1-(3,5-difluorophenylamino)ethyl)-2-((S)-3-methylmorpholino)-4-oxo-4H-chromene-6-carboxylic acid used as starting material was made as follows: —

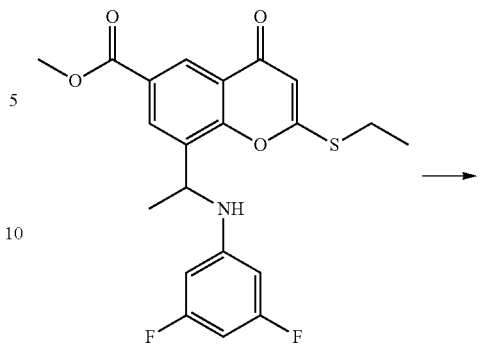

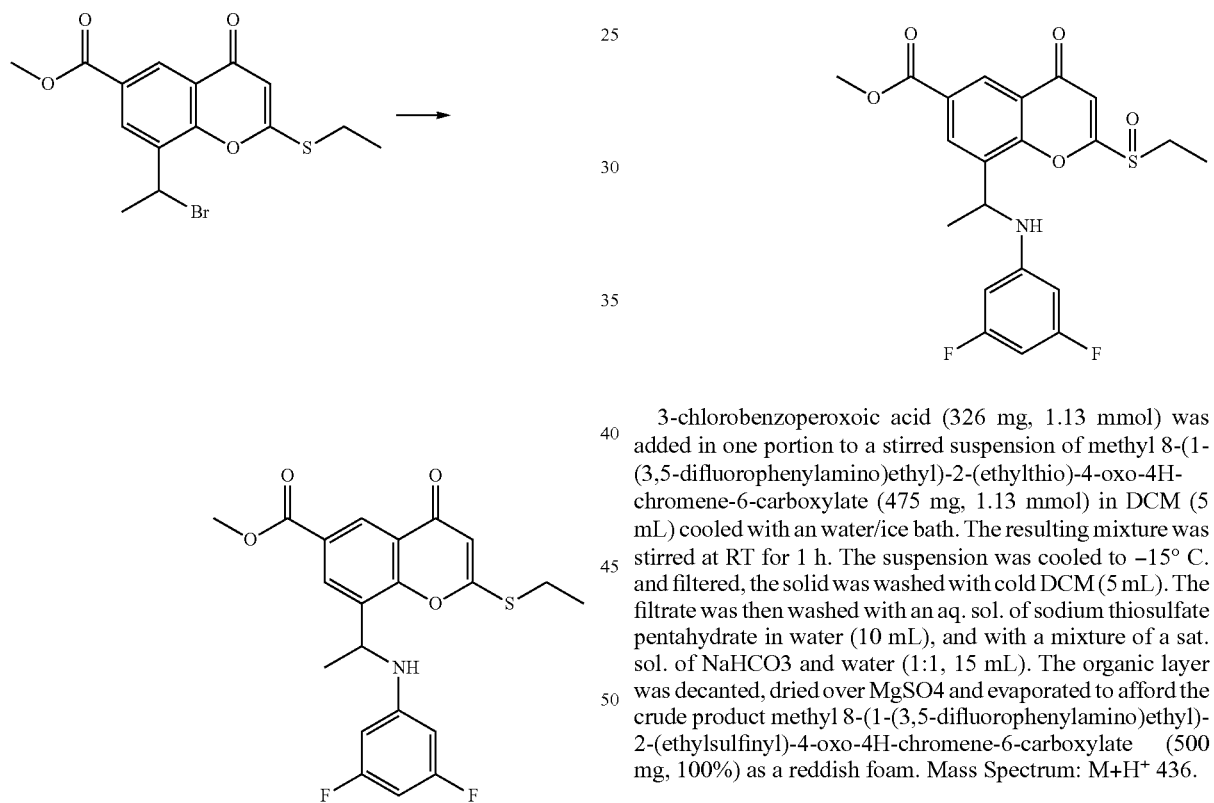

Methyl 8-bromo-2-(ethylthio)-4-oxo-4H-chromene-6-carboxylate (850 mg, 2.29 mmol, prepared as described in Example 9) and 3,5-difluoroaniline (621 mg, 4.81 mmol) in DMA (10 mL) were stirred at 50° C. overnight. The reaction mixture was diluted with water/ethyl acetate. The organic layer was washed with brine, dried over MgSO4 and concentrated. The crude product was purified by flash chromatography on silica gel eluting with 0 to 25% ethyl acetate in dichloromethane. The solvent was evaporated to dryness to afford methyl 8-(1-(3,5-difluorophenylamino)ethyl)-2-(ethylthio)-4-oxo-4H-chromene-6-carboxylate (550 mg, 57%) as a off-white solid. Mass Spectrum: M+H$^+$ 420.

3-chlorobenzoperoxoic acid (326 mg, 1.13 mmol) was added in one portion to a stirred suspension of methyl 8-(1-(3,5-difluorophenylamino)ethyl)-2-(ethylthio)-4-oxo-4H-chromene-6-carboxylate (475 mg, 1.13 mmol) in DCM (5 mL) cooled with an water/ice bath. The resulting mixture was stirred at RT for 1 h. The suspension was cooled to −15° C. and filtered, the solid was washed with cold DCM (5 mL). The filtrate was then washed with an aq. sol. of sodium thiosulfate pentahydrate in water (10 mL), and with a mixture of a sat. sol. of NaHCO3 and water (1:1, 15 mL). The organic layer was decanted, dried over MgSO4 and evaporated to afford the crude product methyl 8-(1-(3,5-difluorophenylamino)ethyl)-2-(ethylsulfinyl)-4-oxo-4H-chromene-6-carboxylate (500 mg, 100%) as a reddish foam. Mass Spectrum: M+H$^+$ 436.

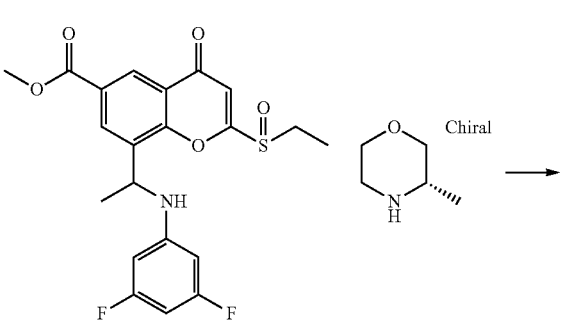

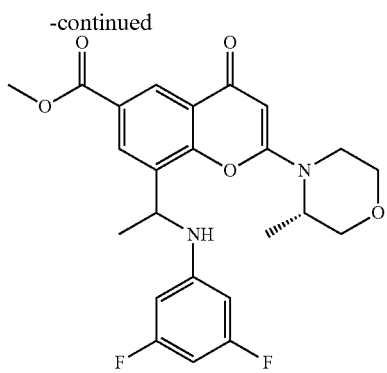

(S)-3-methylmorpholine (87 mg, 0.86 mmol) was added to a stirred solution of methyl 8-(1-(3,5-difluorophenylamino)ethyl)-2-(ethylsulfinyl)-4-oxo-4H-chromene-6-carboxylate (250 mg, 0.57 mmol) and N-ethyl-N-isopropylpropan-2-amine (0.150 mL, 0.86 mmol) in acetonitrile (3 mL) at RT. The resulting brown mixture was stirred at 75° C. for 7 hours. The reaction mixture was concentrated, diluted with DCM, washed with a 1M hydrochloric acid 1M, brine dried over magnesium sulfate and concentrated to afford the crude product which was purified by flash chromatography on silica gel eluting with 0 to 5% MeOH in DCM. The solvent was evaporated to dryness to afford methyl 8-(1-(3,5-difluorophenylamino)ethyl)-2-((S)-3-methylmorpholino)-4-oxo-4H-chromene-6-carboxylate (90 mg, 34%) as a yellow foam. Spectrum: [M−H]⁻ 457.

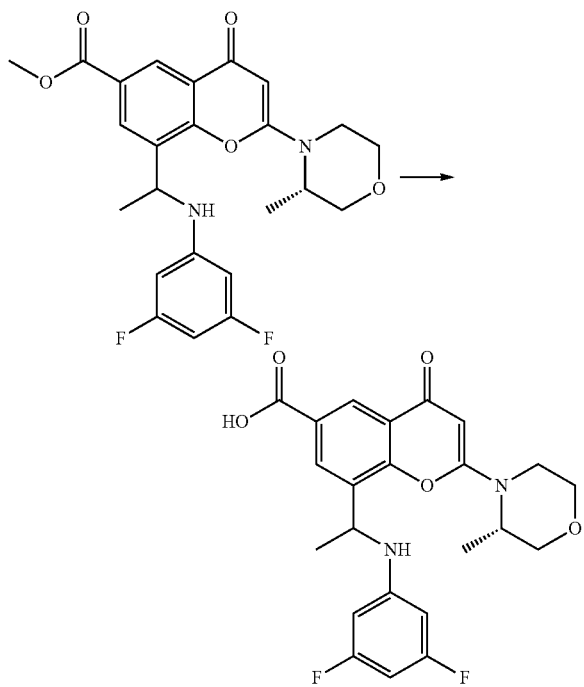

2N NaOH (0.206 mL, 0.41 mmol) was added to a stirred suspension of methyl 8-(1-(3,5-difluorophenylamino)ethyl)-2-((S)-3-methylmorpholino)-4-oxo-4H-chromene-6-carboxylate (90 mg, 0.20 mmol) in MeOH (1 mL)/THF (1 mL) and cooled with an ice-water bath. The resulting suspension was stirred at RT for 2 hours. The reaction was incomplete thus the temperature was increased to 35° C. and stirred for an additional hour. The reaction mixture was cooled with an ice bath, the pH was adjusted to 2-3 with hydrochloric acid 1M and the volatils were evaporated. The resulting precipitate was collected by filtration, dried, triturated with diethyl ether, collected by filtration and dried again under vacuum to give 8-(1-(3,5-difluorophenylamino)ethyl)-2-((S)-3-methylmorpholino)-4-oxo-4H-chromene-6-carboxylic acid (75 mg, 86%). Mass Spectrum: M+H⁺ 445.

The invention claimed is:
1. A compound of the Formula I:

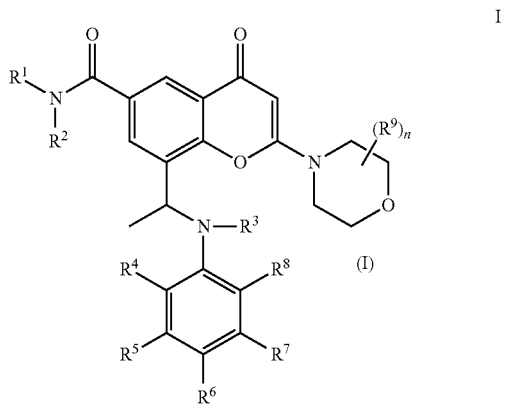

in which:
$R^1$ is H or (1-4C)alkyl optionally substituted by 1, 2 or 3 substituents independently selected from halogeno, hydroxy or (1-3C)alkoxy;
$R^2$ is (1-4C)alkyl or (1-4C)alkoxy, either of which can be optionally substituted by 1, 2 or 3 substituents independently selected from halogeno, hydroxy, (2-3C)alkenyl, (2-3C)alkynyl, (1-3C)alkoxy, cyano, (1-3C)alkylamino or di-[(1-3C)alkyl]amino; or
$R^1$ and $R^2$ together form a 3 to 8 membered nitrogen containing heterocyclyl ring system, which optionally contains 1 or 2 further heteroatoms selected from oxygen, nitrogen and sulphur, wherein a ring sulphur atom is optionally oxidised to form the S-oxide(s), said ring being optionally substituted by 1, 2 or 3 substituents independently selected from halogeno, hydroxy, (1-3C)alkyl, (2-3C)alkenyl, (2-3C)alkynyl, (1-3C)alkoxy, oxo, hydroxy-(1-3C)alkyl, halogeno-(1-3C)alkyl and (1-3C)alkoxy-(1-3C)alkyl;
$R^3$ is H or (1-3C)alkyl;
$R^4$ and $R^5$ are independently selected from H, halogeno, (1-3C)alkyl, (2-3C)alkenyl, (2-3C)alkynyl, (1-3C)alkoxy and cyano; or
$R^4$ and $R^5$ together form a phenyl ring or a 5 or 6 membered heterocyclyl ring or a 5 or 6 membered heteroaryl ring, wherein the heterocyclyl or heteroaryl ring contains 1, 2 or 3 heteroatoms selected from oxygen and nitrogen, said phenyl, heterocyclyl or heteroaryl ring being optionally substituted by 1, 2 or 3 substituents independently selected from halogeno, (1-3C)alkyl, (2-3C)alkenyl, (2-3C)alkynyl, (1-3C)alkoxy and cyano;
$R^6$, $R^7$ and $R^8$ are independently selected from H, halogeno, (1-3C)alkyl, (2-3C)alkenyl, (2-3C)alkynyl, (1-3C)alkoxy and cyano;
n is 0, 1, 2, 3 or 4;
each $R^9$ group is (1-3C)alkyl; or a pharmaceutically-acceptable salt thereof.

2. A compound of the Formula I according to claim 1, wherein:

$R^1$ is H or (1-4C)alkyl;

$R^2$ is (1-4C)alkyl optionally substituted by halogeno, hydroxy, (1-3C)alkoxy, cyano, (1-3C)alkylamino or di-[(1-3C)alkyl]amino; or $R^1$ and $R^2$ together form a 4 to 7 membered nitrogen containing heterocyclyl ring system, which optionally contains 1 further heteroatom selected from oxygen, nitrogen and sulphur, wherein a ring sulphur atom is optionally oxidised to form the S-oxide(s), said ring being optionally substituted by halogeno, hydroxy, (1-3C)alkyl, (1-3C)alkoxy or hydroxy-(1-3C)alkyl; or a pharmaceutically-acceptable salt thereof.

3. A compound of the Formula I according to claim 1, wherein $R^3$ is H or methyl; or a pharmaceutically-acceptable salt thereof.

4. A compound of the Formula I according to claims 1, wherein $R^4$ and $R^5$ are independently selected from H, halogeno, (1-3C)alkyl, (2-3C)alkenyl, (2-3C)alkynyl, (1-3C)alkoxy and cyano; or a pharmaceutically-acceptable salt thereof.

5. A compound of the Formula I according to claims 1, wherein $R^6$, $R^7$ and $R^8$ are independently selected from H, halogeno, (1-3C)alkyl, (2-3C)alkenyl, (2-3C)alkynyl, (1-3C)alkoxy and cyano; or a pharmaceutically-acceptable salt thereof.

6. A compound of the Formula I according to claims 1, wherein n is 1 and $R^9$ is methyl; or a pharmaceutically-acceptable salt thereof.

7. A compound of the Formula I according to claim 1, wherein:

$R^1$ is H or (1-4C)alkyl;

$R^2$ is (1-4C)alkyl optionally substituted by halogeno, hydroxy, (1-3C)alkoxy, cyano, (1-3C)alkylamino or di-[(1-3C)alkyl]amino; or $R^1$ and $R^2$ together form a 4 to 7 membered nitrogen containing heterocyclyl ring system, which optionally contains 1 further heteroatom selected from oxygen, nitrogen and sulphur, wherein a ring sulphur atom is optionally oxidised to form the S-oxide(s), said ring being optionally substituted by halogeno, hydroxy, (1-3C)alkyl, (1-3C)alkoxy or hydroxy-(1-3C)alkyl;

$R^3$ is H or methyl;

$R^4$ and $R^5$ are independently selected from H, halogeno, (1-3C)alkyl, (2-3C)alkenyl, (2-3C)alkynyl, (1-3C)alkoxy and cyano;

$R^6$, $R^7$ and $R^8$ are independently selected from H, halogeno, (1-3C)alkyl, (2-3C)alkenyl, (2-3C)alkynyl, (1-3C)alkoxy and cyano;

n is 0; or a pharmaceutically-acceptable salt thereof.

8. A compound of the Formula I according to claim 1 wherein:

$R^1$ is H, methyl or ethyl;

$R^2$ is (1-4C)alkyl optionally substituted by halogeno, hydroxy, (1-3C)alkoxy, cyano, (1-3C)alkylamino or di-[(1-3C)alkyl]amino; or $R^1$ and $R^2$ together form a nitrogen containing heterocyclyl ring system, selected from azepanyl, oxazepanyl, azetidinyl, pyrrolidinyl, morpholinyl, thiomorpholinyl, piperidinyl and piperazinyl, said ring being optionally substituted by halogeno, hydroxy, (1-3C)alkyl, (1-3C)alkoxy or hydroxy-(1-3C)alkyl;

$R^3$ is H;

$R^4$ and $R^5$ are independently selected from H, fluoro or chloro;

$R^6$, $R^7$ and $R^8$ are independently selected from H or halogeno;

n is 0; or a pharmaceutically-acceptable salt thereof.

9. A compound of the Formula I according to claim 1 wherein:

$R^1$ is H, methyl or ethyl;

$R^2$ is methyl, ethyl, cyclopropylmethyl, 2-fluoroethyl, 2-hydroxyethyl, 2-methoxyethyl, 3-methoxypropyl or 2-(dimethylamino)ethyl; or $R^1$ and $R^2$ together form an optionally substituted nitrogen containing heterocyclyl ring system, selected from azepan-1-yl, 1,4-oxazepan-4-yl, azetidin-1-yl, 3-fluoro-azetidin-1-yl, 3-hydroxyazetidin-1-yl, pyrrolidin-1-yl, (2R)-2-(hydroxymethyl)pyrrolidin-1-yl, (2S)-2-(hydroxymethyl)pyrrolidin-1-yl, morpholin-4-yl, thiomorpholin-4-yl, piperidin-1-yl, 4-hydroxypiperidin-1-yl, 4-methoxypiperidin-1-yl, piperazin-1-yl or 4-methylpiperazin-1-yl;

$R^3$ is H or methyl;

$R^4$ and $R^5$ are independently selected from H, fluoro or chloro;

$R^6$, $R^7$ and $R^8$ are independently selected from H, fluoro or chloro;

n is 0; or a pharmaceutically-acceptable salt thereof.

10. A compound of the Formula I, or a pharmaceutically-acceptable salt thereof, according to claim 1, wherein the compound is a single enantiomer being in an enantiomeric excess (% ee) of ≧95.

11. A pharmaceutical composition, which comprises a compound of the

Formula I, or a pharmaceutically-acceptable salt thereof, according to claim 1 in association with a pharmaceutically-acceptable diluent or carrier.

12. A method for the treatment of tumours which are sensitive to inhibition of PI 3-kinase enzymes in a warm-blooded animal having such tumours, which comprises administering to said animal an effective amount of a compound of the Formula I, or a pharmaceutically-acceptable salt thereof, according to claim 1.

13. 8-(1-(3,5-difluorophenylamino)ethyl)-N,N-dimethyl-2-morpholino-4-oxo-4H-chromene-6-carboxamide or a pharmaceutically acceptable salt thereof.

14. A compound according to claim 13 which is 8((1R)-1-(3,5-difluorophenylamino)ethyl)-N,N-dimethyl-2-morpholino-4-oxo-4H-chromene-6-carboxamide) or a pharmaceutically acceptable salt thereof.

15. A compound according to claim 13 which is 8-((1S)-1-(3,5-difluorophenylamino)ethyl)-N,N-dimethyl-2-morpholino-4-oxo-4H-chromene-6-carboxamide) or a pharmaceutically acceptable salt thereof.

* * * * *